US008389692B2

(12) United States Patent
Takayama et al.

(10) Patent No.: US 8,389,692 B2
(45) Date of Patent: Mar. 5, 2013

(54) ANTI-PLATELET MEMBRANE GLYCOPROTEIN VI MONOCLONAL ANTIBODY

(75) Inventors: Hiroshi Takayama, Ibaraki (JP); Kamon Shirakawa, Tokyo (JP); Shoji Furusako, Tokyo (JP); Yoshitaka Hosaka, Tokyo (JP); Tomokazu Matsusue, Tokyo (JP); Katsuki Naitoh, Tokyo (JP); Yumi Hotta, Tokyo (JP); Tetsushi Kawahara, Tokyo (JP); Motoyasu Honda, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/095,098

(22) Filed: Apr. 27, 2011

(65) Prior Publication Data
US 2011/0217318 A1 Sep. 8, 2011

Related U.S. Application Data

(62) Division of application No. 11/912,757, filed as application No. PCT/JP2006/309431 on Apr. 28, 2006, now Pat. No. 7,977,461.

(30) Foreign Application Priority Data

Apr. 28, 2005 (JP) ................................ 2005-132665
Dec. 1, 2005 (JP) ................................ 2005-348534
Jan. 27, 2006 (WO) .................. PCT/JP2006/301818

(51) Int. Cl.
*C12P 21/08* (2006.01)
(52) U.S. Cl. ............... 530/387.3; 530/388.1; 530/391.3; 530/391.7
(58) Field of Classification Search .................. None
See application file for complete search history.

(56) References Cited

U.S. PATENT DOCUMENTS

| 7,977,461 | B2 * | 7/2011 | Takayama et al. ......... 530/387.1 |
| 2002/0141992 | A1 | 10/2002 | Nieswandt |
| 2009/0041783 | A1 | 2/2009 | Takayama et al. |

FOREIGN PATENT DOCUMENTS

| EP | 1 369 128 A1 | 12/2003 |
| EP | 1 538 165 A1 | 6/2005 |
| EP | 1 647 596 A2 | 4/2006 |
| JP | 11-004694 A | 1/1999 |
| JP | 11-243955 A | 9/1999 |
| JP | 2004-521655 A | 7/2004 |
| JP | 2005-087215 A | 4/2005 |
| WO | WO 90/07861 A1 | 7/1990 |
| WO | WO 91/09967 A1 | 7/1991 |
| WO | WO 00/37504 A2 | 6/2000 |
| WO | WO 00/68377 A1 | 11/2000 |
| WO | WO 01/16321 A1 | 3/2001 |
| WO | WO 02/080968 A1 | 10/2002 |
| WO | WO 03/008454 A2 | 1/2003 |
| WO | WO 03/010202 A1 | 2/2003 |
| WO | WO 03/054020 A2 | 7/2003 |
| WO | WO 2004/035607 A2 | 4/2004 |
| WO | WO 2004/039826 A1 | 5/2004 |
| WO | WO 2004/113517 A2 | 12/2004 |
| WO | WO 2005/007800 A2 | 1/2005 |
| WO | WO 2005/019267 A2 | 3/2005 |

OTHER PUBLICATIONS

Futei et al., "Use of Domain-Swapped Molecules for Conformational Epitope Mapping of Desmoglein 3 in Pemphigus Vulgaris," J. Invest. Derm., Nov. 2000, 115(5):829-834.
Mathonet et al., "Engineering of non-natural receptors," Current Opinion in Structural Biology, 2004, 14:505-511.
Ostermeier et al., "Evolution of Protein Function by Domain Swapping," Advances in Protein Chemistry, 2001, 55:29-77.
Amersdorfer et al., "Molecular Characterization of Murine Humoral Immune Response to Botulinum Neurotoxin Type A Binding Domain as Assessed by Using Phage Antibody Libraries," Infection and Immunity, Sep. 1997, 65(9):3743-3752.
Clemetson et al., "The Platelet Collagen Receptor Glycoprotein VI is a Member of the Immunoglobulin Superfamily Closely Related to FcαR and the Natural Killer Receptors," J. Biol. Chem., Oct. 8, 1999, 274(41):29019-29024.
Cortez-Retamozo et al., "Efficient Cancer Therapy with a Nanobody-Based Conjugate," Cancer Research, Apr. 15, 2004, 64:2853-2857.
Gardiner et al., "Regulation of platelet membrane levels of glycoprotein VI by a platelet-derived metalloproteinase," Blood, 2004, 104(12):3611-3617.
Greenspan et al., "Defining epitopes: It's not as easy as it seems," Nature Biotechnology, Oct. 1999, 17:936-937.
Gussow et al., "Humanization of Monoclonal Antibodies," Methods in Enzymology, 1991, 203:99-121.
Holm et al., "Functional mapping and single chain construction of the anti-cytokeratin 8 monoclonal antibody TS1," Molecular Immunology, 2007, 44:1075-1084.
International Search Report mailed May 16, 2006, in PCT/JP2006/301818, 2 pages.
Lecut et al., "Human platelet glycoprotein VI function is antagonized by monoclonal antibody-derived Fab fragments," Journal of Thrombosis and Haemostasis, Dec. 1, 2003, 1(12):2653-2662.
Lecut et al., "Identification of residues within human glycoprotein VI involved in the binding to collagen," J. Biol. Chem., 2004, 279(50):52293-52299.
MacCallum et al., "Antibody-antigen Interactions: Contact Analysis and Binding Site Topography," J. Mol. Biol., 1996, 262:732-745.
Mariuzza et al., "The Structural Basis of Antigen-Antibody Recognition," Ann. Rev. Biophys. Biophys. Chem., 1987, 16:139-159.

(Continued)

*Primary Examiner* — Brad Duffy
(74) *Attorney, Agent, or Firm* — Foley & Lardner LLP

(57) ABSTRACT

The present invention provides an antibody which has the following features, its active fragment, or a derivative thereof:
a) It specifically binds to human platelet membrane glycoprotein VI (GPVI);
b) The function to activate a platelet and/or the function to induce a thrombocytopenia in vivo are low; and
c) It at least partially depletes GPVI on the platelet membrane by contacting with a platelet.

8 Claims, 47 Drawing Sheets

OTHER PUBLICATIONS

McKean et al., "Mechanisms of antibody diversity: Multiple genes encode structurally related mouse κ variable regions," Proc. Natl. Acad. Sci. USA, Aug. 1978, 75(8):3913-3917.

Moroi et al., "Platelet glycoprotein VI: its structure and function," Thrombosis Research, Jan. 1, 2004, 114(4):221-233.

Nieswandt et al., "Long-term Antithrombotic Protection by In Vivo Depletion of Platelet Glycoprotein VI in Mice," J. Exp. Med., Feb. 19, 2001, 193(4):459-469.

Orita et al., "A novel therapeutic approach for thrombocytopenia by minibody agonist of the thrombopoietin receptor," Blood, Jan. 15, 2005, 105(2):562-566.

Pier et al., Eds., Immunology, Infection and Immunity, 2004, p. 49.

Rudikoff et al., "Single amino acid substitution altering antigen-binding specificity," Proc. Natl. Acad. Sci. USA, Mar. 1982, 79:1979-1983.

Schulte et al., "Evidence for Two Distinct Epitopes within Collagen for Activation of Murine Platelets," J. Biol. Chem., Jan. 5, 2001, 276(1):364-368.

Smethurst et al., "Identification of the primary collagen-binding surface on human glycoprotein VI by site-directed mutagenesis and by a blocking phage antibody," Blood, Feb. 1, 2004, 103(3):903-911.

Stark et al., "Antibodies that are Specific for a Single Amino Acid Interchange in a Protein Epitope Use Structurally Distinct Variable Regions," J. Exp. Med., Sep. 1991, 174:613-624.

Stephens et al., "Platelet activation induces metalloproteinase-dependent GP VI cleavage to down-regulate platelet reactivity to collagen," Blood, Jan. 2005, 105(1):186-191.

Sugiyama et al., "A Novel Platelet Aggregating Factor Found in a Patient with Defective Collagen-Induced Platelet Aggregation and Autoimmune Thrombocytopenia," Blood, Jun. 1987, 69(6):1712-1720.

Supplementary European Search Report dated Dec. 30, 2008, in corresponding European Application No. 0674241.6, 6 pages.

Takayama et al., "A novel antiplatelet antibody therapy that induces cAMP-dependent endocytosis of the GPVI/Fc receptor γ-chain," J. Clin. Invest., May 2008, 118(5):1785-1795.

Takayama, Hiroshi, "Ko Kesshoban Ryoho," Kessen to Junkan, Mar. 10, 2005, 13(1):56-59.

Weigert et al., "Rearrangement of genetic information may produce immunoglobulin diversity," Nature, Dec. 21, 1978, 276 (5690):785-790.

Xia et al., "Mapping of a conformational epitope on the cashew allergen Ana o 2: A discontinuous large subunit epitope dependent upon homologous or heterologous small subunit association," Molecular Immunology, 2010, 47:1808-1816.

Davies et al., "Affinity improvement of single antibody VH domains: residues in all three hypervariable regions affect antigen binding," Immunotechnology, Sep. 1, 1996, 2(3):169-179.

Gruener et al., "Relative antithrombotic effect of soluble GPVI dimmer compared with anti-GPVI antibodies in mice," Blood, American Society of Hematology, Feb. 15, 2005, 105(4):1492-1499.

Holt et al., "Domain antibodies: proteins for therapy," Trends in Biotechnology, Nov. 1, 2003, 21(11):484-490.

O'Connor et al., "Selective Blockade of Glycoprotein VI Clustering on Collagen Helices," Thr Journal of Biological Chemistry, Nov. 3, 2006, 281(44):33505-33510.

Rabie et al., "Diverging signaling events control the pathway of GPVI down-regulation in vivo," Blood, Jul. 1, 2007, 110(2):529-535.

Asturias et al., "Molecular and structural analysis of the panallergen profiling B cell epitopes defined by monoclonal antibodies," International Immunology, 2002, 14(9):993-1001.

Dekker et al., "Inhibitory and neutral antibodies to *Plasmodium falciparum* MSPI19 form ring structures with their antigen," Molecular & Biochemical Parasitology, 2004, 137(1):143-149.

Pearce et al., "Mutational Analysis of thrombopoietin for Identification of Receptor and Neutralizing Antibody Sites," The Journal of Biological Chemistry, Aug. 16, 1997, 272(33):20595-20602.

* cited by examiner

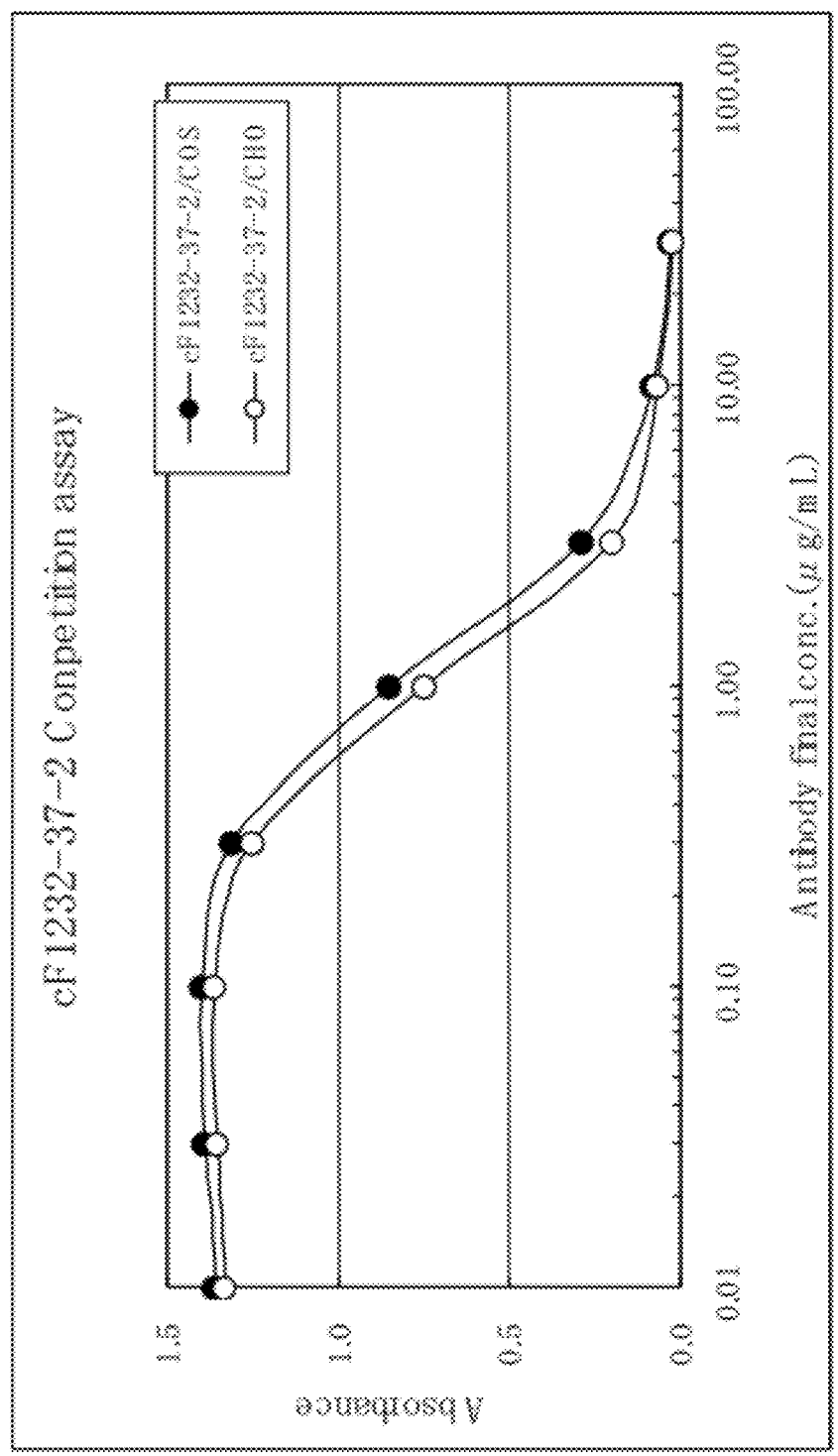

Fig.20

Humanization of heavy chain variable region

|  | FR1 | CDR1 | FR2 | CDR2 |
|---|---|---|---|---|
| F1232-37-2 | QVQLQQSGPELVRPGESVKISCKGSGYTFT | DYAIH | WVKLSHAKSLEWIG | VISIYYDDTNYN |
| NEW-HA | QVQLQESGPGLVRPSQTLSLTCTVSGSTFS | DYAIH | WVRQPPGRGLEWIG | VISIYYDDTNYN |
| NEW-HAN | ....Q..E....G................ | ..... | .............. | ............ |
| Eu-HA | QVQLVESGAGVKKPSSTLSVTCTASGGTFS | DYAIH | WVRQAPGQGLEWMG | VISIYYDDTNYN |
| Eu-HC | ............................. | ..... | .............I | ............ |

|  | FR3 | CDR3 | FR4 |
|---|---|---|---|
| F1232-37-2 | QKFKGRATMTVDKSSSTAYLELARLTSEDSAIYYCAR | RRDSSGPYAMDY | WGQGTSVTVSS |
| NEW-HA | QKFKGRVTMLVDTSKNQFSLRLSSVTAADTAVYYCAR | RRDSSGPYAMDY | WGQGSLVTVSS |
| NEW-HAN | .................................... | ............ | ........... |
| Eu-HA | QKFKGRVTITLADESTNQFSMRLSSVRAADTAFYFCAG | RRDSSGPYAMDY | ENGGLVTVSS |
| Eu-HC | .....KA.............................. | .I.Y..R..... | WGQ.T...... |

Fig.21

Humanization of light chain variable region

|  | FR1 | CDR1 | FR2 | CDR2 |
|---|---|---|---|---|
| F1232-37-2 | DIVLTQSPASLAVSLGQRATISC | RASESVDSYGNSFMH | WYQQKPGQPPKLLIY | RASNLES |
| REI-KA | DIQMTQSPSSLSASVGDRVTITC | RASESVDSYGNSFMH | WYQQKPGKAPKLLIY | RASNLES |
| Eu-KA | DIVLTQSPASLAVSLGQRATISC | RASESVDSYGNSFMH | WYQQKPGQPPKLLIY | RASNLES |

|  | FR3 | CDR3 | FR4 |
|---|---|---|---|
| F1232-37-2 | GIPARFSGSGSRTDFTLTINPVEADDVATYYC | QQSNEDPYT | FGGGTKLEIKRADAA |
| REI-KA | GVPSRFSGSGSGTDFTFTISSLQPEDIATYYC | QQSNEDPYT | FGQGTKVEIKRTDAA |
| Eu-KA | GIPARFSGSGSRTDFTLTINPVEADDVATYYC | QQSNEDPYT | FGGGTKLEIKRTDAA |

Fig. 27
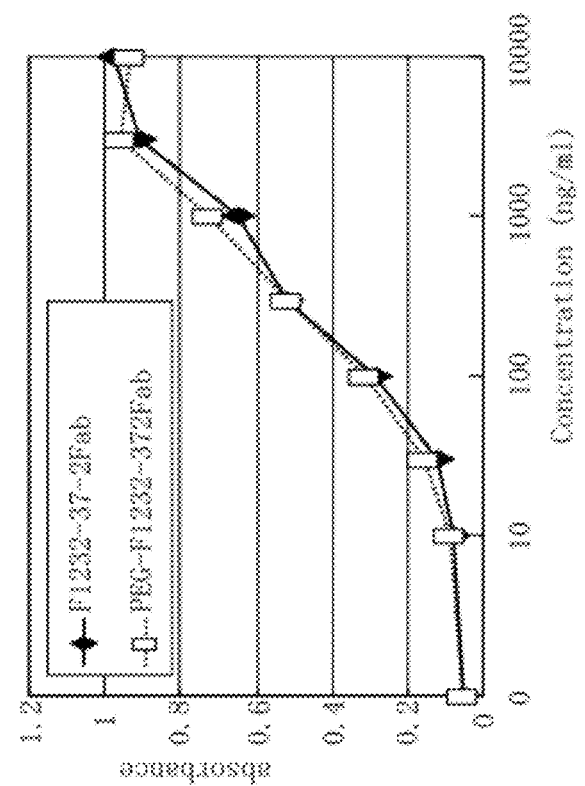
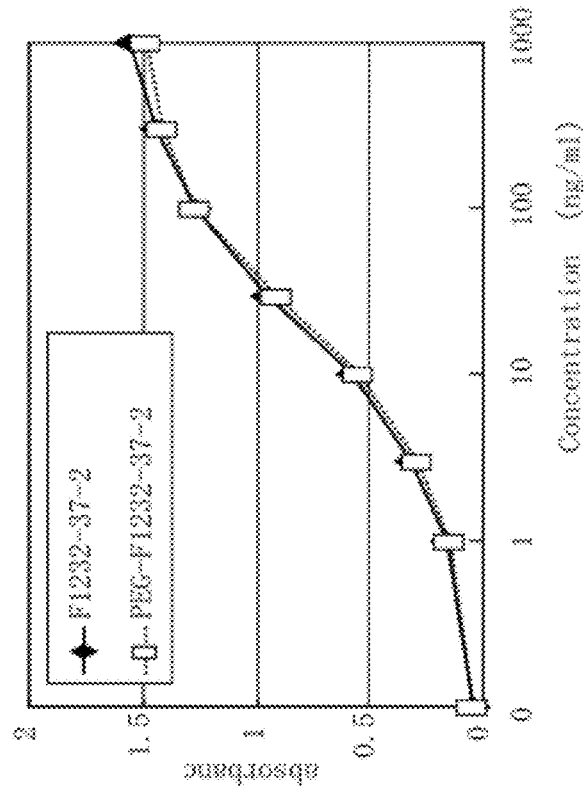

FIG. 28

Nucleotide sequence of rat GPVI

```
  1  ATGTCTCCAGCCTCACTCACTTTCTTCTGTATTGGGCTGTGTGTACTACAAGTGATCCAA   60
     METSerProAlaSerLeuThrPhePheCysIleGlyLeuCysValLeuGlnValIleGln

61  CCACAGCATGGCCCACTCCCCAACCCTTCTCTCCAGCCTCAACCCAGTTCCCTCGTGCCC  120
     AlaGlnHisGlyProLeuProLysProSerLeuGlnAlaGlnProSerSerLeuValPro

121  CTCCCTCATCCACTCACTCTCAGGTGCCCTGGGGCCTTCAGATGCCGCATTTATATCCTCTC 180
     LeuGlyHisProValThrLeuArgCysLeuGlyProSerAspAlaAspLeuTyrArgLeu

181  GAGAAAGTCAAACCCCGCAAGTTCATCTTCATAGATCAAGACTTTCTCTTCATTCCAATC  240
     GluLysValLysProGlyLysLeuIlePheIleAspGlnAspPheLeuPheIleProIle

241  ATGGAAATAAATAATGCTGGACGCTACCGCTGCTCATATCAGAATGAGAGTCATTGGTCT  300
     METGluIleAsnAsnAlaGlyArgTyrArgCysSerTyrGlnAsnGluSerHisTrpSer

301  CTCCCAAGTGACCAGCTTGAGCTAATTGCTACAGGTGTTTACTCTAAGCCCTCACTTTCA  360
     LeuProSerAspGlnLeuGluLeuIleAlaThrGlyValTyrSerLysProSerLeuSer

361  GCTCATCCAGCTCAGCAATCCCTCCAGGCAGGGATGTGACTCTGAAGTGCCAAAGCCAA  420
     AlaHisProSerSerAlaIleProProGlyArgAspValThrLeuLysCysGlnSerGln

421  TATAGTTTTGACGAATTTGTTTTATACAAAGAGGGGGATACTAGGCCTTATAAGAGACCT  480
     TyrSerPheAspGluPheValLeuTyrLysGluGlyAspThrArgProTyrLysArgPro

481  GAGAAATGGTACCGGGCCAATTTCCCCGTCATCACAGTGACTGCTGCTCACAGTGGGACT  540
     GluLysTrpTyrArgAlaAsnPheProValIleThrValThrAlaAlaHisSerGlyThr

541  TACCGGTGTTACAGCTTTTCCAGCTCATCTCCATACCTGTGGTCAGCACCGAGTGACCCT  600
     TyrArgCysTyrSerPheSerSerSerProTyrLeuTrpSerAlaProSerAspPro

601  CTAGTAGTTGTGGTTACTGGACCCTCTGCCACTCCCAGTCAGGTACCCACAGAGGTACCA  660
     LeuValValValValThrGlyProSerAlaThrProSerGlnValProThrGluValPro

661  TCTCCTATGACAGAAGCCTCCAGGAGACCTTCCATGTTACTCACAAACAAAATATCTACA  720
     SerProMETThrGluAlaSerArgArgProSerMETLeuLeuThrAsnLysIleSerThr

721  ACTGAAAAGCCTATGAATATCACTGTCTCTCCAGAGGGGCCAAGCCCTCCATTTGGTTTT  780
     ThrGluLysProMETAsnIleThrValSerProGluGlyProSerProProPheGlyPhe

781  GCTCATCAGCACTATGCCAAGGGGAATCTGGTCCGGATATGCCTTGGTGTCATGATTATA  840
     AlaHisGlnHisTyrAlaLysGlyAsnLeuValArgIleCysLeuGlyValMETIleIle

841  ATGTTCTTGGTGGGGTTTCTGGCAGAGGATTGGCACAGTCGGAAGAAACGCCTACAACAC  900
     METPheLeuValGlyPheLeuAlaGluAspTrpHisSerArgLysLysArgLeuGlnHis

901  AGGATCAGAGCTATGCAAAGGCCACTGCCACCTCTCCCACTGGCCTAG             948
     ArgIleArgAlaMETGlnArgProLeuProProLeuProLeuAla***
```

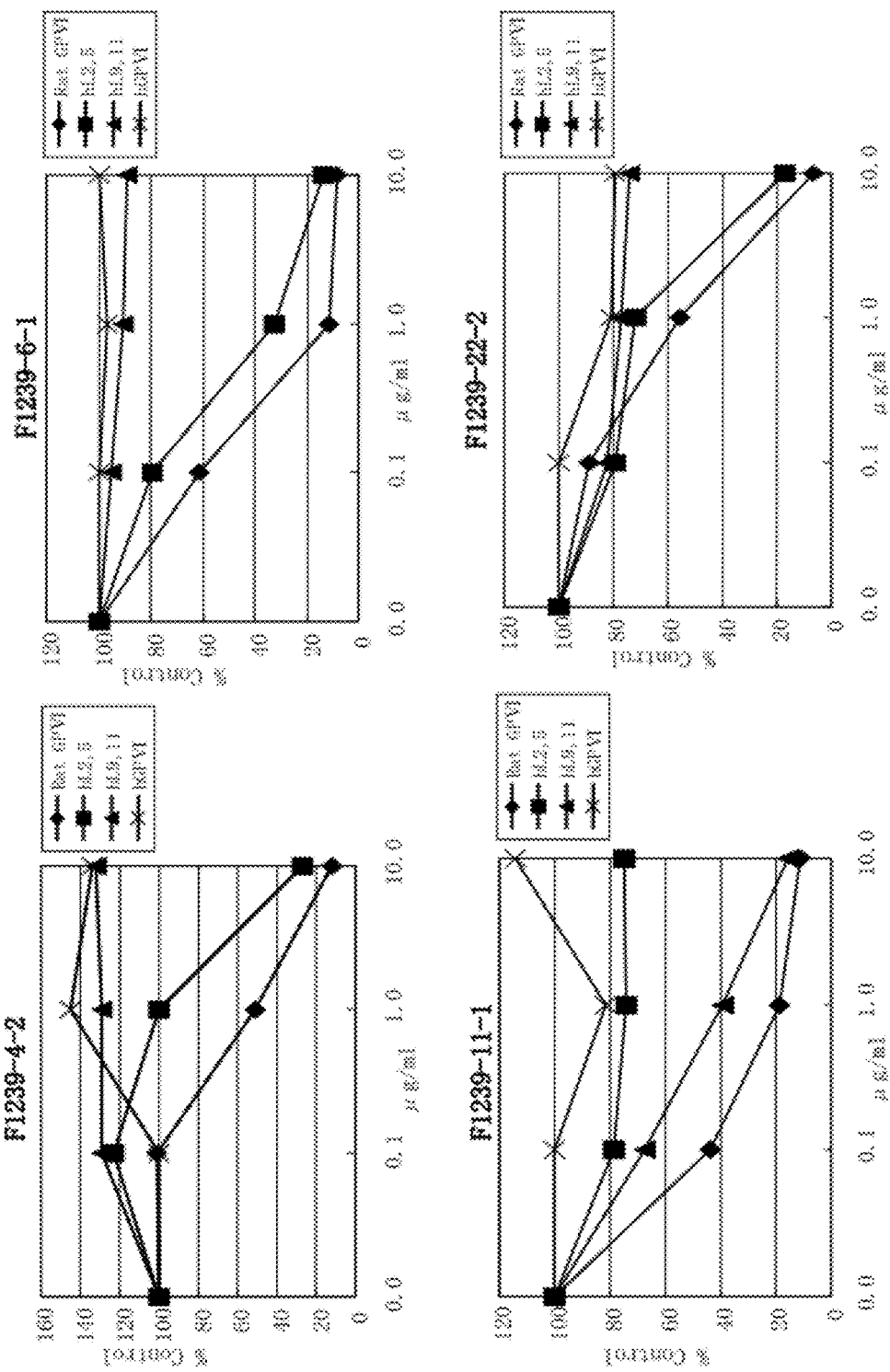

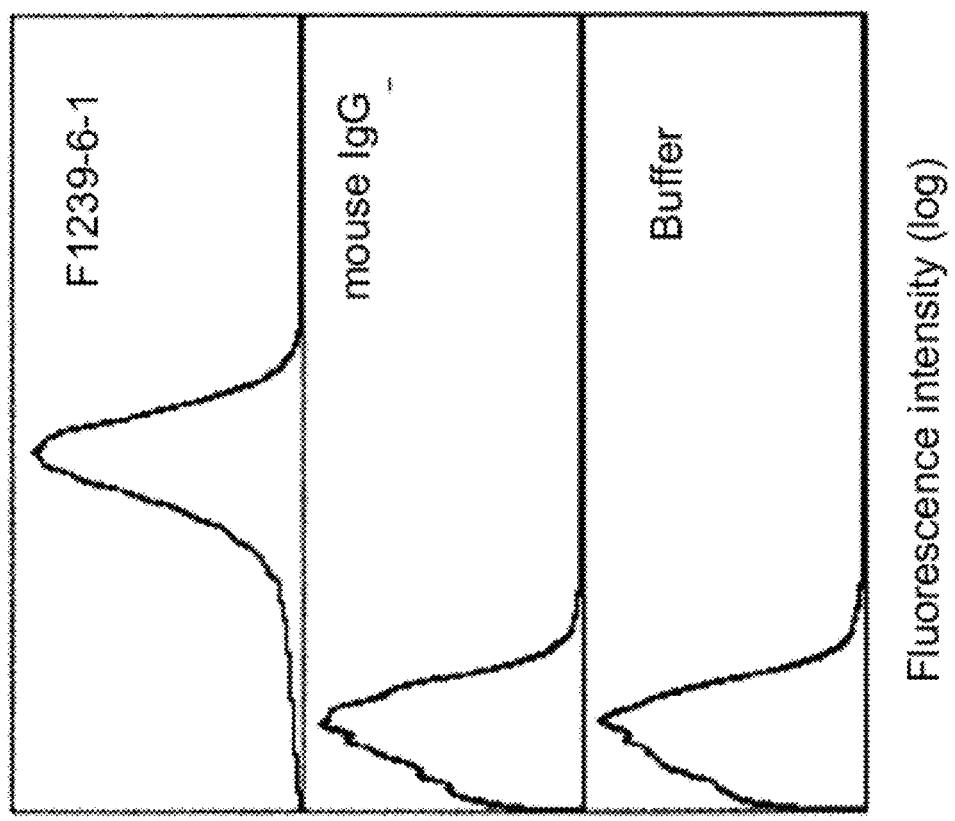

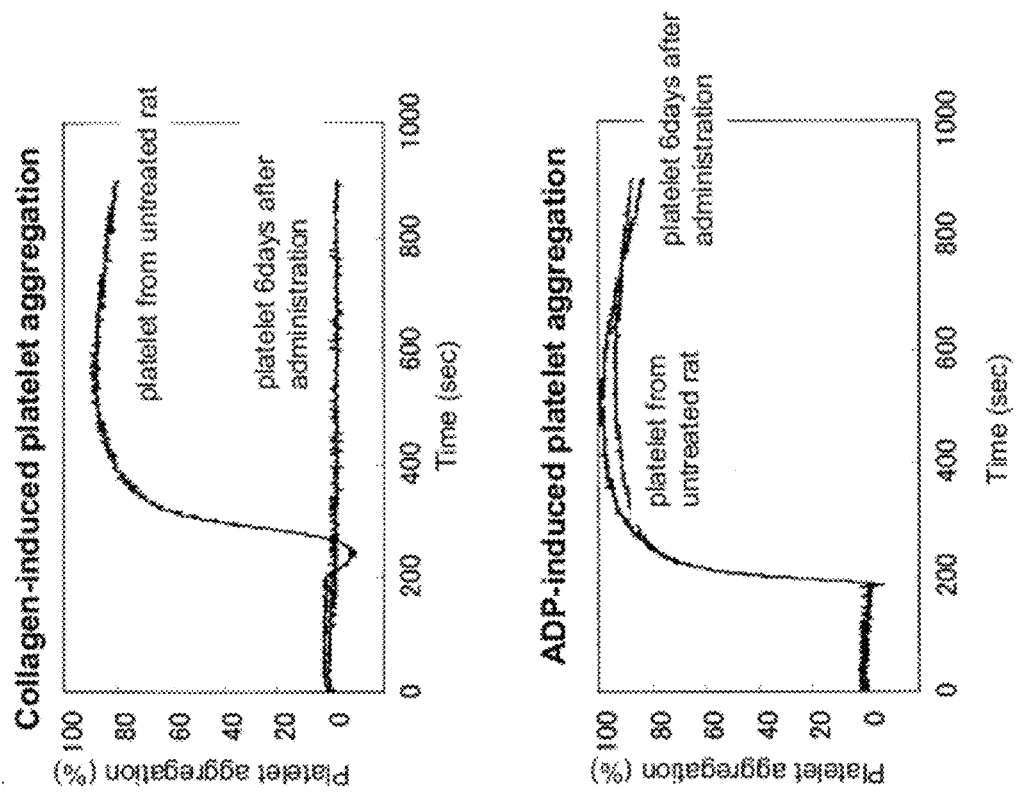

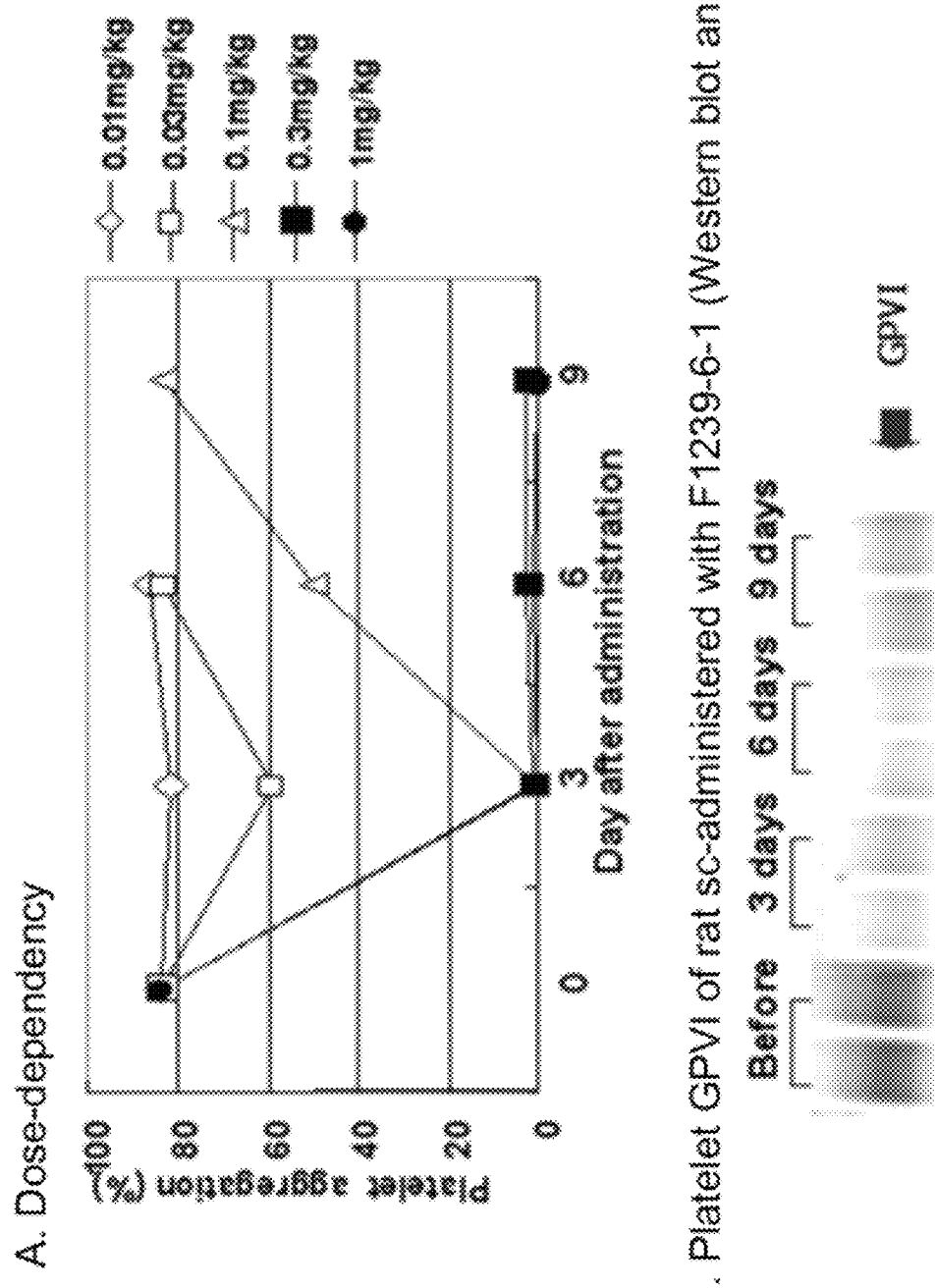

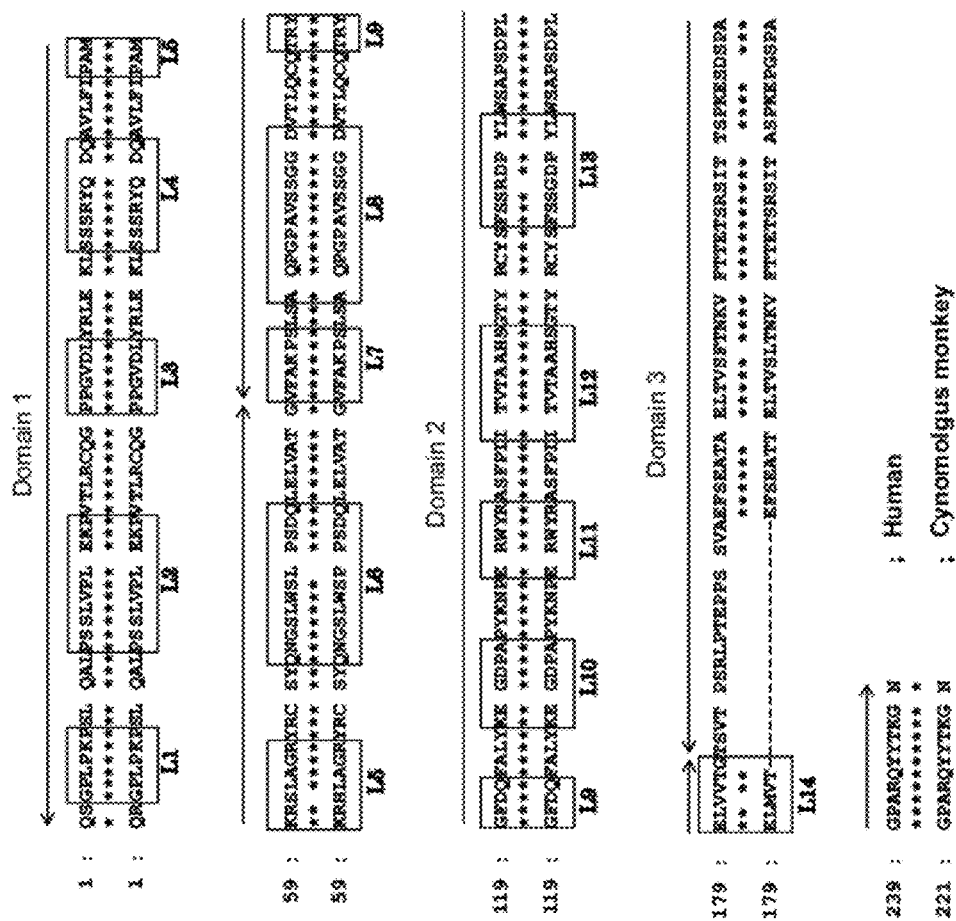

SEQUENCE LISTING

```
<160> NUMBER OF SEQ ID NOS: 429

<210> SEQ ID NO 1
<211> LENGTH: 6
<212> TYPE: PRT
<213> ORGANISM: Homo sapiens

<400> SEQUENCE: 1

Gly Pro Leu Pro Lys Pro
1               5

<210> SEQ ID NO 2
<211> LENGTH: 10
<212> TYPE: PRT
<213> ORGANISM: Homo sapiens

<400> SEQUENCE: 2

Pro Ser Ser Leu Val Pro Leu Glu Lys Pro
1               5                   10

<210> SEQ ID NO 3
<211> LENGTH: 6
<212> TYPE: PRT
<213> ORGANISM: Homo sapiens

<400> SEQUENCE: 3

Pro Pro Gly Val Asp Leu
1               5

<210> SEQ ID NO 4
<211> LENGTH: 8
<212> TYPE: PRT
<213> ORGANISM: Homo sapiens

<400> SEQUENCE: 4

Ser Ser Ser Arg Tyr Gln Asp Gln
1               5

<210> SEQ ID NO 5
<211> LENGTH: 10
<212> TYPE: PRT
<213> ORGANISM: Homo sapiens

<400> SEQUENCE: 5

Pro Ala Met Lys Arg Ser Leu Ala Gly Arg
1               5                   10
```

```
<210> SEQ ID NO 6
<211> LENGTH: 12
<212> TYPE: PRT
<213> ORGANISM: Homo sapiens

<400> SEQUENCE: 6

Gln Asn Gly Ser Leu Trp Ser Leu Pro Ser Asp Gln
1               5                   10

<210> SEQ ID NO 7
<211> LENGTH: 6
<212> TYPE: PRT
<213> ORGANISM: Homo sapiens

<400> SEQUENCE: 7

Val Phe Ala Lys Pro Ser
1               5

<210> SEQ ID NO 8
<211> LENGTH: 12
<212> TYPE: PRT
<213> ORGANISM: Homo sapiens

<400> SEQUENCE: 8

Ala Gln Pro Gly Pro Ala Val Ser Ser Gly Gly Asp
1               5                   10

<210> SEQ ID NO 9
<211> LENGTH: 7
<212> TYPE: PRT
<213> ORGANISM: Homo sapiens

<400> SEQUENCE: 9

Thr Arg Tyr Gly Phe Asp Gln
1               5

<210> SEQ ID NO 10
<211> LENGTH: 6
<212> TYPE: PRT
<213> ORGANISM: Homo sapiens

<400> SEQUENCE: 10

Lys Glu Gly Asp Pro Ala
1               5

<210> SEQ ID NO 11
<211> LENGTH: 5
<212> TYPE: PRT
<213> ORGANISM: Homo sapiens

<400> SEQUENCE: 11

Glu Arg Trp Tyr Arg
1               5

<210> SEQ ID NO 12
<211> LENGTH: 8
<212> TYPE: PRT
<213> ORGANISM: Homo sapiens

<400> SEQUENCE: 12

Ile Thr Val Thr Ala Ala His Ser
1               5

<210> SEQ ID NO 13
<211> LENGTH: 8
<212> TYPE: PRT
```

<213> ORGANISM: Homo sapiens

<400> SEQUENCE: 13

Phe Ser Ser Arg Asp Pro Tyr Leu
1               5

<210> SEQ ID NO 14
<211> LENGTH: 6
<212> TYPE: PRT
<213> ORGANISM: Homo sapiens

<400> SEQUENCE: 14

Glu Leu Val Val Thr Gly
1               5

<210> SEQ ID NO 15
<211> LENGTH: 5
<212> TYPE: PRT
<213> ORGANISM: Mus musculus

<400> SEQUENCE: 15

Asp Tyr Ala Ile His
1               5

<210> SEQ ID NO 16
<211> LENGTH: 17
<212> TYPE: PRT
<213> ORGANISM: Mus musculus

<400> SEQUENCE: 16

Val Ile Ser Ile Tyr Tyr Asp Asp Thr Asn Tyr Asn Gln Lys Phe Lys
1               5                   10                  15

Gly

<210> SEQ ID NO 17
<211> LENGTH: 12
<212> TYPE: PRT
<213> ORGANISM: Mus musculus

<400> SEQUENCE: 17

Arg Arg Asp Ser Ser Gly Pro Tyr Ala Met Asp Tyr
1               5                   10

<210> SEQ ID NO 18
<211> LENGTH: 5
<212> TYPE: PRT
<213> ORGANISM: Mus musculus

<400> SEQUENCE: 18

Ser Tyr Ala Met Ser
1               5

<210> SEQ ID NO 19
<211> LENGTH: 17
<212> TYPE: PRT
<213> ORGANISM: Mus musculus

<400> SEQUENCE: 19

Thr Ile Ser Ser Gly Gly Ser Tyr Thr Tyr Tyr Pro Asp Ser Val Lys
1               5                   10                  15

Gly

<210> SEQ ID NO 20
<211> LENGTH: 7

```
<212> TYPE: PRT
<213> ORGANISM: Mus musculus

<400> SEQUENCE: 20

Asp Tyr Gly Tyr Phe Asp Tyr
1               5

<210> SEQ ID NO 21
<211> LENGTH: 5
<212> TYPE: PRT
<213> ORGANISM: Mus musculus

<400> SEQUENCE: 21

Asp Tyr Tyr Val Asn
1               5

<210> SEQ ID NO 22
<211> LENGTH: 17
<212> TYPE: PRT
<213> ORGANISM: Mus musculus

<400> SEQUENCE: 22

Glu Ile Tyr Pro Gly Ser Gly Asn Thr Tyr Tyr Asn Glu Lys Phe Lys
1               5                   10                  15

Gly

<210> SEQ ID NO 23
<211> LENGTH: 17
<212> TYPE: PRT
<213> ORGANISM: Mus musculus

<400> SEQUENCE: 23

Trp Arg Gly Asn Leu Tyr Tyr Asp Tyr Asp Ala Glu Thr Leu Phe Ala
1               5                   10                  15

Tyr

<210> SEQ ID NO 24
<211> LENGTH: 5
<212> TYPE: PRT
<213> ORGANISM: Mus musculus

<400> SEQUENCE: 24

Ser Tyr Gly Met Ser
1               5

<210> SEQ ID NO 25
<211> LENGTH: 17
<212> TYPE: PRT
<213> ORGANISM: Mus musculus

<400> SEQUENCE: 25

Thr Ile Ser Ser Gly Gly Ser Tyr Thr Tyr Tyr Pro Asp Asn Val Lys
1               5                   10                  15

Gly

<210> SEQ ID NO 26
<211> LENGTH: 10
<212> TYPE: PRT
<213> ORGANISM: Mus musculus

<400> SEQUENCE: 26

Gln Val Tyr Tyr Phe Gly Ser Cys Asp Tyr
1               5                   10
```

```
<210> SEQ ID NO 27
<211> LENGTH: 5
<212> TYPE: PRT
<213> ORGANISM: Mus musculus

<400> SEQUENCE: 27

Ser Tyr Gly Met Ser
1               5

<210> SEQ ID NO 28
<211> LENGTH: 17
<212> TYPE: PRT
<213> ORGANISM: Mus musculus

<400> SEQUENCE: 28

Thr Ile Ser Ser Gly Gly Ser Tyr Thr Tyr Tyr Pro Asp Ser Val Lys
1               5                   10                  15

Gly

<210> SEQ ID NO 29
<211> LENGTH: 10
<212> TYPE: PRT
<213> ORGANISM: Mus musculus

<400> SEQUENCE: 29

Gln Val Tyr Tyr Tyr Gly Ser Ser Asp Tyr
1               5                   10

<210> SEQ ID NO 30
<211> LENGTH: 5
<212> TYPE: PRT
<213> ORGANISM: Mus musculus

<400> SEQUENCE: 30

Tyr Tyr Leu Ile Glu
1               5

<210> SEQ ID NO 31
<211> LENGTH: 17
<212> TYPE: PRT
<213> ORGANISM: Mus musculus

<400> SEQUENCE: 31

Val Ile Asn Pro Gly Ser Gly Val Thr Asn Tyr Asn Glu Lys Phe Lys
1               5                   10                  15

Gly

<210> SEQ ID NO 32
<211> LENGTH: 9
<212> TYPE: PRT
<213> ORGANISM: Mus musculus

<400> SEQUENCE: 32

Ser Ile Tyr Tyr Gly Thr Ile Asp Tyr
1               5

<210> SEQ ID NO 33
<211> LENGTH: 7
<212> TYPE: PRT
<213> ORGANISM: Mus musculus

<400> SEQUENCE: 33

Thr Tyr Gly Ile Gly Val Gly
1               5
```

<210> SEQ ID NO 34
<211> LENGTH: 16
<212> TYPE: PRT
<213> ORGANISM: Mus musculus

<400> SEQUENCE: 34

His Ile Trp Trp Asp Asp Asn Lys Tyr Tyr Asn Thr Ala Leu Lys Ser
1               5                   10                  15

<210> SEQ ID NO 35
<211> LENGTH: 10
<212> TYPE: PRT
<213> ORGANISM: Mus musculus

<400> SEQUENCE: 35

Ile His Tyr Tyr Gly Ser Ser Leu Asp Tyr
1               5                   10

<210> SEQ ID NO 36
<211> LENGTH: 5
<212> TYPE: PRT
<213> ORGANISM: Mus musculus

<400> SEQUENCE: 36

Ser Tyr Ala Met Ser
1               5

<210> SEQ ID NO 37
<211> LENGTH: 17
<212> TYPE: PRT
<213> ORGANISM: Mus musculus

<400> SEQUENCE: 37

Ile Ile Ser Ser Gly Gly Ser Tyr Thr Tyr Tyr Pro Asp Ser Val Lys
1               5                   10                  15

Gly

<210> SEQ ID NO 38
<211> LENGTH: 8
<212> TYPE: PRT
<213> ORGANISM: Mus musculus

<400> SEQUENCE: 38

Gln Gly Gly Gly Tyr Phe Asp Tyr
1               5

<210> SEQ ID NO 39
<211> LENGTH: 7
<212> TYPE: PRT
<213> ORGANISM: Mus musculus

<400> SEQUENCE: 39

Thr Tyr Gly Ile Gly Val Gly
1               5

<210> SEQ ID NO 40
<211> LENGTH: 16
<212> TYPE: PRT
<213> ORGANISM: Mus musculus

<400> SEQUENCE: 40

His Ile Trp Trp Asn Asp Asp Lys Tyr Tyr Asn Thr Ala Leu Lys Ser
1               5                   10                  15

```
<210> SEQ ID NO 41
<211> LENGTH: 10
<212> TYPE: PRT
<213> ORGANISM: Mus musculus

<400> SEQUENCE: 41

Val Tyr Tyr Tyr Gly Ser Ser Phe Asp Tyr
1               5                   10

<210> SEQ ID NO 42
<211> LENGTH: 5
<212> TYPE: PRT
<213> ORGANISM: Mus musculus

<400> SEQUENCE: 42

Asp Tyr Ala Ile His
1               5

<210> SEQ ID NO 43
<211> LENGTH: 17
<212> TYPE: PRT
<213> ORGANISM: Mus musculus

<400> SEQUENCE: 43

Val Ile Ser Ile Tyr Tyr Asp Asp Thr Asn Tyr Asn Gln Lys Phe Lys
1               5                   10                  15

Gly

<210> SEQ ID NO 44
<211> LENGTH: 12
<212> TYPE: PRT
<213> ORGANISM: Mus musculus

<400> SEQUENCE: 44

Arg Arg Asp Ser Ser Gly Pro Tyr Ala Met Asp Tyr
1               5                   10

<210> SEQ ID NO 45
<211> LENGTH: 6
<212> TYPE: PRT
<213> ORGANISM: Mus musculus

<400> SEQUENCE: 45

Ala Ala Ala Ala Ala Ala
1               5

<210> SEQ ID NO 46
<211> LENGTH: 6
<212> TYPE: PRT
<213> ORGANISM: Mus musculus

<400> SEQUENCE: 46

Ala Ala Ala Ala Ala Ala
1               5

<210> SEQ ID NO 47
<211> LENGTH: 6
<212> TYPE: PRT
<213> ORGANISM: Mus musculus

<400> SEQUENCE: 47

Ala Ala Ala Ala Ala Ala
1               5
```

```
<210> SEQ ID NO 48
<211> LENGTH: 5
<212> TYPE: PRT
<213> ORGANISM: Mus musculus

<400> SEQUENCE: 48

Asp Tyr Ala Met His
1               5

<210> SEQ ID NO 49
<211> LENGTH: 17
<212> TYPE: PRT
<213> ORGANISM: Mus musculus

<400> SEQUENCE: 49

Val Ile Ser Thr Tyr Tyr Gly Asp Ala Ser Tyr Asn Gln Lys Phe Lys
1               5                   10                  15

Gly

<210> SEQ ID NO 50
<211> LENGTH: 10
<212> TYPE: PRT
<213> ORGANISM: Mus musculus

<400> SEQUENCE: 50

Ser Tyr Asp Tyr Asp Pro Trp Phe Ala Tyr
1               5                   10

<210> SEQ ID NO 51
<211> LENGTH: 15
<212> TYPE: PRT
<213> ORGANISM: Mus musculus

<400> SEQUENCE: 51

Arg Ala Ser Glu Ser Val Asp Ser Tyr Gly Asn Ser Phe Met His
1               5                   10                  15

<210> SEQ ID NO 52
<211> LENGTH: 7
<212> TYPE: PRT
<213> ORGANISM: Mus musculus

<400> SEQUENCE: 52

Arg Ala Ser Asn Leu Glu Ser
1               5

<210> SEQ ID NO 53
<211> LENGTH: 9
<212> TYPE: PRT
<213> ORGANISM: Mus musculus

<400> SEQUENCE: 53

Gln Gln Ser Asn Glu Asp Pro Tyr Thr
1               5

<210> SEQ ID NO 54
<211> LENGTH: 15
<212> TYPE: PRT
<213> ORGANISM: Mus musculus

<400> SEQUENCE: 54

Arg Ala Ser Glu Ser Val Asp Asn Tyr Gly Ile Ser Phe Met His
1               5                   10                  15

<210> SEQ ID NO 55
```

```
<211> LENGTH: 7
<212> TYPE: PRT
<213> ORGANISM: Mus musculus

<400> SEQUENCE: 55

Arg Ala Ser Asn Leu Glu Ser
1               5

<210> SEQ ID NO 56
<211> LENGTH: 9
<212> TYPE: PRT
<213> ORGANISM: Mus musculus

<400> SEQUENCE: 56

Gln Gln Ser Asn Thr Asp Pro Arg Thr
1               5

<210> SEQ ID NO 57
<211> LENGTH: 11
<212> TYPE: PRT
<213> ORGANISM: Mus musculus

<400> SEQUENCE: 57

Arg Ala Ser Gln Asp Ile Ser Asn Tyr Leu Asn
1               5                   10

<210> SEQ ID NO 58
<211> LENGTH: 7
<212> TYPE: PRT
<213> ORGANISM: Mus musculus

<400> SEQUENCE: 58

Ala Thr Ser Ser Leu Asp Ser
1               5

<210> SEQ ID NO 59
<211> LENGTH: 9
<212> TYPE: PRT
<213> ORGANISM: Mus musculus

<400> SEQUENCE: 59

Leu Gln Tyr Ala Ser Tyr Pro Tyr Thr
1               5

<210> SEQ ID NO 60
<211> LENGTH: 15
<212> TYPE: PRT
<213> ORGANISM: Mus musculus

<400> SEQUENCE: 60

Arg Ala Ser Glu Ser Val Asp Asn Tyr Gly Ile Ser Phe Met His
1               5                   10                  15

<210> SEQ ID NO 61
<211> LENGTH: 7
<212> TYPE: PRT
<213> ORGANISM: Mus musculus

<400> SEQUENCE: 61

Arg Ala Ser Asn Leu Glu Ser
1               5

<210> SEQ ID NO 62
<211> LENGTH: 9
<212> TYPE: PRT
<213> ORGANISM: Mus musculus
```

```
<400> SEQUENCE: 62

Gln Gln Ser Asn Lys Asp Pro Trp Thr
1               5

<210> SEQ ID NO 63
<211> LENGTH: 15
<212> TYPE: PRT
<213> ORGANISM: Mus musculus

<400> SEQUENCE: 63

Arg Ala Ser Glu Ser Val Asp Asn Tyr Gly Ile Ser Phe Met His
1               5                   10                  15

<210> SEQ ID NO 64
<211> LENGTH: 7
<212> TYPE: PRT
<213> ORGANISM: Mus musculus

<400> SEQUENCE: 64

Arg Ala Ser Asn Leu Glu Ser
1               5

<210> SEQ ID NO 65
<211> LENGTH: 9
<212> TYPE: PRT
<213> ORGANISM: Mus musculus

<400> SEQUENCE: 65

Gln Gln Ser Asn Lys Asp Pro Trp Thr
1               5

<210> SEQ ID NO 66
<211> LENGTH: 11
<212> TYPE: PRT
<213> ORGANISM: Mus musculus

<400> SEQUENCE: 66

Arg Ala Ser Gln Asp Ile Ser Asn Tyr Leu Asn
1               5                   10

<210> SEQ ID NO 67
<211> LENGTH: 7
<212> TYPE: PRT
<213> ORGANISM: Mus musculus

<400> SEQUENCE: 67

Tyr Thr Ser Arg Leu His Ser
1               5

<210> SEQ ID NO 68
<211> LENGTH: 9
<212> TYPE: PRT
<213> ORGANISM: Mus musculus

<400> SEQUENCE: 68

Gln Gln Gly Ser Thr Leu Pro Tyr Thr
1               5

<210> SEQ ID NO 69
<211> LENGTH: 11
<212> TYPE: PRT
<213> ORGANISM: Mus musculus

<400> SEQUENCE: 69
```

Arg Ala Ser Glu Asn Ile Tyr Ser Tyr Leu Ala
1               5                   10

<210> SEQ ID NO 70
<211> LENGTH: 7
<212> TYPE: PRT
<213> ORGANISM: Mus musculus

<400> SEQUENCE: 70

Ala Ala Thr Asn Leu Ala Asp
1               5

<210> SEQ ID NO 71
<211> LENGTH: 9
<212> TYPE: PRT
<213> ORGANISM: Mus musculus

<400> SEQUENCE: 71

Gln His Phe Tyr Gly Thr Pro Trp Thr
1               5

<210> SEQ ID NO 72
<211> LENGTH: 15
<212> TYPE: PRT
<213> ORGANISM: Mus musculus

<400> SEQUENCE: 72

Arg Ala Ser Glu Ser Val Asp Ser Tyr Gly Asn Ser Phe Met His
1               5                   10                  15

<210> SEQ ID NO 73
<211> LENGTH: 7
<212> TYPE: PRT
<213> ORGANISM: Mus musculus

<400> SEQUENCE: 73

Arg Ala Ser Asn Val Glu Ser
1               5

<210> SEQ ID NO 74
<211> LENGTH: 9
<212> TYPE: PRT
<213> ORGANISM: Mus musculus

<400> SEQUENCE: 74

Gln Gln Ser Asn Glu Asp Pro Pro Thr
1               5

<210> SEQ ID NO 75
<211> LENGTH: 11
<212> TYPE: PRT
<213> ORGANISM: Mus musculus

<400> SEQUENCE: 75

Arg Ala Ser Glu Asn Ile Phe Ser Ile Leu Ala
1               5                   10

<210> SEQ ID NO 76
<211> LENGTH: 7
<212> TYPE: PRT
<213> ORGANISM: Mus musculus

<400> SEQUENCE: 76

Ala Ala Thr Asn Leu Ala Asp
1               5

```
<210> SEQ ID NO 77
<211> LENGTH: 9
<212> TYPE: PRT
<213> ORGANISM: Mus musculus

<400> SEQUENCE: 77

Gln His Phe Tyr Gly Thr Pro Trp Thr
1               5

<210> SEQ ID NO 78
<211> LENGTH: 15
<212> TYPE: PRT
<213> ORGANISM: Mus musculus

<400> SEQUENCE: 78

Arg Ala Ser Glu Ser Val Asp Ser Tyr Gly Asn Ser Phe Met His
1               5                   10                  15

<210> SEQ ID NO 79
<211> LENGTH: 7
<212> TYPE: PRT
<213> ORGANISM: Mus musculus

<400> SEQUENCE: 79

Arg Ala Ser Asn Leu Glu Ser
1               5

<210> SEQ ID NO 80
<211> LENGTH: 9
<212> TYPE: PRT
<213> ORGANISM: Mus musculus

<400> SEQUENCE: 80

Gln Gln Ser Asn Glu Asp Pro Tyr Thr
1               5

<210> SEQ ID NO 81
<211> LENGTH: 6
<212> TYPE: PRT
<213> ORGANISM: Mus musculus

<400> SEQUENCE: 81

Ala Ala Ala Ala Ala Ala
1               5

<210> SEQ ID NO 82
<211> LENGTH: 6
<212> TYPE: PRT
<213> ORGANISM: Mus musculus

<400> SEQUENCE: 82

Ala Ala Ala Ala Ala Ala
1               5

<210> SEQ ID NO 83
<211> LENGTH: 6
<212> TYPE: PRT
<213> ORGANISM: Mus musculus

<400> SEQUENCE: 83

Ala Ala Ala Ala Ala Ala
1               5

<210> SEQ ID NO 84
<211> LENGTH: 15
```

<210> SEQ ID NO 84
<211> LENGTH: 16 (not shown; inferred)
<212> TYPE: PRT
<213> ORGANISM: Mus musculus

<400> SEQUENCE: 84

Arg Ala Ser Glu Ser Val Asp Asn Tyr Gly Ile Ser Phe Met His
1               5                   10                  15

<210> SEQ ID NO 85
<211> LENGTH: 7
<212> TYPE: PRT
<213> ORGANISM: Mus musculus

<400> SEQUENCE: 85

Arg Ala Ser Asn Leu Glu Ser
1               5

<210> SEQ ID NO 86
<211> LENGTH: 9
<212> TYPE: PRT
<213> ORGANISM: Mus musculus

<400> SEQUENCE: 86

Gln Gln Ser Asn Lys Asp Pro Leu Thr
1               5

<210> SEQ ID NO 87
<211> LENGTH: 360
<212> TYPE: DNA
<213> ORGANISM: Mus musculus

<400> SEQUENCE: 87

```
gtccagctgc agcagtctgg gcctgagctg gtgaggcctg gggaatcagt gaagatttcc      60
tgcaagggtt ccggctacac attcactgat tatgctatac actgggtgaa gctgagtcat     120
gcaaagagtc tagagtggat tggagttatt agtatttact atgatgatac aaactacaac     180
cagaagttta agggcaaggc cacaatgact gtagacaaat cctccagcac agcctatatg     240
gaacttgcca gattgacatc tgaggattct gccatctatt actgtgcaag acgaagggac     300
agctcgggtc cctatgctat ggactactgg ggtcaaggaa cctcagtcac cgtctcctca     360
```

<210> SEQ ID NO 88
<211> LENGTH: 348
<212> TYPE: DNA
<213> ORGANISM: Mus musculus

<400> SEQUENCE: 88

```
gacattgtgc tgacccaatc tccagcttct ttggctgtgt ctctagggca gagggccacc      60
atatcctgca gagccagtga aagtgttgat agttatggca atagttttat gcactggtac     120
cagcagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgatgt tgcaacctat tactgtcagc aaagtaatga ggatccgtac     300
acgttcggag gggggaccaa gctggaaata aaacgggctg atgctgca                  348
```

<210> SEQ ID NO 89
<211> LENGTH: 345
<212> TYPE: DNA
<213> ORGANISM: Mus musculus

<400> SEQUENCE: 89

```
gtgatgctgg tggagtctgg gggaggctta gtgaagcctg agggtccct gaaactctcc       60
```

```
tgtgcagcct ctggattcac tttcagtagc tatgccatgt cttgggttcg ccagactccg    120
gagaagaggc tggagtgggt cgcaaccatt agtagtggtg gtagttacac ctactatcca    180
gacagtgtga aggggcgatt caccatctcc agagacaatg ccagaacacc cctgtacctg    240
caaatgagca gtctgaggtc tgcggacacg gccatgtatt actgtgcaag ggattacggc    300
tactttgact actggggcca aggcaccact ctcacagtct cctca                    345

<210> SEQ ID NO 90
<211> LENGTH: 348
<212> TYPE: DNA
<213> ORGANISM: Mus musculus

<400> SEQUENCE: 90
gacattgtgc tgacccaatc tccagcttct ttggctgtgt ctctagggca gagggccacc     60
atctcctgca gagccagcga aagtgttgat aattatggca ttagtttttat gcactggtac    120 cagcagaaac caggacagcc acccaaactc ctcttctatc gtgcatccaa cctagaatct    180
gggatccctg ccaggttcag tggcagtggg tctaggacag acttcaccct caccattaat    240
cctgtggaga ctgatgatgt tgcaacctat tactgtcagc agagtaatac ggatcctcgg    300
acgttcggtg gaggcaccaa gctggaaata aaacgggctg atgctgca                 348

<210> SEQ ID NO 91
<211> LENGTH: 375
<212> TYPE: DNA
<213> ORGANISM: Mus musculus

<400> SEQUENCE: 91
gttcagctgc agcagtctgg agctgagctg gcgaggcccg ggcttcagt gaagctgtcc      60 tgcgtggctt ctggctacac cttcactgac tactatgtaa actggatgaa gcagaggact    120
ggacagggcc ttgagtggat tggagagatt tatcctggaa gtggtaatac ttactacaat    180
gagaagttca aggcaaggc cacactgact gcagacaaat cctccagcac agcctacatg     240
cagctcagca gcctgacatc tgaggactct gcagtctatt tctgtgcaac atggagggga    300
aacctctact atgattacga cgcagagacc ctgtttgctt actggggcca agggactctg    360
gtcactgtct ctgca                                                     375

<210> SEQ ID NO 92
<211> LENGTH: 336
<212> TYPE: DNA
<213> ORGANISM: Mus musculus

<400> SEQUENCE: 92
gacatccaga tgacccagtc tccatcctcc ttatctgcct ctctgggaga aagaatcagt     60
ctcacttgcc gggcaagtca ggatattagt aattacttaa actggtttca gcagaaacca    120
gatggaactt ttaaacgcct gatctatgcc acatccagtt tagattctgg tgtccccaaa    180
aggttcagtg gcagtaggtc tgggtcagat tattctctca ccatcagcag ccttgagtct    240
gaagattttg cagactatta ctgtctacaa tatgctagtt atccgtacac gttcggaggg    300
gggaccaagc tggaaataaa acgggctgat gctgca                              336

<210> SEQ ID NO 93
<211> LENGTH: 354
<212> TYPE: DNA
<213> ORGANISM: Mus musculus

<400> SEQUENCE: 93
```

-continued

```
gtgcaactgg tggagtctgg gggagactta gtgaagcctg agggtccct gaaactctcc      60 tgtgcagcct ctggattcac tttcagtagc tatggcatgt cttgggttcg ccagactcca    120
gacaagaggc tggagtgggt cgcaaccatt agtagtggtg gtagttacac ctactatcca   180
gacaatgtga aggggcgatt caccatctcc agagacaatg ccaagaacac cctgtacctg    240
caaatgagca gtctgaactc tgaggacaca gccatgtatt actgtgcaag acaggtttat    300
tacttcggta gttgcgacta ctggggccaa ggcaccactc tcacagtctc ctca         354
```

<210> SEQ ID NO 94
<211> LENGTH: 348
<212> TYPE: DNA
<213> ORGANISM: Mus musculus

<400> SEQUENCE: 94

```
gacattgtgc tgacccaatc tccagcttct ttggctgtgt ctctagggca gagggccacc    60
atctcctgca gagccagcga aagtgttgat aattatggca ttagttttat gcactggtac    120
cagcagaaac caggacagcc acccaaactc ctcatctatc gtgcatccaa cctagaatct   180
gggatccctg ccaggttcag tggcagtggg tctaggacag acttcaccct caccattaat    240
cctgtggaga ctgatgatgt tgcaacctat tactgtcagc aaagtaataa ggatccgtgg    300
acgttcggtg aggcaccaa gctggaaatc aaacgggctg atgctgca                 348
```

<210> SEQ ID NO 95
<211> LENGTH: 354
<212> TYPE: DNA
<213> ORGANISM: Mus musculus

<400> SEQUENCE: 95

```
gtgcagctgg tggagtctgg gggagactta gtgaagcctg agggtccct gaaactctcc      60 tgtgcagcct ctggattcac tttcagtagc tatggcatgt cttgggttcg ccagactcca    120
gacaagaggc tggagtgggt cgcaaccatt agtagtggtg gtagttacac ctactatcca   180
gacagtgtga aggggcgatt caccatctcc agagacaatg ccaagaacac cctgtacctg    240
caaatgagca gtctgaagtc tgaggacaca gccatgtatt actgtgcaag acaggtttat    300
tactacggta gtagcgacta ctggggccaa ggcaccactc tcacagtctc ctca         354
```

<210> SEQ ID NO 96
<211> LENGTH: 348
<212> TYPE: DNA
<213> ORGANISM: Mus musculus

<400> SEQUENCE: 96

```
gacattgtgc tgacccaatc tccagcttct ttggctgtgt ctctagggca gagggccacc    60
atctcctgca gagccagcga aagtgttgat aattatggca ttagttttat gcactggtac    120
cagcagaaac caggacagcc acccaaactc ctcatctatc gtgcatccaa cctagaatct   180
gggatccctg ccaggttcag tggcagtggg tctaggacag acttcaccct caccattaat    240
cctgtggaga ctgatgatgt tgcaacctat tactgtcagc aaagtaataa ggatccgtgg    300
acgttcggtg aggcaccaa gctggaaatc aaacgggctg atgctgca                 348
```

<210> SEQ ID NO 97
<211> LENGTH: 351
<212> TYPE: DNA
<213> ORGANISM: Mus musculus

<400> SEQUENCE: 97

```
gtccagctgc agcagtctgg agctgagctg gtaaggcctg ggacttcagt gaaggtgtcc      60
tgcaaggctt ctggatacgc cttcacgtat tacttgatag agtgggtaaa gcagaggcct     120
ggacagggcc ttgagtggat tggagtgatt aatcctggaa gtggtgttac taactacaat     180
gagaagttca agggcaaggc aacactgact gcagacaaat cctccagcac tgcctacatg     240
cagctcagca gcctgacatc tgatgactct gcggtctatt tctgtgcaag atccatttac     300
tacggtacca ttgactactg gggccaaggc accactctca cagtctcctc a              351

<210> SEQ ID NO 98
<211> LENGTH: 336
<212> TYPE: DNA
<213> ORGANISM: Mus musculus

<400> SEQUENCE: 98
gatatccaga tgacacagac tacatcctcc ctgtctgcct ctctgggaga cagagtcacc      60
atcagttgca gggccagtca ggacattagc aattatttaa actggtatca gcagaaccca     120
gatggaactg ttaaactcct gatctactac acatcaagat tacactcagg agtcccatca     180
aggttcagtg ccagtgggtc tgggacagat tattctctca ccattagcaa cctggaacaa     240
gaagatattg ccacttactt tgccaacagg gtagtacgc ttccgtacac gttcggaggg      300
gggaccaagc tggaaataaa acgggctgat gctgca                               336

<210> SEQ ID NO 99
<211> LENGTH: 357
<212> TYPE: DNA
<213> ORGANISM: Mus musculus

<400> SEQUENCE: 99
gttactctga aagagtctgg ccctgggata ttgcagccct cccagaccct cagtctgact      60
tgttctttct ctgggttttc actgagcact tatggtatag agtaggctg gattcgtcag     120 ccttcaggga agggtctgga gtggctggca cacatttggt gggatgataa taagtactat     180
aacacagccc tgaagagccg gctcacaatc tccaaggata cctccaacaa ccaggtattc     240
ctcaagatcg ccagtgtgga cactgcagat actgccacat actactgtgc tcgaatccat     300
tactacggta gtagccttga ctactggggc caaggcacca ctctcacagt ctcctca       357

<210> SEQ ID NO 100
<211> LENGTH: 336
<212> TYPE: DNA
<213> ORGANISM: Mus musculus

<400> SEQUENCE: 100
gacatccaga tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcacctcct ggtctatgct gcaacaaatt tagcagatgg tgtgccatca     180
aggttcagtg gcagtggatc aggcacacag ttttctctga agatcaacag cctgcagcct     240
gaagattttg ggagttatta ctgtcaacat ttttatggta ctccgtggac gttcggtgga     300
ggcaccaagc tggaaatcaa acgggctgat gctgca                               336

<210> SEQ ID NO 101
<211> LENGTH: 348
<212> TYPE: DNA
<213> ORGANISM: Mus musculus

<400> SEQUENCE: 101
```

```
gtgcagctgg tggagtctgg gggaggctta gtgaagcctg gagggtccct gaaactctcc    60
tgtgcagcct ctggattcac tttcagtagc tatgccatgt cttgggttcg ccagactccg   120
gagaagaggc tggagtgggt cgcaatcatt agtagtggtg gtagttacac ctactatcca   180
gacagtgtga agggtcgatt caccatctcc agagacaatg ccaagaacac cctgtacctg   240
cacatgagca gtctgaggtc tgaggacacg gccatgtatt actgtgcaag acagggcggg   300
ggttactttg actactgggg ccaaggcacc actctcacag tctcctca               348

<210> SEQ ID NO 102
<211> LENGTH: 348
<212> TYPE: DNA
<213> ORGANISM: Mus musculus

<400> SEQUENCE: 102
gacattgtgc tgacccaatc tccagcttct ttggctgtgt ctctagggca gagggccacc    60
atatcctgca gagccagtga aagtgttgat agttatggca atagtttat gcactggtac   120 cagcagaaac caggacagcc acccaaactc ctcatctatc gtgcatccaa cgtagaatct   180
gggatccctg ccaggttcag tggcagtggg tctaggacag acttcaccct caccattaat   240
cctgtggagg ctgatgatgt tgcaacctat tactgtcagc aaagtaatga ggatcctcct   300
acgttcggtg ctgggaccaa gctggagctg aaacgggctg atgctgca                348

<210> SEQ ID NO 103
<211> LENGTH: 357
<212> TYPE: DNA
<213> ORGANISM: Mus musculus

<400> SEQUENCE: 103
gttactctga aagagtctgg ccctgggata ttgcagccct cccagaccct cagtctgact    60
tgttctttct ctgggttttc actgagcact tatggtatag gagtaggctg gattcgtcag   120
ccttcaggga agggtctgga gtggctggca cacatttggt ggaatgatga taagtactat   180
aacacagccc tgaagagccg gctcacaatc tccaaggata cctccaacaa ccaggtattc   240
ctcaagatcg ccagtgtgga cactgcagac actgccacat actactgtgc tcagtttat   300 tactacggta gtagttttga ctactggggc caaggcacca ctctcacagt ctcctca      357

<210> SEQ ID NO 104
<211> LENGTH: 336
<212> TYPE: DNA
<213> ORGANISM: Mus musculus

<400> SEQUENCE: 104
gacatccaga tgactcagtc tccagcctcc ctatctgcat ctgtgggaga aactgtcacc    60
atcacatgtc gagcaagtga gaatatttc agtatttag catggtatca gcagaaacag   120
ggaaaatctc ctcaactcct ggtctatgct gcaacaaatt tagcagatgg tgtgccatca   180
aggttcagtg gcagtggatc aggcacacag ttttctctga agatcaacag cctgcagcct   240
gaagattttg ggagttatta ctgtcaacat ttttatggta ctccgtggac gttcggtgga   300
ggcaccaagc tggaaatcaa acgggctgat gctgca                             336

<210> SEQ ID NO 105
<211> LENGTH: 360
<212> TYPE: DNA
<213> ORGANISM: Mus musculus

<400> SEQUENCE: 105
```

```
gtccagctgc agcagtctgg gcctgagctg gtgaggcctg gggaatcagt gaagatttcc      60
tgcaagggtt ccggctacac attcactgat tatgctatac actgggtgaa gctgagtcat     120
gcaaagagtc tagagtggat tggagttatt agtatttact atgatgatac aaactacaac     180
cagaagttta agggcaaggc cacaatgact gtagacaaat cctccagcac agcctatctg     240
gaacttgcca gattgacatc tgaggattct gccatctatt actgtgcaag acgaagggac     300
agctcgggtc cctatgctat ggactactgg ggtcaaggaa cctcagtcac cgtctcctca     360
```

<210> SEQ ID NO 106
<211> LENGTH: 348
<212> TYPE: DNA
<213> ORGANISM: Mus musculus

<400> SEQUENCE: 106

```
gacattgtgc tgacccaatc tccagcttct ttggctgtgt ctctagggca gagggccacc      60
atatcctgca gagccagtga aagtgttgat agttatggca atagtttat gcactggtac      120 cagcagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgatgt tgcaacctat tactgtcagc aaagtaatga ggatccgtac     300
acgttcggag gggggaccaa gctggaaata aaacgggctg atgctgca                  348
```

<210> SEQ ID NO 107
<211> LENGTH: 20
<212> TYPE: DNA
<213> ORGANISM: Mus musculus

<400> SEQUENCE: 107

```
aaaaaaaaaa aaaaaaaaaa                                                  20
```

<210> SEQ ID NO 108
<211> LENGTH: 20
<212> TYPE: DNA
<213> ORGANISM: Mus musculus

<400> SEQUENCE: 108

```
aaaaaaaaaa aaaaaaaaaa                                                  20
```

<210> SEQ ID NO 109
<211> LENGTH: 354
<212> TYPE: DNA
<213> ORGANISM: Mus musculus

<400> SEQUENCE: 109

```
gtccagctgc agcagtctgg ggctgagctg gtgaggcctg gggtctcagt gaagatttcc      60
tgcaagggtt ctggctacac attcactgat tatgctatgc actgggtgaa gcagagtcat     120
gcaaagagtc tagagtggat tggagttatt agtacttact atggtgatgc tagctacaac     180
cagaagttca agggcaaggc cacaatgact gtagacaaat cctccagcac agcctatatg     240
gagcttgcca gactgacatc tgaggattct gccatctatt actgtgcaag atcctatgat     300 tacgaccccct ggtttgctta ctggggccaa gggactctgg tcactgtctc tgca          354
```

<210> SEQ ID NO 110
<211> LENGTH: 348
<212> TYPE: DNA
<213> ORGANISM: Mus musculus

<400> SEQUENCE: 110

```
gacattgtgc tgacccaatc tccagcttct ttggctgtgt ctctagggca gagggccacc    60
atctcctgca gagccagcga aagtgttgat aattatggca ttagtttttat gcactggtac   120 cagcagaaac caggacagcc acccaaactc ctcatctatc gtgcatccaa cctagaatct   180
gggatccctg ccaggttcag tggcagtggg tctaggacag acttcaccct caccattaat   240
cctgtggaga ctgatgatgt tgcaacctat tactgtcagc aaagtaataa ggatccgctc   300
acgttcggtg ctgggaccaa gctggagctg aaacgggctg atgctgca                348
```

<210> SEQ ID NO 111
<211> LENGTH: 120
<212> TYPE: PRT
<213> ORGANISM: Mus musculus

<400> SEQUENCE: 111

```
Val Gln Leu Gln Gln Ser Gly Pro Glu Leu Val Arg Pro Gly Glu Ser
1               5                   10                  15

Val Lys Ile Ser Cys Lys Gly Ser Gly Tyr Thr Phe Thr Asp Tyr Ala
            20                  25                  30

Ile His Trp Val Lys Leu Ser His Ala Lys Ser Leu Glu Trp Ile Gly
        35                  40                  45

Val Ile Ser Ile Tyr Tyr Asp Asp Thr Asn Tyr Asn Gln Lys Phe Lys
    50                  55                  60

Gly Lys Ala Thr Met Thr Val Asp Lys Ser Ser Ser Thr Ala Tyr Met
65                  70                  75                  80

Glu Leu Ala Arg Leu Thr Ser Glu Asp Ser Ala Ile Tyr Tyr Cys Ala
                85                  90                  95

Arg Arg Arg Asp Ser Ser Gly Pro Tyr Ala Met Asp Tyr Trp Gly Gln
            100                 105                 110

Gly Thr Ser Val Thr Val Ser Ser
        115                 120
```

<210> SEQ ID NO 112
<211> LENGTH: 116
<212> TYPE: PRT
<213> ORGANISM: Mus musculus

<400> SEQUENCE: 112

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

Ala Asp Ala Ala
        115
```

<210> SEQ ID NO 113
<211> LENGTH: 115
<212> TYPE: PRT

<213> ORGANISM: Mus musculus

<400> SEQUENCE: 113

Val Met Leu Val Glu Ser Gly Gly Leu Val Lys Pro Gly Gly Ser
1               5                   10                  15

Leu Lys Leu Ser Cys Ala Ala Ser Gly Phe Thr Phe Ser Tyr Ala
                20                  25                  30

Met Ser Trp Val Arg Gln Thr Pro Glu Lys Arg Leu Glu Trp Val Ala
            35                  40                  45

Thr Ile Ser Ser Gly Gly Ser Tyr Thr Tyr Tyr Pro Asp Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Ala Asp Thr Ala Met Tyr Tyr Cys Ala
                85                  90                  95

Arg Asp Tyr Gly Tyr Phe Asp Tyr Trp Gly Gln Gly Thr Thr Leu Thr
            100                 105                 110

Val Ser Ser
        115

<210> SEQ ID NO 114
<211> LENGTH: 116
<212> TYPE: PRT
<213> ORGANISM: Mus musculus

<400> SEQUENCE: 114

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Ile Ser Phe Met His Trp Tyr Gln Gln Lys Pro Gly Gln Pro Pro
            35                  40                  45

Lys Leu Leu Phe Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Thr Asp Pro Arg Thr Phe Gly Gly Gly Thr Lys Leu Glu Ile Lys Arg
            100                 105                 110

Ala Asp Ala Ala
        115

<210> SEQ ID NO 115
<211> LENGTH: 125
<212> TYPE: PRT
<213> ORGANISM: Mus musculus

<400> SEQUENCE: 115

Val Gln Leu Gln Gln Ser Gly Ala Glu Leu Ala Arg Pro Gly Ala Ser
1               5                   10                  15

Val Lys Leu Ser Cys Val Ala Ser Gly Tyr Thr Phe Thr Asp Tyr Tyr
                20                  25                  30

Val Asn Trp Met Lys Gln Arg Thr Gly Gln Gly Leu Glu Trp Ile Gly
            35                  40                  45

Glu Ile Tyr Pro Gly Ser Gly Asn Thr Tyr Tyr Asn Glu Lys Phe Lys
        50                  55                  60

```
Gly Lys Ala Thr Leu Thr Ala Asp Lys Ser Ser Ser Thr Ala Tyr Met
 65                  70                  75                  80

Gln Leu Ser Ser Leu Thr Ser Glu Asp Ser Ala Val Tyr Phe Cys Ala
             85                  90                  95

Thr Trp Arg Gly Asn Leu Tyr Tyr Asp Tyr Asp Ala Glu Thr Leu Phe
            100                 105                 110

Ala Tyr Trp Gly Gln Gly Thr Leu Val Thr Val Ser Ala
            115                 120                 125

<210> SEQ ID NO 116
<211> LENGTH: 112
<212> TYPE: PRT
<213> ORGANISM: Mus musculus

<400> SEQUENCE: 116

Asp Ile Gln Met Thr Gln Ser Pro Ser Ser Leu Ser Ala Ser Leu Gly
  1               5                  10                  15

Glu Arg Ile Ser Leu Thr Cys Arg Ala Ser Gln Asp Ile Ser Asn Tyr
             20                  25                  30

Leu Asn Trp Phe Gln Gln Lys Pro Asp Gly Thr Phe Lys Arg Leu Ile
             35                 40                  45

Tyr Ala Thr Ser Ser Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Tyr
             85                  90                  95

Thr Phe Gly Gly Gly Thr Lys Leu Glu Ile Lys Arg Ala Asp Ala Ala
            100                 105                 110

<210> SEQ ID NO 117
<211> LENGTH: 118
<212> TYPE: PRT
<213> ORGANISM: Mus musculus

<400> SEQUENCE: 117

Val Gln Leu Val Glu Ser Gly Gly Asp Leu Val Lys Pro Gly Gly Ser
  1               5                  10                  15

Leu Lys Leu Ser Cys Ala Ala Ser Gly Phe Thr Phe Ser Ser Tyr Gly
             20                  25                  30

Met Ser Trp Val Arg Gln Thr Pro Asp Lys Arg Leu Glu Trp Val Ala
             35                  40                  45

Thr Ile Ser Ser Gly Gly Ser Tyr Thr Tyr Tyr Pro Asp Asn Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Asn Ser Glu Asp Thr Ala Met Tyr Tyr Cys Ala
             85                  90                  95

Arg Gln Val Tyr Tyr Phe Gly Ser Cys Asp Tyr Trp Gly Gln Gly Thr
            100                 105                 110

Thr Leu Thr Val Ser Ser
            115

<210> SEQ ID NO 118
<211> LENGTH: 116
<212> TYPE: PRT
<213> ORGANISM: Mus musculus

<400> SEQUENCE: 118
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65              70                  75                  80

Pro Val Glu Thr Asp Asp Val Ala Thr Tyr Tyr Cys Gln Gln Ser Asn
                85                  90                  95

Lys Asp Pro Trp Thr Phe Gly Gly Gly Thr Lys Leu Glu Ile Lys Arg
            100                 105                 110

Ala Asp Ala Ala
        115

<210> SEQ ID NO 119
<211> LENGTH: 118
<212> TYPE: PRT
<213> ORGANISM: Mus musculus

<400> SEQUENCE: 119

Val Gln Leu Val Glu Ser Gly Gly Asp Leu Val Lys Pro Gly Gly Ser
1               5                   10                  15

Leu Lys Leu Ser Cys Ala Ala Ser Gly Phe Thr Phe Ser Ser Tyr Gly
            20                  25                  30

Met Ser Trp Val Arg Gln Thr Pro Asp Lys Arg Leu Glu Trp Val Ala
        35                  40                  45

Thr Ile Ser Ser Gly Gly Ser Tyr Thr Tyr Tyr Pro Asp Ser Val Lys
    50                  55                  60

Gly Arg Phe Thr Ile Ser Arg Asp Asn Ala Lys Asn Thr Leu Tyr Leu
65              70                  75                  80

Gln Met Ser Ser Leu Lys Ser Glu Asp Thr Ala Met Tyr Tyr Cys Ala
                85                  90                  95

Arg Gln Val Tyr Tyr Tyr Gly Ser Ser Asp Tyr Trp Gly Gln Gly Thr
            100                 105                 110

Thr Leu Thr Val Ser Ser
        115

<210> SEQ ID NO 120
<211> LENGTH: 116
<212> TYPE: PRT
<213> ORGANISM: Mus musculus

<400> SEQUENCE: 120

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65              70                  75                  80

Pro Val Glu Thr Asp Asp Val Ala Thr Tyr Tyr Cys Gln Gln Ser Asn
            85                  90                  95

Lys Asp Pro Trp Thr Phe Gly Gly Gly Thr Lys Leu Glu Ile Lys Arg
            100                 105                 110

Ala Asp Ala Ala
        115

<210> SEQ ID NO 121
<211> LENGTH: 117
<212> TYPE: PRT
<213> ORGANISM: Mus musculus

<400> SEQUENCE: 121

Val Gln Leu Gln Gln Ser Gly Ala Glu Leu Val Arg Pro Gly Thr Ser
1               5                   10                  15

Val Lys Val Ser Cys Lys Ala Ser Gly Tyr Ala Phe Thr Tyr Tyr Leu
            20                  25                  30

Ile Glu Trp Val Lys Gln Arg Pro Gly Gln Gly Leu Glu Trp Ile Gly
        35                  40                  45

Val Ile Asn Pro Gly Ser Gly Val Thr Asn Tyr Asn Glu Lys Phe Lys
    50                  55                  60

Gly Lys Ala Thr Leu Thr Ala Asp Lys Ser Ser Ser Thr Ala Tyr Met
65                  70                  75                  80

Gln Leu Ser Ser Leu Thr Ser Asp Ser Ala Val Tyr Phe Cys Ala
                85                  90                  95

Arg Ser Ile Tyr Tyr Gly Thr Ile Asp Tyr Trp Gly Gln Gly Thr Thr
            100                 105                 110

Leu Thr Val Ser Ser
        115

<210> SEQ ID NO 122
<211> LENGTH: 112
<212> TYPE: PRT
<213> ORGANISM: Mus musculus

<400> SEQUENCE: 122

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Asn Pro Asp Gly Thr Val Lys Leu Leu Ile
        35                  40                  45

Tyr Tyr Thr Ser Arg Leu His Ser Gly Val Pro Ser Arg Phe Ser Ala
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Ala Asp Ala Ala
            100                 105                 110

<210> SEQ ID NO 123
<211> LENGTH: 119
<212> TYPE: PRT
<213> ORGANISM: Mus musculus

<400> SEQUENCE: 123

Val Thr Leu Lys Glu Ser Gly Pro Gly Ile Leu Gln Pro Ser Gln Thr
1               5                   10                  15

```
Leu Ser Leu Thr Cys Ser Phe Ser Gly Phe Ser Leu Ser Thr Tyr Gly
            20                  25                  30

Ile Gly Val Gly Trp Ile Arg Gln Pro Ser Gly Lys Gly Leu Glu Trp
        35                  40                  45

Leu Ala His Ile Trp Trp Asp Asp Asn Lys Tyr Tyr Asn Thr Ala Leu
    50                  55                  60

Lys Ser Arg Leu Thr Ile Ser Lys Asp Thr Ser Asn Asn Gln Val Phe
65                  70                  75                  80

Leu Lys Ile Ala Ser Val Asp Thr Ala Asp Thr Ala Thr Tyr Tyr Cys
                85                  90                  95

Ala Arg Ile His Tyr Tyr Gly Ser Ser Leu Asp Tyr Trp Gly Gln Gly
            100                 105                 110

Thr Thr Leu Thr Val Ser Ser
            115
```

<210> SEQ ID NO 124
<211> LENGTH: 112
<212> TYPE: PRT
<213> ORGANISM: Mus musculus

<400> SEQUENCE: 124

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro His Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Tyr Gly Thr Pro Trp
                85                  90                  95

Thr Phe Gly Gly Gly Thr Lys Leu Glu Ile Lys Arg Ala Asp Ala Ala
            100                 105                 110
```

<210> SEQ ID NO 125
<211> LENGTH: 116
<212> TYPE: PRT
<213> ORGANISM: Mus musculus

<400> SEQUENCE: 125

```
Val Gln Leu Val Glu Ser Gly Gly Gly Leu Val Lys Pro Gly Gly Ser
1               5                   10                  15

Leu Lys Leu Ser Cys Ala Ala Ser Gly Phe Thr Phe Ser Ser Tyr Ala
            20                  25                  30

Met Ser Trp Val Arg Gln Thr Pro Glu Lys Arg Leu Glu Trp Val Ala
        35                  40                  45

Ile Ile Ser Ser Gly Gly Ser Tyr Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

His Met Ser Ser Leu Arg Ser Glu Asp Thr Ala Met Tyr Tyr Cys Ala
                85                  90                  95

Arg Gln Gly Gly Gly Tyr Phe Asp Tyr Trp Gly Gln Gly Thr Thr Leu
            100                 105                 110
```

-continued

```
Thr Val Ser Ser
        115

<210> SEQ ID NO 126
<211> LENGTH: 116
<212> TYPE: PRT
<213> ORGANISM: Mus musculus

<400> SEQUENCE: 126

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Val Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys Arg
            100                 105                 110

Ala Asp Ala Ala
        115

<210> SEQ ID NO 127
<211> LENGTH: 119
<212> TYPE: PRT
<213> ORGANISM: Mus musculus

<400> SEQUENCE: 127

Val Thr Leu Lys Glu Ser Gly Pro Gly Ile Leu Gln Pro Ser Gln Thr
1               5                   10                  15

Leu Ser Leu Thr Cys Ser Phe Ser Gly Phe Ser Leu Ser Thr Tyr Gly
            20                  25                  30

Ile Gly Val Gly Trp Ile Arg Gln Pro Ser Gly Lys Gly Leu Glu Trp
        35                  40                  45

Leu Ala His Ile Trp Trp Asn Asp Asp Lys Tyr Tyr Asn Thr Ala Leu
    50                  55                  60

Lys Ser Arg Leu Thr Ile Ser Lys Asp Thr Ser Asn Asn Gln Val Phe
65                  70                  75                  80

Leu Lys Ile Ala Ser Val Asp Thr Ala Asp Thr Ala Thr Tyr Tyr Cys
                85                  90                  95

Ala Arg Val Tyr Tyr Tyr Gly Ser Ser Phe Asp Tyr Trp Gly Gln Gly
            100                 105                 110

Thr Thr Leu Thr Val Ser Ser
        115

<210> SEQ ID NO 128
<211> LENGTH: 112
<212> TYPE: PRT
<213> ORGANISM: Mus musculus

<400> SEQUENCE: 128

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Ile
            20                  25                  30
```

```
Leu Ala Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His Phe Tyr Gly Thr Pro Trp
                85                  90                  95

Thr Phe Gly Gly Gly Thr Lys Leu Glu Ile Lys Arg Ala Asp Ala Ala
               100                 105                 110

<210> SEQ ID NO 129
<211> LENGTH: 120
<212> TYPE: PRT
<213> ORGANISM: Mus musculus

<400> SEQUENCE: 129

Val Gln Leu Gln Gln Ser Gly Pro Glu Leu Val Arg Pro Gly Glu Ser
 1               5                  10                  15

Val Lys Ile Ser Cys Lys Gly Ser Gly Tyr Thr Phe Thr Asp Tyr Ala
             20                  25                  30

Ile His Trp Val Lys Leu Ser His Ala Lys Ser Leu Glu Trp Ile Gly
            35                  40                  45

Val Ile Ser Ile Tyr Tyr Asp Asp Thr Asn Tyr Asn Gln Lys Phe Lys
 50                  55                  60

Gly Lys Ala Thr Met Thr Val Asp Lys Ser Ser Ser Thr Ala Tyr Leu
 65                  70                  75                  80

Glu Leu Ala Arg Leu Thr Ser Glu Asp Ser Ala Ile Tyr Tyr Cys Ala
                85                  90                  95

Arg Arg Arg Asp Ser Ser Gly Pro Tyr Ala Met Asp Tyr Trp Gly Gln
               100                 105                 110

Gly Thr Ser Val Thr Val Ser Ser
               115                 120

<210> SEQ ID NO 130
<211> LENGTH: 116
<212> TYPE: PRT
<213> ORGANISM: Mus musculus

<400> SEQUENCE: 130

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys Arg
               100                 105                 110

Ala Asp Ala Ala
     115
```

<210> SEQ ID NO 131
<211> LENGTH: 10
<212> TYPE: PRT
<213> ORGANISM: Mus musculus

<400> SEQUENCE: 131

Ala Ala Ala Ala Ala Ala Ala Ala Ala Ala
1               5                   10

<210> SEQ ID NO 132
<211> LENGTH: 10
<212> TYPE: PRT
<213> ORGANISM: Mus musculus

<400> SEQUENCE: 132

Ala Ala Ala Ala Ala Ala Ala Ala Ala Ala
1               5                   10

<210> SEQ ID NO 133
<211> LENGTH: 118
<212> TYPE: PRT
<213> ORGANISM: Mus musculus

<400> SEQUENCE: 133

Val Gln Leu Gln Gln Ser Gly Ala Glu Leu Val Arg Pro Gly Val Ser
1               5                   10                  15

Val Lys Ile Ser Cys Lys Gly Ser Gly Tyr Thr Phe Thr Asp Tyr Ala
            20                  25                  30

Met His Trp Val Lys Gln Ser His Ala Lys Ser Leu Glu Trp Ile Gly
        35                  40                  45

Val Ile Ser Thr Tyr Tyr Gly Asp Ala Ser Tyr Asn Gln Lys Phe Lys
    50                  55                  60

Gly Lys Ala Thr Met Thr Val Asp Lys Ser Ser Ser Thr Ala Tyr Met
65                  70                  75                  80

Glu Leu Ala Arg Leu Thr Ser Glu Asp Ser Ala Ile Tyr Tyr Cys Ala
                85                  90                  95

Arg Ser Tyr Asp Tyr Asp Pro Trp Phe Ala Tyr Trp Gly Gln Gly Thr
            100                 105                 110

Leu Val Thr Val Ser Ala
        115

<210> SEQ ID NO 134
<211> LENGTH: 116
<212> TYPE: PRT
<213> ORGANISM: Mus musculus

<400> SEQUENCE: 134

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

```
Lys Asp Pro Leu Thr Phe Gly Ala Gly Thr Lys Leu Glu Leu Lys Arg
                100                 105                 110

Ala Asp Ala Ala
        115
```

<210> SEQ ID NO 135
<211> LENGTH: 486
<212> TYPE: PRT
<213> ORGANISM: Artificial Sequence
<220> FEATURE:
<223> OTHER INFORMATION: Description of Artificial Sequence: Synthetic GPVI variant sequence

<400> SEQUENCE: 135

```
Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
                35                  40                  45

Asp Gln Ala Val Leu Phe Ile Pro Ala Met Lys Arg Ser Leu Ala Gly
        50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
        130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
                180                 185                 190

Pro Thr Glu Pro Pro Ser Ser Val Ala Glu Phe Ser Glu Ala Thr Ala
            195                 200                 205

Glu Leu Thr Val Ser Phe Thr Asn Lys Val Phe Thr Thr Glu Thr Ser
        210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
        290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335
```

```
Ser Thr Tyr Arg Val Ser Val Leu Thr Val Leu His Gln Asp Trp
            340                 345                 350

Leu Asn Gly Lys Glu Tyr Lys Cys Val Ser Asn Lys Ala Leu Pro
        355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 136
<211> LENGTH: 483
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 136

Gln Ser Gly Pro Leu Pro Lys Pro Ser Leu Gln Ala Gln Pro Ser Ser
1               5                   10                  15

Leu Val Pro Leu Gly Gln Ser Val Ile Leu Arg Cys Gln Gly Pro Pro
            20                  25                  30

Asp Val Asp Leu Tyr Arg Leu Glu Lys Leu Lys Pro Glu Lys Tyr Glu
        35                  40                  45

Asp Gln Asp Phe Leu Phe Ile Pro Thr Met Glu Arg Ser Asn Ala Gly
    50                  55                  60

Arg Tyr Arg Cys Ser Tyr Gln Asn Gly Ser His Trp Ser Leu Pro Ser
65                  70                  75                  80

Asp Gln Leu Glu Leu Ile Ala Thr Gly Val Tyr Ala Lys Pro Ser Leu
                85                  90                  95

Ser Ala His Pro Ser Ser Ala Val Pro Gln Gly Arg Asp Val Thr Leu
            100                 105                 110

Lys Cys Gln Ser Pro Tyr Ser Phe Asp Glu Phe Val Leu Tyr Lys Glu
        115                 120                 125

Gly Asp Thr Gly Ser Tyr Lys Arg Pro Gly Lys Trp Tyr Arg Ala Asn
    130                 135                 140

Phe Pro Ile Ile Thr Val Thr Ala Ala His Ser Gly Thr Tyr Arg Cys
145                 150                 155                 160

Tyr Ser Phe Ser Ser Ser Ser Pro Tyr Leu Trp Ser Ala Pro Ser Asp
                165                 170                 175

Pro Leu Val Leu Val Val Thr Gly Leu Ser Ala Thr Pro Ser Gln Val
            180                 185                 190

Pro Thr Glu Glu Ser Phe Pro Val Thr Glu Ser Ser Arg Arg Pro Ser
        195                 200                 205
```

```
Ile Leu Pro Thr Asn Lys Ile Ser Thr Thr Glu Lys Pro Met Asn Ile
210                 215                 220

Thr Ala Ser Pro Glu Gly Leu Ser Pro Pro Phe Gly Phe Ala His Gln
225                 230                 235                 240

His Tyr Ala Lys Gly Asn Gly Ser Arg Ser Asn Glu Pro Lys Ser Cys
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Pro Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys

<210> SEQ ID NO 137
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 137

Gln Ser Gly Pro Leu Pro Lys Pro Ser Leu Gln Ala Gln Pro Ser Ser
1               5                   10                  15

Leu Val Pro Leu Gly Gln Ser Val Ile Leu Arg Cys Gln Gly Pro Pro
            20                  25                  30

Asp Val Asp Leu Tyr Arg Leu Glu Lys Leu Lys Pro Glu Lys Tyr Glu
        35                  40                  45

Asp Gln Asp Phe Leu Phe Ile Pro Thr Met Glu Arg Ser Asn Ala Gly
    50                  55                  60

Arg Tyr Arg Cys Ser Tyr Gln Asn Gly Ser His Trp Ser Leu Pro Ser
65                  70                  75                  80

Asp Gln Leu Glu Leu Ile Ala Thr Gly Val Phe Ala Lys Pro Ser Leu
```

```
                    85                  90                  95
Ser Ala Gln Pro Gly Pro Ala Val Ser Ser Gly Gly Asp Val Thr Leu
                100                 105                 110
Gln Cys Gln Thr Arg Tyr Gly Phe Asp Gln Phe Ala Leu Tyr Lys Glu
                115                 120                 125
Gly Asp Pro Ala Pro Tyr Lys Asn Pro Glu Arg Trp Tyr Arg Ala Ser
                130                 135                 140
Phe Pro Ile Ile Thr Val Thr Ala Ala His Ser Gly Thr Tyr Arg Cys
145                 150                 155                 160
Tyr Ser Phe Ser Ser Arg Asp Pro Tyr Leu Trp Ser Ala Pro Ser Asp
                165                 170                 175
Pro Leu Glu Leu Val Val Thr Gly Thr Ser Val Thr Pro Ser Arg Leu
                180                 185                 190
Pro Thr Glu Pro Pro Ser Ser Val Ala Glu Phe Ser Glu Ala Thr Ala
                195                 200                 205
Glu Leu Thr Val Ser Phe Thr Asn Lys Val Phe Thr Thr Glu Thr Ser
                210                 215                 220
Arg Ser Ile Thr Thr Ser Pro Lys Glu Ser Asp Ser Pro Ala Gly Pro
225                 230                 235                 240
Ala Arg Gln Tyr Tyr Thr Lys Gly Asn Gly Ser Arg Ser Asn Glu Pro
                245                 250                 255
Lys Ser Cys Asp Lys Thr His Thr Cys Pro Pro Cys Pro Ala Pro Glu
                260                 265                 270
Leu Leu Gly Gly Pro Ser Val Phe Leu Phe Pro Pro Lys Pro Lys Asp
                275                 280                 285
Thr Leu Met Ile Ser Arg Thr Pro Glu Val Thr Cys Val Val Val Asp
                290                 295                 300
Val Ser His Glu Asp Pro Glu Val Lys Phe Asn Trp Tyr Val Asp Gly
305                 310                 315                 320
Val Glu Val His Asn Ala Lys Thr Lys Pro Arg Glu Glu Gln Tyr Asn
                325                 330                 335
Ser Thr Tyr Arg Val Val Ser Val Leu Thr Val Leu His Gln Asp Trp
                340                 345                 350
Leu Asn Gly Lys Glu Tyr Lys Cys Lys Val Ser Asn Lys Ala Leu Pro
                355                 360                 365
Ala Pro Ile Glu Lys Thr Ile Ser Lys Ala Lys Gly Gln Pro Arg Glu
                370                 375                 380
Pro Gln Val Tyr Thr Leu Pro Pro Ser Arg Asp Glu Leu Thr Lys Asn
385                 390                 395                 400
Gln Val Ser Leu Thr Cys Leu Val Lys Gly Phe Tyr Pro Ser Asp Ile
                405                 410                 415
Ala Val Glu Trp Glu Ser Asn Gly Gln Pro Glu Asn Asn Tyr Lys Thr
                420                 425                 430
Thr Pro Pro Val Leu Asp Ser Asp Gly Pro Phe Phe Leu Tyr Ser Lys
                435                 440                 445
Leu Thr Val Asp Lys Ser Arg Trp Gln Gln Gly Asn Val Phe Ser Cys
450                 455                 460
Ser Val Met His Glu Ala Leu His Asn His Tyr Thr Gln Lys Ser Leu
465                 470                 475                 480
Ser Leu Ser Pro Gly Lys
                485

<210> SEQ ID NO 138
<211> LENGTH: 486
```

```
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 138
```

| | | | | | | | | | | | | | | | |
|---|---|---|---|---|---|---|---|---|---|---|---|---|---|---|---|
| Gln | Ser | Gly | Pro | Leu | Pro | Lys | Pro | Ser | Leu | Gln | Ala | Leu | Pro | Ser | Ser |
| 1 | | | | 5 | | | | | 10 | | | | | 15 | |
| Leu | Val | Pro | Leu | Glu | Lys | Pro | Val | Thr | Leu | Arg | Cys | Gln | Gly | Pro | Pro |
| | | | 20 | | | | | 25 | | | | | 30 | | |
| Gly | Val | Asp | Leu | Tyr | Arg | Leu | Glu | Lys | Leu | Ser | Ser | Ser | Arg | Tyr | Gln |
| | | 35 | | | | | 40 | | | | | 45 | | | |
| Asp | Gln | Ala | Val | Leu | Phe | Ile | Pro | Ala | Met | Lys | Arg | Ser | Leu | Ala | Gly |
| | 50 | | | | | 55 | | | | | 60 | | | | |
| Arg | Tyr | Arg | Cys | Ser | Tyr | Gln | Asn | Gly | Ser | Leu | Trp | Ser | Leu | Pro | Ser |
| 65 | | | | | 70 | | | | | 75 | | | | | 80 |
| Asp | Gln | Leu | Glu | Leu | Val | Ala | Thr | Gly | Val | Tyr | Ala | Lys | Pro | Ser | Leu |
| | | | | 85 | | | | | 90 | | | | | 95 | |
| Ser | Ala | His | Pro | Ser | Ser | Ala | Val | Pro | Gln | Gly | Arg | Asp | Val | Thr | Leu |
| | | | 100 | | | | | 105 | | | | | 110 | | |
| Lys | Cys | Gln | Ser | Pro | Tyr | Ser | Phe | Asp | Glu | Phe | Val | Leu | Tyr | Lys | Glu |
| | | 115 | | | | | 120 | | | | | 125 | | | |
| Gly | Asp | Thr | Gly | Ser | Tyr | Lys | Arg | Pro | Glu | Lys | Trp | Tyr | Arg | Ala | Asn |
| | 130 | | | | | 135 | | | | | 140 | | | | |
| Phe | Pro | Ile | Ile | Thr | Val | Thr | Ala | Ala | His | Ser | Gly | Thr | Tyr | Arg | Cys |
| 145 | | | | | 150 | | | | | 155 | | | | | 160 |
| Tyr | Ser | Phe | Ser | Ser | Ser | Pro | Tyr | Leu | Trp | Ser | Ala | Pro | Ser | Asp |
| | | | | 165 | | | | | 170 | | | | | 175 | |
| Pro | Leu | Val | Leu | Val | Val | Thr | Gly | Thr | Ser | Val | Thr | Pro | Ser | Arg | Leu |
| | | | 180 | | | | | 185 | | | | | 190 | | |
| Pro | Thr | Glu | Pro | Pro | Ser | Ser | Val | Ala | Glu | Phe | Ser | Glu | Ala | Thr | Ala |
| | | 195 | | | | | 200 | | | | | 205 | | | |
| Glu | Leu | Thr | Val | Ser | Phe | Thr | Asn | Lys | Val | Phe | Thr | Thr | Glu | Thr | Ser |
| | 210 | | | | | 215 | | | | | 220 | | | | |
| Arg | Ser | Ile | Thr | Thr | Ser | Pro | Lys | Glu | Ser | Asp | Ser | Pro | Ala | Gly | Pro |
| 225 | | | | | 230 | | | | | 235 | | | | | 240 |
| Ala | Arg | Gln | Tyr | Tyr | Thr | Lys | Gly | Asn | Gly | Ser | Arg | Ser | Asn | Glu | Pro |
| | | | | 245 | | | | | 250 | | | | | 255 | |
| Lys | Ser | Cys | Asp | Lys | Thr | His | Thr | Cys | Pro | Pro | Cys | Pro | Ala | Pro | Glu |
| | | | 260 | | | | | 265 | | | | | 270 | | |
| Leu | Leu | Gly | Gly | Pro | Ser | Val | Phe | Leu | Phe | Pro | Pro | Lys | Pro | Lys | Asp |
| | | 275 | | | | | 280 | | | | | 285 | | | |
| Thr | Leu | Met | Ile | Ser | Arg | Thr | Pro | Glu | Val | Thr | Cys | Val | Val | Val | Asp |
| | 290 | | | | | 295 | | | | | 300 | | | | |
| Val | Ser | His | Glu | Asp | Pro | Glu | Val | Lys | Phe | Asn | Trp | Tyr | Val | Asp | Gly |
| 305 | | | | | 310 | | | | | 315 | | | | | 320 |
| Val | Glu | Val | His | Asn | Ala | Lys | Thr | Lys | Pro | Arg | Glu | Glu | Gln | Tyr | Asn |
| | | | | 325 | | | | | 330 | | | | | 335 | |
| Ser | Thr | Tyr | Arg | Val | Val | Ser | Val | Leu | Thr | Val | Leu | His | Gln | Asp | Trp |
| | | | 340 | | | | | 345 | | | | | 350 | | |
| Leu | Asn | Gly | Lys | Glu | Tyr | Lys | Cys | Lys | Val | Ser | Asn | Lys | Ala | Leu | Pro |
| | | 355 | | | | | 360 | | | | | 365 | | | |
| Ala | Pro | Ile | Glu | Lys | Thr | Ile | Ser | Lys | Ala | Lys | Gly | Gln | Pro | Arg | Glu |
| | 370 | | | | | 375 | | | | | 380 | | | | |

```
Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 139
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 139

Gln Ser Gly Pro Leu Pro Lys Pro Ser Leu Gln Ala Gln Pro Ser Ser
1               5                   10                  15

Leu Val Pro Leu Gly Gln Ser Val Ile Leu Arg Cys Gln Gly Pro Pro
            20                  25                  30

Asp Val Asp Leu Tyr Arg Leu Glu Lys Leu Lys Pro Glu Lys Tyr Glu
        35                  40                  45

Asp Gln Asp Phe Leu Phe Ile Pro Thr Met Glu Arg Ser Asn Ala Gly
    50                  55                  60

Arg Tyr Arg Cys Ser Tyr Gln Asn Gly Ser His Trp Ser Leu Pro Ser
65                  70                  75                  80

Asp Gln Leu Glu Leu Ile Ala Thr Gly Val Tyr Ala Lys Pro Ser Leu
                85                  90                  95

Ser Ala His Pro Ser Ser Ala Val Pro Gln Gly Arg Asp Val Thr Leu
            100                 105                 110

Lys Cys Gln Ser Pro Tyr Ser Phe Asp Glu Phe Val Leu Tyr Lys Glu
        115                 120                 125

Gly Asp Thr Gly Ser Tyr Lys Arg Pro Glu Lys Trp Tyr Arg Ala Asn
    130                 135                 140

Phe Pro Ile Ile Thr Val Thr Ala Ala His Ser Gly Thr Tyr Arg Cys
145                 150                 155                 160

Tyr Ser Phe Ser Ser Ser Pro Tyr Leu Trp Ser Ala Pro Ser Asp
                165                 170                 175

Pro Leu Val Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255
```

```
Lys Ser Cys Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
        290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 140
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 140

Gln Ser Gly Pro Leu Pro Lys Pro Ser Leu Gln Ala Leu Pro Ser Ser
1               5                   10                  15

Leu Val Pro Leu Gly Gln Ser Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125
```

Gly Asp Pro Ala Pro Tyr Lys Asn Pro Glu Arg Trp Tyr Arg Ala Ser
130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Glu Thr Ser
210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
        435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 141
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 141

```
Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Asp Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
            50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
                115                 120                 125

Gly Asp Pro Ala Pro Tyr Lys Asn Pro Glu Arg Trp Tyr Arg Ala Ser
        130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
                180                 185                 190

Pro Thr Glu Pro Pro Ser Ser Val Ala Glu Phe Ser Glu Ala Thr Ala
                195                 200                 205

Glu Leu Thr Val Ser Phe Thr Asn Lys Val Phe Thr Thr Glu Thr Ser
210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
                275                 280                 285

Thr Leu Met Ile Ser Arg Thr Pro Glu Val Thr Cys Val Val Val Asp
        290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
                340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
        370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430
```

Thr Pro Pro Val Leu Asp Ser Asp Gly Pro Phe Phe Leu Tyr Ser Lys
            435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 142
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 142

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Lys Pro Glu Lys Tyr Glu
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65              70                  75                  80

Asp Gln Leu Glu Leu Val Ala Thr Gly Val Phe Ala Lys Pro Ser Leu
            85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
            195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
    290                 295                 300

```
Val Ser His Glu Asp Pro Glu Val Lys Phe Asn Trp Tyr Val Asp Gly
305                 310                 315                 320

Val Glu Val His Asn Ala Lys Thr Lys Pro Arg Glu Gln Tyr Asn
            325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430

Thr Pro Pro Val Leu Asp Ser Asp Gly Pro Phe Phe Leu Tyr Ser Lys
                435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 143
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 143

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Thr Met Glu Arg Ser Asn Ala Gly
50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175
```

```
Pro Leu Glu Leu Val Val Thr Gly Thr Ser Val Thr Pro Ser Arg Leu
                180                 185                 190

Pro Thr Glu Pro Pro Ser Ser Val Ala Glu Phe Ser Glu Ala Thr Ala
            195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
            290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
            370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
            435                 440                 445

Leu Thr Val Asp Lys Ser Arg Trp Gln Gln Gly Asn Val Phe Ser Cys
            450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 144
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 144

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45
```

```
Asp Gln Ala Val Leu Phe Ile Pro Ala Met Lys Arg Ser Leu Ala Gly
    50                  55                  60

Arg Tyr Arg Cys Ser Tyr Gln Asn Gly Ser His Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
                115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
                180                 185                 190

Pro Thr Glu Pro Pro Ser Ser Val Ala Glu Phe Ser Glu Ala Thr Ala
                195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
                275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
                340                 345                 350

Leu Asn Gly Lys Glu Tyr Lys Cys Lys Val Ser Asn Lys Ala Leu Pro
    355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430

Thr Pro Pro Val Leu Asp Ser Asp Gly Pro Phe Phe Leu Tyr Ser Lys
    435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
```

465         470              475              480
Ser Leu Ser Pro Gly Lys
                485

<210> SEQ ID NO 145
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 145

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Tyr Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp

```
                    340             345             350
Leu Asn Gly Lys Glu Tyr Lys Cys Lys Val Ser Asn Lys Ala Leu Pro
            355                 360             365
Ala Pro Ile Glu Lys Thr Ile Ser Lys Ala Lys Gly Gln Pro Arg Glu
        370                 375             380
Pro Gln Val Tyr Thr Leu Pro Pro Ser Arg Asp Glu Leu Thr Lys Asn
385                 390                 395                 400
Gln Val Ser Leu Thr Cys Leu Val Lys Gly Phe Tyr Pro Ser Asp Ile
                405                 410                 415
Ala Val Glu Trp Glu Ser Asn Gly Gln Pro Glu Asn Asn Tyr Lys Thr
            420                 425                 430
Thr Pro Pro Val Leu Asp Ser Asp Gly Pro Phe Phe Leu Tyr Ser Lys
        435                 440                 445
Leu Thr Val Asp Lys Ser Arg Trp Gln Gln Gly Asn Val Phe Ser Cys
        450                 455                 460
Ser Val Met His Glu Ala Leu His Asn His Tyr Thr Gln Lys Ser Leu
465                 470                 475                 480
Ser Leu Ser Pro Gly Lys
                485

<210> SEQ ID NO 146
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 146

Gln Ser Gly Pro Leu Pro Lys Pro Ser Leu Gln Ala Leu Pro Ser Ser
1               5                   10                  15
Leu Val Pro Leu Glu Lys Pro Val Thr Leu Arg Cys Gln Gly Pro Pro
            20                  25                  30
Gly Val Asp Leu Tyr Arg Leu Glu Lys Leu Ser Ser Ser Arg Tyr Gln
        35                  40                  45
Asp Gln Ala Val Leu Phe Ile Pro Ala Met Lys Arg Ser Leu Ala Gly
    50                  55                  60
Arg Tyr Arg Cys Ser Tyr Gln Asn Gly Ser Leu Trp Ser Leu Pro Ser
65                  70                  75                  80
Asp Gln Leu Glu Leu Val Ala Thr Gly Val Phe Ala Lys Pro Ser Leu
                85                  90                  95
Ser Ala His Pro Ser Ser Ala Val Pro Gln Gly Arg Asp Val Thr Leu
            100                 105                 110
Gln Cys Gln Thr Arg Tyr Gly Phe Asp Gln Phe Ala Leu Tyr Lys Glu
        115                 120                 125
Gly Asp Pro Ala Pro Tyr Lys Asn Pro Glu Arg Trp Tyr Arg Ala Ser
    130                 135                 140
Phe Pro Ile Ile Thr Val Thr Ala Ala His Ser Gly Thr Tyr Arg Cys
145                 150                 155                 160
Tyr Ser Phe Ser Ser Arg Asp Pro Tyr Leu Trp Ser Ala Pro Ser Asp
                165                 170                 175
Pro Leu Glu Leu Val Val Thr Gly Thr Ser Val Thr Pro Ser Arg Leu
            180                 185                 190
Pro Thr Glu Pro Pro Ser Ser Val Ala Glu Phe Ser Glu Ala Thr Ala
        195                 200                 205
Glu Leu Thr Val Ser Phe Thr Asn Lys Val Phe Thr Thr Glu Thr Ser
```

```
                    210                 215                 220
Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
                275                 280                 285

Thr Leu Met Ile Ser Arg Thr Pro Glu Val Thr Cys Val Val Val Asp
                290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
                340                 345                 350

Leu Asn Gly Lys Glu Tyr Lys Cys Lys Val Ser Asn Lys Ala Leu Pro
                355                 360                 365

Ala Pro Ile Glu Lys Thr Ile Ser Lys Ala Lys Gly Gln Pro Arg Glu
                370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430

Thr Pro Pro Val Leu Asp Ser Asp Gly Pro Phe Phe Leu Tyr Ser Lys
                435                 440                 445

Leu Thr Val Asp Lys Ser Arg Trp Gln Gln Gly Asn Val Phe Ser Cys
                450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 147
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 147

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
                35                  40                  45

Asp Gln Ala Val Leu Phe Ile Pro Ala Met Lys Arg Ser Leu Ala Gly
                50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
```

```
                        85                  90                  95
Ser Ala Gln Pro Gly Pro Ala Val Ser Ser Gly Gly Asp Val Thr Leu
                100                 105                 110
Gln Cys Gln Ser Pro Tyr Ser Phe Asp Glu Phe Ala Leu Tyr Lys Glu
                115                 120                 125
Gly Asp Pro Ala Pro Tyr Lys Asn Pro Glu Arg Trp Tyr Arg Ala Ser
                130                 135                 140
Phe Pro Ile Ile Thr Val Thr Ala Ala His Ser Gly Thr Tyr Arg Cys
145                 150                 155                 160
Tyr Ser Phe Ser Ser Arg Asp Pro Tyr Leu Trp Ser Ala Pro Ser Asp
                165                 170                 175
Pro Leu Glu Leu Val Val Thr Gly Thr Ser Val Thr Pro Ser Arg Leu
                180                 185                 190
Pro Thr Glu Pro Pro Ser Ser Val Ala Glu Phe Ser Glu Ala Thr Ala
                195                 200                 205
Glu Leu Thr Val Ser Phe Thr Asn Lys Val Phe Thr Thr Glu Thr Ser
                210                 215                 220
Arg Ser Ile Thr Thr Ser Pro Lys Glu Ser Asp Ser Pro Ala Gly Pro
225                 230                 235                 240
Ala Arg Gln Tyr Tyr Thr Lys Gly Asn Gly Ser Arg Ser Asn Glu Pro
                245                 250                 255
Lys Ser Cys Asp Lys Thr His Thr Cys Pro Pro Cys Pro Ala Pro Glu
                260                 265                 270
Leu Leu Gly Gly Pro Ser Val Phe Leu Phe Pro Pro Lys Pro Lys Asp
                275                 280                 285
Thr Leu Met Ile Ser Arg Thr Pro Glu Val Thr Cys Val Val Val Asp
                290                 295                 300
Val Ser His Glu Asp Pro Glu Val Lys Phe Asn Trp Tyr Val Asp Gly
305                 310                 315                 320
Val Glu Val His Asn Ala Lys Thr Lys Pro Arg Glu Glu Gln Tyr Asn
                325                 330                 335
Ser Thr Tyr Arg Val Val Ser Val Leu Thr Val Leu His Gln Asp Trp
                340                 345                 350
Leu Asn Gly Lys Glu Tyr Lys Cys Lys Val Ser Asn Lys Ala Leu Pro
                355                 360                 365
Ala Pro Ile Glu Lys Thr Ile Ser Lys Ala Lys Gly Gln Pro Arg Glu
                370                 375                 380
Pro Gln Val Tyr Thr Leu Pro Pro Ser Arg Asp Glu Leu Thr Lys Asn
385                 390                 395                 400
Gln Val Ser Leu Thr Cys Leu Val Lys Gly Phe Tyr Pro Ser Asp Ile
                405                 410                 415
Ala Val Glu Trp Glu Ser Asn Gly Gln Pro Glu Asn Asn Tyr Lys Thr
                420                 425                 430
Thr Pro Pro Val Leu Asp Ser Asp Gly Pro Phe Phe Leu Tyr Ser Lys
                435                 440                 445
Leu Thr Val Asp Lys Ser Arg Trp Gln Gln Gly Asn Val Phe Ser Cys
450                 455                 460
Ser Val Met His Glu Ala Leu His Asn His Tyr Thr Gln Lys Ser Leu
465                 470                 475                 480
Ser Leu Ser Pro Gly Lys
                485

<210> SEQ ID NO 148
<211> LENGTH: 486
```

<210> 212> TYPE: PRT
<213> ORGANISM: Artificial Sequence
<220> FEATURE:
<223> OTHER INFORMATION: Description of Artificial Sequence: Synthetic GPVI variant sequence

<400> SEQUENCE: 148

```
Gln Ser Gly Pro Leu Pro Lys Pro Ser Leu Gln Ala Leu Pro Ser Ser
1               5                   10                  15
Leu Val Pro Leu Glu Lys Pro Val Thr Leu Arg Cys Gln Gly Pro Pro
            20                  25                  30
Gly Val Asp Leu Tyr Arg Leu Glu Lys Leu Ser Ser Ser Arg Tyr Gln
        35                  40                  45
Asp Gln Ala Val Leu Phe Ile Pro Ala Met Lys Arg Ser Leu Ala Gly
    50                  55                  60
Arg Tyr Arg Cys Ser Tyr Gln Asn Gly Ser Leu Trp Ser Leu Pro Ser
65                  70                  75                  80
Asp Gln Leu Glu Leu Val Ala Thr Gly Val Phe Ala Lys Pro Ser Leu
                85                  90                  95
Ser Ala Gln Pro Gly Pro Ala Val Ser Ser Gly Gly Asp Val Thr Leu
            100                 105                 110
Gln Cys Gln Thr Arg Tyr Gly Phe Asp Gln Phe Ala Leu Tyr Lys Glu
        115                 120                 125
Gly Asp Thr Gly Ser Tyr Lys Asn Pro Glu Arg Trp Tyr Arg Ala Ser
    130                 135                 140
Phe Pro Ile Ile Thr Val Thr Ala Ala His Ser Gly Thr Tyr Arg Cys
145                 150                 155                 160
Tyr Ser Phe Ser Ser Arg Asp Pro Tyr Leu Trp Ser Ala Pro Ser Asp
                165                 170                 175
Pro Leu Glu Leu Val Val Thr Gly Thr Ser Val Thr Pro Ser Arg Leu
            180                 185                 190
Pro Thr Glu Pro Pro Ser Ser Val Ala Glu Phe Ser Glu Ala Thr Ala
        195                 200                 205
Glu Leu Thr Val Ser Phe Thr Asn Lys Val Phe Thr Thr Glu Thr Ser
    210                 215                 220
Arg Ser Ile Thr Thr Ser Pro Lys Glu Ser Asp Ser Pro Ala Gly Pro
225                 230                 235                 240
Ala Arg Gln Tyr Tyr Thr Lys Gly Asn Gly Ser Arg Ser Asn Glu Pro
                245                 250                 255
Lys Ser Cys Asp Lys Thr His Thr Cys Pro Pro Cys Pro Ala Pro Glu
            260                 265                 270
Leu Leu Gly Gly Pro Ser Val Phe Leu Phe Pro Pro Lys Pro Lys Asp
        275                 280                 285
Thr Leu Met Ile Ser Arg Thr Pro Glu Val Thr Cys Val Val Val Asp
    290                 295                 300
Val Ser His Glu Asp Pro Glu Val Lys Phe Asn Trp Tyr Val Asp Gly
305                 310                 315                 320
Val Glu Val His Asn Ala Lys Thr Lys Pro Arg Glu Glu Gln Tyr Asn
                325                 330                 335
Ser Thr Tyr Arg Val Val Ser Val Leu Thr Val Leu His Gln Asp Trp
            340                 345                 350
Leu Asn Gly Lys Glu Tyr Lys Cys Lys Val Ser Asn Lys Ala Leu Pro
        355                 360                 365
Ala Pro Ile Glu Lys Thr Ile Ser Lys Ala Lys Gly Gln Pro Arg Glu
    370                 375                 380
```

```
Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 149
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 149

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Lys Trp Tyr Arg Ala Ser
        130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255
```

-continued

```
Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 150
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 150

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125
```

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Ser Pro Tyr Leu Trp Ser Ala Pro Ser Asp
            165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
            195                 200                 205

Glu Leu Thr Val Ser Phe Thr Asn Lys Val Phe Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
            370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Pro Phe Phe Leu Tyr Ser Lys
            435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
            485

<210> SEQ ID NO 151
<211> LENGTH: 486
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 151

```
Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
        50                  55                  60

Arg Tyr Arg Cys Ser Tyr Gln Asn Gly Ser Leu Trp Ser Leu Pro Ser
65                      70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Val Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430
```

-continued

```
Thr Pro Pro Val Leu Asp Ser Asp Gly Pro Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
            485

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 152
ggatccaaaa caacagcccc atcggtctat                                     30

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 153
tggacaagaa aattgagccc agagtgccca                                     30

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 154
tgggcactct gggctcaatt ttcttgtcca                                     30

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 155
gtcccccatg cgcagctcca gacctcttgg                                     30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 156
ccaagaggtc tggagctgcg catgggggac                                     30

<210> SEQ ID NO 157
```

```
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 157
tctcaaaacc cagagggcca gtaagagctc                                      30

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 158
gagctcttac tggccctctg gttttgaga                                       30

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 159
agatcttcat ttacccagag accgggagat                                      30

<210> SEQ ID NO 160
<211> LENGTH: 25
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 160
gggatccatt ccccttggca tagtg                                           25

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 161
gtgtactgca agtgatccaa acacagagtg                                      30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 162
agctaattgc tacaggtgtg tatgctaaac                                      30

<210> SEQ ID NO 163
<211> LENGTH: 30
<212> TYPE: DNA
```

```
<213> ORGANISM: Artificial Sequence
<220> FEATURE:
<223> OTHER INFORMATION: Description of Artificial Sequence:
      Synthetic primer

<400> SEQUENCE: 163
gagtggcaga gagtccagta accacaagca                                          30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 164
tgcttgtggt tactggactc tctgccactc                                          30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 165
gtctcctgga ggattctgtc acaggaaatg                                          30

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 166
catttcctgt gacagaatcc tccaggagac                                          30

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 167
tattcatagg cttttcagtt gtagatattt                                          30

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 168
aaatatctac aactgaaaag cctatgaata                                          30

<210> SEQ ID NO 169
<211> LENGTH: 30
<212> TYPE: DNA
<213> ORGANISM: Artificial Sequence
<220> FEATURE:
```

<223> OTHER INFORMATION: Description of Artificial Sequence:
      Synthetic primer

<400> SEQUENCE: 169
gctgatgagc aaaaccaaat ggagggctca                                    30

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 170
tgagccctcc atttggtttt gctcatcagc                                    30

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 171
tctgtattgg gctgtgtgta ctgcaagtga                                    30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 172
cctcacccac tttcttctgt attgggctgt                                    30

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 173
gggctagcca tgtctccagc ctcacccact                                    30

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 174
gggctagcca tgtctccatc cccgaccacc                                    30

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 175
gccccagaca cagcccgaga cagaagaggg					30

<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 176
gcttaggcag cggtcctctc tgcgctggca					30

<210> SEQ ID NO 177
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 177
tgccagcgca gagaggaccg ctgcctaagc					30

<210> SEQ ID NO 178
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 178
gctgggggtc acagaggttc ctgtgaccat					30

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 179
atggtcacag gaacctctgt gacccccagc					30

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 180
ccctcttctg tcttgggctg tgtctggggc					30

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 181

```
tcgttgccac gggagttttt gccaaaccct                                         30

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 182
gtttggcaaa aactcccgtg gcaacgagct                                         30

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 183
ccaggagttc aggtgctggg cacggtgggc                                         30

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 184
ttcattctca agcctcagac                                                    20

<210> SEQ ID NO 185
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 185
ccaggagttc aggtgctggg cacggtgggc                                         30

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 186
gggtttggca aaacacctg tagcaattag                                          30

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 187
ctaattgcta caggtgtttt tgccaaaccc                                         30
```

```
<210> SEQ ID NO 188
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 188
gggtttagca tacactcccg tggcaacgag                                           30

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 189
ctcgttgcca cgggagtgta tgctaaaccc                                           30

<210> SEQ ID NO 190
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 190
gctgggggtc acagagagtc cagtaaccac                                           30

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 191
gtggttactg gactctctgt gaccccagc                                            30

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 192
cggagggtca ctgactgccc caggggcacc                                           30

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 193 ggtgccctg gggcagtcag tgaccctccg                                            30
```

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 194
ggtacaggtc cacgtccgga ggtccctggc                                    30

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 195
gccagggacc tccggacgtg gacctgtacc                                    30

<210> SEQ ID NO 196
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 196
cctcgtactt ctcgggtttc agcttctcca                                    30

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 197
gaaacccgag aagtacgagg atcaggcagt                                    30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 198
gttacttctc tccatggtcg ggatgaagag                                    30

<210> SEQ ID NO 199
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 199
accatggaga gaagtaacgc tggacgctac                                    30

<210> SEQ ID NO 200
<211> LENGTH: 30

```
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 200
gggcagggac cagtggcttc cgttctggta                              30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 201
accagaacgg aagccactgg tccctgccca                              30

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 202
agcgagggtt tggcataaac tcccgtggca                              30

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 203
tgccacggga gtttatgcca aaccctcgct                              30

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 204
cggcaccgcc gagctgggat gggctgagag                              30

<210> SEQ ID NO 205
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 205
tcggcggtgc cgcaaggaag ggacgtaacc                              30

<210> SEQ ID NO 206
<211> LENGTH: 30
<212> TYPE: DNA
<213> ORGANISM: Artificial Sequence
```

```
<220> FEATURE:
<223> OTHER INFORMATION: Description of Artificial Sequence:
      Synthetic primer

<400> SEQUENCE: 206
ttcgtcaaag ctatacggag actgacactg                                        30

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 207
tctccgtata gctttgacga atttgctctg                                        30

<210> SEQ ID NO 208
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 208
tcttgtaggg cccagtgtcc ccttccttgt                                        30

<210> SEQ ID NO 209
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 209
acaaggaagg ggacactggg ccctacaaga                                        30

<210> SEQ ID NO 210
<211> LENGTH: 29
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 210
agcccggtac catttctcgg gattcttgt                                         29

<210> SEQ ID NO 211
<211> LENGTH: 29
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 211
acaagaatcc cgagaaatgg taccgggct                                         29

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence:
```

-continued

Synthetic primer

<400> SEQUENCE: 212
gaccacaggt atggggaact gctggagaag                                      30

<210> SEQ ID NO 213
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 213
cttctccagc agttccccat acctgtggtc                                      30

<210> SEQ ID NO 214
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 214
cctgtgacca caagcaccag ggggtcgctg                                      30

<210> SEQ ID NO 215
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 215
cagcgacccc ctggtgcttg tggtcacagg                                      30

<210> SEQ ID NO 216
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 216
gggaattcca tgggttggag ctgtatcatc                                      30

<210> SEQ ID NO 217
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 217
ggggctagcg ctggagacgg tgactgaggt                                      30

<210> SEQ ID NO 218
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

```
<400> SEQUENCE: 218
gggaattcca tggagacaga cacactcctg                                          30

<210> SEQ ID NO 219
<211> LENGTH: 27
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 219
gggcgtacgt tttatttcca gcttggt                                             27

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 220
cgtacggtgg ctgcaccatc tgtc                                                24

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 221
gcacttctcc ctctaacact                                                     20

<210> SEQ ID NO 222
<211> LENGTH: 543
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 222

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140
```

-continued

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
            165                 170                 175

Pro Leu Glu Leu Val Val Thr Gly Ser Val Thr Pro Ser Arg Leu
        180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Leu Ser Ser
            245                 250                 255

Gly Val His Thr Phe Pro Ala Leu Leu Gln Ser Gly Leu Tyr Thr Leu
        260                 265                 270

Ser Ser Ser Val Thr Val Thr Ser Asn Thr Trp Pro Ser Gln Thr Ile
        275                 280                 285

Thr Cys Asn Val Ala His Pro Ala Ser Ser Thr Lys Val Asp Lys Lys
290                 295                 300

Ile Glu Pro Arg Val Pro Ile Thr Gln Asn Pro Cys Pro Pro Leu Lys
305                 310                 315                 320

Glu Cys Pro Pro Cys Ala Ala Pro Asp Leu Leu Gly Gly Pro Ser Val
            325                 330                 335

Phe Ile Phe Pro Pro Lys Ile Lys Asp Val Leu Met Ile Ser Leu Ser
        340                 345                 350

Pro Met Val Thr Cys Val Val Asp Val Ser Glu Asp Pro Asp
        355                 360                 365

Val Gln Ile Ser Trp Phe Val Asn Asn Val Glu Val His Thr Ala Gln
370                 375                 380

Thr Gln Thr His Arg Glu Asp Tyr Asn Ser Thr Leu Arg Val Val Ser
385                 390                 395                 400

Ala Leu Pro Ile Gln His Gln Asp Trp Met Ser Gly Lys Glu Phe Lys
            405                 410                 415

Cys Lys Val Asn Asn Arg Ala Leu Pro Ser Pro Ile Glu Lys Thr Ile
        420                 425                 430

Ser Lys Pro Arg Gly Pro Val Arg Ala Pro Gln Val Tyr Val Leu Pro
        435                 440                 445

Pro Pro Ala Glu Glu Met Thr Lys Lys Glu Phe Ser Leu Thr Cys Met
450                 455                 460

Ile Thr Gly Phe Leu Pro Ala Glu Ile Ala Val Asp Trp Thr Ser Asn
465                 470                 475                 480

Gly Arg Thr Glu Gln Asn Tyr Lys Asn Thr Ala Thr Val Leu Asp Ser
            485                 490                 495

Asp Gly Ser Tyr Phe Met Tyr Ser Lys Leu Arg Val Gln Lys Ser Thr
        500                 505                 510

Trp Glu Arg Gly Ser Leu Phe Ala Cys Ser Val Val His Glu Gly Leu
        515                 520                 525

His Asn His Leu Thr Thr Lys Thr Ile Ser Arg Ser Leu Gly Lys
530                 535                 540

<210> SEQ ID NO 223
<211> LENGTH: 486
<212> TYPE: PRT

<213> ORGANISM: Artificial Sequence
<220> FEATURE:
<223> OTHER INFORMATION: Description of Artificial Sequence: Synthetic GPVI variant sequence

<400> SEQUENCE: 223

Gln Arg Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg His Leu Ala Gly
    50                  55                  60

Arg Tyr Arg Cys Ser Tyr Gln Asn Gly Ser Leu Trp Ser Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Gly Asp Pro Tyr Leu Trp Ser Ala Pro Ser Asp
                165                 170                 175

Pro Leu Glu Leu Met Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Ser Arg Ser Asn Glu Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
    420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465                 470

Ser Leu Ser Pro Gly Lys
                475                 480

Ser Leu Ser Pro Gly Lys
            485

<210> SEQ ID NO 224
<211> LENGTH: 351
<212> TYPE: DNA
<213> ORGANISM: Mus musculus

<400> SEQUENCE: 224
caggtccaac tgcagcagcc tggggctgag ctggtaaagc ctggggcttc agtgaagttg    60
tcctgcaagg cttctggctg cactttcacc agctactgga tgcactgggt gaagcagagg   120
cctggacagg gccttgagtg gattggaatg attcatccta atagtgataa tactaactac   180
aatgagaagt tcaagagcaa ggccacactg actgtagaca atcctccag cacagcctac   240 atgcatctca gcagcctgac atctgaggac tctgcggtct attactgtgc aacccactac   300
tatgattacg tcgactactg gggccaaggc accactctca cagtctcctc g            351

<210> SEQ ID NO 225
<211> LENGTH: 117
<212> TYPE: PRT
<213> ORGANISM: Mus musculus

<400> SEQUENCE: 225

Gln Val Gln Leu Gln Gln Pro Gly Ala Glu Leu Val Lys Pro Gly Ala
1               5                   10                  15

Ser Val Lys Leu Ser Cys Lys Ala Ser Gly Cys Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Asp Asn Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Thr His Tyr Tyr Asp Tyr Val Asp Tyr Trp Gly Gln Gly Thr Thr
            100                 105                 110

Leu Thr Val Ser Ser
        115

<210> SEQ ID NO 226
<211> LENGTH: 336
<212> TYPE: DNA
<213> ORGANISM: Mus musculus

<400> SEQUENCE: 226

```
aatattgtga tgacccagac tcccaaattc ctgcttgtat cagcaggaga cagggttacc     60
ataacctgca aggccagtca gagtgtgagt aatgatgtag cttggtacca acagaagcca    120
gggcagtctc ctaaactgct gatatactat gcatccaatc gctacactgg agtccctgat    180
cgcttcactg gcagtggata tgggacggat ttcactttca ccatcagcac tgtgcaggct    240
gaagacctgg cagtttattt ctgtcagcag gattatagct ctccgtggac gttcggtgga    300
ggcaccaagc tggaaatcaa acgggctgat gctgca                              336
```

<210> SEQ ID NO 227
<211> LENGTH: 112
<212> TYPE: PRT
<213> ORGANISM: Mus musculus

<400> SEQUENCE: 227

```
Asn Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys Arg Ala Asp Ala Ala
            100                 105                 110
```

<210> SEQ ID NO 228
<211> LENGTH: 351
<212> TYPE: DNA
<213> ORGANISM: Mus musculus

<400> SEQUENCE: 228

```
caggtccaac tgcagcagcc tggggctgag ctggtaaagc ctggggcttc agtgaagttg     60
tcctgcaagg cttctggcta cactttcatc agctactgga tgcactgggt gaagcagagg    120
cctggacaag gccttgagtg gattggaatg attcatccta atagtggtag tactcactac    180
aatgagaagt tcaagagcaa ggccacactg actgtagaca atcctccag cacagcctac    240 atgcaactca gcagcctgac atctgaggac tctgcggtct attactgtgc aagaggggga    300
gtaaccccgg ttgcttactg gggccaaggg actctggtca ctgtctctgc a             351
```

<210> SEQ ID NO 229
<211> LENGTH: 117
<212> TYPE: PRT
<213> ORGANISM: Mus musculus

<400> SEQUENCE: 229

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr His Tyr Asn Glu Lys Phe
    50                  55                  60
```

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Val Thr Pro Val Ala Tyr Trp Gly Gln Gly Thr Leu
            100                 105                 110

Val Thr Val Ser Ala
        115

<210> SEQ ID NO 230
<211> LENGTH: 336
<212> TYPE: DNA
<213> ORGANISM: Mus musculus

<400> SEQUENCE: 230
agtattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctccgtggac gttcggtgga     300
ggcaccaagc tggaaatcaa acgggctgat gctgca                               336

<210> SEQ ID NO 231
<211> LENGTH: 112
<212> TYPE: PRT
<213> ORGANISM: Mus musculus

<400> SEQUENCE: 231

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys Arg Ala Asp Ala Ala
            100                 105                 110

<210> SEQ ID NO 232
<211> LENGTH: 354
<212> TYPE: DNA
<213> ORGANISM: Mus musculus

<400> SEQUENCE: 232
caggtccaac tgcagcaacc tggggctgag ctggtaaagc ctggggcttc agtgaagttg      60
tcctgcaagg cttctggcta cactttcacc agctactgga tgcactgggt gaagcagagg     120
cctggacaag gccttgagtg gattggaatg attcatccta atagtggtag tactaactac     180
aatgagaagt tcaagagcaa ggccacactg actgtagaca atcctccag cacagcctac      240 atgcaactca gcagcctgac atctgaggac tctgcggtct attactgtgc aagaggggga     300 gtaacccccgg ttgcttactg gggccaaggg actctggtca ctgtctctgc agcc    354

<210> SEQ ID NO 233
<211> LENGTH: 118
<212> TYPE: PRT
<213> ORGANISM: Mus musculus

<400> SEQUENCE: 233

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Met Ile His Pro Asn Ser Gly Ser Thr Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Val Thr Pro Val Ala Tyr Trp Gly Gln Gly Thr Leu
                100                 105                 110

Val Thr Val Ser Ala Ala
            115

<210> SEQ ID NO 234
<211> LENGTH: 336
<212> TYPE: DNA
<213> ORGANISM: Mus musculus

<400> SEQUENCE: 234
agtattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct gatatactat gcatccaatc gctacactgg agtcccttat   180
cgcttcactg gcagtggata tgggacggat ttcactttca ccatcagcac tgtgcaggct   240
gaagacctgg cagtttattt ctgtcagcag gattatagct ctccgtggac gttcggtgga   300
ggcaccaagc tggaaatcaa acgggctgat gctgca                             336

<210> SEQ ID NO 235
<211> LENGTH: 112
<212> TYPE: PRT
<213> ORGANISM: Mus musculus

<400> SEQUENCE: 235

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Tyr Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

```
Thr Phe Gly Gly Gly Thr Lys Leu Glu Ile Lys Arg Ala Asp Ala Ala
            100                 105                 110
```

```
<210> SEQ ID NO 236
<211> LENGTH: 363
<212> TYPE: DNA
<213> ORGANISM: Mus musculus

<400> SEQUENCE: 236
caggtccaac tgcagcagcc tggggctgag ctggtaaagc ctggggcttc agtgaagttg      60
tcctgcaagg cttctggcta cactttcacc agctactgga tgcactgggt gaagcagagg     120
cctggacaag gccttgagtg gattggaatg attcatccta atagtggtag tactaactac     180
aatgagaagt tcaagagcaa ggccacactg actgtagaca atcctccag cacagcctac      240 atgcaactca gcagcctgac atctgaggac tctgcggtct attactgtgc aagccccgtt     300
actgcggtag tagagtacta ctttgactac tggggccaag caccactct cacagtctcc      360 tca                                                                   363

<210> SEQ ID NO 237
<211> LENGTH: 121
<212> TYPE: PRT
<213> ORGANISM: Mus musculus

<400> SEQUENCE: 237

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Val Thr Ala Val Val Glu Tyr Tyr Phe Asp Tyr Trp Gly
            100                 105                 110

Gln Gly Thr Thr Leu Thr Val Ser Ser
        115                 120

<210> SEQ ID NO 238
<211> LENGTH: 333
<212> TYPE: DNA
<213> ORGANISM: Mus musculus

<400> SEQUENCE: 238
agtattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctctcacgtt cggctcgggg     300
acaaaattgg aaataaaacg ggctgatgct gca                                  333

<210> SEQ ID NO 239
<211> LENGTH: 111
```

<212> TYPE: PRT
<213> ORGANISM: Mus musculus

<400> SEQUENCE: 239

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Leu Thr
                85                  90                  95

Phe Gly Ser Gly Thr Lys Leu Glu Ile Lys Arg Ala Asp Ala Ala
            100                 105                 110

<210> SEQ ID NO 240
<211> LENGTH: 354
<212> TYPE: DNA
<213> ORGANISM: Mus musculus

<400> SEQUENCE: 240
gaggtgcagc tggtggagtc tgggggagac ttagtgaagc tggagggtc cctgaaactc      60 tcctgtgcag cctctggatt cactttcagt agctatggca tgtcttgggt tcgccagact    120
ccagacaaga ggctggagtg ggtcgcaacc attagtaatg gtggtactta cacctactat    180
ccagacagtg tgaaggggcg attcaccatc tccagagaca atgccaagaa caccctgtac    240
ctgcaaatga gcagtctgaa gtctgacgac acagccatgt attactgtgg acggctacgg    300
gattactatg ctatggacta ctggggtcaa ggaacctcag tcaccgtctc ctca           354

<210> SEQ ID NO 241
<211> LENGTH: 118
<212> TYPE: PRT
<213> ORGANISM: Mus musculus

<400> SEQUENCE: 241

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Asn Gly Gly Thr Tyr Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Asp Asp Thr Ala Met Tyr Tyr Cys
                85                  90                  95

Gly Arg Leu Arg Asp Tyr Tyr Ala Met Asp Tyr Trp Gly Gln Gly Thr
            100                 105                 110

Ser Val Thr Val Ser Ser
        115

<210> SEQ ID NO 242

<211> LENGTH: 348
<212> TYPE: DNA
<213> ORGANISM: Mus musculus

<400> SEQUENCE: 242

```
gacattgtgc tgacccaatc tccagcttct ttggctgtgt ctctagggca gagggccacc    60
atatcctgca gagccagtga aagtgttgat agttatggca atagttttat gcactggtac   120
cagcagaaac caggacagcc acccaaactc ctcatctatc gtgcatccaa cctagaatct   180
gggatccctg ccaggttcag tggcagtggg tctaggacag acttcaccct caccattaat   240
cctgtgagg ctgatgatgt tgcaacctat tactgtcagc aaagtaatga ggatccgtgg   300
acgttcggtg gaggcaccaa gctggaaatc aaacgggctg atgctgca                348
```

<210> SEQ ID NO 243
<211> LENGTH: 116
<212> TYPE: PRT
<213> ORGANISM: Mus musculus

<400> SEQUENCE: 243

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Ser Tyr
            20                  25                  30
Gly Asn Ser Phe Met His Trp Tyr Gln Gln Lys Pro Gly Gln Pro Pro
        35                  40                  45
Lys Leu Leu Ile Tyr Arg Ala Ser Asn Leu Glu Ser Gly Ile Pro Ala
    50                  55                  60
Arg Phe Ser Gly Ser Gly Ser Arg Thr Asp Phe Thr Leu Thr Ile Asn
65                  70                  75                  80
Pro Val Glu Ala Asp Asp Val Ala Thr Tyr Tyr Cys Gln Gln Ser Asn
                85                  90                  95
Glu Asp Pro Trp Thr Phe Gly Gly Gly Thr Lys Leu Glu Ile Lys Arg
            100                 105                 110
Ala Asp Ala Ala
        115
```

<210> SEQ ID NO 244
<211> LENGTH: 348
<212> TYPE: DNA
<213> ORGANISM: Mus musculus

<400> SEQUENCE: 244

```
gaagtgcagc tggtggagtc tgggggaggc ttagtgaagc ctggagggtc cctgaaactc    60
tcctgtgcag cctctggatt cactttcagt agctatggca tgtcttgggt tcgccagact   120
ccagacaaga ggctggagtg ggtcgcaacc attagtagtg gtggtagtta cacctactat   180
tcagacagtg tgaaggggcg attcaccatc tccagagaca atgccaagaa caacctgtac   240
ctgcaattga gcagtctgaa gtctcaggac acagccatat attactgtgc aagagatagt   300
ggttactttg actactgggg ccaaggcacc actctcacag tctcctca                348
```

<210> SEQ ID NO 245
<211> LENGTH: 116
<212> TYPE: PRT
<213> ORGANISM: Mus musculus

<400> SEQUENCE: 245

```
Glu Val Gln Leu Val Glu Ser Gly Gly Gly Leu Val Lys Pro Gly Gly
1               5                   10                  15
```

```
Ser Leu Lys Leu Ser Cys Ala Ala Ser Gly Phe Thr Phe Ser Ser Tyr
             20                  25                  30

Gly Met Ser Trp Val Arg Gln Thr Pro Asp Lys Arg Leu Glu Trp Val
         35                  40                  45

Ala Thr Ile Ser Ser Gly Gly Ser Tyr Thr Tyr Tyr Ser Asp Ser Val
 50                  55                  60

Lys Gly Arg Phe Thr Ile Ser Arg Asp Asn Ala Lys Asn Asn Leu Tyr
65                  70                  75                  80

Leu Gln Leu Ser Ser Leu Lys Ser Gln Asp Thr Ala Ile Tyr Tyr Cys
                 85                  90                  95

Ala Arg Asp Ser Gly Tyr Phe Asp Tyr Trp Gly Gln Gly Thr Thr Leu
            100                 105                 110

Thr Val Ser Ser
        115

<210> SEQ ID NO 246
<211> LENGTH: 348
<212> TYPE: DNA
<213> ORGANISM: Mus musculus

<400> SEQUENCE: 246
aacattgtgc tgacccaatc tccagcttct ttggctgtgt ctctagggca gagggccacc      60
atatcctgca gagccagtga aagtgttgat agttatggca atagttttat gcactggtac     120
cagcagaaac caggacagcc acccaaactc ctcatctatc ttgcatccaa cctagaatct     180
ggggtccctg ccaggttcag tggcagtggg tctaggacag acttcaccct caccattgat     240
cctgtggagg ctgatgatgc tgcaacctat tactgtcagc aaaataatga ggatcctcgg     300
acgttcggtg gaggcaccaa gctggaaatc aaacgggctg atgctgca                  348

<210> SEQ ID NO 247
<211> LENGTH: 116
<212> TYPE: PRT
<213> ORGANISM: Mus musculus

<400> SEQUENCE: 247

Asn Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                 85                  90                  95

Glu Asp Pro Arg Thr Phe Gly Gly Gly Thr Lys Leu Glu Ile Lys Arg
            100                 105                 110

Ala Asp Ala Ala
        115

<210> SEQ ID NO 248
<211> LENGTH: 354
<212> TYPE: DNA
<213> ORGANISM: Mus musculus
```

<400> SEQUENCE: 248

```
caggtccaac tgcagcagcc tggggctgag ctggtaaagc ctggggcttc agtgaagttg      60
tcctgcaagg cttctggcta cactttcacc agctactgga tgcactggtt gaagcagagg     120
cctggacaag gccttgagtg gattggaatg attcatccta atagtgatat tactaactac     180
aatgagaagt tcaagaacaa ggccacactg actgtagcca aatcctccag cacagcctac     240
atgcaactca gcagcctgac atctgaggac tctgcggtct attactgtgc aagattgggg     300
gactactatg ctatggacta ctggggtcaa ggaaccctcag tcaccgtctc ctca          354
```

<210> SEQ ID NO 249
<211> LENGTH: 118
<212> TYPE: PRT
<213> ORGANISM: Mus musculus

<400> SEQUENCE: 249

```
Gln Val Gln Leu Gln Gln Pro Gly Ala Glu Leu Val Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Leu Lys Gln Arg Pro Gly Gln Gly Leu Glu Trp Ile
        35                  40                  45
Gly Met Ile His Pro Asn Ser Asp Ile Thr Asn Tyr Asn Glu Lys Phe
    50                  55                  60
Lys Asn Lys Ala Thr Leu Thr Val Ala Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Leu Gly Asp Tyr Tyr Ala Met Asp Tyr Trp Gly Gln Gly Thr
            100                 105                 110
Ser Val Thr Val Ser Ser
        115
```

<210> SEQ ID NO 250
<211> LENGTH: 336
<212> TYPE: DNA
<213> ORGANISM: Mus musculus

<400> SEQUENCE: 250

```
agtattgtga tgacccagac tcccaaattc ctgcttgtat cagcaggaga cagggttacc      60
ataacctgca aggccagtca gagtgtgagt aatgatgtaa cttggtacca acagaagcca     120
gggcagtctc ctaaactgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctcctccgac gttcggtgga     300
ggcaccaagc tggaaatcaa acgggctgat gctgca                              336
```

<210> SEQ ID NO 251
<211> LENGTH: 112
<212> TYPE: PRT
<213> ORGANISM: Mus musculus

<400> SEQUENCE: 251

```
Ser Ile Val Met Thr Gln Thr Pro Lys Phe Leu Leu Val Ser Ala Gly
1               5                   10                  15
Asp Arg Val Thr Ile Thr Cys Lys Ala Ser Gln Ser Val Ser Asn Asp
            20                  25                  30
```

Val Thr Trp Tyr Gln Gln Lys Pro Gly Gln Ser Pro Lys Leu Leu Ile
    35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Pro
                85                  90                  95

Thr Phe Gly Gly Gly Thr Lys Leu Glu Ile Lys Arg Ala Asp Ala Ala
            100                 105                 110

<210> SEQ ID NO 252
<211> LENGTH: 354
<212> TYPE: DNA
<213> ORGANISM: Mus musculus

<400> SEQUENCE: 252
caggtccaac tgcagcagcc tggggctgag ctggtaaagc ctggggcttc agtgaagttg     60
tcctgcaagg cttctggcta cactttcacc agctactgga tgcactggtt gaagcagagg    120
cctggacaag gccttgagtg gattggaatg attcatccta atagtgatat tactaactac    180
aatgagaagt tcaagaacaa ggccacactg actgtagaca atcctccag cacagcctac     240 atgcaactca gcagcctgac atctgaggac tctgcggtct attactgtgc aagatcgggg    300
gattactatg ctatggacta ctggggtcaa ggaacctcag tcaccgtctc ctca          354

<210> SEQ ID NO 253
<211> LENGTH: 118
<212> TYPE: PRT
<213> ORGANISM: Mus musculus

<400> SEQUENCE: 253

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Leu Lys Gln Arg Pro Gly Gln Gly Leu Glu Trp Ile
        35                  40                  45

Gly Met Ile His Pro Asn Ser Asp Ile Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Gly Asp Tyr Tyr Ala Met Asp Tyr Trp Gly Gln Gly Thr
            100                 105                 110

Ser Val Thr Val Ser Ser
        115

<210> SEQ ID NO 254
<211> LENGTH: 336
<212> TYPE: DNA
<213> ORGANISM: Mus musculus

<400> SEQUENCE: 254
agtattgtga tgacccagac tcccaaattc ctgcttgtat cagcaggaga cagggttacc     60
ataacctgca aggccagtca gagtgtgagt aatgatgtag cttggtacca acagaagcca    120
gggcagtctc ctaaactgct gatatactat gcatccaatc gctacactgg agtccctgat    180

```
cgcttcactg gcagtggata tgggacggat ttcactttca ccatcagcac tgtgcaggct     240
gaagacctgg cagtttattt ctgtcagcag gattatagct ctcctccgac gttcggtgga     300
ggcaccaagc tggaaatcaa acgggctgat gctgca                               336
```

```
<210> SEQ ID NO 255
<211> LENGTH: 112
<212> TYPE: PRT
<213> ORGANISM: Mus musculus

<400> SEQUENCE: 255

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Pro
                85                  90                  95

Thr Phe Gly Gly Gly Thr Lys Leu Glu Ile Lys Arg Ala Asp Ala Ala
            100                 105                 110
```

```
<210> SEQ ID NO 256
<211> LENGTH: 360
<212> TYPE: DNA
<213> ORGANISM: Mus musculus

<400> SEQUENCE: 256
caggtccagc tgcagcagtc tggggctgag ctggtgaggc ctggggtctc agtgaagatt     60
tcctgcaagg gttctggcta cacattcact gattatgcta tgcactgggt gaagcagagt    120
catgcaaaga gtctagagtg gattggagtt attagtactt actacggtga ctactagctac   180 aaccagaagt tcaagggcaa ggccacaatg actgtagaca atcctccag cacagcctat     240 atggaacttg ccagactgac atctgaggat tctgccatct attactgtgc aagagcagag    300
gattacgacc cctggtttgc ttactggggc caagggactc tggtcaccgt ctctgcagcc   360
```

```
<210> SEQ ID NO 257
<211> LENGTH: 120
<212> TYPE: PRT
<213> ORGANISM: Mus musculus

<400> SEQUENCE: 257

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Tyr Gly Asp Thr Ser Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
```

Ala Arg Ala Glu Asp Tyr Asp Pro Trp Phe Ala Tyr Trp Gly Gln Gly
                85                  90                  95

Thr Leu Val Thr Val Ser Ala Ala
        115                 120

<210> SEQ ID NO 258
<211> LENGTH: 348
<212> TYPE: DNA
<213> ORGANISM: Mus musculus

<400> SEQUENCE: 258
gacattgtgc tgacccaatc cccagcttcc ttggctgtgt ctctagggca gagggccacc      60
atatcctgca gagccagtga aagtgttgac agttatggca atagtttat gtactggtac     120 cagcagaaac aggacagcc acccaaactc ctcatctatc gtgcatccaa cctagaatct     180
gggatccctg ccaggttcag tggcagtggg tctaggacag acttcaccct caccattaat    240
cctgtggagg ctgatgatgt tgcaacctat tactgtcagc aaagtgatga ggatccgctc    300
acgttcggtg ctgggaccaa gctggagctg aaacgggctg atgctgca                 348

<210> SEQ ID NO 259
<211> LENGTH: 116
<212> TYPE: PRT
<213> ORGANISM: Mus musculus

<400> SEQUENCE: 259

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met Tyr Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asp
                85                  90                  95

Glu Asp Pro Leu Thr Phe Gly Ala Gly Thr Lys Leu Glu Leu Lys Arg
            100                 105                 110

Ala Asp Ala Ala
        115

<210> SEQ ID NO 260
<211> LENGTH: 357
<212> TYPE: DNA
<213> ORGANISM: Mus musculus

<400> SEQUENCE: 260
caggtccaac tgcagcagcc tggggctgag cttgtgaagc ctggggcttc agtgaagctg      60
tcctgcaagg cttctggcta caccttcacc agctactgga tgcagtgggt aaaagagagg     120
cctggacagg gccttgagtg gatcggagag attgatcctt ctgatagcta tactaactac     180
aatcaaaagt tcaagggcaa ggccacattg actgtagaca tcctccag cacagcctgc      240 atgcagctca gcagcctgac atctgaggac tctgcggtct attactgtgc aagaggggca    300
attactacgg ctactcttga ctactggggc caaggcacca ctctcacagt ctcctca       357

<210> SEQ ID NO 261
<211> LENGTH: 119
<212> TYPE: PRT
<213> ORGANISM: Mus musculus

<400> SEQUENCE: 261

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Glu Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Thr Ala Cys
65                  70                  75                  80

Met Gln Leu Ser Ser Leu Thr Ser Glu Asp Ser Ala Val Tyr Tyr Cys
                85                  90                  95

Ala Arg Gly Ala Ile Thr Thr Ala Thr Leu Asp Tyr Trp Gly Gln Gly
            100                 105                 110

Thr Thr Leu Thr Val Ser Ser
        115

<210> SEQ ID NO 262
<211> LENGTH: 354
<212> TYPE: DNA
<213> ORGANISM: Mus musculus

<400> SEQUENCE: 262
gacattgtga tgacacagtc tccatcctcc ctggctatgt cagtaggaca gaaggtcact      60
atgagctgca gtccagtca gagccttta aatagtaaca atcaaaagaa ctatttggcc      120
tggtaccagc agaaaccagg acagtctcct aaacttctgg tatactttgc atccactagg    180
gaatctgggg tccctgatcg cttcataggc agtggatctg gacagattt cactcttacc     240 atcagcagtg tgcaggctga agacctggca gattacttct gtcagcaaca ttatatcact    300
ccgctcacgt tcggtgctgg gaccaagctg gaactgaaac gggctgatgc tgca          354

<210> SEQ ID NO 263
<211> LENGTH: 118
<212> TYPE: PRT
<213> ORGANISM: Mus musculus

<400> SEQUENCE: 263

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Asn Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ile Thr Pro Leu Thr Phe Gly Ala Gly Thr Lys Leu Glu Leu
            100                 105                 110

<210> SEQ ID NO 264
<211> LENGTH: 357
<212> TYPE: DNA
<213> ORGANISM: Mus musculus

<400> SEQUENCE: 264

```
caggtccagc tgcagcagtc tggggctgag ctggtgaggc ctggggtctc agtgaagatt    60
tcctgcaagg gttctggcta cacattcact gattatgcta tgcactgggt gaagcagagt   120
catgcaaaga gtctagagtg gattggagtt attagtactt actatggtga tactagctac   180
aaccagaagt tcaagggcaa ggccacaatg actgtagaca atcctccag cacagcctat    240
atggaacttg ccagactgac atctgaggat tctgccatct attactgtgc aagagcagag   300
gattacgacc cctggtttgc ttactggggc caagggactc tggtcactgt ctctgca      357
```

<210> SEQ ID NO 265
<211> LENGTH: 119
<212> TYPE: PRT
<213> ORGANISM: Mus musculus

<400> SEQUENCE: 265

```
Gln Val Gln Leu Gln Gln Ser Gly Ala Glu Leu Val Arg Pro Gly Val
  1               5                  10                  15

Ser Val Lys Ile Ser Cys Lys Gly Ser Gly Tyr Thr Phe Thr Asp Tyr
             20                  25                  30

Ala Met His Trp Val Lys Gln Ser His Ala Lys Ser Leu Glu Trp Ile
         35                  40                  45

Gly Val Ile Ser Thr Tyr Tyr Gly Asp Thr Ser Tyr Asn Gln Lys Phe
     50                  55                  60

Lys Gly Lys Ala Thr Met Thr Val Asp Lys Ser Ser Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Ala Glu Asp Tyr Asp Pro Trp Phe Ala Tyr Trp Gly Gln Gly
            100                 105                 110

Thr Leu Val Thr Val Ser Ala
        115
```

<210> SEQ ID NO 266
<211> LENGTH: 348
<212> TYPE: DNA
<213> ORGANISM: Mus musculus

<400> SEQUENCE: 266

```
gacattgtgc tgacccaatc tccagcttct ttggctgtgt ctctagggca gagggccacc    60
atatcctgca gagccagtga aagtgttgat agttatggca atagttttat gcactggtac   120
cagcagaaac aggacagcc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaacctat tactgtcagc aaagtgatga ggatccgctc   300
acgttcggtg ctgggaccaa gctggagctg aaacgggctg atgctgca                348
```

<210> SEQ ID NO 267
<211> LENGTH: 116
<212> TYPE: PRT

<213> ORGANISM: Mus musculus

<400> SEQUENCE: 267

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asp
                85                  90                  95

Glu Asp Pro Leu Thr Phe Gly Ala Gly Thr Lys Leu Glu Leu Lys Arg
            100                 105                 110

Ala Asp Ala Ala
        115
```

<210> SEQ ID NO 268
<211> LENGTH: 357
<212> TYPE: DNA
<213> ORGANISM: Mus musculus

<400> SEQUENCE: 268

```
caggtccagc tgcagcagtc tggggctgag ctggtgaggc ctggggtctc agtgaagatt      60
tcctgcaagg gttctggcta cacattcact gattatgcta tgcactgggt gaagcagagt     120
catgcaaaga gtctagagtg gattggagtt attagtactt actatggtga ctactagctac    180
aaccagaagt tcaagggcaa ggccgcaatg actgtagaca atcctccag cacagcctat      240
atggaacttg ccagactgac atctgacgat tctgccatct attactgtgc aagagcagag     300
gattacgacc cctggtttgc ttactggggc caagggactc tggtcactgt ctctgca        357
```

<210> SEQ ID NO 269
<211> LENGTH: 119
<212> TYPE: PRT
<213> ORGANISM: Mus musculus

<400> SEQUENCE: 269

```
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Tyr Gly Asp Thr Ser Tyr Asn Gln Lys Phe
    50                  55                  60

Lys Gly Lys Ala Ala Met Thr Val Asp Lys Ser Ser Thr Ala Tyr
65                  70                  75                  80

Met Glu Leu Ala Arg Leu Thr Ser Asp Asp Ser Ala Ile Tyr Tyr Cys
                85                  90                  95

Ala Arg Ala Glu Asp Tyr Asp Pro Trp Phe Ala Tyr Trp Gly Gln Gly
            100                 105                 110

Thr Leu Val Thr Val Ser Ala
        115
```

<210> SEQ ID NO 270
<211> LENGTH: 348
<212> TYPE: DNA
<213> ORGANISM: Mus musculus

<400> SEQUENCE: 270

```
gacattgtgc tgacccaatc tccagcttct ttggctgtgt ctctagggca gagggccacc    60
atatcctgca gagccagtga aagtgttgat agttatggca atagttttat gcactggtac   120
cagcagaaac caggacagcc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaacctat tactgtcagc aaagtgatga ggatccgctc   300
acgttcggtg ctgggaccaa gctggagctg aaacgggctg atgctgca                348
```

<210> SEQ ID NO 271
<211> LENGTH: 116
<212> TYPE: PRT
<213> ORGANISM: Mus musculus

<400> SEQUENCE: 271

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Ser Tyr
            20                  25                  30
Gly Asn Ser Phe Met His Trp Tyr Gln Gln Lys Pro Gly Gln Pro Pro
        35                  40                  45
Lys Leu Leu Ile Tyr Arg Ala Ser Asn Leu Glu Ser Gly Ile Pro Ala
    50                  55                  60
Arg Phe Ser Gly Ser Gly Ser Arg Thr Asp Phe Thr Leu Thr Ile Asn
65                  70                  75                  80
Pro Val Glu Ala Asp Asp Val Ala Thr Tyr Tyr Cys Gln Gln Ser Asp
                85                  90                  95
Glu Asp Pro Leu Thr Phe Gly Ala Gly Thr Lys Leu Glu Leu Lys Arg
            100                 105                 110
Ala Asp Ala Ala
        115
```

<210> SEQ ID NO 272
<211> LENGTH: 360
<212> TYPE: DNA
<213> ORGANISM: Rattus norvegicus

<400> SEQUENCE: 272

```
caggtcaacc tactgcagtc tggggctgca ctggtgaagc ctggggcctc tgtgaagttg    60
tcttgcaaag cttctggtta tacattcact gactactata cactgggt gaagcagagt    120
catggaaaga gccttgagtg gattgggtat attaatccta cagtggtta tactaactac   180
aatgaaaagt tcaagagcaa ggccacattg actgtagaca atccaccaa tacagcctat   240
atggagctta gcagattgac atctgaggac tctgcaacct attactgtac aagatgtaat   300
tcggggtacg gggattggtt tgcttactgg ggccaaggca ctctgctcac tgtctcttca   360
```

<210> SEQ ID NO 273
<211> LENGTH: 120
<212> TYPE: PRT
<213> ORGANISM: Rattus norvegicus

<400> SEQUENCE: 273

-continued

```
Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Lys Gln Ser His Gly Lys Ser Leu Glu Trp Ile
        35                  40                  45

Gly Tyr Ile Asn Pro Asn Ser Gly Tyr Thr Asn Tyr Asn Glu Lys Phe
    50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Glu Asp Ser Ala Thr Tyr Tyr Cys
                85                  90                  95

Thr Arg Cys Asn Ser Gly Tyr Gly Asp Trp Phe Ala Tyr Trp Gly Gln
            100                 105                 110

Gly Thr Leu Leu Thr Val Ser Ser
        115                 120

<210> SEQ ID NO 274
<211> LENGTH: 336
<212> TYPE: DNA
<213> ORGANISM: Rattus norvegicus

<400> SEQUENCE: 274
gacatccaga tgacccagtc tcctccagtc ctgtctgcat ctgtgggaga cagagtcact    60
ctcagctgca aagcaagtca gaatattaat aagaacttag actggtatca gcaaaagcat   120
ggagaagctc caaaactcct gatatattat acgaacaatt tgcaaacgga catcccatca   180
aggttcagtg gcagtggatc tggtacagat tacacactca ccatcagcag cctgcagcct   240
gaagatgttg ccactttta ctgctatcag tataacagtg ggcccggcac gtttggagct   300
gggaccaagc tggagctgaa acgggctgat gctgca                             336

<210> SEQ ID NO 275
<211> LENGTH: 112
<212> TYPE: PRT
<213> ORGANISM: Rattus norvegicus

<400> SEQUENCE: 275

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Ile
        35                  40                  45

Tyr Tyr Thr Asn Asn Leu Gln Thr Asp Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Phe Tyr Cys Tyr Gln Tyr Asn Ser Gly Pro Gly
                85                  90                  95

Thr Phe Gly Ala Gly Thr Lys Leu Glu Leu Lys Arg Ala Asp Ala Ala
            100                 105                 110

<210> SEQ ID NO 276
<211> LENGTH: 372
<212> TYPE: DNA
<213> ORGANISM: Rattus norvegicus

<400> SEQUENCE: 276
```

```
caggttactc tgaaagagtc tggtcctggg atgttacagc cctccaagac cctaagcctg      60
acttgctctt tttctgggtt ttcactgagc acttctggta tggttgtgag ctggattcgg     120
cagccttcag ggaagagtct cgagtggctg cagccattg attgggatgg tgataagtac      180 tacaaccat ctctgaaaag caggctcaca gtctccaagg acacctccaa cacccaagta      240
ttcctcaaga tcagtagtgt ggacattgca gatactgcca catactactg tgctcggaca     300
ccatactatg ggtataagga ggcctactac tttgattact ggggccaagg agtcaaggtc     360
acagtctcct ca                                                         372
```

<210> SEQ ID NO 277
<211> LENGTH: 124
<212> TYPE: PRT
<213> ORGANISM: Rattus norvegicus

<400> SEQUENCE: 277

```
Gln Val Thr Leu Lys Glu Ser Gly Pro Gly Met Leu Gln Pro Ser Lys
1               5                   10                  15

Thr Leu Ser Leu Thr Cys Ser Phe Ser Gly Phe Ser Leu Ser Thr Ser
            20                  25                  30

Gly Met Val Val Ser Trp Ile Arg Gln Pro Ser Gly Lys Ser Leu Glu
        35                  40                  45

Trp Leu Ala Ala Ile Asp Trp Asp Gly Asp Lys Tyr Tyr Asn Pro Ser
    50                  55                  60

Leu Lys Ser Arg Leu Thr Val Ser Lys Asp Thr Ser Asn Thr Gln Val
65                  70                  75                  80

Phe Leu Lys Ile Ser Ser Val Asp Ile Ala Asp Thr Ala Thr Tyr Tyr
                85                  90                  95

Cys Ala Arg Thr Pro Tyr Tyr Gly Tyr Lys Glu Ala Tyr Tyr Phe Asp
            100                 105                 110

Tyr Trp Gly Gln Gly Val Lys Val Thr Val Ser Ser
        115                 120
```

<210> SEQ ID NO 278
<211> LENGTH: 336
<212> TYPE: DNA
<213> ORGANISM: Rattus norvegicus

<400> SEQUENCE: 278

```
gacatccaga tgacacagtc tcctgcctcc ctgtctgctt ctctggaaga aattgtcacc      60
atcacctgca aggcaagccg ggccattgat gattacttat catggtatca gcagaaacca    120
gggaaatctc ctcagctcct gatctatgat gcaaccagct ggcagatgg ggtcccatca     180 cggttcagcg gcagtagatc tggcacacag tattctctta agatcagcag accacaggtt    240
gatgattctg gaatctatta ctgtctacag agttacagta ctccgtggac gttcggtgga    300
ggcaccaagc tggacttgaa acgggctgat gctgca                              336
```

<210> SEQ ID NO 279
<211> LENGTH: 112
<212> TYPE: PRT
<213> ORGANISM: Rattus norvegicus

<400> SEQUENCE: 279

```
Asp Ile Gln Met Thr Gln Ser Pro Ala Ser Leu Ser Ala Ser Leu Glu
1               5                   10                  15

Glu Ile Val Thr Ile Thr Cys Lys Ala Ser Arg Ala Ile Asp Asp Tyr
            20                  25                  30
```

```
Leu Ser Trp Tyr Gln Gln Lys Pro Gly Lys Ser Pro Gln Leu Leu Ile
            35                  40                  45

Tyr Asp Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Pro Gln Val
 65                  70                  75                  80

Asp Asp Ser Gly Ile Tyr Tyr Cys Leu Gln Ser Tyr Ser Thr Pro Trp
                 85                  90                  95

Thr Phe Gly Gly Gly Thr Lys Leu Asp Leu Lys Arg Ala Asp Ala Ala
            100                 105                 110
```

<210> SEQ ID NO 280
<211> LENGTH: 363
<212> TYPE: DNA
<213> ORGANISM: Artificial Sequence
<220> FEATURE:
<223> OTHER INFORMATION: Description of Artificial Sequence: Synthetic
      GPVI variant sequence

<400> SEQUENCE: 280

```
caggtccaac tgcagcagag cggtccagaa cttgtgagac tggccagac  cctgagcctg    60 acctgcaccg gtccggatc  gaccttcagc gattatgcta tacactgggt gagacagcca   120
cctggacgag gtctcgagtg gattggagtt attagtattt actatgatga tacaaactac   180
aaccagaagt ttaagggcag agtgacaatg ctggtcgaca ccagcaagaa ccagttcagc   240
ctgagactca gcagcgtgac agccgccgac accgcggtct attattgtgc gcgccgaagg   300
gacagctcgg gtccctatgc tatggactac tggggtcaag gcagcctcgt caccgtgtcc   360
agc                                                                 363
```

<210> SEQ ID NO 281
<211> LENGTH: 121
<212> TYPE: PRT
<213> ORGANISM: Artificial Sequence
<220> FEATURE:
<223> OTHER INFORMATION: Description of Artificial Sequence: Synthetic
      humanized antibody sequence

<400> SEQUENCE: 281

```
Gln Val Gln Leu Gln Gln Ser Gly Pro Glu Leu Val Arg Pro Gly Gln
 1               5                  10                  15

Thr Leu Ser Leu Thr Cys Thr Gly Ser Gly Ser Thr Phe Ser Asp Tyr
            20                  25                  30

Ala Ile His Trp Val Arg Gln Pro Pro Gly Arg Gly Leu Glu Trp Ile
        35                  40                  45

Gly Val Ile Ser Ile Tyr Tyr Asp Asp Thr Asn Tyr Asn Gln Lys Phe
    50                  55                  60

Lys Gly Arg Val Thr Met Leu Val Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Arg Arg Asp Ser Ser Gly Pro Tyr Ala Met Asp Tyr Trp Gly
            100                 105                 110

Gln Gly Ser Leu Val Thr Val Ser Ser
        115                 120
```

<210> SEQ ID NO 282
<211> LENGTH: 363
<212> TYPE: DNA

```
<213> ORGANISM: Artificial Sequence
<220> FEATURE:
<223> OTHER INFORMATION: Description of Artificial Sequence: Synthetic
      humanized antibody sequence

<400> SEQUENCE: 282
caggtccaac tggtccagag cggtgctgaa gtcaagaaac tgggtcgag cgtgaaggtc      60 tcctgcaagg cttctggcgg tacctttagc gattatgcta tacactgggt gagacaggcc    120
cctggacagg gtcttgagtg gattggagtt attagtattt actatgatga taaaactac    180 aaccagaagt ttaagggcaa ggccacaatt actgcagacg aatccaccaa cacagcctac    240
atggaactca gcagcctgag gtctgaggac accgcgatct attattgtgc gcgccgaagg    300
gacagctcgg gtccctatgc tatggactac tggggtcaag caccctcgt caccgtgtcc    360 agc                                                                 363

<210> SEQ ID NO 283
<211> LENGTH: 121
<212> TYPE: PRT
<213> ORGANISM: Artificial Sequence
<220> FEATURE:
<223> OTHER INFORMATION: Description of Artificial Sequence: Synthetic
      humanized antibody sequence

<400> SEQUENCE: 283

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile His Trp Val Arg Gln Ala Pro Gly Gln Gly Leu Glu Trp Ile
        35                  40                  45

Gly Val Ile Ser Ile Tyr Tyr Asp Asp Thr Asn Tyr Asn Gln Lys Phe
    50                  55                  60

Lys Gly Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Arg Arg Asp Ser Ser Gly Pro Tyr Ala Met Asp Tyr Trp Gly
            100                 105                 110

Gln Gly Thr Leu Val Thr Val Ser Ser
        115                 120

<210> SEQ ID NO 284
<211> LENGTH: 339
<212> TYPE: DNA
<213> ORGANISM: Artificial Sequence
<220> FEATURE:
<223> OTHER INFORMATION: Description of Artificial Sequence: Synthetic
      humanized antibody sequence

<400> SEQUENCE: 284
gacatccaga tgacccagag cccaagcagc ctgagcgcca gcgtgggtga cagagtgacc      60
atcacctgta gagccagtga agtgtttgat agttatggca atagtttat gcactggtac    120 cagcagaagc caggtaaggc tccaaagctg ctgatctacc gtgcatccaa cctagaatct    180
ggtgtgccaa gcagattcag cggtagcggt agcggtaccg acttcacctt caccatcagc    240
agcctccagc cagaggacat cgccacctac tactgccagc aaagtaatga ggacccgtac    300
acgttcggcc aagggaccaa ggtggaaatc aaacgtacg                         339
```

```
<210> SEQ ID NO 285
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody sequence

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Asn
                85                  90                  95

Glu Asp Pro Tyr Thr Phe Gly Gln Gly Thr Lys Val Glu Ile Lys Arg
            100                 105                 110

Thr

<210> SEQ ID NO 286
<211> LENGTH: 339
<212> TYPE: DNA
<213> ORGANISM: Artificial Sequence
<220> FEATURE:
<223> OTHER INFORMATION: Description of Artificial Sequence: Synthetic
      humanized antibody sequence

<400> SEQUENCE: 286
gacatccaga tgacccagag cccaagcacg ctgagcgcca gcgtgggtga cagagtgacc      60
atcacctgta gagccagtga aagtgttgat agttatggca atagtttttat gcactggtac    120 cagcagaagc caggtaaggc tccaaagctg ctgatgtacc gtgcatccaa cctagaatct    180
ggtgtgccaa gcagattcat cggtagcggt agcggtaccg agttcaccct caccatcagc    240
agcctccagc cagacgactt cgccacctac tactgccagc aaagtaatga ggacccgtac    300
acgttcggcc aagggaccaa ggtggaagtc aaacgtacg                           339

<210> SEQ ID NO 287
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody sequence

<400> SEQUENCE: 287

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Met Tyr Arg Ala Ser Asn Leu Glu Ser Gly Val Pro Ser
    50                  55                  60

Arg Phe Ile Gly Ser Gly Ser Gly Thr Glu Phe Thr Leu Thr Ile Ser
```

```
                65                  70                  75                  80
Ser Leu Gln Pro Asp Asp Phe Ala Thr Tyr Tyr Cys Gln Gln Ser Asn
                    85                  90                  95

Glu Asp Pro Tyr Thr Phe Gly Gln Gly Thr Lys Val Glu Val Lys Arg
                100                 105                 110

Thr

<210> SEQ ID NO 288
<211> LENGTH: 542
<212> TYPE: PRT
<213> ORGANISM: Artificial Sequence
<220> FEATURE:
<223> OTHER INFORMATION: Description of Artificial Sequence: Synthetic
      GPVI variant sequence

<400> SEQUENCE: 288

Gln His Gly Pro Leu Pro Lys Pro Ser Leu Gln Ala Gln Pro Ser Ser
1               5                   10                  15

Leu Val Pro Leu Gly His Pro Val Thr Leu Arg Cys Leu Gly Pro Ser
                20                  25                  30

Asp Ala Asp Leu Tyr Arg Leu Glu Lys Val Lys Pro Gly Lys Leu Ile
                35                  40                  45

Phe Ile Asp Gln Asp Phe Leu Phe Ile Pro Ile Met Glu Ile Asn Asn
            50                  55                  60

Ala Gly Arg Tyr Arg Cys Ser Tyr Gln Asn Glu Ser His Trp Ser Leu
65                  70                  75                  80

Pro Ser Asp Gln Leu Glu Leu Ile Ala Thr Gly Val Tyr Ser Lys Pro
                85                  90                  95

Ser Leu Ser Ala His Pro Ser Ser Ala Ile Pro Pro Gly Arg Asp Val
                100                 105                 110

Thr Leu Lys Cys Gln Thr Arg Tyr Gly Phe Asp Gln Phe Val Leu Tyr
                115                 120                 125

Lys Glu Gly Asp Thr Arg Pro Tyr Lys Arg Pro Glu Arg Trp Tyr Arg
            130                 135                 140

Ala Asn Phe Pro Val Ile Thr Val Thr Ala Ala His Ser Gly Thr Tyr
145                 150                 155                 160

Arg Cys Tyr Ser Phe Ser Ser Ser Pro Tyr Leu Trp Ser Ala Pro
                165                 170                 175

Ser Asp Pro Leu Val Val Val Thr Gly Pro Ser Ala Thr Pro Ser
                180                 185                 190

Gln Val Pro Thr Glu Val Pro Ser Pro Met Thr Glu Ala Ser Arg Arg
                195                 200                 205

Pro Ser Met Leu Leu Thr Asn Lys Ile Ser Thr Thr Glu Lys Pro Met
210                 215                 220

Asn Ile Thr Val Ser Pro Glu Gly Pro Ser Pro Phe Gly Phe Ala
225                 230                 235                 240

His Gln His Tyr Ala Lys Gly Asn Gly Ser Arg Ser Leu Ser Ser Gly
                245                 250                 255

Val His Thr Phe Pro Ala Leu Leu Gln Ser Gly Leu Tyr Thr Leu Ser
                260                 265                 270

Ser Ser Val Thr Val Thr Ser Asn Thr Trp Pro Ser Gln Thr Ile Thr
            275                 280                 285

Cys Asn Val Ala His Pro Ala Ser Ser Thr Lys Val Asp Lys Lys Ile
            290                 295                 300

Glu Pro Arg Val Pro Ile Thr Gln Asn Pro Cys Pro Pro Leu Lys Glu
305                 310                 315                 320
```

Cys Pro Pro Cys Ala Ala Pro Asp Leu Leu Gly Gly Pro Ser Val Phe
                325                 330                 335

Ile Phe Pro Pro Lys Ile Lys Asp Val Leu Met Ile Ser Leu Ser Pro
                340                 345                 350

Met Val Thr Cys Val Val Val Asp Val Ser Glu Asp Asp Pro Asp Val
            355                 360                 365

Gln Ile Ser Trp Phe Val Asn Asn Val Glu Val His Thr Ala Gln Thr
        370                 375                 380

Gln Thr His Arg Glu Asp Tyr Asn Ser Thr Leu Arg Val Val Ser Ala
385                 390                 395                 400

Leu Pro Ile Gln His Gln Asp Trp Met Ser Gly Lys Glu Phe Lys Cys
                405                 410                 415

Lys Val Asn Asn Arg Ala Leu Pro Ser Pro Ile Glu Lys Thr Ile Ser
                420                 425                 430

Lys Pro Arg Gly Pro Val Arg Ala Pro Gln Val Tyr Val Leu Pro Pro
            435                 440                 445

Pro Ala Glu Glu Met Thr Lys Lys Glu Phe Ser Leu Thr Cys Met Ile
        450                 455                 460

Thr Gly Phe Leu Pro Ala Glu Ile Ala Val Asp Trp Thr Ser Asn Gly
465                 470                 475                 480

Arg Thr Glu Gln Asn Tyr Lys Asn Thr Ala Thr Val Leu Asp Ser Asp
                485                 490                 495

Gly Ser Tyr Phe Met Tyr Ser Lys Leu Arg Val Gln Lys Ser Thr Trp
                500                 505                 510

Glu Arg Gly Ser Leu Phe Ala Cys Ser Val Val His Glu Gly Leu His
            515                 520                 525

Asn His Leu Thr Thr Lys Thr Ile Ser Arg Ser Leu Gly Lys
        530                 535                 540

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 289
ccacatagct caggactggg                                              20

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 290
ccaagttatt tctaggccag tgg                                          23

<210> SEQ ID NO 291
<211> LENGTH: 14
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 291

```
aattcgccgc cacc                                                          14
```

<210> SEQ ID NO 292
<211> LENGTH: 13
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 292

```
catggtggcg gcg                                                           13
```

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 293

```
ggagtgcatc cgccccaacc ctt                                                23
```

<210> SEQ ID NO 294
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 294

```
gcagctcggc aatcactgga agaggcacgt                                         30
```

<210> SEQ ID NO 295
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 295

```
acgtgcctct tccagtgatt gccgagctgc                                         30
```

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 296

```
tggctgtgtc ttgatcgggg ccacacatgg                                         30
```

<210> SEQ ID NO 297
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 297

```
ccatgtgtgg ccccgatcaa gacacagcca                                         30
```

<210> SEQ ID NO 298
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 298
tgtgcagggc caccccttg ggccgggaga                              30

<210> SEQ ID NO 299
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 299
tctcccggcc caaggggtg gccctgcaca                              30

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 300
gttgacacgg ttagtttgca tgca                                   24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 301
gccggcagtg catccgcccc aacc                                   24

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 302
cactccttat agatcacaca cct                                    23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 303
aagtgaagtc aagatgaaga acc                                    23

<210> SEQ ID NO 304

```
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 304
ctgttcatgt gaaagcccaa gaagatgaaa                                      30

<210> SEQ ID NO 305
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 305
tttcatcttc ttgggctttc acatgaacag                                      30

<210> SEQ ID NO 306
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 306
aaacatccga attattgttc ctctgaacaa                                      30

<210> SEQ ID NO 307
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 307
ttgttcagag gaacaataat tcggatgttt                                      30

<210> SEQ ID NO 308
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 308
ccatttgtct gacctctgta aaaaatgtga                                      30

<210> SEQ ID NO 309
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 309
tcacattttt tacagaggtc agacaaatgg                                      30

<210> SEQ ID NO 310
<211> LENGTH: 23
<212> TYPE: DNA
```

<213> ORGANISM: Artificial Sequence
<220> FEATURE:
<223> OTHER INFORMATION: Description of Artificial Sequence:
      Synthetic primer

<400> SEQUENCE: 310
ttagtcagga tagcaggcat ctg                                             23

<210> SEQ ID NO 311
<211> LENGTH: 17
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 311
agagctatgc agtcagc                                                    17

<210> SEQ ID NO 312
<211> LENGTH: 945
<212> TYPE: DNA
<213> ORGANISM: Rattus norvegicus

<400> SEQUENCE: 312
atgtctccag cctcactcac tttcttctgt attgggctgt gtgtactaca agtgatccaa      60
gcacagcatg gcccactccc caagccttct ctccaggctc aacccagttc cctggtgccc     120
ctgggtcatc cagtcactct gaggtgcctg gggccttcag atgcggattt atatcgtctg     180
gagaaagtga aacccgggaa gttgatcttc atagatcaag actttctctt cattccaatc     240
atggaaataa ataatgctgg acgctaccgc tgctcatatc agaatgagag tcattggtct     300
ctcccaagtg accagcttga gctaattgct acaggtgttt actctaagcc ctcactttca     360
gctcatccca gctcagcaat ccctccaggc agggatgtga ctctgaagtg ccaaagccaa     420
tatagttttg acgaatttgt tttatacaaa gagggggata ctaggcctta taagagacct     480
gagaaatggt accgggccaa tttccccgtc atcacagtga ctgctgctca gtgggact       540 taccggtgtt acagcttttc cagctcatct ccatacctgt ggtcagcacc gagtgaccct     600
ctagtagttg tggttactgg accctctgcc actcccagtc aggtacccac agaggtacca     660
tctcctatga cagaagcctc caggagacct tccatgttac tcacaaacaa aatatctaca     720
actgaaaagc ctatgaatat cactgtctct ccagaggggc caagccctcc atttggtttt     780
gctcatcagc actatgccaa ggggaatctg gtccggatat gccttggtgt catgattata     840
atgttcttgg tggggttct ggcagaggat tggcacagtc ggaagaaacg cctacaacac      900
aggatcagag ctatgcaaag gccactgcca cctctcccac tggcc                    945

<210> SEQ ID NO 313
<211> LENGTH: 315
<212> TYPE: PRT
<213> ORGANISM: Rattus norvegicus

<400> SEQUENCE: 313

Met Ser Pro Ala Ser Leu Thr Phe Phe Cys Ile Gly Leu Cys Val Leu
1               5                   10                  15

Gln Val Ile Gln Ala Gln His Gly Pro Leu Pro Lys Pro Ser Leu Gln
            20                  25                  30

Ala Gln Pro Ser Ser Leu Val Pro Leu Gly His Pro Val Thr Leu Arg
        35                  40                  45

Cys Leu Gly Pro Ser Asp Ala Asp Leu Tyr Arg Leu Glu Lys Val Lys

```
                 50                  55                  60
Pro Gly Lys Leu Ile Phe Ile Asp Gln Asp Phe Leu Phe Ile Pro Ile
 65                  70                  75                  80

Met Glu Ile Asn Asn Ala Gly Arg Tyr Arg Cys Ser Tyr Gln Asn Glu
                 85                  90                  95

Ser His Trp Ser Leu Pro Ser Asp Gln Leu Glu Leu Ile Ala Thr Gly
                100                 105                 110

Val Tyr Ser Lys Pro Ser Leu Ser Ala His Pro Ser Ala Ile Pro
                115                 120                 125

Pro Gly Arg Asp Val Thr Leu Lys Cys Gln Ser Gln Tyr Ser Phe Asp
130                 135                 140

Glu Phe Val Leu Tyr Lys Glu Gly Asp Thr Arg Pro Tyr Lys Arg Pro
145                 150                 155                 160

Glu Lys Trp Tyr Arg Ala Asn Phe Pro Val Ile Thr Val Thr Ala Ala
                165                 170                 175

His Ser Gly Thr Tyr Arg Cys Tyr Ser Phe Ser Ser Ser Pro Tyr
                180                 185                 190

Leu Trp Ser Ala Pro Ser Asp Pro Leu Val Val Val Thr Gly Pro
                195                 200                 205

Ser Ala Thr Pro Ser Gln Val Pro Thr Glu Val Pro Ser Pro Met Thr
210                 215                 220

Glu Ala Ser Arg Arg Pro Ser Met Leu Leu Thr Asn Lys Ile Ser Thr
225                 230                 235                 240

Thr Glu Lys Pro Met Asn Ile Thr Val Ser Pro Glu Gly Pro Ser Pro
                245                 250                 255

Pro Phe Gly Phe Ala His Gln His Tyr Ala Lys Gly Asn Leu Val Arg
                260                 265                 270

Ile Cys Leu Gly Val Met Ile Ile Met Phe Leu Val Gly Phe Leu Ala
                275                 280                 285

Glu Asp Trp His Ser Arg Lys Lys Arg Leu Gln His Arg Ile Arg Ala
                290                 295                 300

Met Gln Arg Pro Leu Pro Pro Leu Pro Leu Ala
305                 310                 315

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 314
ccctcagcgc atcctgttcc tat                                          23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 315
tttcccaggt caccttcagg act                                          23

<210> SEQ ID NO 316
<211> LENGTH: 22
<212> TYPE: DNA
```

```
<213> ORGANISM: Artificial Sequence
<220> FEATURE:
<223> OTHER INFORMATION: Description of Artificial Sequence:
      Synthetic primer

<400> SEQUENCE: 316
ttaagggagt ctctagcctc tg                                              22

<210> SEQ ID NO 317
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 317
gtttagcata cacacctgta gcaattagct                                      30

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 318
cctgtttcct gtctttaata gag                                             23

<210> SEQ ID NO 319
<211> LENGTH: 22
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 319
ccttgcccac acctctgact cc                                              22

<210> SEQ ID NO 320
<211> LENGTH: 25
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 320
gtgagaaaat caagtcacag aaatg                                           25

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 321
ttcagacaca tttgtagtag aac                                             23

<210> SEQ ID NO 322
<211> LENGTH: 23
<212> TYPE: DNA
<213> ORGANISM: Artificial Sequence
<220> FEATURE:
```

-continued

<223> OTHER INFORMATION: Description of Artificial Sequence:
      Synthetic primer

<400> SEQUENCE: 322
ggagcacttg ggatgaactg tca                                           23

<210> SEQ ID NO 323
<211> LENGTH: 22
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 323
gagaaaccca tcctcttgcc ac                                            22

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 324
gcttcacaag catatgagca cgtg                                          24

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 325
attatagctc tatagattcc atg                                           23

<210> SEQ ID NO 326
<211> LENGTH: 27
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 326
gggaattcca tgtctccagc ctcactc                                       27

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 327
ccaagttatt tctaggccag tgg                                           23

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

```
<400> SEQUENCE: 328
ccaggagttc aggtgctggg cacggtgggc                                            30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 329 gtggttactg␣gaccctctgc␣cactcccagc                                            30

<210> SEQ ID NO 330
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 330
gctgggagtg gcagagggtc cagtaaccac                                            30

<210> SEQ ID NO 331
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 331
ggtgctgggc ctgatgggcc tgggggacca                                            30

<210> SEQ ID NO 332
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 332
agcgctagca ccaagggccc atccgtcttc                                            30

<210> SEQ ID NO 333
<211> LENGTH: 30
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 333
tggtccccca ggcccatcag gcccagcacc                                            30

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 334
```

```
catcaatgta tcttatcatg tct                                              23
```

<210> SEQ ID NO 335
<211> LENGTH: 5
<212> TYPE: PRT
<213> ORGANISM: Mus musculus

<400> SEQUENCE: 335

Ser Tyr Trp Met His
1               5

<210> SEQ ID NO 336
<211> LENGTH: 17
<212> TYPE: PRT
<213> ORGANISM: Mus musculus

<400> SEQUENCE: 336

Met Ile His Pro Asn Ser Asp Asn Thr Asn Tyr Asn Glu Lys Phe Lys
1               5                   10                  15

Ser

<210> SEQ ID NO 337
<211> LENGTH: 8
<212> TYPE: PRT
<213> ORGANISM: Mus musculus

<400> SEQUENCE: 337

His Tyr Tyr Asp Tyr Val Asp Tyr
1               5

<210> SEQ ID NO 338
<211> LENGTH: 5
<212> TYPE: PRT
<213> ORGANISM: Mus musculus

<400> SEQUENCE: 338

Ser Tyr Trp Met His
1               5

<210> SEQ ID NO 339
<211> LENGTH: 17
<212> TYPE: PRT
<213> ORGANISM: Mus musculus

<400> SEQUENCE: 339

Met Ile His Pro Asn Ser Gly Ser Thr His Tyr Asn Glu Lys Phe Lys
1               5                   10                  15

Ser

<210> SEQ ID NO 340
<211> LENGTH: 8
<212> TYPE: PRT
<213> ORGANISM: Mus musculus

<400> SEQUENCE: 340

Gly Gly Val Thr Pro Val Ala Tyr
1               5

<210> SEQ ID NO 341
<211> LENGTH: 5
<212> TYPE: PRT
<213> ORGANISM: Mus musculus

<400> SEQUENCE: 341

Ser Tyr Trp Met His
1               5

<210> SEQ ID NO 342
<211> LENGTH: 17
<212> TYPE: PRT
<213> ORGANISM: Mus musculus

<400> SEQUENCE: 342

Met Ile His Pro Asn Ser Gly Ser Thr Asn Tyr Asn Glu Lys Phe Lys
1               5                   10                  15

Ser

<210> SEQ ID NO 343
<211> LENGTH: 8
<212> TYPE: PRT
<213> ORGANISM: Mus musculus

<400> SEQUENCE: 343

Gly Gly Val Thr Pro Val Ala Tyr
1               5

<210> SEQ ID NO 344
<211> LENGTH: 5
<212> TYPE: PRT
<213> ORGANISM: Mus musculus

<400> SEQUENCE: 344

Ser Tyr Trp Met His
1               5

<210> SEQ ID NO 345
<211> LENGTH: 17
<212> TYPE: PRT
<213> ORGANISM: Mus musculus

<400> SEQUENCE: 345

Met Ile His Pro Asn Ser Gly Ser Thr Asn Tyr Asn Glu Lys Phe Lys
1               5                   10                  15

Ser

<210> SEQ ID NO 346
<211> LENGTH: 12
<212> TYPE: PRT
<213> ORGANISM: Mus musculus

<400> SEQUENCE: 346

Pro Val Thr Ala Val Val Glu Tyr Tyr Phe Asp Tyr
1               5                   10

<210> SEQ ID NO 347
<211> LENGTH: 5
<212> TYPE: PRT
<213> ORGANISM: Mus musculus

<400> SEQUENCE: 347

Ser Tyr Gly Met Ser
1               5

<210> SEQ ID NO 348
<211> LENGTH: 17
<212> TYPE: PRT
<213> ORGANISM: Mus musculus -continued

```
<400> SEQUENCE: 348

Thr Ile Ser Asn Gly Gly Thr Tyr Thr Tyr Tyr Pro Asp Ser Val Lys
1               5                   10                  15

Gly

<210> SEQ ID NO 349
<211> LENGTH: 9
<212> TYPE: PRT
<213> ORGANISM: Mus musculus

<400> SEQUENCE: 349

Leu Arg Asp Tyr Tyr Ala Met Asp Tyr
1               5

<210> SEQ ID NO 350
<211> LENGTH: 5
<212> TYPE: PRT
<213> ORGANISM: Mus musculus

<400> SEQUENCE: 350

Ser Tyr Gly Met Ser
1               5

<210> SEQ ID NO 351
<211> LENGTH: 17
<212> TYPE: PRT
<213> ORGANISM: Mus musculus

<400> SEQUENCE: 351

Thr Ile Ser Ser Gly Gly Ser Tyr Thr Tyr Tyr Ser Asp Ser Val Lys
1               5                   10                  15

Gly

<210> SEQ ID NO 352
<211> LENGTH: 7
<212> TYPE: PRT
<213> ORGANISM: Mus musculus

<400> SEQUENCE: 352

Asp Ser Gly Tyr Phe Asp Tyr
1               5

<210> SEQ ID NO 353
<211> LENGTH: 5
<212> TYPE: PRT
<213> ORGANISM: Mus musculus

<400> SEQUENCE: 353

Ser Tyr Trp Met His
1               5

<210> SEQ ID NO 354
<211> LENGTH: 17
<212> TYPE: PRT
<213> ORGANISM: Mus musculus

<400> SEQUENCE: 354

Met Ile His Pro Asn Ser Asp Ile Thr Asn Tyr Asn Glu Lys Phe Lys
1               5                   10                  15

Asn

<210> SEQ ID NO 355
<211> LENGTH: 9
```

```
<212> TYPE: PRT
<213> ORGANISM: Mus musculus

<400> SEQUENCE: 355

Leu Gly Asp Tyr Tyr Ala Met Asp Tyr
1               5

<210> SEQ ID NO 356
<211> LENGTH: 5
<212> TYPE: PRT
<213> ORGANISM: Mus musculus

<400> SEQUENCE: 356

Ser Tyr Trp Met His
1               5

<210> SEQ ID NO 357
<211> LENGTH: 17
<212> TYPE: PRT
<213> ORGANISM: Mus musculus

<400> SEQUENCE: 357

Met Ile His Pro Asn Ser Asp Ile Thr Asn Tyr Asn Glu Lys Phe Lys
1               5                   10                  15

Asn

<210> SEQ ID NO 358
<211> LENGTH: 9
<212> TYPE: PRT
<213> ORGANISM: Mus musculus

<400> SEQUENCE: 358

Ser Gly Asp Tyr Tyr Ala Met Asp Tyr
1               5

<210> SEQ ID NO 359
<211> LENGTH: 5
<212> TYPE: PRT
<213> ORGANISM: Mus musculus

<400> SEQUENCE: 359

Asp Tyr Ala Met His
1               5

<210> SEQ ID NO 360
<211> LENGTH: 17
<212> TYPE: PRT
<213> ORGANISM: Mus musculus

<400> SEQUENCE: 360

Val Ile Ser Thr Tyr Tyr Gly Asp Thr Ser Tyr Asn Gln Lys Phe Lys
1               5                   10                  15

Gly

<210> SEQ ID NO 361
<211> LENGTH: 10
<212> TYPE: PRT
<213> ORGANISM: Mus musculus

<400> SEQUENCE: 361

Ala Glu Asp Tyr Asp Pro Trp Phe Ala Tyr
1               5                   10

<210> SEQ ID NO 362
```

```
<211> LENGTH: 5
<212> TYPE: PRT
<213> ORGANISM: Mus musculus

<400> SEQUENCE: 362

Ser Tyr Trp Met Gln
1               5

<210> SEQ ID NO 363
<211> LENGTH: 17
<212> TYPE: PRT
<213> ORGANISM: Mus musculus

<400> SEQUENCE: 363

Glu Ile Asp Pro Ser Asp Ser Tyr Thr Asn Tyr Asn Gln Lys Phe Lys
1               5                   10                  15

Gly

<210> SEQ ID NO 364
<211> LENGTH: 10
<212> TYPE: PRT
<213> ORGANISM: Mus musculus

<400> SEQUENCE: 364

Gly Ala Ile Thr Thr Ala Thr Leu Asp Tyr
1               5                   10

<210> SEQ ID NO 365
<211> LENGTH: 5
<212> TYPE: PRT
<213> ORGANISM: Mus musculus

<400> SEQUENCE: 365

Asp Tyr Ala Met His
1               5

<210> SEQ ID NO 366
<211> LENGTH: 17
<212> TYPE: PRT
<213> ORGANISM: Mus musculus

<400> SEQUENCE: 366

Val Ile Ser Thr Tyr Tyr Gly Asp Thr Ser Tyr Asn Gln Lys Phe Lys
1               5                   10                  15

Gly

<210> SEQ ID NO 367
<211> LENGTH: 10
<212> TYPE: PRT
<213> ORGANISM: Mus musculus

<400> SEQUENCE: 367

Ala Glu Asp Tyr Asp Pro Trp Phe Ala Tyr
1               5                   10

<210> SEQ ID NO 368
<211> LENGTH: 5
<212> TYPE: PRT
<213> ORGANISM: Mus musculus

<400> SEQUENCE: 368

Asp Tyr Ala Met His
1               5
```

```
<210> SEQ ID NO 369
<211> LENGTH: 17
<212> TYPE: PRT
<213> ORGANISM: Mus musculus

<400> SEQUENCE: 369

Val Ile Ser Thr Tyr Tyr Gly Asp Thr Ser Tyr Asn Gln Lys Phe Lys
1               5                   10                  15

Gly

<210> SEQ ID NO 370
<211> LENGTH: 10
<212> TYPE: PRT
<213> ORGANISM: Mus musculus

<400> SEQUENCE: 370

Ala Glu Asp Tyr Asp Pro Trp Phe Ala Tyr
1               5                   10

<210> SEQ ID NO 371
<211> LENGTH: 5
<212> TYPE: PRT
<213> ORGANISM: Rattus norvegicus

<400> SEQUENCE: 371

Asp Tyr Tyr Ile His
1               5

<210> SEQ ID NO 372
<211> LENGTH: 17
<212> TYPE: PRT
<213> ORGANISM: Rattus norvegicus

<400> SEQUENCE: 372

Tyr Ile Asn Pro Asn Ser Gly Tyr Thr Asn Tyr Asn Glu Lys Phe Lys
1               5                   10                  15

Ser

<210> SEQ ID NO 373
<211> LENGTH: 11
<212> TYPE: PRT
<213> ORGANISM: Rattus norvegicus

<400> SEQUENCE: 373

Cys Asn Ser Gly Tyr Gly Asp Trp Phe Ala Tyr
1               5                   10

<210> SEQ ID NO 374
<211> LENGTH: 7
<212> TYPE: PRT
<213> ORGANISM: Rattus norvegicus

<400> SEQUENCE: 374

Thr Ser Gly Met Val Val Ser
1               5

<210> SEQ ID NO 375
<211> LENGTH: 16
<212> TYPE: PRT
<213> ORGANISM: Rattus norvegicus

<400> SEQUENCE: 375

Ala Ile Asp Trp Asp Gly Asp Lys Tyr Tyr Asn Pro Ser Leu Lys Ser
1               5                   10                  15
```

```
<210> SEQ ID NO 376
<211> LENGTH: 14
<212> TYPE: PRT
<213> ORGANISM: Rattus norvegicus

<400> SEQUENCE: 376

Thr Pro Tyr Tyr Gly Tyr Lys Glu Ala Tyr Tyr Phe Asp Tyr
 1               5                  10

<210> SEQ ID NO 377
<211> LENGTH: 11
<212> TYPE: PRT
<213> ORGANISM: Mus musculus

<400> SEQUENCE: 377

Lys Ala Ser Gln Ser Val Ser Asn Asp Val Ala
 1               5                  10

<210> SEQ ID NO 378
<211> LENGTH: 7
<212> TYPE: PRT
<213> ORGANISM: Mus musculus

<400> SEQUENCE: 378

Tyr Ala Ser Asn Arg Tyr Thr
 1               5

<210> SEQ ID NO 379
<211> LENGTH: 9
<212> TYPE: PRT
<213> ORGANISM: Mus musculus

<400> SEQUENCE: 379

Gln Gln Asp Tyr Ser Ser Pro Trp Thr
 1               5

<210> SEQ ID NO 380
<211> LENGTH: 11
<212> TYPE: PRT
<213> ORGANISM: Mus musculus

<400> SEQUENCE: 380

Lys Ala Ser Gln Ser Val Ser Asn Asp Val Ala
 1               5                  10

<210> SEQ ID NO 381
<211> LENGTH: 7
<212> TYPE: PRT
<213> ORGANISM: Mus musculus

<400> SEQUENCE: 381

Tyr Ala Ser Asn Arg Tyr Thr
 1               5

<210> SEQ ID NO 382
<211> LENGTH: 9
<212> TYPE: PRT
<213> ORGANISM: Mus musculus

<400> SEQUENCE: 382

Gln Gln Asp Tyr Ser Ser Pro Trp Thr
 1               5

<210> SEQ ID NO 383
<211> LENGTH: 11
```

```
<212> TYPE: PRT
<213> ORGANISM: Mus musculus

<400> SEQUENCE: 383

Lys Ala Ser Gln Ser Val Ser Asn Asp Val Ala
1               5                   10

<210> SEQ ID NO 384
<211> LENGTH: 7
<212> TYPE: PRT
<213> ORGANISM: Mus musculus

<400> SEQUENCE: 384

Tyr Ala Ser Asn Arg Tyr Thr
1               5

<210> SEQ ID NO 385
<211> LENGTH: 9
<212> TYPE: PRT
<213> ORGANISM: Mus musculus

<400> SEQUENCE: 385

Gln Gln Asp Tyr Ser Ser Pro Trp Thr
1               5

<210> SEQ ID NO 386
<211> LENGTH: 11
<212> TYPE: PRT
<213> ORGANISM: Mus musculus

<400> SEQUENCE: 386

Lys Ala Ser Gln Ser Val Ser Asn Asp Val Ala
1               5                   10

<210> SEQ ID NO 387
<211> LENGTH: 7
<212> TYPE: PRT
<213> ORGANISM: Mus musculus

<400> SEQUENCE: 387

Tyr Ala Ser Asn Arg Tyr Thr
1               5

<210> SEQ ID NO 388
<211> LENGTH: 8
<212> TYPE: PRT
<213> ORGANISM: Mus musculus

<400> SEQUENCE: 388

Gln Gln Asp Tyr Ser Ser Leu Thr
1               5

<210> SEQ ID NO 389
<211> LENGTH: 15
<212> TYPE: PRT
<213> ORGANISM: Mus musculus

<400> SEQUENCE: 389

Arg Ala Ser Glu Ser Val Asp Ser Tyr Gly Asn Ser Phe Met His
1               5                   10                  15

<210> SEQ ID NO 390
<211> LENGTH: 7
<212> TYPE: PRT
<213> ORGANISM: Mus musculus
```

```
<400> SEQUENCE: 390

Arg Ala Ser Asn Leu Glu Ser
1               5

<210> SEQ ID NO 391
<211> LENGTH: 9
<212> TYPE: PRT
<213> ORGANISM: Mus musculus

<400> SEQUENCE: 391

Gln Gln Ser Asn Glu Asp Pro Trp Thr
1               5

<210> SEQ ID NO 392
<211> LENGTH: 15
<212> TYPE: PRT
<213> ORGANISM: Mus musculus

<400> SEQUENCE: 392

Arg Ala Ser Glu Ser Val Asp Ser Tyr Gly Asn Ser Phe Met His
1               5                   10                  15

<210> SEQ ID NO 393
<211> LENGTH: 7
<212> TYPE: PRT
<213> ORGANISM: Mus musculus

<400> SEQUENCE: 393

Leu Ala Ser Asn Leu Glu Ser
1               5

<210> SEQ ID NO 394
<211> LENGTH: 10
<212> TYPE: PRT
<213> ORGANISM: Mus musculus

<400> SEQUENCE: 394

Gln Gln Ser Asn Asn Glu Asp Pro Arg Thr
1               5                   10

<210> SEQ ID NO 395
<211> LENGTH: 11
<212> TYPE: PRT
<213> ORGANISM: Mus musculus

<400> SEQUENCE: 395

Lys Ala Ser Gln Ser Val Ser Asn Asp Val Thr
1               5                   10

<210> SEQ ID NO 396
<211> LENGTH: 7
<212> TYPE: PRT
<213> ORGANISM: Mus musculus

<400> SEQUENCE: 396

Tyr Ala Ser Asn Arg Tyr Thr
1               5

<210> SEQ ID NO 397
<211> LENGTH: 9
<212> TYPE: PRT
<213> ORGANISM: Mus musculus

<400> SEQUENCE: 397

Gln Gln Asp Tyr Ser Ser Pro Pro Thr
```

<210> SEQ ID NO 398
<211> LENGTH: 11
<212> TYPE: PRT
<213> ORGANISM: Mus musculus

<400> SEQUENCE: 398

Lys Ala Ser Gln Ser Val Ser Asn Asp Val Ala
1               5                   10

<210> SEQ ID NO 399
<211> LENGTH: 7
<212> TYPE: PRT
<213> ORGANISM: Mus musculus

<400> SEQUENCE: 399

Tyr Ala Ser Asn Arg Tyr Thr
1               5

<210> SEQ ID NO 400
<211> LENGTH: 9
<212> TYPE: PRT
<213> ORGANISM: Mus musculus

<400> SEQUENCE: 400

Gln Gln Asp Tyr Ser Ser Pro Pro Thr
1               5

<210> SEQ ID NO 401
<211> LENGTH: 15
<212> TYPE: PRT
<213> ORGANISM: Mus musculus

<400> SEQUENCE: 401

Arg Ala Ser Glu Ser Val Asp Ser Tyr Gly Asn Ser Phe Met Tyr
1               5                   10                  15

<210> SEQ ID NO 402
<211> LENGTH: 7
<212> TYPE: PRT
<213> ORGANISM: Mus musculus

<400> SEQUENCE: 402

Arg Ala Ser Asn Leu Glu Ser
1               5

<210> SEQ ID NO 403
<211> LENGTH: 9
<212> TYPE: PRT
<213> ORGANISM: Mus musculus

<400> SEQUENCE: 403

Gln Gln Ser Asp Glu Asp Pro Leu Thr
1               5

<210> SEQ ID NO 404
<211> LENGTH: 17
<212> TYPE: PRT
<213> ORGANISM: Mus musculus

<400> SEQUENCE: 404

Lys Ser Ser Gln Ser Leu Leu Asn Ser Asn Asn Gln Lys Asn Tyr Leu
1               5                   10                  15
Ala

```
<210> SEQ ID NO 405
<211> LENGTH: 7
<212> TYPE: PRT
<213> ORGANISM: Mus musculus

<400> SEQUENCE: 405

Phe Ala Ser Thr Arg Glu Ser
1               5

<210> SEQ ID NO 406
<211> LENGTH: 9
<212> TYPE: PRT
<213> ORGANISM: Mus musculus

<400> SEQUENCE: 406

Gln Gln His Tyr Ile Thr Pro Leu Thr
1               5

<210> SEQ ID NO 407
<211> LENGTH: 15
<212> TYPE: PRT
<213> ORGANISM: Mus musculus

<400> SEQUENCE: 407

Arg Ala Ser Glu Ser Val Asp Ser Tyr Gly Asn Ser Phe Met His
1               5                   10                  15

<210> SEQ ID NO 408
<211> LENGTH: 7
<212> TYPE: PRT
<213> ORGANISM: Mus musculus

<400> SEQUENCE: 408

Arg Ala Ser Asn Leu Glu Ser
1               5

<210> SEQ ID NO 409
<211> LENGTH: 9
<212> TYPE: PRT
<213> ORGANISM: Mus musculus

<400> SEQUENCE: 409

Gln Gln Ser Asp Glu Asp Pro Leu Thr
1               5

<210> SEQ ID NO 410
<211> LENGTH: 15
<212> TYPE: PRT
<213> ORGANISM: Mus musculus

<400> SEQUENCE: 410

Arg Ala Ser Glu Ser Val Asp Ser Tyr Gly Asn Ser Phe Met His
1               5                   10                  15

<210> SEQ ID NO 411
<211> LENGTH: 7
<212> TYPE: PRT
<213> ORGANISM: Mus musculus

<400> SEQUENCE: 411

Arg Ala Ser Asn Leu Glu Ser
1               5

<210> SEQ ID NO 412
```

```
<211> LENGTH: 9
<212> TYPE: PRT
<213> ORGANISM: Mus musculus

<400> SEQUENCE: 412

Gln Gln Ser Asp Glu Asp Pro Leu Thr
1               5

<210> SEQ ID NO 413
<211> LENGTH: 11
<212> TYPE: PRT
<213> ORGANISM: Rattus norvegicus

<400> SEQUENCE: 413

Lys Ala Ser Gln Asn Ile Asn Lys Asn Leu Asp
1               5                   10

<210> SEQ ID NO 414
<211> LENGTH: 7
<212> TYPE: PRT
<213> ORGANISM: Rattus norvegicus

<400> SEQUENCE: 414

Tyr Thr Asn Asn Leu Gln Thr
1               5

<210> SEQ ID NO 415
<211> LENGTH: 9
<212> TYPE: PRT
<213> ORGANISM: Rattus norvegicus

<400> SEQUENCE: 415

Tyr Gln Tyr Asn Ser Gly Pro Gly Thr
1               5

<210> SEQ ID NO 416
<211> LENGTH: 11
<212> TYPE: PRT
<213> ORGANISM: Rattus norvegicus

<400> SEQUENCE: 416

Lys Ala Ser Arg Ala Ile Asp Asp Tyr Leu Ser
1               5                   10

<210> SEQ ID NO 417
<211> LENGTH: 7
<212> TYPE: PRT
<213> ORGANISM: Rattus norvegicus

<400> SEQUENCE: 417

Asp Ala Thr Ser Leu Ala Asp
1               5

<210> SEQ ID NO 418
<211> LENGTH: 9
<212> TYPE: PRT
<213> ORGANISM: Rattus norvegicus

<400> SEQUENCE: 418

Leu Gln Ser Tyr Ser Thr Pro Trp Thr
1               5

<210> SEQ ID NO 419
<211> LENGTH: 249
<212> TYPE: PRT
<213> ORGANISM: Homo sapiens
```

```
<400> SEQUENCE: 419

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
            85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
            195                 200                 205

Glu Leu Thr Val Ser Phe Thr Asn Lys Val Phe Thr Thr Glu Thr Ser
210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn
                245

<210> SEQ ID NO 420
<211> LENGTH: 246
<212> TYPE: PRT
<213> ORGANISM: Mus musculus

<400> SEQUENCE: 420

Gln Ser Gly Pro Leu Pro Lys Pro Ser Leu Gln Ala Gln Pro Ser Ser
1               5                   10                  15

Leu Val Pro Leu Gly Gln Ser Val Ile Leu Arg Cys Gln Gly Pro Pro
            20                  25                  30

Asp Val Asp Leu Tyr Arg Leu Glu Lys Leu Lys Pro Glu Lys Tyr Glu
        35                  40                  45

Asp Gln Asp Phe Leu Phe Ile Pro Thr Met Glu Arg Ser Asn Ala Gly
    50                  55                  60

Arg Tyr Arg Cys Ser Tyr Gln Asn Gly Ser His Trp Ser Leu Pro Ser
65                  70                  75                  80

Asp Gln Leu Glu Leu Ile Ala Thr Gly Val Tyr Ala Lys Pro Ser Leu
            85                  90                  95

Ser Ala His Pro Ser Ser Ala Val Pro Gln Gly Arg Asp Val Thr Leu
            100                 105                 110
```

```
Lys Cys Gln Ser Pro Tyr Ser Phe Asp Glu Phe Val Leu Tyr Lys Glu
            115                 120                 125

Gly Asp Thr Gly Ser Tyr Lys Arg Pro Glu Lys Trp Tyr Arg Ala Asn
130                 135                 140

Phe Pro Ile Ile Thr Val Thr Ala Ala His Ser Gly Thr Tyr Arg Cys
145                 150                 155                 160

Tyr Ser Phe Ser Ser Ser Pro Tyr Leu Trp Ser Ala Pro Ser Asp
                165                 170                 175

Pro Leu Val Leu Val Val Thr Gly Leu Ser Ala Thr Pro Ser Gln Val
            180                 185                 190

Pro Thr Glu Glu Ser Phe Pro Val Thr Glu Ser Ser Arg Arg Pro Ser
            195                 200                 205

Ile Leu Pro Thr Asn Lys Ile Ser Thr Thr Glu Lys Pro Met Asn Ile
210                 215                 220

Thr Ala Ser Pro Glu Gly Leu Ser Pro Pro Gly Phe Ala His Gln
225                 230                 235                 240

His Tyr Ala Lys Gly Asn
                245

<210> SEQ ID NO 421
<211> LENGTH: 248
<212> TYPE: PRT
<213> ORGANISM: Rattus norvegicus

<400> SEQUENCE: 421

Gln His Gly Pro Leu Pro Lys Pro Ser Leu Gln Ala Gln Pro Ser Ser
1               5                   10                  15

Leu Val Pro Leu Gly His Pro Val Thr Leu Arg Cys Leu Gly Pro Ser
            20                  25                  30

Asp Ala Asp Leu Tyr Arg Leu Glu Lys Val Lys Pro Gly Lys Leu Ile
            35                  40                  45

Phe Ile Asp Gln Asp Phe Leu Phe Ile Pro Ile Met Glu Ile Asn Asn
50                  55                  60

Ala Gly Arg Tyr Arg Cys Ser Tyr Gln Asn Glu Ser His Trp Ser Leu
65                  70                  75                  80

Pro Ser Asp Gln Leu Glu Leu Ile Ala Thr Gly Val Tyr Ser Lys Pro
            85                  90                  95

Ser Leu Ser Ala His Pro Ser Ala Ile Pro Pro Gly Arg Asp Val
            100                 105                 110

Thr Leu Lys Cys Gln Ser Gln Tyr Ser Phe Asp Glu Phe Val Leu Tyr
            115                 120                 125

Lys Glu Gly Asp Thr Arg Pro Tyr Lys Arg Pro Glu Lys Trp Tyr Arg
            130                 135                 140

Ala Asn Phe Pro Val Ile Thr Val Thr Ala Ala His Ser Gly Thr Tyr
145                 150                 155                 160

Arg Cys Tyr Ser Phe Ser Ser Ser Pro Tyr Leu Trp Ser Ala Pro
                165                 170                 175

Ser Asp Pro Leu Val Val Val Thr Gly Pro Ser Ala Thr Pro Ser
            180                 185                 190

Gln Val Pro Thr Glu Val Pro Ser Pro Met Thr Glu Ala Ser Arg Arg
            195                 200                 205

Pro Ser Met Leu Leu Thr Asn Lys Ile Ser Thr Thr Glu Lys Pro Met
210                 215                 220
```

```
Asn Ile Thr Val Ser Pro Glu Gly Pro Ser Pro Phe Gly Phe Ala
225                 230                 235                 240

His Gln His Tyr Ala Lys Gly Asn
                245
```

<210> SEQ ID NO 422
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

```
Gln Val Gln Leu Gln Gln Ser Gly Pro Glu Leu Val Arg Pro Gly Glu
1               5                   10                  15

Ser Val Lys Ile Ser Cys Lys Gly Ser Gly Tyr Thr Phe Thr Asp Tyr
                20                  25                  30

Ala Ile His Trp Val Lys Leu Ser His Ala Lys Ser Leu Glu Trp Ile
            35                  40                  45

Gly Val Ile Ser Ile Tyr Tyr Asp Asp Thr Asn Tyr Asn Gln Lys Phe
        50                  55                  60

Lys Gly Lys Ala Thr Met Thr Val Asp Lys Ser Ser Thr Ala Tyr
65                  70                  75                  80

Leu Glu Leu Ala Arg Leu Thr Ser Glu Asp Ser Ala Ile Tyr Tyr Cys
                85                  90                  95

Ala Arg Arg Arg Asp Ser Ser Gly Pro Tyr Ala Met Asp Tyr Trp Gly
                100                 105                 110

Gln Gly Thr Ser Val Thr Val Ser Ser
            115                 120
```

<210> SEQ ID NO 423
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Asp Tyr
                20                  25                  30

Ala Ile His Trp Val Arg Gln Pro Pro Gly Arg Gly Leu Glu Trp Ile
            35                  40                  45

Gly Val Ile Ser Ile Tyr Tyr Asp Asp Thr Asn Tyr Asn Gln Lys Phe
        50                  55                  60

Lys Gly Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Arg Arg Asp Ser Ser Gly Pro Tyr Ala Met Asp Tyr Trp Gly
                100                 105                 110

Gln Gly Ser Leu Val Thr Val Ser Ser
            115                 120
```

```
<210> SEQ ID NO 424
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Gln Val Gln Leu Val Glu Ser Gly Ala Gly Val Lys Lys Pro Ser Ser
1               5                   10                  15

Thr Leu Ser Val Thr Cys Thr Ala Ser Gly Gly Thr Phe Ser Asp Tyr
            20                  25                  30

Ala Ile His Trp Val Arg Gln Ala Pro Gly Gln Gly Leu Glu Trp Met
        35                  40                  45

Gly Val Ile Ser Ile Tyr Tyr Asp Asp Thr Asn Tyr Asn Gln Lys Phe
    50                  55                  60

Lys Gly Arg Val Thr Ile Leu Ala Asp Glu Ser Thr Asn Gln Phe Ser
65                  70                  75                  80

Met Arg Leu Ser Ser Val Arg Ala Ala Asp Thr Ala Phe Tyr Phe Cys
                85                  90                  95

Ala Gly Arg Arg Asp Ser Ser Gly Pro Tyr Ala Met Asp Tyr Glu Tyr
            100                 105                 110

Asn Gly Gly Leu Val Thr Val Ser Ser
        115                 120

<210> SEQ ID NO 425
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Gln Val Gln Leu Val Glu Ser Gly Ala Gly Val Lys Lys Pro Ser Ser
1               5                   10                  15

Thr Leu Ser Val Thr Cys Thr Ala Ser Gly Gly Thr Phe Ser Asp Tyr
            20                  25                  30

Ala Ile His Trp Val Arg Gln Ala Pro Gly Gln Gly Leu Glu Trp Met
        35                  40                  45

Gly Val Ile Ser Ile Tyr Tyr Asp Asp Thr Asn Tyr Asn Gln Lys Phe
    50                  55                  60

Lys Gly Lys Ala Thr Ile Leu Ala Asp Glu Ser Thr Asn Gln Phe Ser
65                  70                  75                  80

Met Arg Leu Ser Ser Val Arg Ala Ala Asp Thr Ala Ile Tyr Tyr Cys
                85                  90                  95

Ala Arg Arg Arg Asp Ser Ser Gly Pro Tyr Ala Met Asp Tyr Trp Gly
            100                 105                 110

Gln Gly Thr Leu Val Thr Val Ser Ser
        115                 120

<210> SEQ ID NO 426
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 426

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Asn
                85                  90                  95

Glu Asp Pro Tyr Thr Phe Gly Gln Gly Thr Lys Val Glu Ile Lys Arg
            100                 105                 110

Thr Asp Ala Ala
        115

<210> SEQ ID NO 427
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

Thr Asp Ala Ala
        115

<210> SEQ ID NO 428
<211> LENGTH: 249
<212> TYPE: PRT
<213> ORGANISM: Homo sapiens

<400> SEQUENCE: 428

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
50                  55                  60
```

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn
                245

<210> SEQ ID NO 429
<211> LENGTH: 231
<212> TYPE: PRT
<213> ORGANISM: Macaca fascicularis

<400> SEQUENCE: 429

Gln Arg Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg His Leu Ala Gly
        50                  55                  60

Arg Tyr Arg Cys Ser Tyr Gln Asn Gly Ser Leu Trp Ser Pro Ser Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
130                 135                 140

Phe Pro Ile Ile Thr Val Thr Ala Ala His Ser Gly Thr Tyr Arg Cys
145                 150                 155                 160

Tyr Ser Phe Ser Ser Gly Asp Pro Tyr Leu Trp Ser Ala Pro Ser Asp
                165                 170                 175

Pro Leu Glu Leu Met Val Thr Glu Phe Ser Glu Ala Thr Thr Glu Leu
            180                 185                 190

-continued

```
Thr Val Ser Leu Thr Asn Lys Val Phe Thr Thr Glu Thr Ser Arg Ser
        195                 200                 205

Ile Thr Ala Ser Pro Lys Glu Pro Gly Ser Pro Ala Gly Pro Ala Arg
        210                 215                 220

Gln Tyr Tyr Thr Lys Gly Asn
225             230
```

ANTI-PLATELET MEMBRANE GLYCOPROTEIN VI MONOCLONAL ANTIBODY

CROSS-REFERENCE TO RELATED APPLICATIONS

This application is a Divisional of U.S. application Ser. No. 11/912,757, now U.S. Pat. No. 7,977,461 which issued Jul. 12, 2011, which is the U.S. National Stage application of PCT/JP2006/309431, filed Apr. 28, 2006, and which was published in Japanese as WO 2006/118350 on Nov. 9, 2006; which claims priority from Japanese patent applications JP 2005-132665, filed Apr. 28, 2005, and JP 2005-348534, filed Dec. 1, 2005, and is a Continuation of International Application PCT/JP2006/301818, filed Jan. 27, 2006. The entire contents of each of the aforementioned applications are incorporated herein by reference.

In addition, a nucleotide and/or amino acid sequence listing is incorporated by reference of the material on computer readable form (via EFS-Web; "sequence.txt" 242 KB).

TECHNICAL FIELD

The present invention relates to an antibody to platelet membrane glycoprotein VI (hereinafter, sometimes abbreviated as GPVI) and a recognition region of the antibody.

BACKGROUND ART

The platelet plays a very important role in the clot formation and the biophylaxis, and its concerning in various clinical conditions is being elucidated from the physiological role. In particular, it is remarkable about the function that the platelet forms a hemostatic plug. For example, when the vascular endothelial cell suffers damage, the collagen that is the major matrix protein of the subcutaneous vascular endothelium is exposed and the platelet adheres thereto. Next, the platelet is activated by the signal from the collagen and when finally, the platelet agglutinates through the fibrinogen. Then, since this fact causes morbidity such as thromboembolic disease depending on the situation, it is remarkable as a target for therapy.

In the past, for the purpose of the treatment and the prevention of the thrombosis based on the platelet aggregation, an anti-platelet agent such as aspirin, ticlopidine, GPIIb/IIIa antagonist and the like has been used. However, a lot of problems are pointed out from the aspect of the effectiveness and the side effects such as bleeding. Therefore, the excellent platelet inhibitor having the enough safety and the sure and appropriate function without the above-mentioned problems is desired to arrive.

GPVI that is present on the platelet membrane is the collagen receptor of the platelet, and it has been elucidated that the GPVI plays a central role for an activation of the platelet by collagen stimulation (see, Hiroshi Takayama, The Japanese Journal of Thrombosis and Hemostasis, 2003, volume 14, No. 2, pp. 75-81). That is, Sugiyama et al. has been reported that the membrane protein of 62 kDa is specifically depleted in the platelet of a patient with autoimmune thrombocytopenia and the platelet aggregation by collagen cannot be detected (see, Tateo Sugiyama and five other members, Blood (USA), 1987, volume 69, No. 6, pp. 1712-1720), and further that the protein that has been deleted in the platelet of the patient is GPVI and the Fab fragment of the antibody purified from the serum of the patient suppresses a collagen-induced platelet aggregation (see, Tateo Sugiyama and five other members, Blood (USA), 1987, volume 69, No. 6, pp. 1712-1720, and Masaaki Moroi and three other members, The Journal of Clinical Investigation (USA), 1989, volume 84, No. 5, pp. 1440-1445).

So far, Sugiyama et al. (see, Tateo Sugiyama and five other members, Blood (USA), 1987, volume 69, No. 6, pp. 1712-1720) and Takahashi et al. (see, Hoyu Takahashi and one other member, American Journal of Hematology (USA), 2001, volume 67, No. 4, pp. 262-267) have been reported about the anti-human GPVI autoantibody derived from the patient with autoimmune disease. However, since, according to the report by Sugiyama et al., the anti-human GPVI autoantibody purified from the patient's plasma has a function to induce platelet aggregation, it cannot be applied for medicaments immediately. Takahashi et al. (Hoyu Takahashi and one other member, American Journal of Hematology (USA), 2001, volume 67, No. 4, pp. 262-267) describes that an autoantibody to the protein of ca. 62 kDa that is speculated to be GPVI is present, and that this antibody induces a platelet aggregation. In addition, to apply these anti-GPVI antibodies derived from the patient clinically as a medicament, the antibody with high safety must be produced in quantities in stable quality. However, the method of producing industrially is not yet established.

The anti-GPVI antibody, which has been prepared by the present, includes a monoclonal rat antibody to mouse GPVI (see, Publication number 1228768 of the European Patent Application) and a monoclonal mouse antibody to human GPVI (see, Publication number 01/00810 of International Patent Application and Publication number 02/080968 of International Patent Application, Thromb Haemost. 2003 June; 89(6): 996-1003).

In addition, human single-stranded antibody (scFv: single chain Fv) that recognizes human GPVI has been prepared using the phage display method (see, Publication number 01/00810 of International Patent Application, Publication number 02/080968 of International Patent Application, and Peter A Smethurst and 15 other members, Blood (USA), 2002, volume 100, number 11, p. 474a). These single-stranded antibodies are the antibody that combines heavy chain variable region (VH) and light chain variable region (VL) of the human antibody by the peptide linker and has a variable region derived from the human. However, compared with normal immunoglobulin that the cell produces, it generally possesses a low affinity to an antigen thereof and is short in the half-life in vivo, too. Further, Smethurst analyzed an epitope on GPVI in the term of clone 10B12 that suppresses platelet aggregation among the single-stranded antibodies, and suggested that lysine at the 59th position (Lys59) has a possibility to involve (Hoyu Takahashi and one other member, American Journal of Hematology (USA), 2001, volume 67, No. 4, pp. 262-267; and Peter A Smethurst and 15 other members, Blood (USA), 2002, volume 100, number 11, p. 474a).

As described above, most of the antibodies to human GPVI that have been reported until now, including the aforementioned human autoantibody, possess an activity of activating the platelet only by the antibody in vitro, and/or an activity of inducing or enhancing platelet aggregation. Thus, when administering the same in vivo, a probability to cause thrombocytopenia is considered. In fact, Nieswandt et al. has reported several monoclonal antibodies (JAQ1, JAQ2 and JAQ3) that deplete GPVI on the platelet in vivo. All antibodies caused thrombocytopenia after administration.

Recently, there have been reported that collagen, the agonist for GPVI, convulxin and CRP, and an antibody (9012.2) that inhibits the binding of collagen to GPVI activate the platelet, followed by, a shedding of GPVI from the platelet occurs by metalloprotease-mediated cleavage (Stephens G and four other members, Blood, 2005, 105(1): 186-191; Gardiner E E and four other members, Blood, 2004, 104: 3611-3617; Bergmeier W and six other members, Thromb Haemost., 2004, 91: 951-958). Further, the prediction of the amino acid residues on GPVI associated with the interaction with collagen (Val34, Leu36) was performed using the 9012.2 antibody, etc. (Lecut C and seven other members, J Biol Chem, 2004, 279: 52293-52299).

In addition, Takayama et al. cloned anti-human GPVI antibodies using lymphocytes from the patient with autoimmune disease, and investigated about the feature of the antibodies in vitro (Publication number 05/007800 of International Patent Application).

However, in all reports that have been published until now, no antibody having the activity to deplete GPVI on the platelet membrane without activating the platelet and/or without inducing thrombocytopenia in vivo has been disclosed.

DISCLOSURE OF THE INVENTION

In the context of requirement for a medicament that has high safety and excellent efficacy, and is easy-to-use as an anti-platelet agent as described above, an anti-GPVI antibody applicable in vivo is desired.

The present invention intends to provide a novel antibody that specifically binds to GPVI, which is the glycoprotein that exists on a platelet such as a mammalian platelet, specifically a platelet from human, monkey, rat or mouse, especially the human platelet membrane, preferably a monoclonal antibody. Particularly, there is provided the anti-GPVI antibody that is applicable in vivo, has efficacy and no problem in the aspect of side effects such as thrombocytopenia. Also, the invention provides the antibody that specifically binds to GPVI, especially human GPVI and comprises a novel CDR sequence. Moreover, the cell that produces these antibodies is provided.

To solve the above-mentioned problems, the inventors have conceived of establishing a lot of mouse hybridomas that produce an antibody to GPVI and analyzing properties of the antibodies produced by the hybridomas. Based on the conception, the present inventors have made extensive investigations and have succeeded to obtain the hybridomas that produce the antibody having a binding ability to GPVI and an activity for decreasing the collagen-induced platelet aggregation. Then the inventors further analyzed recognition region on GPVI of each antibody to obtain useful information about epitope of GPVI. As a result of further investigation after isolating the clones, the inventors succeeded in obtaining a gene encoding the antibody. In addition, it was found that the amino acid sequence of CDR of the antibody is a novel one. Moreover, the inventors have completed the present invention by preparing recombinant antibodies using gene recombination technology.

In addition, throughout the specification, an antibody that is produced by a hybridoma, e.g. clone F1232-18 is sometimes referred to as F1232-18 antibody.

The first embodiment of the present invention is an antibody which exhibits a specific function or feature, and specifically binds to GPVI such as a mammalian GPVI, specifically GPVI from human, monkey, rat or mouse, especially the human GPVI, preferably a monoclonal antibody (hereinafter, sometimes referred to as anti-human GPVI antibody and anti-human GPVI monoclonal antibody, respectively), its active fragment, or derivatives thereof. Specifically, it includes as follows.

(1) An antibody having the following features, its active fragment, or derivatives thereof:
a) It specifically binds to GPVI, especially human platelet membrane glycoprotein VI (GPVI);
b) The action to activate a platelet and/or the action to induce a thrombocytopenia in vivo are weak; and
c) It at least partially depletes GPVI on the platelet membrane by contacting with a platelet.
(2) An anti-GPVI antibody, its active fragment, or derivatives thereof which at least partially depletes GPVI on the platelet membrane by contacting with a platelet without shedding of platelet GPVI, especially, shedding of platelet GPVI by methalloprotease-mediated cleavage accompanying platelet activation, especially an antibody having the features of (1) above, its active fragment, or derivatives thereof.
(3) An anti-GPVI antibody, its active fragment, or derivatives thereof which at least partially depletes GPVI on the platelet membrane via internalization of the platelet GPVI.
(4) The antibody of (1) to (3), its active fragment, or derivatives thereof which at least partially depletes GPVI on the platelet membrane via internalization of the platelet GPVI.
(5) The antibody of (1) to (4), its active fragment or derivatives thereof, which at least partially depletes GPVI on the platelet membrane by contacting with a platelet in vivo.
(6) The antibody of (1) to (5), its active fragment or derivatives thereof, which decreases or deletes an ability of platelet to aggregate responsive to collagen by contacting with a platelet by administered in vivo.
(7) The antibody of (1) to (6), its active fragment, or derivatives thereof, wherein its action to prolong bleeding time is weak.
(8) The antibody of (1) to (7), its active fragment or derivatives thereof, wherein the dissociation constant with GPVI is equal to or less than $4 \times 10^{-8}$ M.

The antibody of the aforementioned (1) to (8) is preferably an antibody which does not induce human platelet aggregation solely. Adequate examples of the antibody include antibody clones listed in Tables 6 and 11, preferably an antibody that recognizes loop 9 of GPVI, or a chimeric antibody or a humanized antibody, wherein the above antibody is recombined with human IgG, more preferably human IgG4. Further, the antibody of the present invention is an antibody, wherein the dissociation constant (Kd value) between GPVI, especially human GPVI and the antibody is preferably equal to or less than $10^{-8}$ M, more preferably equal to or less than $4 \times 10^{-9}$ M. The antibody, its active fragment or derivatives thereof of the present invention encompass, as long as they have a binding ability to GPVI, for example, a chimeric antibody and a humanized antibody, Fab (Fragment of antigen binding), Fab', F(ab')$_2$, a single-chain antibody (scFv), a disulfide stabilized antibody (dsFv), diabody, nanobody and a peptide comprising CDR, and a labeled antibody, a conjugated antibody and a antibody-fused protein, etc.

Moreover, the antibody of the first embodiment of the present invention, or the like, is preferably an antibody which specifically binds to GPVI such as a mammalian GPVI, specifically GPVI from human, monkey, rat or mouse, especially the human GPVI and specifically decreases platelet aggregability against collagen, but has no effect on the aggregability against other agonists, e.g. ADP or thrombin. Preferably, the antibody cannot induce human platelet aggregation solely. The antibody cannot significantly induce human platelet aggregation solely in the concentration or the dosage equivalent to those, preferably 10-fold, more preferably 100-fold, further preferably 1000-fold of those, in which it suppresses collagen-induced human platelet aggregation.

Herein, the antibody of the aforementioned (1) to (8) may be an antibody which inhibits the binding of GPVI, especially human GPVI to collagen as long as it has its properties, preferably an antibody which inhibits the binding of GPVI, especially human GPVI to collagen with the dissociation constant (Kd) equal to or less than $10^{-8}$ M, more preferably equal to or less than $10^{-9}$ M, further preferably equal to or less than $10^{-10}$ M.

The antibody of the present invention is not necessarily limited to the specific clone, and the antibody having a similar function to that of the preferred examples of the present invention (or antibody, etc.) is encompassed within the scope of the present invention. The existence or non-existence of the function of the antibody of the present invention can be confirmed by the method shown in Examples or the publicly known method.

In addition, an antibody, wherein its recognition region, binding site or epitope on GPVI is the same or at least partially common to those of the preferred antibody of the present invention, for example, an antibody which competes with each other for binding with GPVI, is included within the scope of the present invention. Whether an antibody has a commonality in recognition region or binding site with the antibody of the present invention or not can be confirmed according to the method described in EXAMPLES or by publicly known methods. That is, the present invention provides an antibody which competes with a specified antibody of the present invention for GPVI binding. In the classification based on the competition experiment in EXAMPLES of the present invention, antibodies classified into eight groups in Table 1, preferably groups d, e or h, more preferably group d or e are exemplified as the antibody of the present invention. Preferred examples of the antibody of (1) to (8) aforementioned include an antibody that recognizes at least a part of loop 9 of GPVI, especially human GPVI.

The second embodiment of the present invention is an anti-GPVI antibody which is defined by novel recognition region, binding site or epitope on GPVI such as mammalian GPVI, specifically GPVI from human, monkey, rat or mouse, especially human GPVI, preferably a monoclonal antibody. Specifically, it includes:

(9) An antibody, its active fragment or derivatives thereof, which specifically recognizes an amino acid sequence or a structure on the GPVI comprising at least a part of loop 2, loop 3 and loop 5, or loop 4 and loop 5 in GPVI, especially human GPVI domain 1, or loop 9, or loop 9 and loop 11 in domain 2, preferably loop 9, or loop 9 and loop 11 in domain 2 or loop 2 in domain 1, more preferably loop 9, or loop 9 and loop 11 in domain 2, further preferably loop 9 in domain 2;

(10) The antibody of (9), its active fragment or derivatives thereof, wherein at least a part of loop 2, loop 3 and loop 5, or loop 4 and loop 5 in GPVI domain 1, or loop 9, or loop 9 and loop 11 in domain 2 are E21, K22 and P23 of loop 2 of the human GPVI, G33 of loop 3 and A57, K59 and L62 of loop 5, or S43, S44, S45, R46, and E48 of loop 4 and A57, K59 and L62 of loop 5, or T116, R117, G119 and Q122 of loop 9 or T116, R117, G119, and Q122 of loop 9 and R139 of loop 11;

(11) The antibody of (9) or (10), its active fragment or derivatives thereof, which specifically binds to loop 2, loop 3 and loop 5, or loop 4 and loop 5 in GPVI, especially human GPVI domain 1, or loop 9, or loop 9 and loop 11 in domain 2, preferably loop 9, or loop 9 and loop 11 in domain 2 or loop 2 in domain 1, more preferably loop 9, or loop 9 and loop 11 in domain 2, further preferably loop 9 in domain 2; more preferably,

(12) The antibody of (1) to (8), its active fragment or derivatives thereof, which recognizes an amino acid sequence or a structure on the GPVI comprising at least a part of loop 2, loop 3 and loop 5, or loop 4 and loop 5 in GPVI, especially human GPVI domain 1, or loop 9, or loop 9 and loop 11 in domain 2, preferably loop 9, or loop 9 and loop 11 in domain 2 or loop 2 in domain 1, more preferably loop 9, or loop 9 and loop 11 in domain 2, further preferably loop 9 in domain 2;

(13) The antibody of (1) to (8), its active fragment or derivatives thereof, which specifically recognizes an amino acid sequence or a structure on the GPVI comprising E21, K22 and P23 of loop 2, G33 of loop 3 and A57, K59 and L62 of loop 5, or S43, S44, S45, R46, and E48 of loop 4 and A57, K59 and L62 of loop 5, or T116, 8117, G119 and Q122 of loop 9 or T116, R117, G119, and Q122 of loop 9 and R139 of loop 11; and

(14) The antibody of (1) to (8), its active fragment or derivatives thereof, which specifically binds to loop 2, loop 3 and loop 5, or loop 4 and loop 5 in GPVI, especially human GPVI domain 1, or loop 9, or loop 9 and loop 11 in domain 2, preferably loop 9, or loop 9 and loop 11 in domain 2 or loop 2 in domain 1, more preferably loop 9, or loop 9 and loop 11 in domain 2, further preferably loop 9 in domain 2.

Herein, at least a part of each loop described above is, for example, the residues, which are different from the corresponding amino acid residues of heterogeneous GPVI such as monkey, mouse or rat GPVI. A modeling structure of GPVI such as human GPVI is presumable by the method described in EXAMPLES. A position of each loop structure is shown in FIGS. 1, 3 and 47. Among the abovementioned loops, loop 9, or loop 9 and loop 11 in domain 2 and loop 2 in domain 1, preferably loop 9, loop 9 and loop 11 in domain 2, further preferably loop 9 in domain 2 are important as a recognition region of the antibody of the present invention, and the antibody which can recognize the region is preferred. Preferred examples are an antibody listed in Tables 6 and 11, or a chimeric or humanized antibody which is recombined with human IgG, more preferably human IgG4.

The antibody of the second embodiment of the present invention can be classified or can be confirmed as for its binding region by the binding property with the peptide of the eighth embodiment of the present invention and/or the polypeptide of the ninth embodiment of the present invention. That is, the present invention provides an anti-GPVI antibody which has a distinct binding property, preferably a decreased binding property with the specified substance among the peptide of the eighth embodiment of the present invention and/or the polypeptide of the ninth embodiment of the present invention. Specifically, it is an anti-GPVI antibody which has a binding property with the specified GPVI mutant significantly different from that with human GPVI and/or other GPVI mutants, preferably a decreased binding property. Specific examples of the method of confirmation, polypeptides to be used, preferred classification and preferred antibodies are illustrated in EXAMPLES. An antibody of the present invention is not necessarily limited regarding its antigen-binding valency and may be a monovalent antibody such as Fab or scFv. From the aspect of stability in vivo, especially in the blood, and/or binding property to GPVI or strength of action, preferred is a multivalent antibody having two or more valencies, e.g., a divalent, trivalent, tetravalent or decavalent antibody; a divalent antibody is more preferable. Accordingly, in the second embodiment of the present invention, a monovalent antibody and a polyvalent antibody having two or more valency which recognizes a specific region, especially loop 9 on GPVI, such as a divalent, trivalent, tetravalent or decavalent antibody; preferably a divalent antibody can be provided. Herein, examples of tetravalent antibody include IgA, and examples of decavalent antibody include IgM. However, they are not limited to these examples. Further, a trivalent antibody does not phisologically exit. However, by chemically or through genetic engineering binding a natural or synthetic peptide having an intrinsic trimerization property such as the domain of tenascin molecule (AA 110-139, Swissprot #P10039 (chicken) or Swissprot #P24821 (human)) to a monovalent antibody (scFv or Fab and so on), a trivalent antibody can be prepared (see, JP 2004-508828 publication). In addition, the antibody of the second embodiment of the invention is preferably an antibody which exhibits a specific function or property of the antibody of the first embodiment.

The third embodiment of the present invention is an anti-GPVI antibody which comprises a novel amino acid sequence of CDR or variable region, preferably a chimeric antibody which is recombined with human IgG, especially human IgG4, more preferably a CDR grafted antibody, especially a humanized antibody. Specifically, it includes:

(15) An anti-GPVI antibody, its active fragment or derivatives thereof, wherein at least three CDR of either H-chain or L-chain in the antibody, preferably six CDR of both H-chain and L-chain in the antibody comprises an amino acid sequence of CDR in the clones listed in Tables 8, 9, 12 and 13, preferably an antibody which recognizes loop 9 of GPVI as an amino acid sequence of the corresponding CDR;

(16) A heavy chain of anti-GPVI antibody, its active fragment, or derivatives thereof, wherein the amino acid sequences of SEQ ID NOs: 15, 16, and 17, the amino acid sequences of SEQ ID NOs: 18, 19, and 20, the amino acid sequences of SEQ ID NOs: 21, 22, and 23, the amino acid sequences of SEQ ID NOs: 24, 25, and 26, the amino acid sequences of SEQ ID NOs: 27, 28, and 29, the amino acid sequences of SEQ ID NOs: 30, 31, and 32, the amino acid sequences of SEQ ID NOs: 33, 34, and 35, the amino acid sequences of SEQ ID NOs: 36, 37, and 38, the amino acid sequences of SEQ ID NOs: 39, 40, and 41, the amino acid sequences of SEQ ID NOs: 42, 43, and 44, the amino acid sequences of SEQ ID NOs: 45, 46, and 47, or the amino acid sequences of SEQ ID NOs: 48, 49, and 50, or VH CDR1, VH CDR2, and VH CDR3 of any clone listed in Table 12 are comprised in VH CDR1, VH CDR2, and VH CDR3, respectively;

(17) A light chain of anti-GPVI antibody, its active fragment, or derivatives thereof, wherein the amino acid sequences of SEQ ID NOs: 51, 52 and 53, the amino acid sequences of SEQ ID NOs: 54, 55 and 56, the amino acid sequences of SEQ ID NOs: 57, 58 and 59, the amino acid sequences of SEQ ID NOs: 60, 61 and 62, the amino acid sequences of SEQ ID NOs: 63, 64 and 65, the amino acid sequences of SEQ ID NOs: 66, 67 and 68, the amino acid sequences of SEQ ID NOs: 69, 70 and 71, the amino acid sequences of SEQ ID NOs: 72, 73 and 74, the amino acid sequences of SEQ ID NOs: 75, 76 and 77, the amino acid sequences of SEQ ID NOs: 78, 79 and 80, the amino acid sequences of SEQ ID NOs: 81, 82 and 83, or the amino acid sequences of SEQ ID NOs: 84, 85 and 86, or VL CDR1, VL CDR2, and VL CDR3 of any clone listed in Table 13 are comprised in VL CDR1, VL CDR2 and VL CDR3, respectively;

(18) An anti-GPVI antibody, its active fragment, or derivatives thereof, wherein the amino acid sequences of SEQ ID NOs: 15, 16, 17, 51, 52 and 53, the amino acid sequences of SEQ ID NOs: 18, 19, 20, 54, 55 and 56, the amino acid sequences of SEQ ID NOs: 21, 22, 23, 57, 58 and 59, the amino acid sequences of SEQ ID NOs: 24, 25, 26, 60, 61 and 62, the amino acid sequences of SEQ ID NOs: 27, 28, 29, 63, 64 and 65, the amino acid sequences of SEQ ID NOs: 30, 31, 32, 66, 67 and 68, the amino acid sequences of SEQ ID NOs: 33, 34, 35, 69, 70 and 71, the amino acid sequenced of SEQ ID NOs: 36, 37, 38, 72, 73 and 74, the amino acid sequences of SEQ ID NOs: 39, 40, 41, 75, 76 and 77, the amino acid sequences of SEQ ID NOs: 42, 43, 44, 78, 79 and 80, the amino acid sequences of SEQ ID NOs: 45, 46, 47, 81, 82 and 83, or the amino acid sequences of SEQ ID NOs: 48, 49, 50, 84, 85 and 86, or VH CDR1, VH CDR2, VH CDR3, VL CDR1, VL CDR2, and VL CDR3 of any clone listed in Tables 12 and 13 are comprised in VH CDR1, VH CDR2, VH CDR3, VL CDR1, VL CDR2 and VL CDR3, respectively;

(19) An anti-GPVI antibody, their active fragments or derivatives thereof, wherein at least variable region of either H-chain or L-chain in the antibody, preferably variable regions of both H-chain and L-chain in the antibody comprises an amino acid sequence of variable region in the clones listed in Table 7 or Table 14, preferably an antibody which recognizes loop 9 of GPVI as an amino acid sequence of the corresponding variable regions, especially a chimeric antibody which is recombined with human IgG, preferably human IgG4. The antibody of the third embodiment of the present invention is preferably an antibody which possesses characteristics and/or specificity for recognition region of the antibody of the first and/or the second embodiment.

The fourth embodiment of the present invention is a polynucleotide or nucleic acid which comprises the base sequence encoding at least three CDR of either H-chain or L-chain, preferably six CDR of both H-chain and L-chain, or variable region in the antibody of the first to the third embodiments, its active fragment or derivatives thereof. Specifically, it includes:

(20) A polynucleotide which comprises the base sequence encoding H-chain and/or L-chain of the antibody of the first to the third embodiments, its active fragment or derivatives thereof;

(21) The polynucleotide of (20) which comprises the base sequence encoding the corresponding CDR in the clones listed in Tables 8 and 9, or Tables 12 and 13, preferably an antibody which recognizes loop 9 of GPVI as the base sequence encoding at least three CDR of either H-chain or L-chain in the antibody, preferably six CDR of both H-chain and L-chain in the antibody;

(22) A polynucleotide which comprises the base sequence encoding the corresponding variable region in the gene of any clone, preferably an antibody which recognizes loop 9 of GPVI, listed in Tables 7 and 14, as the base sequence encoding at least variable region of either H-chain or L-chain in the antibody, preferably variable regions of both H-chain and L-chain in the antibody;

(23) A polynucleotide comprising the base sequence having SEQ ID NO: 280 and encoding variable region of the H-chain and the base sequence having SEQ ID NO: 284 and encoding variable region of the L-chain, and a polynucleotide comprising the base sequence having SEQ ID NO: 282 and encoding variable region of the H-chain and the base sequence having SEQ ID NO: 284 and encoding variable region of the L-chain.

Further, the present invention provides an anti-human GPVI antibody gene, or its heavy chain or light chain variable region gene thereof, which is derived from an antibody gene comprising a combination of specific mouse germ-line antibody gene segments. That is,

(24) An anti-human GPVI antibody gene, or a heavy chain variable region gene thereof, which is derived from an antibody heavy chain gene comprising any combination of mouse germ-line antibody gene segments $V_H$, $D_H$ and $J_H$ listed in Table 16.

(25) An anti-human GPVI antibody gene, or a heavy chain variable region gene thereof, comprising a nucleotide sequence encoding CDR amino acid sequence in the aforementioned antibody heavy chain variable gene.

(26) An anti-human GPVI antibody gene, or a light chain variable region gene thereof, which is derived from an antibody light chain gene comprising any combination of mouse germ-line antibody gene segments $V_L$ and $J_L$ listed in Table 16.

(27) An anti-human GPVI antibody gene, or a light chain variable region gene thereof comprising a nucleotide sequence encoding CDR amino acid sequence in the aforementioned antibody light chain variable gene.

Herein, among the mouse germ-line antibody gene segments listed in Table 16, a combination of segments having a high score indicated on the first line of each antibody clones, for example, a combination of $V_H$ (3:3.9), $D_H$ (DSP2.7 or DSP2.5) and $J_H$ (JH4) in the heavy chain gene of clone F1246-1-1 is preferred. Further, a gene derived from the above-mentioned antibody gene includes the antibody gene itself or a gene with mutation in one base or more as long as an antibody encoded by the gene exhibits a similar antigen-binding specificity. In addition, both of naturally occurring or artificially introduced mutations may be acceptable. At the same time as the above, the present invention provides an antibody, its active fragment or derivatives thereof, encoded by the anti-human GPVI antibody gene or its heavy chain or light chain variable region gene, which is derived from an antibody gene comprising a combination of specific mouse germ-line antibody gene segments. That is,

(28) An anti-human GPVI antibody or its heavy chain variable region polypeptide encoded by the antibody gene or its heavy chain variable region gene of (24) to (25).

(29) An anti-human GPVI antibody or its light chain variable region polypeptide encoded by the antibody gene or its light chain variable region gene of (26) to (27).

In addition, the present invention provides an anti-GPVI antibody, especially anti-human GPVI antibody, specifically, the above-mentioned antibody of the present invention, preferably the antibody recognizing loop 9 of GPVI, or its active fragment or derivatives thereof, which is polyethyleneglycolated (PEGylated). The method for PEGylating the antibody etc. may be in accordance with publicly known method (for example, Roberts M. J. et al., Advanced Drug Delivery Reviews 54 (2002) 459-476), and specifically is described in EXAMPLE 31.

The fifth embodiment of the present invention is a cell which produces the antibody of the first through the third embodiment, its active fragment or derivatives thereof, or a cell which comprises the polynucleotide of the fourth embodiment. Specifically, it includes:

(30) A cell which produces any antibody described in the aforementioned (1) through (19), its active fragment, or derivatives thereof, especially a transformant or a hybridoma;
(31) A cell which comprises any polynucleotide described in the aforementioned (20) through (23), especially a transformant or a hybridoma.

The sixth embodiment of the present invention is a method of manufacturing the antibody of the first through the third embodiment, which is characterized by using the polynucleotide of the fourth embodiment or an expression vector comprising the same, or the cell of the fifth embodiment. Specifically, it includes:

(32) A method of manufacturing the antibody of the first through the third embodiment, which comprises a process, in which the cell of the aforementioned (30) or (31) is cultured, and a process, in which a monoclonal antibody produced by the cell is collected;

(33) A method of manufacturing the antibody of the first through the third embodiment, which comprises a process, in which any among the polynucleotide of the aforementioned (19) through (23), an expression vector comprising the same, and the cell of the above (30) or (31) is used.

The seventh embodiment of the present invention relates to a medical composition comprising the antibody of the first to the third embodiment of the present invention, its active fragment or derivatives thereof as an effective ingredient, and preferably is a medical composition for prophylaxis and/or therapy of thrombotic, embolic or arteriosclerotic disease. The antibody of the present invention hardly has side effects such as activation of platelet, platelet aggregation, thrombocytopenia and prolongation of bleeding time and so on, and is useful for prevention and/or therapy of the above-mentioned diseases.

The eighth embodiment of the present invention is a peptide which constitutes the specific structure, especially a loop structure on GPVI, specifically,

(34) a peptide which comprises loop 2, loop 3 and loop 5, or loop 4 and loop 5 in domain 1, or loop 9, or loop 9 and loop 11 in domain 2 of GPVI, especially human GPVI, especially, a peptide which consists of any one of amino acid sequence among them. Herein, the peptide may comprise an amino acid sequence derived from heterogeneous GPVI or an amino acid sequence of a polypeptide other than GPVI such as Fc.

The ninth embodiment of the'present invention is a specified GPVI mutant, for example, a mutant with an amino acid substitution, a domain substitution between species or a partial sequence substitution between species such as a loop substitution, and the like. Preferred is a mutant wherein amino acids constituting one or more loop structures of GPVI shown in FIGS. 1 and 3 may be substituted with other amino acids or amino acids of the corresponding loop of other species such as human, monkey, mouse and rat. Specific examples are described in Table 4 or EXAMPLES. Specifically,

(35) a polypeptide which comprises the amino acid sequence of SEQ ID NOs: 137 through 151.

The tenth embodiment of the present invention is a method of screening an antibody, its active fragment or derivatives thereof, which comprises the following process:

a) A process for measuring the binding property with platelet membrane glycoprotein VI (GPVI), especially human GPVI;
b) A process for measuring the action to activate a platelet and/or the function to induce thrombocytopenia in vivo; and
c) A process for measuring the activity to at least partially deplete GPVI on the platelet membrane by contacting with a platelet.

The eleventh embodiment of the present invention is a method of estimating an epitope of an antibody or a method of identifying a recognition region of an antibody, which comprises a process for measuring the reactivity, for example, the binding property with the antibody of the peptide of the eighth embodiment or the polypeptide of the ninth embodiment.

The twelfth embodiment is a method of manufacturing an antibody specific for GPVI, which is characterized by using the peptide of the eighth embodiment or the polypeptide of the ninth embodiment, specifically,

(36) a method of manufacturing an antibody specific for GPVI, preferably the antibody of the first to the third embodiments of the present invention, which is characterized by using the peptide of the eighth embodiment or the polypeptide of the ninth embodiment as an antigen for immunization or as an antigen for in vitro immunization;

(37) a method of manufacturing an antibody specific for GPVI, preferably the antibody of the first to the third embodiments of the present invention, which is characterized by using the peptide of the eighth embodiment or the polypeptide of the ninth embodiment as an antigen for detection or identification of the antibody. That is, using a recombinant GPVI as an immunogen and/or an antigen for detection, wherein the amino acid sequence on human GPVI, such as the amino acid sequence corresponding to the loop structure, which can be recognized by the antibody of the present invention, is integrated into mouse GPVI, a novel antibody which can recognize the same recognition region can be obtained. As a more preferred method of preparing an antibody for human therapy, the method using human antibody gene-transgenic non-human animal has been disclosed (WO 2002/070648 (Tokuhyou 2005-504507) and WO 2002/043478 (Tokuhyou 2004-515230)). When using a protein, wherein a partial amino acid sequence of human GPVI is integrated into a heterogeneous GPVI, for example, mouse GPVI, the above-mentioned transgenic animal such as a mouse is immunized, it will be considered that a human antibody which reacts with the integrated amino acid sequence from human, preferably epitope, but not the amino acid sequence from mouse on GPVI can be obtained efficiently. Therefore, the human antibody obtained by such method is useful as a human antibody having the features of the antibody of the first or the second embodiment, and said method is particularly useful.

The thirteenth embodiment of the present invention is a method of detecting or quantifying GPVI in the test sample using the antibody of the first to the third embodiments. By the method, GPVI on the platelet or in the body fluid, especially in the blood can be measured. Further, it can be applied to a method of diagnosing diseases, preferably a method of diagnosing diseases associated with clot formation. Furthermore, the method can be applied to monitoring for treatment relating to GPVI, particularly prediction or determination of efficacy of anti-GPVI antibody, or prognostic determination using GPVI on the platelet as an index.

BRIEF DESCRIPTION OF DRAWINGS

FIG. 19 shows a reactivity for antigen binding of cF1232-37-2 expressed in COS cells and CHO cells.

FIG. 20 shows an amino acid sequence of heavy chain variable region and humanization thereof. Figure discloses SEQ ID NOS 422-423, 281 and 424-425, respectively, in order of appearance.

FIG. 21 shows an amino acid sequence of light chain variable region and humanization thereof. Figure discloses SEQ ID NOS 112 and 426-427, respectively, in order of appearance.

FIG. 27 shows the result of GPVI antigen binding assay for PEGylated anti-GPVI antibody.

FIG. 28 shows a nucleotide sequence (SEQ ID NO: 312) of the rat GPVI gene and an amino acid sequence (SEQ ID NO: 313) encoded by the same.

FIG. 29 presents a result of SDS-PAGE for rGPVI-Fc fusion protein obtained in EXAMPLE 35. Lanes 1, 2 and 3 show a molecular weight marker, rGPVI-hFc fusion protein and rGPVI-mFc fusion protein, respectively.

FIG. 30 presents a result of assay for binding ability to GPVI loop substitution mutant.

FIG. 31 presents a result of assay for binding ability of anti-rat GPVI antibody to rat platelet.

FIG. 32 presents a result of assay for aggregation ability of rat platelet to which the anti-rat GPVI antibody was administered.

FIG. 33 shows a result of GPVI depletion in EXAMPLE 40.

FIG. 47 shows an alignment of the amino acid sequences of both human soluble GPVI (SEQ ID NO: 428) and cynomolgus soluble GPVI (SEQ ID NO: 429). Box indicates respective domain regions of GPVI and the position of loop regions (L1-L14) predicted by modeling.

Figure 1:
FIG. 1 is the alignment of the amino acid sequence of human soluble GPVI (SEQ ID NO: 419) and mouse soluble GPVI (SEQ ID NO: 420). The squares show the positions of each domain region of GPVI and the loop region deduced by the modeling (L1-L14).

BEST MODE FOR CARRYING OUT THE INVENTION (Constitution)

The antibody of the present invention is the one which specifically recognizes GPVI, the membrane glycoprotein existing on platelet such as mammalian platelet GPVI, specifically the platelet from human, monkey, rat or mouse, especially the human platelet. Further, the GPVI which is recognized by the antibody of the present invention is not always limited to the GPVI on the platelet, and for example, GPVI on megakaryocyte can also be recognized. Herein, the GPVI which is subjected by the present invention is a mammalian GPVI. For example, the GPVI from human, monkey, rat or mouse, especially the human GPVI is exemplified. The present invention will be described in detail as follows. In addition, in the specification, sometimes, an amino acid residue is denoted as one-letter code or three-letter code.

The antibody of the present invention may be a polyclonal antibody, or preferably is a monoclonal antibody. A method of preparing the monoclonal antibody is not limited to the specified method. The monoclonal antibody may be any of a monoclonal antibody produced by hybridoma, a monoclonal antibody produced by a recombinant cell, in which a gene encoding the antibody is incorporated, or a monoclonal antibody produced by the transformed cell with Epstein-Barr virus (EBV). In addition, it may be a mixture of antibodies or a polyclonal antibodies comprising at least one of the monoclonal antibodies of the present invention, or a mixture of plural monoclonal antibodies of the present invention. Further, the antibody of the present invention encompasses a bispecific antibody or a polyspecific antibody.

The antibody of the present invention is an antibody which specifically binds to mammalian GPVI, specifically GPVI from human, monkey, rat or mouse, especially human GPVI. The binding of the antibody of the present invention with GPVI, especially human GPVI can be measured by publicly known methods, specifically the method described in EXAMPLES. Dissociation constant (Kd value) between GPVI, especially human GPVI and the antibody of the present invention is $4 \times 10^{-8}$ M, preferably equal to or less than $10^{-8}$ M, more preferably equal to or less than $4 \times 10^{-9}$ M, further preferably equal to or less than $10^{-9}$ M. A method of determining dissociation constant between human GPVI and the antibody is not limited to the specified method, and the conventional method can be used. For example, it can be measured with the protein interaction analyzer such as BIACORE® (SPR-MALDI system for measuring molecular interactions) 3000 using GPVI-Fc immobilized on chip. Alternatively, using a platelet, especially human or monkey platelet, it can be assayed with a publicly known method such as a method using RI-labeled antibody. Specifically, it can be illustrated in EXAMPLE 5 and EXAMPLE 52.

The antibody of the first embodiment of the present invention has an activity for disappearing GPVI on the platelet membrane at least partially by bringing in contact with the platelet, in particular, by bringing in contact with the platelet in vivo. The activity can be confirmed by bringing the antibody of the present invention in contact with the platelet for a given time followed by isolating the platelet, and assaying the expression level of GPVI on the surface. The expression level of GPVI can be measured by the conventional method using FACS, etc., and the specific method is illustrated in EXAMPLES. The antibody of the present invention has an activity for depleting GPVI on the platelet equal to or more than 20%, preferably equal to or more than 40%, more preferably equal to or more than 60%, further preferably equal to or more than 80% in comparison with the value prior to administration or the control value at the dosage of 3 mg/kg, preferably 1 mg/kg, more preferably 0.3 mg/kg, further preferably 0.1 mg/kg.

The antibody of the present invention is an antibody which has GPVI-depleting ability without mediating shedding of platelet GPVI, in particular, shedding of GPVI from platelets by methalloprotease-mediated cleavage accompanying with platelet activation, or an antibody having a weak function of the shedding induction, preferably no significant inducing function, more preferably no substantial inducing function, which at least partially depletes GPVI on the platelet membrane by contacting with platelets. Herein, shedding can be detected by the publicly known method (Stephens G and other four members, Blood, 2005 Jan. 1; 105 (1): 186-191; Gardiner E E et al., Blood 2004, 104: 3611-3617; Bergmeier W et al., Thromb Haemost. 2004; 91: 951-958), and specifically the method described in EXAMPLE 30 may be applicable.

The antibody of the present invention is an antibody, its active fragment or derivatives thereof which at least partially depletes GPVI on the platelet membrane by contacting with the platelet via internalization of the platelet GPVI. These antibodies are different from an antibody which induces the shedding of GPVI from the platelet by cleavage via methalloprotease associated with platelet activation. As described below, since they themselves have a weak action for activating platelets and/or inducing thrombocytopenia in vivo, preferably little action, they are useful. Preferred examples of such antibody include an antibody which recognizes loop 9 in GPVI.

The internalization of the platelet GPVI by the antibody of the present invention may be detected with a publicly known method. Preferably, by a method using a labeling substance as shown in EXAMPLES, such as fluorescent material, preferably pH-sensitive fluorescent material, specifically by a method labeling the antibody of the present invention directly or indirectly with these labeling substances, uptake of antibody-bound GPVI into platelets can be detected, or an amount of the uptake can be determined. Preferred method is shown in EXAMPLES.

The antibody of the present invention per se has a low activity for activating a platelet and/or inducing thrombocytopenia in vivo, preferably no activity. The activation of platelet can be measured by known methods, and an expression level of a platelet surface antigen, preferably CD62P can be used as an index. For example, a method of isolating a platelet from a living body that the antibody has been administered after a given period and measuring the expression level of CD62P by a conventional method, a method of bringing the antibody of the present invention in contact with a platelet isolated from a living body, and assaying the expression level of CD62P after a given period by a conventional method, and the like are included. The specific method is shown in EXAMPLES. The activation of platelet by the antibody of the present invention is, when the expression level of CD62P is used as an index, at the dose or the concentration that at least partially depletes GPVI on the platelet, equal to or less than five-fold, preferably equal to or less than two-fold, more preferably equal to or less than 1.5-fold, further preferably almost the same as the platelet for control.

Thrombocytopenia in vivo can be confirmed by collecting blood with time after in vivo administration of the antibody of the present invention, calculating the number of platelets with a conventional method and comparing the number with a value prior to administration or the number of platelets of an individual as a control. The specific method is shown in EXAMPLES. The platelet number by the antibody of the present invention is, at the dose or the concentration that at least partially disappears GPVI on the platelet, when the value prior to administration or the control value is set as 100%, equal to or more than 50%, preferably equal to or more than 70%, more preferably equal to or more than 90%, further preferably almost the same.

The antibody of the present invention has the activity that suppresses the human platelet aggregability against the collagen, that is, the activity that attenuates or deletes aggregability of the platelet responsive to collagen by contacting with the platelet in vivo. The activity can be confirmed by administering the antibody of the present invention in vivo to make contact with the platelet, followed by isolating the platelet with time, and measuring a collagen-induced platelet aggregation. Herein, the platelet aggregation can be measured by the publicly known method. For example, it can be measured by calculating an aggregation rate using a light transmission with the platelet aggregometer as an index, and in general, may be represented by the aggregation rate at the point that exhibits a maximum light transmission (hereinafter, sometimes referred to as the maximum aggregation rate). In the method described in EXAMPLE 8 later, the antibody of the present invention has an activity that at the dosage of 3 mg/kg, preferably 1 mg/kg, more preferably 0.3 mg/kg, further preferably 0.1 mg/kg, makes the collagen-induced aggregability of the platelet decrease by 20%, preferably equal to or more than 40%, more preferably equal to or more than 60%, further preferably equal to or more than 80% in comparison to the value prior to the administration or the control value.

Preferably, the antibody of the present invention hardly has an effect on aggregation induced by platelet aggregation-inducing substances except for collagen, for example, ADP or thrombin. At the dosage or the concentration that affects on collagen-induced aggregability, the maximum aggregation rate is preferably equal to or more than 80% of the control, more preferably equal to or more than 90% of the control, further preferably equal to or more than 95% of the control. A method of assaying suppression of a human platelet aggregation by platelet aggregation-inducing substances except for collagen can be performed by the conventional methods.

In addition, the antibody of the present invention is an antibody that has a weak prolonging activity on bleeding time, preferably no significant prolonging activity, more preferably no substantial prolonging activity. The bleeding time can be assayed by the publicly known method, and specifically the method described in EXAMPLE 28 or 50 may be applicable. The antibody of the present invention substantially does not prolong the bleeding time at the therapeutic dosage or more, for example, 0.3 mg/kg, preferably 1 mg/kg, more preferably 3 mg/kg, further preferably 10 mg/kg. Specifically, the bleeding time is less or equal to 5-fold, preferably less or equal to 3-fold, further preferably less or equal to 2-fold, particularly preferably less or equal to 1.5-fold as the value prior to administration, normal value or control. Such preferred examples include an antibody that recognizes loop 9 of GPVI, especially human GPVI.

Since most of the antibodies to the human GPVI, including the above-mentioned human autoantibody, that have been reported until now, possess, in vitro, an activity that activates a platelet by the antibody itself, and/or an activity that induces or enhance a platelet aggregation, when they are administered in vivo, the possibility to cause a thrombocytopenia may be considered. In the form of the Fab fragment and so on, the one that does not induce a platelet aggregation is also reported, meanwhile in vivo, a possibility that Fab behaves in a similar manner to IgG by cross-linking or aggregating from any cause cannot fully be denied. Therefore, in an intact antibody molecule, but not an active fragment of the antibody, for example, IgG form, an anti-GPVI antibody that does not exhibit the above-mentioned activity, or has a low activity is preferred.

Also, for behavior and stability in vivo, the antibody molecule that is the natural form, e.g. IgG, is superior. Generally, a half-life of the IgG in the blood is much longer than that of the fragment such as Fab. Thus especially, for chronic diseases such as thrombosis, especially thrombosis associated with atrial fibrillation, or clinical conditions that necessitate an antibody administration over long period, a molecular form having a long half-life in the blood, particularly IgG is desirable.

The antibody of the present invention may specifically inhibit the binding of GPVI on the platelet to collagen. For example, in the method described in EXAMPLES later, the antibody of the present invention is an antibody that inhibits the binding of GPVI and collagen by 50% at the concentration preferably equal to or less than 100 μg/mL, more preferably equal to or less than 10 μg/mL, further preferably equal to or less than 1 μg/mL, especially preferably equal to or less than 0.1 μg/mL. A method of measuring the binding of collagen and GPVI is not limited to a specific method and can also be done by the other conventional method.

The second embodiment of the present invention is an anti-GPVI antibody that is defined by novel recognition region, binding site or epitope on GPVI, preferably a monoclonal antibody. The recognition region on GPVI by the antibody of the present invention and the like can be confirmed or deduced by publicly known methods. For example, by applying the method of the eleventh embodiment of the present invention and measuring a reactivity with the peptide of the eighth embodiment or the polypeptide of the ninth embodiment, it can be performed. The specific method is illustrated in EXAMPLES. For example, in the method described in EXAMPLE 7 or EXAMPLE 18, on the basis where the reactivity or inhibition rate is significantly varied in comparison to the control (e.g., hGPVI-Fc), for example, it is reduced to 50%, preferably 30%, more preferably less or equal to 10%; or where a value for IC50 and the like are significantly changed, for example, it is increased three-fold, ten-fold, more preferably 30-fold, further preferably 100-fold, the antibody can be confirmed or deduced. The antibody, wherein recognition region, binding site or epitope on GPVI is confirmed, is useful for detection of specific GPVI molecular species, or for analysis of relationship between the structure and the function of GPVI, solely or by combination with other antibodies.

As the third embodiment of the present invention, there is an anti-GPVI antibody comprising a novel amino acid sequence of CDR or variable region.

On the N-terminal end of heavy chain and light chain of antibody, variable region exists, and is designated heavy chain variable region (VH) and light chain variable region (VL), respectively. Within the variable region, complementarity determining region (CDR) is present, and assumes specificity for recognition of antigen. A region except CDR in variable region has the role that maintains the structure of CDR and is called framework region (FR). On the C-terminal end of heavy chain and light chain of antibody, constant region exists, and is designated heavy chain constant region (CH) and light chain constant region (CL), respectively.

In the heavy chain variable region, three complementarity determining regions exist: the first complementarity determining region (CDR1), the second complementarity determining region (CDR2) and the third complementarity determining region (CDR3). These three complementarity determining regions in the heavy chain variable region collectively mean a heavy chain complementarity determining region. As is the case with the heavy chain, in the light chain variable region, three complementarity determining regions exist: the first complementarity determining region (CDR1), the second complementarity determining region (CDR2) and the third complementarity determining region (CDR3). These three complementarity determining regions in the light chain variable region collectively mean a light chain complementarity determining region.

CDR sequence in the antibody of the present invention is not always limited. Preferred combination of the amino acid sequences as VH CDR1, VH CDR2 and VH CDR3, preferred combination of the amino acid sequences as VL CDR1, VL CDR2 and VL CDR3, and further, preferred combination of the amino acid sequences as VH CDR1, VH CDR2, VH CDR3, VL CDR1, VL CDR2 and VL CDR3, are listed in Tables 8 and 9, and Tables 12 and 13. Preferably, it is an antibody that comprises any one or more, preferably three of heavy chains, more preferably all among the amino acid sequences of CDR of an antibody that recognizes loop 9 of GPVI. The amino acid sequences except for CDR are not particularly limited. The antibody of the present invention includes so-called CDR-grafted antibody, wherein the amino acid sequences except for CDR are derived from another antibody, especially the antibody from other species. Among them, preferred is a humanized antibody, wherein the amino acid sequences except for CDR are derived from human. The humanized antibody may have addition, deletion, substitution and/or insertion of one to several amino acid residues in the framework (FR) region, if desired. As a method of preparing the humanized antibody, publicly known methods can be used, and the specific method is shown in EXAMPLES.

The amino acid sequence of VH and VL of the antibody of the present invention is not always limited, but preferred antibody is an antibody that comprises any one or more among the amino acid sequence of SEQ ID NO: 281 as VH or the amino acid sequence of SEQ ID NO: 285 as VL, or an antibody that comprises any one or more among the amino acid sequence of SEQ ID NO: 283 as VH or the amino acid sequence of SEQ ID NO: 285 as VL.

In addition, the antibody of the present invention is not always limited to that with the specific amino acid sequence, and within the range where there is virtually no influence on its activity and/or antigenecity, as for the amino acid sequence of the antibody of the present invention, for example, variable region, especially FR, addition, deletion, substitution and/or insertion of one to several amino acid residues are permissible.

The antibody of the present invention is an antibody that the constant region of the antibody consists of an amino acid sequence derived from preferably human antibody, more preferably human IgG, further preferably human IgG4.

The antibody of this invention is not always limited to the specific molecular species. The structure of an antibody, i.e. an immunoglobulin consists of heavy chain (H-chain) and light chain (L-chain) and is divided into five isotypes (IgG, IgA, IgM, IgD, IgE) based on the class of the heavy chain (γ, α, μ, δ, ε). Among them, IgG and IgA are divided, based on difference of the heavy chain (e.g., in the case of the human, γ1, γ2, γ3, γ4, α1, α2), into subclasses (e.g., in the case of the human, IgG1, IgG2, IgG3, IgG4, IgA1, IgA2). The light chain is classified into either κ or λ type. The class, the subtype or the isotype of the antibody of the present invention is not limited, and may be the one that is classified into either. Preferred isotype is IgG, and further preferably, the subclass is IgG4 in the point that there is no complement fixation.

The antibody of the present invention, as long as the antibody has the activity such as a binding ability to GPVI, may be the fragment, particularly the active fragment or the part of the antibody. Herein, the active fragment of the antibody means to be a fragment having at least one activity, especially antigen binding activity of the antibody. For example, Fab (fragment of antigen binding), Fab', (Fab')$_2$, single-chain antibody (scFv), disulfide stabilizing antibody (dsFv), diabody, sc(Fv)2 (see, e.g., Orita T, Blood. 2005; 105: 562-566), nanobody (see, e.g., Cortez-Retamozo V., Cancer Research 64, 2853-2857, 2004) and the peptide comprising CDR and so on are included. Also, a derivative of an antibody can be a substance derived from the antibody, having at least one activity of the antibody, especially the antigen binding activity. Examples include an antibody bound to other substance or active fragment thereof, modified antibody that is modified by other substance or active fragment thereof, or a molecule wherein a mutation is introduced to the structure of the antibody, especially the amino acid sequence. An antibody of the present invention is not always limited regarding antigen binding valency and may be monovalent antibody such as Fab or scFv. From the perspective of stability in vivo, especially in the blood, and/or binding property to GPVI or strength of action, preferred is a polyvalent antibody having two or more valencies, e.g., a divalent, trivalent, tetravalent or decavalent antibody; a divalent antibody is more preferable.

In the fourth embodiment of the present invention, a polynucleotide or nucleic acid encoding the antibody of the first embodiment to the third embodiment of the present invention is provided. The polynucleotide is not always limited as long as that encodes the amino acid sequence of the antibody of the present invention, and includes DNA and RNA.

A polynucleotide encoding CDR sequence in the antibody of the present invention is not always limited. Preferred combination of the base sequences encoding the amino acid sequence as VH CDR1, VH CDR2 and VH CDR3, preferred combination of the base sequences encoding the amino acid sequence as VL CDR1, VL CDR2 and VL CDR3, and further, preferred combination of the base sequences encoding the amino acid sequence as VH CDR1, VH CDR2, VH CDR3, VL CDR1, VL CDR2 and VL CDR3, are listed in Tables 8 and 9, and Tables 12 and 13.

The polynucleotide encoding the amino acid sequence of VH and VL of the antibody of the present invention is not always limited, and preferably is a polynucleotide that comprises any one of the base sequences of SEQ ID NOs: 87, 89, 91, 93, 95, 97, 99, 101, 103, 105, 107 and 109 encoding the amino acid sequence as VH or the base sequences of SEQ ID NOs: 88, 90, 92, 94, 96, 98, 100, 102, 104, 106, 108 and 110 encoding the amino acid sequence as VL, more preferably both base sequences, or a polynucleotide that comprises either the base sequences having the corresponding sequence identification number and encoding the amino acid sequence as VH or the base sequences having the corresponding sequence identification number and encoding the amino acid sequence as VL, more preferably both base sequences.

The polynucleotide encoding the constant region of the antibody of the present invention comprises a base sequence derived from preferably human antibody, more preferably human IgG, further preferably human IgG4.

By transferring the vector comprising a nucleotide sequence encoding the antibody of the present invention, or the gene into a cell, a cell that produces the antibody of the present invention can be manufactured. A method of transfer may be according to publicly known methods, and the specific methods are illustrated in EXAMPLES.

As the fifth embodiment of the present invention, a cell that produces the antibody of the present invention is provided. Examples of such cell include hybridoma, transformant, or recombinant cell, in which a gene encoding the antibody of the present invention is introduced. Hybridoma that produces the antibody specifically includes clones listed in Tables 6 and 11. In addition, the present invention provides an antibody that is produced by the abovementioned cells of the present invention.

The eighth and the ninth embodiments of the present invention provide a novel peptide or polypeptide relating to GPVI. These peptides can be prepared by publicly known methods, and the specific method is shown in EXAMPLES. The peptide of the eighth embodiment and the polypeptide of the ninth embodiment can be used as an antigen for immunization, or as an antigen for detection of the anti-GPVI antibody.

(Manufacturing Process)

The sixth embodiment of the present invention provides a method of manufacturing an antibody. The method of preparing the antibody of the present invention is not always limited, and the antibody can be prepared by the method described below. That is, by administering human GPVI, its fragment or derivatives thereof, for example, human GPVI-Fc as an antigen to animal such as mouse, collecting lymphocytes from the peripheral blood, hybridoma with mouse myeloma cell may be prepared. An antibody that is produced by the prepared hybridoma is recovered to select the antibody having a binding ability to GPVI and characteristics of the first to the third antibody. Thereby, a cell, in which the antibody is produced, can be obtained. By culturing the cell, the antibody of the present invention can be obtained.

The antibody of the present invention can be prepared as the recombinant human antibody using publicly known methods (a lot of methods are developed since Nature, 312: 643, 1984, and Nature, 321: 522, 1986 were published, respectively). Firstly, from the cells that produce the antibody of the present invention, e.g. the lymphocytes, preferably, the hybridoma which produces anti-GPVI monoclonal antibody, nucleic acid encoding VH or VL, e.g. cDNA may be obtained, and the base sequence and the amino acid sequence are determined. Then, by inserting the obtained cDNA encoding VH and VL into the expression vector for animal cells comprising a gene encoding human antibody CH and/or human antibody CL that has been prepared from the same or other human cell, respectively, human antibody-expressing vector may be constructed. By introducing the vector into the animal cell and expressing it, the antibody of the present invention can be manufactured. A method of preparing the gene to be introduced to the animal cell is not limited, and may be obtained from genomic DNA or cDNA derived from hybridoma, by PCR from mRNA of hybridoma, or also by the chemical synthesis.

The vector, into which to the nucleic acid encoding VH or VL of the antibody of the present invention is incorporated, is not always limited, but a vector or a vector for high expression that generally is used for expression of gene encoding protein and adapted to expression of the antibody gene is preferred. Preferred example includes a vector containing EF promoter and/or CMV enhancer, specifically pEF-BOS or the vector used in EXAMPLES. In addition, the vector that the nucleic acid encoding VH or VL is incorporated is usually prepared independently, and co-transfected into host cells. However, the nucleic acid may be incorporated into a single expression vector.

The host cell, in which the expression vector is introduced, is not always limited, and the cell that generally is used for expression of gene encoding protein and adapted to expression of the antibody gene is preferred. For example, bacteria (*Escherichia coli*, etc.), *actinomyces*, yeasts, insect cell (SF9, etc.), mammalian cell (COS-1, CHO, myeloma cell, etc.) are included.

To industrially produce a recombinant antibody, generally a recombinant animal cell line that stably and highly expresses the antibody, for example, a CHO cell line may be utilized. For preparation of such recombinant cell lines, cloning, gene amplification for high expression and screening, a publicly known method can be used (see, e.g., Omasa T.: J. Biosci. Bioeng., 94, 600-605, 2002; and others). Further, two kinds of promoters can be used for establishment of animal cell line for stably high expression. Herein, by using combination of different promoter activities such as high activity and low activity, preferably utilizing a promoter having a relatively weak activity as an expression promoter for selection marker, a clone having an high expression ability can be efficiently (or selectively) acquired. Examples of preferred combination of promoters and specific methods are indicated in EXAMPLES.

As the constant region of the human antibody to use for preparing a recombinant human antibody, any human antibody constant region, for example, Cγ1 and Cγ4 for the human antibody heavy chain constant region, and Cκ for the human antibody light chain constant region can be used.

Among the antibodies of the present invention, the antibody comprising an amino acid sequence derived from human includes, as well as an antibody that is naturally occurring in the human body, a combinatorial library consisting of variable heavy chain and variable light chain, for example, a phage library for human antibody, and an antibody obtained from human antibody producing-transgenic animal, etc. The phage library for human antibody is a library, wherein an active fragment of antibody such as Fab and single-stranded antibody is made express on the phage surface by inserting a gene encoding the antibody prepared from human B cell into phage gene. The antibody of the present invention can be obtained by screening these libraries. These and other methods are well-known by persons skilled in the art (Huse et al., Science 246: 1275-1281 (1989); Winter and Harris, Immunol. Today 14: 243-246 (1993); Ward et al., Nature 341: 544-546 (1989); Harlow and Lane, supra, 1988); Hilyard et al., Protein Engineering: A practical approach (IRL Press 1992); Borrabeck, Antibody Engineering, 2nd Ed. (Oxford University Press 1995)). From the library, using an binding activity to the substrate immobilized an antigen as an index, a phage expressing an active fragment of the antibody having the desired antigen binding activity can be recovered. The active fragment of the antibody can further be converted into a human antibody molecule consisting of two intact H-chains and two intact L-chains by genetic engineering techniques.

The present invention includes, in addition to the antibody consisting of two heavy chains and two light chains, the active-fragment of the antibody of the present invention. For example, the active fragment of the antibody includes Fab (fragment of antigen binding), Fab', F(ab')$_2$. The substance that the active fragment of the antibody is linked by linker and so on includes, for example, single-stranded antibody (single chain Fv: scFv) and disulfide stabilized Fv: dsFv. The peptide that contains the active fragment of the antibody includes, for example, a peptide containing CDR. These can be manufactured by the method of processing the antibody of the present invention with the suitable protease or the publicly known methods such as the recombinant DNA techniques.

Fab of the present invention can be obtained by treating the anti-GPVI antibody of the present invention with pepsin, the proteolytic enzyme in case of IgM, or by processing it with the protease papain in case of IgG. Alternatively, Fab can be produced by inserting DNA encoding Fab of the antibody into prokaryotic or eukaryotic expression vector, introducing the vector into prokaryotes or eukaryotes, and expressing the same.

F(ab')$_2$ of the present invention can be obtained by treating the anti-GPVI antibody of the present invention with pepsin, the proteolytic enzyme. Alternatively, it can be prepared by linking the following Fab' with the thioether bond or the disulfide bond.

Fab' of the present invention can be obtained by treating F(ab')$_2$ that specifically reacts to GPVI with the reducing agent, dithiothreitol.

As VH and VL that are comprised in scFv of the present invention, those derived from either the antibody or the human antibody, which the hybridoma of the present invention produces, can be used. The scFv of the present invention can be manufactured by obtaining cDNA encoding VH and VL of the anti-GPVI antibody of the present invention, constructing the DNA encoding scFv, inserting the DNA into prokaryotic expression vector or eukaryotic expression vector, and introducing the vector into prokaryotes or eukaryotes to express the vector.

The term "dsFv" means an antibody that two polypeptides, wherein one amino acid residue in each of VH and VL is substituted with cysteine residue, bind each other via disulfide bond between said cysteine residues. The amino acid residue to be substituted for the cysteine residue can be selected based on the three-dimensional structure prediction of the antibody according to the method shown by Reiter et al. [Protein Engineering, 7, 697 (1994)]. As for VH and VL that is contained in dsFv of the present invention, the ones, which are derived from the antibody of either the first or second embodiment of the present invention may be used.

The dsFv of the present invention can be manufactured by obtaining cDNA encoding VH and VL of the anti-GPVI antibody of the present invention, constructing DNA encoding dsFv, inserting the DNA into prokaryotic or eukaryotic expression vector, and introducing the expression vector into prokaryotes or eukaryotes to express the same.

The peptide containing CDR is constituted by including at least one region or more of the H-chain CDR or of L-chain CDR. Plural CDRs can be bound directly or through the appropriate peptide linker. The peptide that contains CDR of the present invention can be manufactured by obtaining cDNA encoding VH and VL of the anti-GPVI antibody of the present invention, constructing DNA encoding CDR, inserting the DNA into prokaryotic or eukaryotic expression vector, and introducing the expression vector into prokaryotes or eukaryotes to express the same. Alternatively, the peptide that contains CDR can be manufactured by the chemical synthesis such as the Fmoc method (the fluorenylmethyloxycarbonyl method), the tBoc method (t-butyloxycarbonyl method), or the like.

The antibody of the present invention, its active fragment or derivatives thereof include, for example, an antibody that is produced by hybridoma, an antibody that is produced by the cell transformed with EBV, a recombinant antibody expressed from cDNA, or an antibody, wherein a radioisotope, protein, peptide or low molecular, etc. is chemically conjugated or through genetic engineering fused with the active fragment of the antibody. For example, an antibody bound to polyethyleneglycol etc. is highly useful in respect of stability, and is one of preferred examples. To the N-terminal or the C-terminal end of H-chain or L-chain in the anti-GPVI antibody of the present invention or an active fragment thereof, an appropriate residue or a side chain in the antibody or an active fragment of the antibody, and further a sugar chain in the antibody or an active fragment of the antibody, a radioisotope, protein, peptide or low molecular weight compound, etc. can be conjugated by a chemical method [The introduction to antibody engineering (Koutai kougaku nyuumon) (written by Osamu Kanemitsu, 1994, Chijin Shokan)].

Hybridoma means a cell that produces the monoclonal antibody having the desired antigen specificity, wherein it is obtained by fusing a lymphocyte with the myeloma cell derived from human, mouse, rat and so on, and can be prepared by publicly known methods.

When preparing a monoclonal antibody, in consideration of the compatibility with myeloma cell used for the cell fusion, selection is preferably performed. As for the myeloma cell, publicly known various cells are usable. These include SKO-007 from human, SHM-D33, which is a human-mouse heterozygous myeloma, P3, P3U1, SP2/O, NS-1 derived from mouse, and YB2/0 and Y3-Ag1 through Ag3 from rat.

In the case of human antibody, a method of preparing hybridomas utilizing activation of lymphocytes by in vitro immunization and a method of preparing hybridomas using an animal, in which human antibody gene is recombined, in particular, a transgenic mouse such as KM mouse are included (WO 2002/070648 (Tokuhyou 2005-504507) and WO 2002/043478 (Tokuhyou 2004-515230)). When using a heterogeneous GPVI, for example, a protein, wherein a partial amino acid sequence of human GPVI is integrated into mouse GPVI, the above-mentioned transgenic animal such as a mouse is immunized, it will be considered that a human antibody that reacts with the integrated amino acid sequence from human, preferably epitope, but not the amino acid sequence from mouse on GPVI can be obtained efficiently. Therefore, the human antibody obtained by such method is useful as a human antibody having the features of the antibody of the first or the second embodiment, and said method is particularly useful. A cell used for preparation of hybridomas is not always limited. In the case of preparing human antibody, among plural cells for preparation of hybridomas, at least one is preferably a cell derived from human. As the cell derived from human, lymphocytes from peripheral blood, lymph nodes or spleen can be used, and especially, human lymphocytes, in which production of autoantibody is confirmed, is preferred.

Activation of lymphocyte can be according to the publicly known method. For example, preferred are a method of preparing hybridoma with the myeloma cell derived from the human B cell or the mouse myeloma cell by collecting B cell from peripheral blood or spleen of the human and stimulating an antigen with in vitro immunization, a method of fusing with the mouse myeloma cell by transforming with EBV, and a method of fusing by stimulating with mitogen such as PWM and activating B cell to polyclonal antibody (Immunological experiment procedures (Men-eki jikken sousa-hou) I and II, edited by Shunsuke Migita et al., Nankoudo).

The antigen used for immunizing an animal or for stimulation of the cell is not always limited. The animal, from which the protein as an antigen is originated, can be appropriately selected for any purpose of the antibody. The protein as an antigen may be naturally occurring product, genetically engineered product, chemically synthesized product, or fusion protein with other protein or peptide, and the like. For example, the platelet, the membrane of the platelet, purified GPVI, recombinant GPVI, and GPVI-Fc, preferably GPVI-Fc can be used. In addition, the peptide of the eighth embodiment of the present invention and the polypeptide of the ninth embodiment can appropriately be used as an antigen for immunization to prepare an anti-GPVI antibody.

Fusion of the activated lymphocytes with myeloma cells can be performed using the publicly known methods such as the method by Milstein et al. (Methods in Enzymol., volume 73, pages 3). The methods include, for example, the method using polyethylene glycol (PEG) as a fusing agent (Introduction to the monoclonal antibody experiment procedure (Tan-kuron koutai jikken sousahou nyuumon), written by Tamie Ando and Takeshi Chiba, Kodansha) or the electrofusion method. The mixing ratio of the immunocyte and the myeloma cell is not limited as long as it is the ratio that the cells can be fused. Preferably, 1/10 to equal amount of the myeloma cells to the activated lymphocytes may be used. In the cell fusion using PEG (average molecular weight: 1,000-4,000), PEG concentration is not always limited, but 50% is preferable. In addition, as the fusion efficiency accelerator, auxiliary substance such as dimethylsulfoxide (DMSO) may be added. The fusion is started by adding pre-warmed PEG solution at 37° C. to the mixed cells, and is terminated by adding medium after the reaction for 1-5 minutes.

The hybridoma, which was formed by this fusion is cultured for one (1) to ten (10) days in selection medium such as the medium containing hypoxanthine, thymidine and aminopterin (HAT medium) to isolate unfused cells. The obtained hybridoma is further selected based on the antibody to be produced. The selected hybridoma is isolated to a single clone by the publicly known limiting dilution. Thereby, a monoclonal antibody-producing hybridoma is established.

For a method of detecting the activity of the antibody that is produced by the hybridoma, the publicly known method can be used. Herein, the activity of the antibody is detected in the following two steps: the binding ability to GPVI antigen as the first step and the activity of inhibiting the binding of GPVI and collagen as the second step. Examples of the detection method for the first step include ELISA, Western blotting, radioimmunoassay and the like. As the detection method for the second step, ELISA (inhibiting the binding), protein interaction analysis (BIACORE® and so on), and a platelet aggregation suppression assay are given. In addition, the peptide of the eighth embodiment of the present invention and the polypeptide of the ninth embodiment can be used as an antigen for detecting the anti-GPVI antibody. The specific method is illustrated in EXAMPLES.

The established hybridoma can be cultured by publicly known method, and from the culture supernatant, a monoclonal antibody can be obtained.

The antibody can be purified using the publicly known purification means such as the salting-out method, gel filtration, ion exchange chromatography or affinity chromatography.

The concentration of the antibody can be measured by the publicly known quantification method of protein, e.g. the measurement of absorbance at 280 nm absorbance.

For a method of confirming the antigen binding property of the anti-GPVI antibody of the present invention or a method of detecting GPVI in the biological sample using the anti-GPVI antibody of the present invention, fluorescence antibody technique, enzyme linked immunosorbent assay (ELISA), radioimmunoassay (RIA), immunohistochemical method such as immunohistological staining and immunocytological staining (ABC method, the CSA method and so on), the Western blotting method, immuno-precipitation method, enzyme-linked immunoassay as described above, sandwich ELISA method [Tan-kuron koutai jikken manual (The Monoclonal Antibody Experiment Manual) (Kodansha Scientific, 1987), Zoku seikagaku jikken kouza (The Continued Biochemical Experiment Course 5) Menneki-seikagaku kenkyuuhou (Immunobiochemical Research Method) (TOKYO KAGAKU DOZIN, 1986)] can be used.

(Uses)

The antibody of the present invention is an antibody that specifically binds to human GPVI. The antibody of the present invention, the active fragment of the antibody, the modified antibody that binds to the chemicals or the composition that comprises these mixtures have a variety of uses including prevention, diagnosis and treatment of the human diseases, and detection of human GPVI in test sample, cells, tissues and the like.

Uses: Medicaments

Since the antibody of the present invention has a high specificity for binding to GPVI, and solely has little activity that enhances or induces human platelet activation and/or thrombocytopenia, in particular, it is useful for prevention and/or treatment of human diseases, for example, diseases caused by activation or aggregation of platelet, or vascular endothelial disorders or arteriosclerotic reaction. In addition, it can be used for prevention and/or treatment of diseases caused by thrombus or embolus such as thrombosis, embolism and the like. Examples of these diseases include venous thrombosis as well as arterial thrombosis, or cerebral infarction caused by atrial fibrillation.

Specific examples of human diseases or clinical conditions that are able to prevent and treat by the antibody of the present invention include myocardial infarction, vascular endothelial hypertrophy, restenosis of blood vessel, angina pectoris or myocardial infarction at the time of thrombolytic therapy, percutaneous transluminal coronary angioplasty (PTCA), stent operation, bypass surgery or artificial blood vessel operation, or thereafter; atrial fibrillation or atrial flutter, and thrombosis, embolism or cerebral infarction caused by these diseases; thromboangiitis obliterans; acute arterial occlusion; arteriosclerosis obliterans or deep venous thrombosis etc.; cerebral infarction (atheromatous thrombotic infarction, lacunar infarction, cardiogenic infarction); transient cerebral ischemic attack; cerebrovascular spasm after subarachnoid bleeding; pulmonary thrombosis; pulmonary embolism; vascular purpura; idiopathic thrombocytopenic purpura; thrombotic thrombocytopenic purpura; disseminated intravascular coagulation; prevention of blood coagulation at the time of extracorporeal circulation; systemic lupus erythematosus; multiple arteritis; anti-phospholipid antibody syndrome; purpura nephritis; endothelial cell injury associated with diabetes mellitis; diabetic nephritis; diabetic retinopathy; nephritic embolism; complications associated with transplantation (veno-occlusive disease of liver, graft-versus-host disease); and so on.

The antibody of the present invention can be administered to the diseases to be objective for the aforementioned prevention and/treatment solely or in combination with other pharmacologically active ingredient. Examples of such pharmacologically active ingredient include publicly known thrombolytic agents such as tissue plasminogen activator(t-PA) and derivatives thereof (including mutant or so-called second generation); urokinase, streptokinase or publicly known platelet inhibitor (e.g. aspirin, ticlopidine, clopidogrel, thromboxane antagonist, thromboxane synthesis inhibitor, GPIIb/GPIIIa antagonist); publicly known anticoagulant (e.g. warfarin, heparin, low molecular weight heparin, pentasaccharide, thrombin inhibitor, FXa inhibitor, FVIIa inhibitor); and the like. Herein, the term "combination" includes the case where combined formulation comprising both the antibody of the present invention and the pharmacologically active ingredient is administered and the case where the antibody of the present invention and the pharmacologically active ingredient are administered as an independent formulation at the same time or time difference, and for the dosage form, no object as long as both exist simultaneously in the blood of a patient.

A medicament comprising the antibody of the present invention and pharmaceutically acceptable composition as an effective ingredient can be prepared as tablet, injectable solution, powdered drug, suppository and the like using carrier for formulation, excipient and other additives used generally, and administered to human and other animals.

When applied to the human, route for administration includes oral, intraveneous (bolus, continuous drip, intermittent drip), subcutaneous, intramuscular, intra-articular, transdermal, and transnasal administration. In general, oral administration or intraveneous administration may be used. Clinical dose of the antibody of the present invention to the human may appropriately be determined in consideration of conditions, body weight, ages, sex, etc. of the patient to be administered. In general, to adult, by intraveneous administration, dose of 1-10000 mg, preferably 10-1000 mg per day may be used, and the amount can be administered at one time or within several times. Since dosage varies depending on various conditions, there is a case where the amount less than the above-mentioned range is effectively administered.

Herein, the antibody of the present invention includes various antibodies having different mechanisms meanwhile sharing recognition of GPVI in common. For example, since in the antibody that directly inhibits the binding of GPVI to collagen, or that suppresses activation and/or aggregation of platelet by cleaving GPVI, a relatively immediate effect can be expected, there have possibilities that the antibody is useful at least in the acute period of the disease (for example, in the time of myocardial infarction or PTCA implementation, or right before or after the events). In such a case, preferably, to make the antibody of the present invention bind to most of GPVI on the surface of platelet in the blood, relatively massive antibodies can be administered, e.g. by a single or divided intravenous injection or an intravenous drip. Also, in the antibody, in which GPVI is incorporated internally, a continuous effect, but not an immediate effect can be expected considering a life-time of human platelet in the blood (about 9-10 days) and a half-life period of human antibody in the blood (in the case of IgG, several weeks). Thus, for example, there have a possibility that it is useful in chronic stage of diseases (several days to several months after development of myocardial infarction or PTCA implementation). In such a case, the antibody, whose amount is necessitated for depleting GPVI on the platelet surface to the extent of inhibiting a reactivity of platelet in the blood against collagen partially, preferably fully, can be administered at intervals of relatively long duration, e.g. from several days to several weeks per cycle, for example, by single dose or divisional intravenous injection, or the intravenous drip infusion. Therefore, in the preferred embodiment, the antibody of the present invention may possess these effects in parallel. In addition, a treatment, wherein multiple anti-GPVI antibodies that respective effects can be expected are combined, may be performed.

A composition for parenteral administration generally includes a solution of the immunoglobulin dissolved into the acceptable carrier, preferably aqueous carrier or its mixture. Various aqueous carriers such as water, buffer solution, a phosphate buffered saline (PBS), 0.4% of saline, 0.3% of glycine, human albumin solution and the like can be used. These solutions are aseptic, and generally, microparticle material does not exist in these solutions. These compositions can be sterilized by the conventional and well-known method of sterilization. To approximate physiological conditions, the compositions may be included, on demand, pharmacologically acceptable auxiliary substance such as pH adjusting and buffering agent, toxicity regulating agent, and the like, specifically sodium acetate, sodium chloride, potassium chloride, calcium chloride and sodium lactate. The concentration of the antibody in these formulations can vary extensively, i.e. change from less than about 0.005% by weight (usually, at least about 1% by weight) to the large quantity, i.e. 15% or 20% by weight, and may be selected according to the selected and specific mode of administration, mainly based on the volume of the solution, the viscosity and the like.

An actual method of preparing a parenteral administration composition is publicly known or obvious for persons skilled in the art, and further is described in detail in Remington's Pharmaceutical Sciences (15th Edition, Mack Publishing Company, Easton, Pa., 1980), wherein the reference is incorporated by reference in its entirety. A composition suitable for wash (lavage) or the other route is selected according to the intended specific use. Some pharmaceutical compositions can include an anti-GPVI antibody and the other treatment agent which is regularly used in the disease. In any cases, the bolus administration and the continuous administration can be applied. In addition, an effective amount for prevention or treatment is arbitrarily determined depending on object diseases, clinical condition and the condition of the patient and the like.

The antibody of the present invention may be frozen or lyophilized for storage, and prior to use, can be reconstituted in the suitable carrier. This technique is known to be effective in the conventional immunoglobulin. Further the publicly known techniques for lyophilization and reconstitution can be used. It is recognized for persons skilled in the art that lyophilization and reconstitution bring about activity loss of the antibody at various degrees (e.g. in the conventional immunoglobulin, IgM antibody, larger activity loss than that of IgG antibody tends to occur), and that use level may have to be regulated for compensation of loss.

Use: Detection of GPVI

A method of detecting GPVI in test sample using the antibody of the present invention or an active fragment thereof comprises the process, in which the test sample is brought in contact with the antibody of the present invention or an active fragment thereof, and the process, in which GPVI in the test sample bound to the antibody of the present invention or an active fragment thereof is detected. The process for quantifying GPVI in the test sample may further be comprised. Using the method of detecting GPVI in test sample, diseases can be diagnosed. In particular, it is possible to use for diagnosing human diseases such as thrombotic, embolic or arteriosclerosis diseases.

Examples of the method of detecting GPVI in the test sample using the antibody of the present invention includes, but is limited to, the sandwich ELISA system, the inhibition-ELISA system, fluorescence antibody method, immunohistochemical staining method, radioisotope-labeled antibody method, Western blotting method, immunoprecipitation method and so on. As a target test sample, a biological sample is used, but is not limited. Examples of the sample include body fluid, tissues or cells from animal, particularly human, bacterial cells, and extracts thereof, culture supernatant, smears and sections, but preferred is platelet or plasma or serum.

In addition, measurement of GPVI on the platelet can be applied to monitoring of therapy associated with GPVI, especially prediction or determination of the effect of anti-GPVI antibody, or prognostic determination using disappearance of GPVI on the platelet as an index.

EXAMPLES

By the following examples, the present invention will further be described in detail. However, the present invention should not be understood by the limitation of these examples.

Example 1

Preparation of GPVI Extracellular Region-Fc Fusion Protein
A. Preparation of Human GPVI Extracellular Region-Mouse Fc Fusion Protein (hGPVI-mFc)
(1) Construction of the Expression Plasmid for hGPVI-mFc Fusion Protein Using mouse genomic DNA as a template, gene regions encoding respective domains of mouse immunoglobulin (mIgG2a) heavy chain constant region were amplified. That is, with the following primer pair, PCR reaction was performed. As a result, CH1 domain, hinge region, CH2 domain and CH3 domain were amplified with mIgG2a-a (SEQ ID NO: 152) and mIgG2a-c (SEQ ID NO: 154), mIgG2a-b (SEQ ID NO: 153) and mIgG2a-e (SEQ ID NO: 156), mIgG2a-d (SEQ ID NO: 155) and mIgG2a-g (SEQ ID NO: 158), and mIgG2a-f (SEQ ID NO: 157) and mIgG2a-h (SEQ ID NO: 159), respectively. Then these four amplified products were mixed, and PCR reaction using primers mIgG2a-a and mIgG2a-h was performed to obtain an amplified product, wherein respective domains were ligated (DNA fragment encoding heavy chain constant region (Cγ2a)). After the amplified product was cloned into pT7-BlueT vector, DNA fragment encoding mouse Fc region was excised with restriction enzymes Bam HI and Kpn I to obtain fragment A. On the other hand, from pCAGGS-GPVI-Fc plasmid, DNA fragment encoding an extracellular domain of human GPVI was excised with restriction enzymes Xba I and Bgl II to obtain fragment B. These fragments were ligated to the downstream of EF promoter in the expression vector pEF2cew, which was prepared by cleavage with Xba I and Kpn I, so that fragment A+fragment B was made. As a result, a plasmid (pTK-2249) that expresses hGPVI-mFc (SEQ ID NO: 222) was constructed.

(2) Expression and Purification of hGPVI-mFc Fusion Protein

Cos-1 cells were cultured with Dulbecco's MEM medium supplemented with 10% fetal bovine serum. Transfection was performed by mixing an appropriate amount of pTK-2249 with transfection reagent (FUGENE® (reagent for transferring nucleic acid inside cells)6, Roche Diagnostics), dropping the above mixture into serum-free Dulbecco's MEM medium, and replacing this with culture fluid. Under condition of 5% CO2, the cells were cultured at 37° C. for three days. The culture supernatant was subjected to the purification through Protein A column (PROSEP® (reagents for use in biological processing)-A, MILLIPORE), and the purified preparation was used as an antigen for preparation of anti-GPVI antibody.

B. Construction and Expression of Expression Plasmid pTK-2233 for Human GPVI Extracellular Region-Human Fc Fusion Protein Fragment J that is obtained by cleaving the plasmid pCAGGS-GPVI-Fc harboring a gene encoding human GPVI-hFc with restriction enzymes Xba I and Eco T22I, and fragment K that is obtained by cleaving it with restriction enzymes Eco T22I and Bgl II was prepared respectively. By ligating the two fragments to the downstream of EF-1α promoter on the expression vector pEF2cew to make fragments J+K, a hGPVI-hFc expressing plasmid pTK-2233 was constructed. In addition, the expression and purification of hGPVI-hFc was performed in a similar manner of the case for hGPVI-mFc.

C. Construction of Expression Plasmid pTK-2440 for Mouse GPVI Extracellular Region-Human Fc Fusion Protein (mGPVI-hFc)

Using mouse genomic DNA as a template and primer pairs listed, PCR reaction was performed. As a result, the PCR amplified product 'hi' was obtained with mGPVI-h (SEQ ID NO: 162) and mGPVI-i (SEQ ID NO: 163); the PCR amplified product 'jk' with mGPVI-j (SEQ ID NO: 164) and mGPVI-k (SEQ ID NO: 165); the PCR amplified product 'lm' with mGPVI-l (SEQ ID NO: 166) and mGPVI-m (SEQ ID NO: 167); the PCR amplified product 'no' with mGPVI-n (SEQ ID NO: 168) and mGPVI-o (SEQ ID NO: 169); and the PCR amplified product 'pc' with mGPVI-p (SEQ ID NO: 170) and mGPVI-c (SEQ ID NO: 160). Using a mixture of these amplified products as a template and a mixture of primers mGPVI-e (SEQ ID NO: 161), mGPVI-q (SEQ ID NO: 171), mGPVI-r (SEQ ID NO: 172), mGPVI-s (SEQ ID NO: 173) and mGPVI-c, PCR reaction was performed to obtain an amplified product, wherein each fragment is ligated. This amplified product was cloned into pT7-BlueT vector and designated pTK-2437. Since in the gene region including mouse GPVI extracellular domain in pTK-2437, there have Nhe I restriction enzyme recognition site at 5' side and Bam HI restriction enzyme recognition site at 3' side, DNA fragment was prepared by cleavage with these enzymes. Then the fragment was inserted into pTK-2233, which is prepared by cleaving with restriction enzymes Xba I and Bam HI, to construct a mouse mGPVI-Fc expressing plasmid, pTK-2440.

D. Construction of Expression Plasmid for Cynomolgus Monkey GPVI Extracellular Region-Human Fc Fusion Protein (1) Construction of Expression Plasmid for Cynomolgus Monkey D1 D2-Human D3 Chimeric GPVI-Human Fc Fusion Protein Based on the information of human GPVI gene that is a known sequence, an appropriate primer pairs were designed and prepared. Then, using these primers and cynomolgus monkey genomic DNA as a template, PCR was performed to determine a part of gene sequence encoding cynomolgus monkey GPVI. Then, based on the obtained sequence, novel primer pairs for cynomolgus monkey were designed and prepared. Using each primer pairs and cynomolgus monkey genomic DNA as a template, PCR reaction was performed again. As a result, the amplified product 'ab' was obtained with macGPVI-a (SEQ ID NO: 174) and macGPVI-b (SEQ ID NO: 175); the amplified product 'dc' with hGPVI-d (SEQ ID NO: 180) and macGPVI-c (SEQ ID NO: 176); the amplified product 'dh' with macGPVI-d (SEQ ID NO: 177) and hGPVI-h (SEQ ID NO: 182) and the amplified product 'gg' with hGPVI-g (SEQ ID NO: 181) and macGPVI-g (SEQ ID NO: 178). Meanwhile, using pTK-2233 as a template and macGPVI-h (SEQ ID NO: 179) and IgG1-i (SEQ ID NO: 183), PCR reaction was performed to obtain the amplified product 'hi'. Using a mixture of the above-mentioned five amplified products as a template, PCR reaction with macGPVI-a and IgG1-i was performed once again. The amplified product obtained by this procedure includes a chimeric GPVI gene, in which cynomolgus monkey GPVI D1 and D2 and human D3 are fused. After cleavage with restriction enzymes Nhe I and Bam HI, the amplified product was inserted into pTK-2233 prepared by cleavage with restriction enzymes Xba I and Bam HI to construct an expression plasmid, pTK-2462 for cynomolgus monkey D1D2-human D3 chimeric GPVI-human Fc fusion protein (GPVI-FFH-hFc; SEQ ID NO: 223).

Example 2

Preparation of Anti-GPVI Antibody

A. Preparation of Rabbit Polyclonal Antibody

To prepare a polyclonal antibody to human GPVI, rabbit was immunized. That is, 20 μg of hGPVI-mFc prepared in EXAMPLE 1A was diluted with 500 μl of saline mixed with 500 μl of Freund complete adjuvant (DIFCO). And the mixture was subcutaneously administered to the dorsal of female New Zealand white rabbit (KITAYAMA LABES) whose weight was 2.1-2.2 kg. Two weeks later, once again, 20 μg of hGPVI-mFc was diluted with 500 μl of saline and mixed with 500 μl of Freund incomplete adjuvant (DIFCO). Then, the mixture was subcutaneously administered to the dorsal. One week after the administration, the blood was collected from the ear vein, and according to the conventional method, antiserum was prepared to purify an antibody. That is, to the anti-serum ammonium sulfate was added to make the final concentrations of saturated solution 33%. After stirring at 4° C. for one hour, the precipitate was isolated by centrifugation. Next, the precipitate was dissolved in the Dulbecco's phosphate buffered saline (hereinafter, referred to as D-PBS) and dialyzed against D-PBS for overnight. After filtration of the dialysate, it was applied to Protein A column (PROSEP®-A, Millipore) to get a purified antibody by eluting a bound IgG fraction with 0.1-M Glycine-hydrochloride buffer solution (pH3.0). The obtained eluate fraction was immediately neutralized in 1 M Tris-HCl buffer (pH7.0) and dialyzed against D-PBS. After dialysis, protein concentration was calculated from the absorbance at 280 nm (The absorbance coefficient: 0.714 mg/mL). Hereinafter, the obtained antibody is denoted as the anti-GPVI polyclonal antibody.

B. Preparation of an Anti-human GPVI Monoclonal Antibody

By mixing 20 μg of GPVI-mFc and Freund complete adjuvant (DIFCO) at equal volume, an antigen for immunization was prepared. The antigen was administered twice to female ddY mouse (8-week age, SLC), and 3 days later, lymphocyte was isolated from the lymph node. The obtained lymphocyte was mixed with P3×63-Ag. 8. U1 (ATTC), and according to "The Introduction to Monoclonal Antibody Experimental Procedure" written by Tamie Andoh and Takeshi Chiba (Kodansha, p83), using polyethylene glycol (PEG1500, Sigma) a cell fusion was performed. Hybridoma was selected by HAT medium and one week later, the screening of the hybridoma that produces a desired antibody was performed by two ways. That is, a method of using a binding activity to hGPVI-hFc immobilized to a plate as an index, and a method of using an inhibiting activity for binding of collagen with GPVI as an index were utilized.

(1) Screening of Hybridoma Using the Binding Activity as an Index

The hGPVI-hFc prepared by EXAMPLE 1B was diluted with D-PBS to 2 μg/mL and added to immunoplate (Maxisorp, NUNC) at 50 μL/well. After incubation at 37° C. for one hour, the well was washed five times with ion-exchanged water, and D-PBS (pH7.4) containing 2% STABILGUARD® (chemical solutions for stabilizing biological molecules) (Surmodics) was added to each well in 100 μL for blocking. Next, culture supernatant was added to each well and incubated at 37° C. for one hour. After incubation, the well was washed three times with the saline containing 0.05% TWEEN®20 (Polyoxyethylene (20) sorbitan monolaurate). Peroxidase-labeled anti-mouse immunoglobulin antibody (DAKO, P260) was 1000-fold diluted with D-PBS containing 10% rabbit serum and added to each well at 50 μL. After incubation at 37° C. for one hour, washing in a similar manner was performed five times and TMB solution (BIOFX® (reagents for scientific or medical research) was added to each well. After ten minutes at room temperature, the reaction was terminated with 0.5 M sulfuric acid solution. Subsequently, absorbance at 450 nm was measured with the plate spectrophotometer (Multiscan JX, Dainippon Pharmaceutical). As a result, the cell whose culture supernatant reacted to hGPVI-hFc was selected and a cloning with limiting dilution method ("The Introduction to Monoclonal Antibody Experimental Procedure" written by Tamie Andoh and Takeshi Chiba (Kodansha, p97)) was performed. Eight days later, screening was done in a similar manner and the antibody which reacts to hGPVI-hFc was selected.

(2) Screening of Hybridoma Using an Inhibiting Activity for Binding of Collagen with GPVI as an Index Collagen (Horn) was diluted with D-PBS to 10 μg/mL and added to immunoplate (Maxisorp, NUNC) at 50 μl/well. After incubation at 4° C. for overnight, the well was washed five times with ion-exchanged water and blocked with D-PBS containing 5% BSA. Next, culture supernatant was added to each well at 25 μL/well. Further, hGPVI-hFc prepared to 2 μg/mL with D-PBS was added to the well at 25 μL/well. After incubation at 37° C. for one hour, the well was washed three times with the saline containing 0.05% TWEEN®20. Peroxidase-labeled anti-human IgG antibody (BioMeda) was 1000-fold diluted with D-PBS containing 10% goat serums and added to each well at 50 μL. After incubation at 37° C. for one hour, washing in a similar manner was performed five times and TMB solution (BIOFX®) was added to each well. After ten minutes at room temperature, the reaction was terminated with 0.5 M sulfuric acid solution. Subsequently, absorbance at 450 nm was measured with the plate spectrophotometer (Multiscan JX, Dainippon Pharmaceutical). The well, wherein the absorbance decreased by equal to or more than 50% in comparison with the well without the antibody, was selected as a hybridoma that produces an anti-GPVI antibody.

As a result, by performing the multiple cell fusion (the F number shows 1 batch), hybridoma having an inhibiting activity for the binding of collagen with GPVI was selected.

(3) Preparation of Antibody Produced by Hybridoma

Hybridoma that produces an anti-GPVI antibody was cultured in 10% FCS/RPMI-1640 medium (Sigma). After replacement of the medium with Hybridoma-SFM medium (Invitrogen), hybridoma was further cultured to produce the antibody. From the culture supernatant, the antibody was purified using Protein A column (PROSEP®-rA, Millipore). That is, the obtained culture supernatant was subjected to Protein A column (PROSEP®-A, Millipore) pre-equilibrated with D-PBS. After washing non-adsorbed protein with D-PBS, adsorbed fraction was eluted with 25 mM Glycine-hydrochloride buffer (pH3.0). Thereafter, the fraction was dialyzed against saline. Concentration of the obtained antibody was calculated from absorbance at 280 nm using an absorption coefficient (E1%: 1.4). Hereinafter, the obtained antibody is referred to as the anti-GPVI monoclonal antibody.

Example 3

Group Classification of the Anti-GPVI Monoclonal Antibody

In order to classify the antibody obtained in EXAMPLE 2 by the binding property to GPVI, i.e. the difference of the binding region, using F1199, F1201, F1202, F1210 and F1211 antibodies, respectively, competitive assay was performed. Firstly, according to the method described by Nakane et al. (J. Histochem. Cytochem., 22, 1084, 1974), each peroxidase-labeled anti-GPVI monoclonal antibody was prepared.

Then, using the peroxidase-labeled antibody, competitive assay for respective purified antibodies was carried out to classify them. That is, hGPVI-hFc was diluted with D-PBS to 2 μg/mL, and the diluted solution was added to immunoplate (Maxisorp, NUNC) at 50 μL/well. After reaction at 37° C. for one hour, the well was washed five times with ion-exchanged water, and D-PBS containing 2% STABILGUARD® was added to each well for blocking. Then, 25 μL each of the above-mentioned labeled antibody and the purified antibody were added to the well and incubated at 37° C. for one hour. After washing five times with saline containing 0.05% TWEEN®20, color development was done by TMB solution (BIOFX®). After reacting at room temperature for 10 minutes, the reaction was terminated with 0.5 M sulfuric acid solution. With plate spectrophotometer (Multiscan JX, Dainippon Pharmaceutical Co. Ltd.), absorbance at 450 nm was measured The absorbance in the absence of a purified antibody was made 100%, and the inhibiting activity to each labelled antibody was calculated to classify each purified antibody. As a result, the one which competes with labeled antibodies (i), (ii), (v) and (viii) was designated group a. The one which competes with labelled antibodies (i), (v) and (vii) was designated group b. The one which competes with labelled antibodies (i), (ii), (vii) and (viii) was designated group c. Also, the one which competes with labeled antibodies (iii) and (iv) was designated group d. The one which competes with labeled antibodies (iii), (iv) and (vi) was designated group e. The one which competes with labeled antibodies (iii) and (vi) was designated group f. Also, the one whose regularity cannot be seen was designated groups g and h. Since the groups g and h did not compete with each other, they formed another group. Therefore, antibodies are classified into eight groups in their recognition site of the surface of GPVI.

Example 4

Group Classification of the Antibodies Used in the Monkey Ex Vivo Test

Among the prepared anti-human GPVI monoclonal antibodies, antibodies that bind to monkey GPVI and are applicable for ex vivo test were classified according to the method for the group classification performed in EXAMPLE 3. That is, using each labeled antibody prepared in EXAMPLE 3, in a similar method to that of EXAMPLE 3, the competitive assay was done to classify each antibody. As shown in Table 1, just like EXAMPLE 3, the antibodies were classified into seven groups of the antibody that recognizes at least seven regions.

TABLE 1

| Group a | F1232-10-1 | | | |
| Group b | F1232-16-1 | | | |
| Group c | F1232-39-3 | F1232-21-1 | F1232-13-3 | |
| Group d | F1232-7-1 | F1232-9-1 | F1232-11-1 | |
| | F1232-19-1 | F1232-37-2 | F1201-18 | |
| Group e | F1232-17-1 | F1232-18-3 | | |
| Group f | F1232-8-3 | F1232-14-2 | F1232-15-1 | F1232-24-1 |
| | F1232-38-1 | F1232-45-1 | F1232-29-2 | |
| Group g | F1201-20 | F1232-27-1 | | |
| Group h | F1232-43-3 | | | |

Example 5

Determination of Dissociation Constant for the Anti-GPVI Monoclonal Antibody

Dissociation constant for the anti-GPVI monoclonal antibodies prepared in EXAMPLE 2 was measured using protein interaction analyzer BIACORE® 3000 (BIACORE). That is, GPVI substitution mutant (hGPVIHHH-hFc and FFH-hFc) that is prepared in EXAMPLE 1 was coupled to sensor chip, CM5 chip (BIACORE), according to the manual. Then each antibody was diluted with HBS-EP buffer solution (BIACORE) to prepare a series of diluted solution from 1.25 to 40 nM, and analyzed with BIACORE® 3000. Every each antibody bound chip, the chip was regenerated with glycine buffer solution at pH1.5. The obtained result was analyzed by the evaluation software (BIACORE) with Bivalent analyte, to calculate dissociation constant. The result was shown in Table 2. It was shown that each anti-GPVI monoclonal antibody has a sufficient affinity to GPVI-HHH-hFc.

TABLE 2

| Classification | Antibody | Dissociation Constant (KD) M | |
| --- | --- | --- | --- |
| | | ヒトGPVI | サルGPVI |
| Group a | F1232-10-2 | $8.33 \times 10^{-10}$ | $1.09 \times 10^{-9}$ |
| Group c | F1232-21-1 | $1.39 \times 10^{-9}$ | $3.56 \times 10^{-9}$ |
| Group d | F1232-7-1 | $3.47 \times 10^{-8}$ | $3.43 \times 10^{-7}$ |
| | F1232-19-1 | $1.75 \times 10^{-9}$ | $2.35 \times 10^{-9}$ |
| | F1232-37-2 | $4.03 \times 10^{-10}$ | $1.00 \times 10^{-9}$ |
| | F1201-18 | $1.16 \times 10^{-9}$ | $6.19 \times 10^{-10}$ |
| Group e | F1232-17-1 | $5.22 \times 10^{-10}$ | $1.77 \times 10^{-10}$ |
| | F1232-18-3 | $1.65 \times 10^{-9}$ | $3.65 \times 10^{-7}$ |
| Group f | F1232-14-2 | $1.56 \times 10^{-8}$ | $2.14 \times 10^{-8}$ |
| | F1232-24-1 | $2.5 \times 10^{-10}$ | $7.1 \times 10^{-10}$ |
| Group g | F1201-20 | $1.50 \times 10^{-8}$ | $7.55 \times 10^{-9}$ |
| Group h | F1232-43-3 | $1.36 \times 10^{-9}$ | $1.69 \times 10^{-9}$ |

Example 6

Preparation of Sandwich EIA System Using Anti-GPVI Polyclonal Antibody

In order to prepare sandwich EIA system, the anti-GPVI polyclonal antibody obtained in EXAMPLE 2 was labeled with peroxidase just like EXAMPLE 3. Then a plate coated with anti-GPVI polyclonal antibody was prepared. That is, the antibody was diluted with D-PBS to 10 μg/mL and 50 μL of the antibody was added to each well of immunoplate (Maxisorp, NUNC) to incubate at 45° C. for 30 minutes. Then, the well was washed five times with ion-exchanged water and to each well, 100 μL of D-PBS containing 2% STABILGUARD® (Surmodics) was added for blocking. As a standard sample, the purified GPVI-hFc was diluted with 0.1% BSA/D-PBS to 0.75 ng/ml, 1.5 ng/ml, 3.1 ng/ml, 6.25 ng/ml, 12.5 ng/ml, 25 ng/ml and 50 ng/ml. As a blank, D-PBS containing 0.1% BSA was used. At first, a blocking agent on the plate was discarded and 50 μL of the prepared standard sample and the blank was dispensed to each well for incubation at 25° C. for overnight. The plate was washed three times with saline containing 0.05% TWEEN®20. Subsequently, 50 μL of the peroxidase-labeled anti-GPVI polyclonal antibody that was diluted with D-PBS containing 10% rabbit serum and 0.1% TWEEN®20 to 10 μg/ml was added to the well to incubate at 37° C. Similarly, after washing five times, TMB solution (BIOFX®) was added to each well to incubate at room temperature for 20 minutes, and the reaction was terminated with 0.5 M sulfuric acid solution. With the plate spectrophotometer (Multiscan JX, Dainippon Pharmaceutical), an absorbance at 450 nm was measured to prepare standard curve.

Example 7

Analysis for Recognition Region of the GPVI Antibody

By replacing a part of the amino acid sequence in human GPVI with the corresponding amino acid sequence of mouse GPVI and examining the change of the antibody reactivity, the recognition region of each anti-GPVI antibody was refined. That is, since an extracellular region of GPVI, the platelet membrane protein is composed of three domains, i.e. immunoglobulin-like regions 1 and 2 (sometimes referred to as domain 1 or D1, and domain 2 or D2) and mucin-like domain (sometimes referred to as domain 3 or D3) (FIG. 1), substitution mutants for each domain were prepared and a binding assay of anti-GPVI antibody for each substitution mutants was performed.

In addition, with the purpose of further refinement of the anti-GPVI antibody recognition region, among the proteins registered to the Protein Databank (PDB), based on the information of human NK cell activating receptor Nkp46, Ig-like transcript 2 (ILT2), whose homology of the amino acid sequence to GPVI immunoglobulin-like region is relatively high, a modeling for human GPVI was conducted to deduce the regions in which amino acid mutations can be introduced (FIG. 1). Then, expression plasmids for human GPVI mutants having amino acid substitutions in those loop regions with mouse GPVI were constructed, and the binding assay of the anti-GPVI antibodies to each mutants was performed. As a result, each domain and loop region of GPVI, which each anti-GPVI monoclonal antibody recognizes could be confirmed. In addition, in the specification, the domain or the amino acid substitution mutant of GPVI is sometimes merely referred to as GPVI substitution mutants.

TABLE 3

Amino acid sequence of each loop in domain 1 and domain 2 of soluble human GPVI

| Loop No. | Sequence No. | Amino acid sequence |
| --- | --- | --- |
| Loop 1 | 1 | GPLPKP |
| Loop 2 | 2 | PSSLVPLEKP |
| Loop 3 | 3 | PPGVDL |
| Loop 4 | 4 | SSSRYQDQ |
| Loop 5 | 5 | PAMKRSLAGR |
| Loop 6 | 6 | QNGSLWSLPSDQ |
| Loop 7 | 7 | VFAKPS |
| Loop 8 | 8 | AQPGPAVSSGGD |
| Loop 9 | 9 | TRYGFDQ |
| Loop 10 | 10 | KEGDPA |
| Loop 11 | 11 | ERWYR |
| Loop 12 | 12 | ITVTAAHS |
| Loop 13 | 13 | FSSRDPYL |
| Loop 14 | 14 | ELVVTG |

(1) Construction of Expression Plasmids for Human-Mouse GPVI Domain Substitution Mutants Using hGPVI-hFc (hereinafter referred to as GPVI-HHH-hFc; SEQ ID NO: 135) expressing plasmid (pTK2233) and mGPVI-hFc (hereinafter referred to as GPVI-MMM-hFc; SEQ ID NO: 136) expression plasmid (pTK2440), which are prepared in EXAMPLE 1, as a template, an expressing plasmid for GPVI substitution mutant, wherein the domains of human GPVI and mouse GPVI are exchanged, was constructed.

That is, to construct an expression plasmid for GPVI substitution mutant comprising mouse GPVI domain 1 and human domains 2 and 3 (hereinafter referred to as GPVI-MHH-hFc; SEQ ID NO: 137), using pTK2440 as a template and sense primer 1 that is designed at the position upstream mouse GPVI sequence (Table 4; SEQ ID NO: 184) and antisense primer 3, wherein 15mer of the N-terminus of domain 2 in human GPVI is ligated to 15mer of the C-terminus of domain 1 in mouse GPVI (Table 4; SEQ ID NO: 186), PCR was performed to amplify DNA fragment of domain 1 in mouse GPVI (417 bp). Next, using pTK2233 as a template and anti-sense primer 2 that is designed at the position on hFc sequence (Table 4; SEQ ID NO: 185) and sense primer 4, wherein 15mer of the N-terminus of domain 2 in human GPVI is ligated to 15mer of the C-terminus of domain 1 in mouse GPVI (Table 4; SEQ ID NO: 187), PCR was performed to amplify DNA fragment (571 bp) comprising human GPVI domain 2, domain 3 and the N-terminus of hFc. Then, by performing PCR using the amplified two DNA fragments, sense primer 1, anti-sense primer 2, DNA fragment (973 bp), wherein the domain 1 of mouse GPVI, the domain 2 and domain 3 of human GPVI, and the N-terminal sequence of hFc, was amplified. After cutting this amplified DNA fragment with restriction enzymes XbaI and BamHI, the fragment was inserted into XbaI-BamHI site of pTK2233 to construct GPVI-MHH-hFc expressing plasmid.

With respect to the expression plasmids for GPVI substitution mutants comprising sequences of human domain 1, mouse domain 2 and human domain 3 in GPVI (hereinafter represented by GPVI-HMH-hFc; SEQ ID NO: 138) and GPVI substitution mutant comprising sequences of mouse domain 1 and domain 2, and human domain 3 in GPVI (hereinafter represented by GPVI-MMH-hFc; SEQ ID NO: 139), in a similar manner, using sense and anti-sense primers (Table 4; SEQ ID NOs: 191 and 190, respectively) that are prepared by ligating 15mer each of human and mouse GPVI sequences at the joint position of the domain in GPVI desired to replace, sense primer 1 and anti-sense primer 2, needed DNA fragment was amplified. After cleaving with restriction enzymes XbaI and BamHI, by inserting the fragment into the XbaI-BamHI site of pTK2233, the expression plasmid was constructed. In addition, the amino acid sequences of five GPVI mutants were shown in SEQ ID NOs: 141-151.

(2) Construction of Expression Plasmids for GPVI Substitution Mutants, Wherein a Loop Region of Human GPVI is Replaced with the Corresponding Amino Acid Sequence Derived from Mouse Expression plasmids for GPVI substitution mutants, wherein a single loop region to be a recognition region of an anti-GPVI monoclonal antibody is replaced with the corresponding amino acid sequence of mouse GPVI, was constructed as follows. First, in the loop region L2 of human GPVI, the base sequence was replaced so that the amino acid sequence from human was substituted for that from mouse. Further, sense primer 10, wherein 11mer of human GPVI base sequence was ligated upstream from the replaced base (Table 4) and anti-sense primer 9, wherein 13mer of human GPVI base sequence was ligated downstream from the replaced base (Table 4) were prepared. Next, by performing PCR using pTK2233 as a template, and sense primer 1 and anti-sense primer 9, DNA fragment (215 bp) corresponding to the N-terminus of the human GPVI, wherein the loop region L2 is substituted for the sequence from mouse, was amplified. In a similar manner, using pTK2233 as a template, and sense primer 10 and anti-sense primer 2, PCR was performed to amplify DNA fragment (773 bp), wherein the N-terminal sequence of hFc is connected to the C-terminal region of human GPVI, in which the loop region L2 is substituted for the sequence from mouse. Then, by performing PCR using the amplified two DNA fragments, sense primer 1, and anti-sense primer 2, DNA fragment (958 bp), wherein the N-terminal sequence of hFc is connected to the C-terminal region of human GPVI, in which the loop region L2 is substituted for the sequence from mouse, was amplified. After cutting this amplified DNA fragment with restriction enzymes XbaI and BamHI, the fragment was inserted into XbaI-BamHI site of pTK2233 to construct an expressing plasmid for GPVI substitution mutant, wherein the region L2 of human GPVI is replaced with the amino acid sequence of mouse GPVI (hereinafter represented by hGPVI-mL2-hFc; SEQ ID NO: 140).

Expression plasmid for GPVI substitution mutants, wherein other loop regions are replaced, such as hGPVI-mL3-hFc, hGPVI-mL4-hFc, hGPVI-mL5-hFc, hGPVI-mL6-hFc, hGPVI-mL7-hFc, hGPVI-mL8-hFc, hGPVI-mL9-hFc, hGPVI-mL10-hFc, hGPVI-mL11-hFc, hGPVI-mL13-hFc, hGPVI-mL14-hFc, were constructed in a similar manner. The primer sequences that are used for construction of each GPVI substitution mutant-expressing plasmid were shown in Table 4. In addition, the amino acid sequences of the GPVI substitution mutants prepared, was shown by SEQ ID NOs: 141-151.

TABLE 4

Primer sets and PCR-amplified regions for the construction of expression plasmid of each domain-substituted or loop-substituted GPVI mutant

| GPVI mutant | PCR-amplified region | Sense primer | Anti-sense primer |
|---|---|---|---|
| GPVI-HHH-hFc (Seq. ID. 135) | | | |
| GPVI-MMM-hFc (Seq. ID. 136) | | | |
| GPVI-MHH-hFc (Seq. ID. 137) | Mouse domain 1 | Seq. ID. 184 | Seq. ID. 186 |
| | Human domain 2, 3 | Seq. ID. 187 | Seq. ID. 185 |
| GPVI-HMH-hFc (Seq. ID. 138) | Human domain 1 | Seq. ID. 184 | Seq. ID. 188 |
| | Mouse domain 2 | Seq. ID. 189 | Seq. ID. 190 |
| | Human domain 3 | Seq. ID. 191 | Seq. ID. 185 |
| GPVI-MMH-hFc (Seq. ID. 139) | Mouse domain1, 2 | Seq. ID. 184 | Seq. ID. 190 |
| | Human domain 3 | Seq. ID. 191 | Seq. ID. 185 |
| hGPVI-mL2-hFc (Seq. ID. 140) | N-terminus side | Seq. ID. 184 | Seq. ID. 192 |
| | C-terminus side | Seq. ID. 193 | Seq. ID. 185 |
| hGPVI-mL3-hFc (Seq. ID. 141) | N-terminus side | Seq. ID. 184 | Seq. ID. 194 |
| | C-terminus side | Seq. ID. 195 | Seq. ID. 185 |
| hGPVI-mL4-hFc (Seq. ID. 142) | N-terminus side | Seq. ID. 184 | Seq. ID. 196 |
| | C-terminus side | Seq. ID. 197 | Seq. ID. 185 |
| hGPVI-mL5-hFc (Seq. ID. 143) | N-terminus side | Seq. ID. 184 | Seq. ID. 198 |
| | C-terminus side | Seq. ID. 199 | Seq. ID. 185 |
| hGPVI-mL6-hFc (Seq. ID. 144) | N-terminus side | Seq. ID. 184 | Seq. ID. 200 |
| | C-terminus side | Seq. ID. 201 | Seq. ID. 185 |
| hGPVI-mL7-hFc (Seq. ID. 145) | N-terminus side | Seq. ID. 184 | Seq. ID. 202 |
| | C-terminus side | Seq. ID. 203 | Seq. ID. 185 |
| hGPVI-mL8-hFc (Seq. ID. 146) | N-terminus side | Seq. ID. 184 | Seq. ID. 204 |
| | C-terminus side | Seq. ID. 205 | Seq. ID. 185 |
| hGPVI-mL9-hFc (Seq. ID. 147) | N-terminus side | Seq. ID. 184 | Seq. ID. 206 |
| | C-terminus side | Seq. ID. 207 | Seq. ID. 185 |
| hGPVI-mL10-hFc (Seq. ID. 148) | N-terminus side | Seq. ID. 184 | Seq. ID. 208 |
| | C-terminus side | Seq. ID. 209 | Seq. ID. 185 |
| hGPVI-mL11-hFc (Seq. ID. 149) | N-terminus side | Seq. ID. 184 | Seq. ID. 210 |
| | C-terminus side | Seq. ID. 211 | Seq. ID. 185 |
| hGPVI-mL13-hFc (Seq. ID. 150) | N-terminus side | Seq. ID. 184 | Seq. ID. 212 |
| | C-terminus side | Seq. ID. 213 | Seq. ID. 185 |
| hGPVI-mL14-hFc (Seq. ID. 151) | N-terminus side | Seq. ID. 184 | Seq. ID. 214 |
| | C-terminus side | Seq. ID. 215 | Seq. ID. 185 |

(3) Preparation of GPVI Substitution Mutants

The GPVI substitution mutant-expressing plasmid constructed in EXAMPLE 7 (1) and (2), pTK2233 and pTK2440 were introduced into the COS-1 cell and expressed in a similar manner shown in EXAMPLE 1. From culture supernatants obtained, the desired GPVI substitution mutants were purified by the Protein A column (PROSEP®-A, Millipore).

Purity of GPVI substitution mutants obtained was confirmed by SDS-PAGE under both reducing and non-reducing conditions, and silver staining.

(4) Binding Activity with Human-Mouse GPVI Domain Substitution Mutant

By replacing the domain of human GPVI with the corresponding domain of mouse GPVI, the recognition region of the antibody was refined. That is, the binding activity of GPVI-HHH-hFc, GPVI-MHH-hFc, GPVI-HMH-hFc, GPVI-MMH-hFc and GPVI-MMM-hFc with each anti-GPVI monoclonal antibody was assayed.

First, rabbit anti-human IgG antibody (DAKO) was immobilized to the plate (Maxisorp, Nunc) at 5 μg/mL, and the plate was blocked with 2% STABILGUARD® (SurModics). Next, after removing blocking solution, the GPVI substitution mutant diluted with 0.1% BSA/PBS was added to react at 37° C. for one hour. After washing with 0.9% saline containing 0.05% TWEEN®20, blocking with 1% human serum (Cosmo Bio) diluted with 0.1% BSA/PBS was done at 37° C. for one hour. Once again, after washing with 0.9% saline containing 0.05% TWEEN®20, the peroxidase-labeled antibody prepared in EXAMPLE 3 was diluted to 0.5 μg/mL with 0.1% BSA/PBS, and added to the plate to incubate at 37° C. for one hour. Finally, after washing with 0.9% saline containing 0.05% TWEEN®20, the reaction mixture was developed using H2O2/TMB solution. The reaction was terminated with 0.5 M sulfuric acid, and an absorbance at 450 nm of wavelength was measured.

As a result, in F1232-10-2, F1232-21-1, F1201-20, F1232-43-3 and F1232-14-2 antibodies, the binding activity to GPVI-MHH-hFc, GPVI-MMH-hFc and GPVI-MMM-hFc, wherein domain 1 was substituted for mouse GPVI, remarkably reduced. From the fact, it became clear that the recognition region of these antibodies existed in the domain 1 of GPVI. On the other hand, in F1232-7-1, F1232-19-1, F1232-37-2, F1232-17-1, F1232-18-3 and F1232-24-1 antibodies, the binding activity to GPVI-HMH-hFc, GPVI-MMH-hFc, GPVI-MMM-hFc, wherein domain 2 was substituted for mouse GPVI, declined remarkably. It was supposed that the recognition region of these antibodies existed in the domain 2 of GPVI.

The antigen recognition region of each anti-GPVI antibody was shown in Table 5.

(5) Binding Activity with GPVI Substitution Mutant, Wherein the Loop Region in Human GPVI was Replaced with the Corresponding Amino Acid Sequence Derived from Mouse The binding activity of GPVI-HHH-hFc, hGPVI-mL2-hFc, hGPVI-mL3-hFc, hGPVI-mL4-hFc, hGPVI-mL5-hFc, hGPVI-mL6-hFc, hGPVI-mL7-hFc, hGPVI-mL8-hFc, hGPVI-mL9-hFc, hGPVI-mL10-hFc, hGPVI-mL11-hFc, hGPVI-mL13-hFc and hGPVI-mL14-hFc with each anti-GPVI monoclonal antibody was measured.

By comparing the binding activity to GVI substitution mutant, wherein the loop region in human GPVI was replaced with the loop region from mouse, with that to human GPVI, the recognition region of the antibody was refined to the loop region replaced.

In a similar manner as described in EXAMPLE 7 (4), peroxidase-labeled antibody prepared in EXAMPLE 3 was diluted to a measurable concentration with 0.1% BSA/PBS in conformity with the affinity of each antibody to GPVI-HHH-hFc, and used for the measurement. As a result, in F1232-10-2, F1232-21-1 and F1232-43-3 antibodies, the binding activity to hGPVI-mL2-hFc remarkably decreased. In F1232-14-2 antibody, the activity to hGPVI-mL3-hFc and hGPVI-mL5-hFc declined. In F1201-20 antibody, the activity to hGPVI-mL4-hFc and hGPVI-mL5-hFc declined. Also, in F1232-7-1, F1232-37-2, F1232-17-1, F1232-18-3 and F1232-24-1 antibodies, the activity to hGPVI-mL9-hFc and in F1232-19-1 antibody, the activity to hGPVI-mL9-hFc and hGPVI-mL11-hFc reduced, respectively. The antigen recognition region of each anti-GPVI antibody was shown in Table 5.

TABLE 5

| Clone No. | Recognition domain | D1 | | | | | D2 | | | | | | |
|---|---|---|---|---|---|---|---|---|---|---|---|---|---|
| | | L2 | L3 | L4 | L5 | L6 | L7 | L8 | L9 | L10 | L11 | L13 | L14 |
| F1232-21-1 | D1 | ● | | | | | | | | | | | |
| F1232-10-2 | D1 | ● | | | | | | | | | | | |
| F1201-20 | D1 | | | ● | ● | | | | | | | | |
| F1232-14-2 | D1 | | ● | | ● | | | | | | | | |
| F1232-43-3 | D1 | | ● | | | | | | | | | | |
| F1232-7-1 | D2 | | | | | | | | ● | | | | |
| F1232-19-1 | D2 | | | | | | | | ● | | ● | | |
| F1232-37-2 | D2 | | | | | | | | ● | | | | |
| F1232-18-3 | D2 | | | | | | | | ● | | | | |
| F1232-17-1 | D2 | | | | | | | | ● | | | | |
| F1232-24-1 | D2 | | | | | | | | ● | | | | |

●: maens a case of ressuls that the antibody binding with a loop-substituted hGPVI is 30% or less of binding with hGPVI-hFc.

TABLE 6

| | Results of ex vivo test | | | | | | |
|---|---|---|---|---|---|---|---|
| | | | depletion of membran protein | | | Depletion of platelet aggregation | |
| Clone No | Thronbocytopenia | Platelet activation | CD41a | CD42a | GPVI | Collagen-induced | ADP-induced |
| F1232-7-1 | + | − | − | − | ++ | + | − |
| F1232-18-3 | − | − | − | − | ++ | ++ | − |
| F1232-24-1 | + | − | − | − | ± | ± | − |
| F1232-10-2 | − | − | − | − | ++ | ++ | ± |
| F1232-21-1 | + | − | ± | ± | ++ | ++ | ± |
| F1232-14-2 | − | − | − | − | ± | − | − |
| F1201-18 | ± | − | − | − | + | ++ | − |
| F1232-43-3 | − | − | − | − | ++ | ++ | − |
| F1201-20 | − | − | − | − | + | + | − |

TABLE 6-continued

Results of ex vivo test

| Clone No | Thronbocytopenia | Platelet activation | depletion of membran protein | | | Depletion of platelet aggregation | |
|---|---|---|---|---|---|---|---|
| | | | CD41a | CD42a | GPVI | Collagen-induced | ADP-induced |
| F1232-37-2 | − | − | − | − | + | ++ | − |
| F1232-17-1 | ± | − | − | − | ++ | ++ | − |
| F1232-19-1 | ++ | − | ± | ± | ++ | ++ | − |

Thronbocytopenia: −; 20%>, ±; 20%~40%, +; 40%~60%, ++; 60%<
Platelet activation: −; 2-fold, ±; 2-fold~5-fold, +; 5-fold~10-fold, ++; 10-fold<
Depletion of platelet membrane protein (FACS): −; 30%> (1 mg/kg administration), ±; 30%~70% (1 mg/kg administration), +; 70% (1 mg/kg administration), ++; 70%< (0.3 mg/kg administration)
Loss of platelet aggregability: −; 30% (1 mg/kg administration), ±; 30%~70% (1 mg/kg administration), +; 70%< (1 mg/kg administration), ++; 70%< (0.3 mg/kg administration)

Example 8

Evaluation of Anti-GPVI Monoclonal Antibody by Ex Vivo Experiment Using Cynomolgus Monkey Each anti-GPVI monoclonal antibody prepared in EXAMPLE 2 was intravenously administered to male cynomolgus monkey (about 6 kg) at intervals of 24 hours in the dose of 0.3 mg/kg and 1 mg/kg. Prior to administration, 24 hours and 48 hours after the first administration, blood was collected, and number of platelet, expression level of CD62P protein (marker for platelet activation), expression level of platelet membrane protein (GPIIb/IIIa; CD41a and GPVI; CD42a), expression level of platelet GPVI and platelet aggregability (the reactivity to collagen and ADP) were assayed.

A. Measurement of Number of Platelet

Number of platelet of citrated blood was counted using Sysmex F-820. In the monkeys, to which clones F1232-18-3, F1232-10-2, F1232-14-2, F1232-43-3, F1201-20 and F1232-37-2 were administered respectively, no decrease in platelet number was observed (the decreasing rate was less than 20%; in Table 6, represented by symbol "−"). Further, in the monkeys, to which F1201-18 and F1232-17-1 were administered, downward trend of platelet number was observed (the decreasing rate was 20% to 40%; in Table 6, represented by symbol "±"). Meanwhile, in the monkeys, to which F1232-7-1, F1232-24-1 and F1232-21-1 were administered, apparent decreasing of platelet counts was observed (the decreasing rate was 40% to 60%; in Table 6, represented by symbol "+"), especially the decreasing was remarkable in the case of F1232-19-1 (the decreasing rate was equal to or more than 60%; in Table 6, represented by symbol "++").

B. Detection of CD62P Protein on Platelet

Citrated blood was centrifuged at 100×g at 25° C. for 20 minutes to prepare platelet rich plasma (PRP). After PRP was diluted with PBS containing 0.5% heat-inactivated FBS and 2.5 mM EDTA (hereinafter referred to as FACS buffer) to make platelet number of PRP 1×10$^8$ cells/mL, using anti-human CD62P-PE (BD Biosciences Pharmingen), expression of CD62P protein on the platelet from monkey was analyzed by FACS. That is, anti-human CD62P-PE was added to PRP and the mixture was stood at room temperature for 30 minutes. After that, the platelet was washed with FACS buffer, and fluorescent intensity of the platelet was measured by flow cytometer CYTOMICS FC500 (BECKMAN COLETER). As a result, in any PRP prepared from the monkeys, to which anti-GPVI monoclonal antibody was administered, no increasing of expression of CD62P was observed in comparison with the level before administration (induction of expression was less than two-fold; in Table 6, represented by symbol "−").

C. Detection of CD41a and CD42a Proteins on Platelet

A measurement of the expression level of CD41a and CD42a proteins on monkey platelet was performed by FACS analysis using anti-human CD41a-FITC (BD Biosciences Pharmingen) and anti-human CD42a-PE (BD Biosciences Pharmingen) respectively after preparation of PRP in a similar manner to the case of CD62P. As a result, in the PRP prepared from the monkey, to which F1232-21-1 and F1232-19-1 have been administered, a slight decrease in CD41a and CD42a proteins was observed (the depletion rate after administration of 1 mg/kg was 30% to 70%; in Table 6, represented by symbol "±"). However, in the PRP prepared from the monkey, to which other anti-GPVI monoclonal antibodies have been administered, no effect on the expression of CD41a and CD42a proteins was observed (the depletion rate after administration of 1 mg/kg was less than 30%; in Table 6, represented by symbol "−").

D. Detection of GPVI Protein on Platelet

Confirmation of GPVI protein on monkey platelet was performed by FACS analysis using anti-GPVI polyclonal antibody labeled with fluorescent dye Af488 after preparation of PRP in a similar manner to the case of CD62P. As a result, in the PRP prepared from the monkey, to which F1201-18, F1201-20 and F1232-37-2 had been administered, depletion of GPVI protein was observed (the depletion rate after administration of 1 mg/kg was equal to or more than 70%; in Table 6, represented by symbol "++"). Particularly, in F1232-7-1, F1232-18-3, F1232-10-2, F1232-21-1, F1232-43-3, F1232-17-1 and F1232-19-1, depletion was remarkable (the depletion rate after administration of 0.3 mg/kg was equal to or more than 70%; in Table 6, represented by symbol "++"). Meanwhile, in the PRP prepared from the monkey, to which F1232-24-1 and F1232-14-2 have been administered, partial disappearance was observed (the depletion rate after administration of 1 mg/kg was 30% to 70%; in Table 6, represented by symbol "±").

E. Assay for Platelet Aggregability

The platelet aggregation response to collagen or ADP was measured using platelet aggregation analyzer (PA-200 Aggregation Analyzer, Kowa). Firstly, after dilution of PRP with saline to make platelet number 3×10$^8$ cells/mL, CaCl$_2$ solution at the final concentration of 1 mM was added, and the mixture was incubated at 37° C. for 3 minutes. Further, collagen solution at the final concentration of 2 μg/ml or ADP solution at the final concentration of 10 μM was added for incubation at 37° C. for 12 minutes. The platelet aggregation rate was calculated by measuring light transmission with PA-200 Aggregation Analyzer (Kowa). As a result, in the PRP prepared from the monkey, to which F1232-7-1 and F1201-20 have been administered, decrease in collagen-responsive platelet aggregability was observed (the rate of loss after administration of 1 mg/kg was equal to or more than 70%; in Table 6, represented by symbol "+"). Particularly, in F1232-18-3, F1232-10-2, F1232-21-1, F1201-18, F1232-43-3, F1232-37-2, F1232-17-1 and F1232-19-1, the decrease was remarkable (the decreasing rate after administration of 0.3 mg/kg was equal to or more than 70%; in Table 6, represented by symbol "++"). Further, in the PRP prepared from the monkey, to which F1232-24-1 has been administered, partial decrease was observed (the decreasing rate after administration of 1 mg/kg was 30% to 70%; in Table 6, represented by symbol "±"). On the other hand, in F1232-14-2, little effect on aggregability was detected (the rate of loss after administration of 1 mg/kg was less than 30%; in Table 6, represented by symbol "−").

In addition, ADP-induced platelet aggregability, in PRP prepared from the monkey, to which F1232-10-2 or F1232-21-1 have been administered, was partial decreased (the rate of loss after administration of 1 mg/kg was 30% to 70%; in Table 6, represented by symbol "±"). However, in PRP prepared from the monkey, to which other anti-GPVI monoclonal antibodies have been administered, no effect on the platelet aggregation induced by ADP was observed (the rate of loss after administration of 1 mg/kg was less than 30%; in Table 6, represented by symbol "−").

Example 9

Determination of the Amino Acid Sequence of Variable Region of the Anti-GPVI Antibody Example of determining the amino acid sequence of variable region of the anti-GPVI antibody (clone F1232-7-1) was illustrated below. Regarding other anti-GPVI antibodies, using a similar experimental procedure, the amino acid sequence of variable region was determined.

That is, from hybridoma that produces the intended anti-GPVI monoclonal antibody, total RNA was extracted using RNEasy® (kit for purification of RNA from small cell and tissue samples) Micro Kit (QIAGEN), and single-stranded cDNA was synthesized with SUPERSCRIPT® (reverse transcriptase kit) III First-Strand Synthesis System for RT-PCR kit (Invitrogen). By PCR using the obtained single-stranded cDNA as a template and with Mouse Ig-Primer Set (Novagen), variable region was amplified and the base sequence was determined. The sequence information on database was retrieved to obtain the sequence around initiation codon, and 5'-primer was designed once again (F1232-7-1 heavy chain 5'-primer: 1232H-b (SEQ ID NO: 216); light chain 5'-primer: 1232K-a (SEQ ID NO: 218)). On the other hand, with respect to 3'-sequence of variable region, primers, to which restriction enzyme recognition site (Nhe I recognition sequence for the heavy chain and Bsi WI recognition sequence for the light chain) is attached, were designed without changing the amino acid sequence (F1232-7-1 heavy chain 3'-primer: 1031H-b (SEQ ID NO: 217); light chain 3'-primer: mIgK-BsiWI (SEQ ID NO: 219)). Herein, the restriction enzyme recognition site is able to ligate to human constant region. Using these primers, PCR was performed again to amplify heavy chain variable region and light chain variable region. Subsequently, using pT7BlueT vector (Novagen), the obtained amplified product was cloned. A plasmid harboring a gene fragment encoding heavy chain variable region and a plasmid harboring a gene fragment encoding light chain variable region were designated pTK-2464 and pTK-2466, respectively. Then, according to the conventional method, the base sequences of heavy chain variable region and light chain variable region were determined. The base sequences (SEQ ID NO: 87 for the heavy chain variable region and SEQ ID NO: 88 for the light chain variable region) and the amino acid sequences encoded by those (SEQ ID NO: 111 for the heavy chain variable region and SEQ ID NO: 112 for the light chain variable region) were shown in Table 7. Further, regarding clones other than F1232-7-1, the base sequences and the amino acid sequences were determined in a similar manner (Table 7). In addition, the sequence of CDR region in the amino acid sequence of variable region was shown in Tables 8 and 9.

TABLE 7

| Clone No. | Nucleotide sequence | | Amino acid sequence | |
|---|---|---|---|---|
| | Heavy chain | Light chain | Heavy chain | Light chain |
| F1232-7-1 | Seq. ID. 87 | Seq. ID. 88 | Seq. ID. 111 | Seq. ID. 112 |
| F1232-18-3 | Seq. ID. 89 | Seq. ID. 90 | Seq. ID. 113 | Seq. ID. 114 |
| F1201-20 | Seq. ID. 91 | Seq. ID. 92 | Seq. ID. 115 | Seq. ID. 116 |
| F1232-17-1 | Seq. ID. 93 | Seq. ID. 94 | Seq. ID. 117 | Seq. ID. 118 |
| F1232-19-1 | Seq. ID. 95 | Seq. ID. 96 | Seq. ID. 119 | Seq. ID. 120 |
| F1232-21-1 | Seq. ID. 97 | Seq. ID. 98 | Seq. ID. 121 | Seq. ID. 122 |
| F1232-43-3 | Seq. ID. 99 | Seq. ID. 100 | Seq. ID. 123 | Seq. ID. 124 |
| F1201-18 | Seq. ID. 101 | Seq. ID. 102 | Seq. ID. 125 | Seq. ID. 126 |
| F1232-10-1 | Seq. ID. 103 | Seq. ID. 104 | Seq. ID. 127 | Seq. ID. 128 |
| F1232-37-2 | Seq. ID. 105 | Seq. ID. 106 | Seq. ID. 129 | Seq. ID. 130 |
| F1232-14-2 | Seq. ID. 107 | Seq. ID. 108 | Seq. ID. 131 | Seq. ID. 132 |
| F1232-24-1 | Seq. ID. 109 | Seq. ID. 110 | Seq. ID. 133 | Seq. ID. 134 |

TABLE 8

| | Heavy chain | | |
|---|---|---|---|
| Clone No. | CDR1 | CDR2 | CDR3 |
| F1232-7-1 | DYAIH (SEQ ID NO: 15) | VISIYYDDT NYNQKFKG (SEQ ID NO: 16) | RRDSSG PYAMDY (SEQ ID NO: 17) |
| F1232-18-3 | SYAMS (SEQ ID NO: 18) | TISSGGSYT YYPDSVKG (SEQ ID NO: 19) | DYGYFDY (SEQ ID NO: 20) |
| F1201-20 | DYYVN (SEQ ID NO: 21) | EIYPGSGNT YYNEKFKG (SEQ ID NO: 22) | WRGNLYYDY DAETLFAY (SEQ ID NO: 23) |
| F1232-17-1 | SYGMS (SEQ ID NO: 24) | TISSGGSYT YYPDNVKG (SEQ ID NO: 25) | QVYYFGSCDY (SEQ ID NO: 26) |
| F1232-19-1 | SYGMS (SEQ ID NO: 27) | TISSGGSYT YYPDSVKG (SEQ ID NO: 28) | QVYYYGSSDY (SEQ ID NO: 29) |
| F1232-21-1 | YYLIE (SEQ ID NO: 30) | VINPGSGVT NYNEKFKG (SEQ ID NO: 31) | SIYYGTIDY (SEQ ID NO: 32) |
| F1232-43-3 | TYGIGVG (SEQ ID NO: 33) | HIWWDDNK YYNTALKS (SEQ ID ) NO: 34 | IHYYGSSLDY (SEQ ID NO: 35) |
| F1201-18 | SYAMS (SEQ ID NO: 36) | IISSGGSYT YYPDSVKG (SEQ ID NO: 37) | QGGGYFDY (SEQ ID NO: 38) |

TABLE 8-continued

| Clone No. | Heavy chain | | |
|---|---|---|---|
| | CDR1 | CDR2 | CDR3 |
| F1232-10-1 | TYGIGVG (SEQ ID NO: 39) | HIWWNDDK YYNTALKS (SEQ ID NO: 40) | VYYYGSSFDY (SEQ ID NO: 41) |
| F1232-37-2 | DYAIH (SEQ ID NO: 42) | VISIYYDDT NYNQKFKG (SEQ ID NO: 43) | RRDSSGP YAMDY (SEQ ID NO: 44) |
| F1232-14-2 | AAAAAA (SEQ ID NO: 45) | AAAAAA (SEQ ID NO: 46) | AAAAAA (SEQ ID NO: 47) |
| F1232-24-1 | DYAMH (SEQ ID NO: 48) | VISTYYGDA SYNQKFKG (SEQ ID NO: 49) | SYDYDPWFAY (SEQ ID NO: 50) |

TABLE 9

| Clone No. | Light chain | | |
|---|---|---|---|
| | CDR1 | CDR2 | CDR3 |
| F1232-7-1 | RASESVDS YGNSFMH (SEQ ID NO: 51) | RASNLES (SEQ ID NO: 52) | QQSNEDPYT (SEQ ID NO: 53) |
| F1232-18-3 | RASESVDN YGISFMH (SEQ ID NO: 54) | RASNLES (SEQ ID NO: 55) | QQSNTDPRT (SEQ ID NO: 56) |
| F1201-20 | RASQDISN YLN (SEQ ID NO: 57) | ATSSLDS (SEQ ID NO: 58) | LQYASYPYT (SEQ ID NO: 59) |
| F1232-17-1 | RASESVDN YGISFMH (SEQ ID NO: 60) | RASNLES (SEQ ID NO: 61) | QQSNKDPWT (SEQ ID NO: 62) |
| F1232-19-1 | RASESVDN YGISFMH (SEQ ID NO: 63) | RASNLES (SEQ ID NO: 64) | QQSNKDPWT (SEQ ID NO: 65) |
| F1232-21-1 | RASQDISN YLN (SEQ ID NO: 66) | YTSRLHS (SEQ ID NO: 67) | QQGSTLPYT (SEQ ID NO: 68) |
| F1232-43-3 | RASENIYS YLA (SEQ ID NO: 69) | AATNLAD (SEQ ID NO: 70) | QHFYGTPWT (SEQ ID NO: 71) |
| F1201-18 | RASESVDS YGNSFMH (SEQ ID NO: 72) | RASNVES (SEQ ID NO: 73) | QQSNEDPPT (SEQ ID NO: 74) |
| F1232-10-1 | RASENIFS ILA (SEQ ID NO: 75) | AATNLAD (SEQ ID NO: 76) | QHFYGTPWT (SEQ ID NO: 77) |
| F1232-37-2 | RASESVDS YGNSFMH (SEQ ID NO: 78) | RASNLES (SEQ ID NO: 79) | QQSNEDPYT (SEQ ID NO: 80) |
| F1232-14-2 | AAAAAA (SEQ ID NO: 81) | AAAAAA (SEQ ID NO: 82) | AAAAAA (SEQ ID NO: 83) |
| F1232-24-1 | RASESVDN YGISFMH (SEQ ID NO: 84) | RASNLES (SEQ ID NO: 85) | QQSNKDPLT (SEQ ID NO: 86) |

Example 10

Production of Mouse-Human Chimeric Antibody by Genetic Manipulation

An antibody, wherein V region having an antigen binding activity is derived from hybridoma antibody, i.e. mouse antibody, and C region is derived from human, that is, a chimeric antibody was prepared.

(1) Construction of Mouse-Human Chimeric Antibody-Expressing Plasmid

Construction of expression plasmid for anti-GPVI mouse-human chimeric antibody (Clone No. F1232-7-1) was performed as follows.

First, by cleaving pTK-2464 with restriction enzymes EcoR I and Nhe I, a gene fragment C encoding heavy chain region was prepared. On the other hand, by cleaving pTK-2232 (see, EXAMPLE 10 of WO 2005/7800) with restriction enzymes Eco 47111 and Bam HI, a gene fragment D encoding heavy chain constant region (Cγ4) was prepared. These fragments were ligated to the downstream of EF promoter in the expression vector pEF2cew preliminarily cleaved with Eco RI and Bam HI, to become fragment C+fragment D for construction of heavy chain-expressing plasmid (pTK-2468).

Next, by cleaving pTK-2466 with restriction enzymes EcoR I and BsiW I, DNA fragment E encoding the light chain variable region was prepared. On the other hand, using HeLa genomic DNA as a template and primers BsiWI-hIgK (SEQ ID NO: 220) and IgK-e (SEQ ID NO: 221), PCR was performed and human light chain constant region (Cκ) was cloned into pT-7BlueT (pT7-hIgK). To obtain the DNA fragments encoding a human light chain constant region from pT7-hIgK, pT7-hIgK was cleaved with restriction enzymes Bsi WI and Bam HI to prepare DNA fragment F. These fragments were ligated to the downstream of EF promoter in the expression vector pEF2cew preliminarily cleaved with Eco RI and Bam HI, to become fragment E+fragment F for construction of light chain-expressing plasmid (pTK-2474).

(2) Expression of Recombinant Mouse-Human Chimeric Antibody and Confirmation of the Binding Activity to GPVI Expression and purification of mouse-human chimeric antibody that is constructed were performed in a similar method as shown in EXAMPLE 1. That is, expression plasmids for heavy chain and light chain of the mouse-human chimeric antibody of intended clones were co-transfected to the COS-1 cell, and cultured at 37° C. for three days. After cultivation, the culture supernatant was purified by Protein A column. Purity of the obtained mouse-human chimeric antibody was confirmed by SDS-PAGE. Further, a binding ability to human GPVI and monkey GPVI was confirmed. First, GPVI substitution mutant, hGPVI-hFc or GPVI-FFH-hFc that were prepared in EXAMPLE 1 were diluted to 2 µg/mL with D-PBS and 50 µL/well of the solution was added to immunoplate (Maxisorp, NUNC). Next, after incubation at 37° C. for one hour, the well was washed five times with ion-exchanged water, and 100 µL of D-PBS containing 2% STABILGUARD® (Surmodics) was added to each well for blocking. Then, the purified mouse-human chimeric antibody was added to each well and incubated at 37° C. for one hour. After incubation, the well was washed three times with saline containing 0.05% TWEEN®20. Peroxidase-labeled anti-human light chain kappa antibody (DAKO) was 1000-fold diluted with D-PBS containing 10% rabbit serum and 50 µL was added to each well. After incubation at 37° C. for one hour, five times washing was performed in a similar manner. Subsequently, TMB solution (BIOFX®) was added to each well. After incubation at room temperature for 10 minutes, the reaction was terminated by adding 0.5 M sulfuric acid solution. With the plate spectrophotometer (Multi-Scan JX, Dainippon Pharmaceutical), absorbance at 450 nm was measured. As a result, it was confirmed that the prepared mouse-human chimeric antibody specifically binds to human and monkey GPVI.

Example 11

Preparation of Humanized Antibody
A. Preparation of Humanized Antibody (Method 1)
(1) Computer Modeling for Humanized F Antibody Variable Region To maintain high affinity in humanized antibody, framework residue is selected according to general method by Queen et al. (Proc. Natl. Acad. Sci. USA 86: 10029, 1989). As to a sequence from human, based on the database for κ light chain and heavy chain sequences by Kabat et al. (Sequences of proteins of immunological interest, 5th ed., U.S. Department of Health and Human Services, 1991), a sequence having a high framework homology in mouse anti-GPVI monoclonal antibody (clone No. F1232-7-1) is selected. Moreover, by computer analysis, amino acids in the most suitable framework are altered. Specifically, using computer program ENCAD (Levitt, J. Mol. Boil. 168: 595 (1983)), and protein modeling tools such as Hommology (accelris) and FAMS (SGI), a molecular model for F1232-7-1 antibody variable region is constructed. CDR sequences of F1232-7-1 antibody may be transplanted into FR of the human Eu antibody molecular model obtained from the antibody database (Stephens et al., Immunology 85 (4), 668-674 (1995)). Through optimization or simulation such as molecular optimized calculation and molecular dynamical calculation, in FR region, in which a significant contact between CDR and FR is shown on the computer model, being different from the intrinsic human antibody model, substitution of amino acid derived from mouse antibody may be performed in the position where the contact between CDR and FR is expected to be improved by an amino acid substitution. Also, the amino acid residues in FR that infrequently appears at the position in the human antibody database are replaced with the amino acids consensus to human at those positions. Since the quality for the amino acid substitution must be confirmed by actual activity, several kinds of antibodies with the different type of the amino acid substitution may be prepared.
(2) Construction of Humanized Antibody Based on the sequence selected in EXAMPLE 11A (1), a gene encoding the amino acid sequence comprising a signal peptide, a splice donor signal and a restriction site (e.g. Eco RI) is constructed. Several synthetic nucleotides (about 80 bases) based on the constructed gene were prepared to make them overlap. That is, the oligonucleotide are paired and annealed. Then they are extended by the Klenow fragment of DNA polymerase to obtain double-stranded fragments. After denaturing this fragment to become a single strand and annealing them, they are extended by the Klenow fragment of DNA polymerase to obtain double-stranded fragments encoding entire gene. The obtained fragment is amplified by PCR and purified. After cleavage with restriction enzymes such as Eco RI and Nhe I, the fragment is re-purified. The purified fragment is ligated to a gene fragment comprising CH1 exon to CH3 exon of human IgG4 constant region gene (Cγ4), wherein, for example, pTK-2232 is cleaved with Nhe I and Bam HI, and inserted into the downstream of EF promoter in expression vector pEF2cew, which is preliminarily cleaved with Eco RI and Bam HI to construct an expression plasmid for humanized heavy chain. Also, when the amino acid residues to be substituted are a little, it is possible to introduce the mutated amino acids into expression plasmid by site-directed mutagenesis. The sequence for light chain variable region can be constructed as described above. In this case, human Cκ region is excised from pT7-hIgK, ligated to the light-chain variable region sequence and incorporated downstream EF promoter of the expression vector pEF2cew.

To prepare a transformant which produces an antibody, a heavy chain plasmid and a light chain plasmid are linearized with restriction enzymes and is introduced into mouse myeloma cell, Sp2-O-ag14 (ATCC CRL1581) using Genepulsar (BIORAD). For example, 20 µg of the linearized DNA fragment is electroporated into $1 \times 10^7$ cells at capacitance of 360 V, 25 µFD. Next, the cells are inoculated to 96-well plate and cultured for two days. After cultivation, to select the cell, in which the fragment of plasmid is incorporated, D-MEM (Sigma) containing 10% FCS, 1×HT (Invitrogen), 0.25 mg/ml Xanthine, 1 µg/ml Mycophenolic acid is added and is further cultivated for two weeks. After cultivation, by analyzing an antibody in the supernatant, the intended humanized F1232-7-1 antibody-producing cell line is selected. That is, the antibody in the supernatant is bound to the immobilized GPVI antigen and the bound antibody can be detected with peroxidase-labeled anti-human IgG4 antibody. The antibody producing cell line, wherein the binding has been detected, is cultured to become confluent in the medium containing 10% FCS, and the medium is replaced with serum-free medium (Hybridoma SFM, Invitrogen). Culture supernatant is recovered, and the antibody that is contained in the culture supernatant is bound to Protein A (PROSEP®-A, Millipore) to elute with 0.1 M Glycine-HCl (pH3.0). The purified antibody is dialyzed against PBS- (Sigma). Antibody concentration is calculated from absorbance at 280 nm (1 mg/mL of human antibody shows an absorbance of about 1.3).
(3) Evaluation of Humanized Antibody The binding ability of humanized antibody to GPVI antigen of the parent mouse antibody can be measured with BIACORE® system (BIACORE) and can be compared. That is, according to the manual of BIACORE® 3000, the purified hGPVI-mFc is immobilized to CM5 chip (BIACORE). Then a series of diluents of the antibody diluted with HBS-EP buffer (BIACORE) is prepared, and each sample may be injected. The obtained data are analyzed using program for analysis available from BIACORE (BIA Evaluation, BIACORE), and an affinity value (Kd) can be calculated.
B. Preparation of Humanized Antibody (Method 2)
(1) Preparation of a Gene Encoding Humanized Antibody In the humanized antibody, for maintaining CDR sequence to be grafted as an appropriate domain structure having an activity, a method of grafting the CDR sequence together with original FR region is also available. Whether any amino acid residue is involved in maintenance of the CDR domain structure is estimated from properties (hydrophobicity, hydrophilicity, acidity, basic, molecular size, etc.) of the amino acid in FR, and is presumable by modeling using computer. That is, modeling may be performed with the software QUANTA/CHARMm run on Silicon Graphics, or Modeler (Molecular Simulations). From the sequence of human antibody registered on Brookhaven Protein Data Bank (PDB), 3D structure of the antibody having a high homology to VH and VL regions of F1232-7 antibody is searched, and based on the result, the 3D structure of F1232-7 antibody is estimated. The amino acids in FR region, which binds via hydrogen bond to CDR of the heavy chain and the light chain on the deduced 3D structure (the first group), are selected, and further the amino acids in FR region, which binds via hydrogen bond to the first group, is selected (the second group). In a similar manner, the amino acids in FR region, which is estimated to bind to CDR by energy bond such as electrostatic interaction or van der Waal's force (the first group) and the amino acids in FR region, which further binds thereto (the second group) are selected. The amino acids in FR region thus selected, is grafted onto the sequence of human antibody together with the amino acid of CDR. However, when a sequence obtained by classification by Kabat et al. (Sequence of proteins of immunological interest, 5th ed., U.S. Department of Health and Human Services, 1991) or NCBI (National Center for Biotechnology Information), wherein the sequence does not exist in the amino acid sequence of variable region of human antibody, occurs, such sequence may not be grafted. Based on the thus obtained information, the sequence to be grafted to VH and VL of human antibody sequence can be determined, and the gene to be used for preparation of humanized antibody can be constructed.

The constructed gene may be prepared by a method in combination with the kit available from Amersham (Oligonucleotide-directed in vitro mutagenesis system version 2) and PCR method, a method of amplifying in combination with several kinds of nucleotides for long chain synthesis, or a method of amplifying using a gene encoding VH or VL of the chimeric antibody as a template and several primers followed by obtaining an intact gene fragment with their amplified gene fragment as a template. By ligating the obtained amplified gene fragment to the fragment of constant region in the plasmid (pTK-2232 or pT7-IgK) described in EXAMPLE 11A (2) and incorporating it into the downstream of EF promoter in the expression vector pEF2cew, an expression vector for humanized antibody can be constructed. By introducing the prepared plasmid into a cell by the method of EXAMPLE 11A (2) and obtaining a transformant, a purified antibody can equally be prepared. Further, as well as EXAMPLE 11A (3), evaluation of the antibody may be performed.

Example 12

Antigen Binding Property of GPVI Antibody Derived from a Patient with GPVI Deficiency and Antigen Binding Property of Mouse Anti-Human GPVI Monoclonal Antibody 12-1 Analysis for Antigen Binding Property of Anti-GPVI Antibody Derived from a Patient with GPVI Deficiency Using Human GPVI Loop Substitution Mutants The recognition domain of anti-GPVI antibody in the blood of a patient with GPVI deficiency (Tateo Sugiyama and five other members, Blood (USA), 1987, volume 69, No. 6, pp. 1712-1720) was analyzed using a variety of recombinant proteins. A purified specific antibody from the patient and a recombinant human GPVI loop substitution mutant described in EXAMPLE 7 were admixed. After reacting on polypropylene plate at 37° C. for two hours, 50 μL/well of the mixture was added to recombinant hGPVI-hFc-coated plate, which was prepared as with the method in EXAMPLE 2, and the plate was incubated at 37° C. for one hour. Then peroxidase-labeled anti-human κ and λ-chain antibody (DAKO, P130, P129) was 1000 fold diluted with D-PBS (pH7.4) containing 10% rabbit serums and 50 μL of the diluent was added to each well. After incubation at 37° C. for one hour, an absorbance was measured as with the method in EXAMPLE 2. A measurement value was compared with an absorbance in the case where the recombinant human GPVI loop substitution mutant was not added. From the result with loop substitution mutant without absorbance reduction or with a little extent of absorbance reduction, the antigen recognition site of anti-GPVI antibody included in GPVI-deficient patient's autoantibody was deduced.

The result was shown in Table 10. In the case where an antibody (#930819) of patient at early stage after developing of ITP was used as a subject, the absorbance obtained from hGPVI-hFc-mL4 (a protein wherein loop 4 of recombinant human GPVI-hFc is replaced with mouse loop 4; hereinafter, described as the same), hGPVI-hFc-mL5, hGPVI-hFc-mL9 and hGPVI-hFc-mL13 was not reduced. That is, it was found that the anti-GPVI antibody derived from GPVI deficient patient as an experiment subject comprises an antibody that recognizes loop 4, 5, 9 or 13. Meanwhile, in the case where an antibody (#021004) of patient with a long period after developing of ITP was used as a subject, the absorbance for hGPVI-hFc-mL9 and hGPVI-hFc-mL13 was not reduced. That is, it was found that the anti-GPVI antibody derived from GPVI deficient patient as an experiment subject comprises an antibody that recognizes loop 9 or 13.

TABLE 10

Absorption assay of the GPVI-deficient patient's antibody by mouse loop substitution mutant

| Patient's antibody | mL1 | mL2 | mL3 | mL4 | mL5 | mL6 | mL7 | mL9 | mL10 | mL11 | mL12 | mL13 | mL14 |
|---|---|---|---|---|---|---|---|---|---|---|---|---|---|
| # 930819 | − | − | − | + | + | − | − | + | − | − | − | + | − |
| # 021004 | − | − | − | − | − | − | − | + | − | − | − | + | − |

+: shows the case where no or little decrease in absorbance was observed when it was added as an absorption antigen.

−: shows the case where decrease in absorbance to the same extent as the unsubstituted protein (hGPVI-hFc) was observed when it was added as an absorption antigen.

Figure 2:
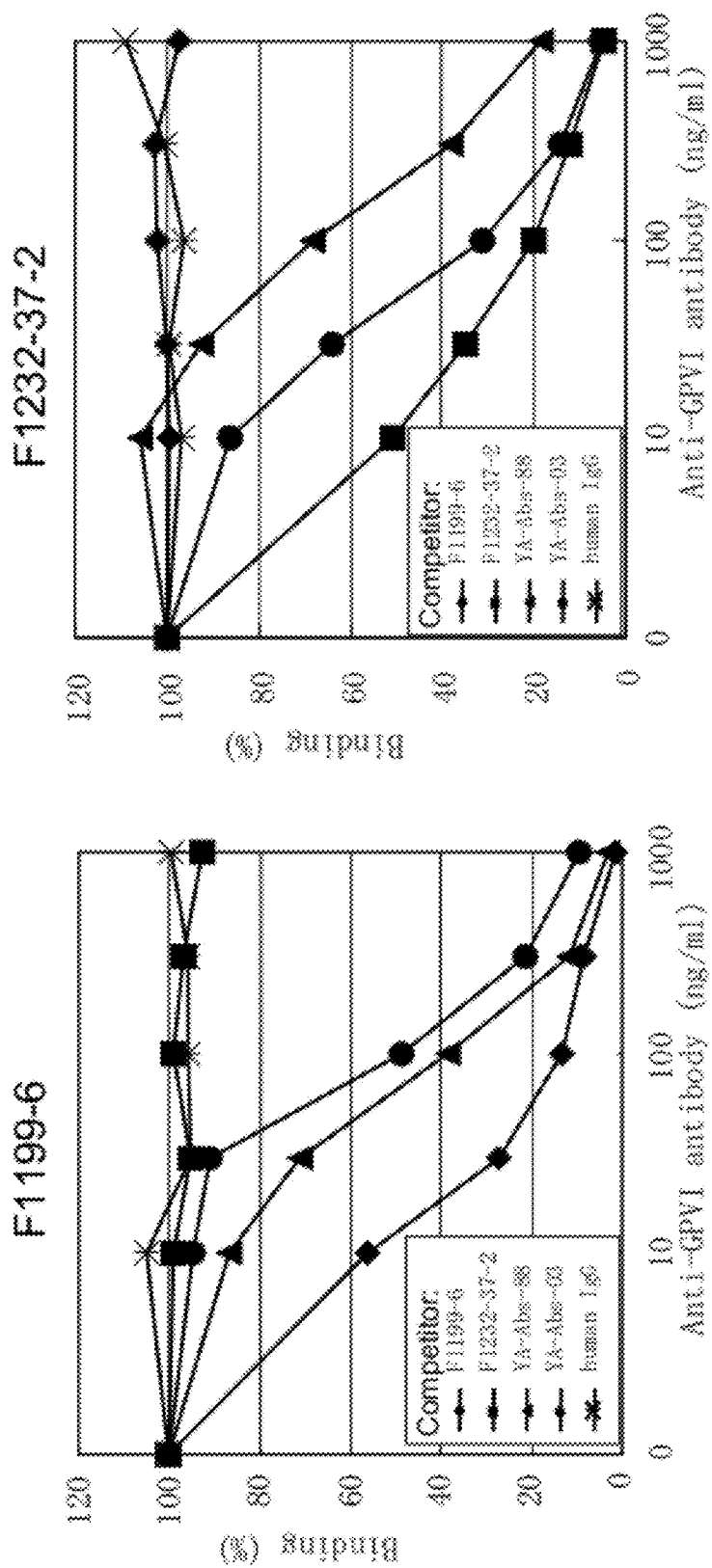
FIG. 2 presents the results of the competitive test of an antibody from a patient with GPVI deficiency with mouse anti-human GPVI monoclonal antibody. YA-Abs-88 and YA-Abs-03 mean anti-GPVI antibodies derived from a patient with GPVI deficiency.

12-2 Competitive Test of the Antibody of GPVI-Deficient Patient with the Mouse Anti-Human GPVI Monoclonal Antibody A competitive test of mouse anti-GPVI hybridoma antibody prepared in EXAMPLE 2 with anti-GPVI antibody included in the blood of GPVI-deficient patient was performed. That is, 50 µL/well of anti-GPVI antibody derived from a patient with GPVI deficiency was added to hGPVI-hFc-coated plate, which was described in 12-1, and the plate was incubated at 4° C. for overnight. Thereto peroxidase-labeled mouse anti-GPVI hybridoma antibody was added to make the absorbance 0.5 through 1.0. The mixture was reacted at 37° C. for 45 minutes, and the absorbance was measured as with the method in EXAMPLE 2. As a result, the mouse anti-human GPVI monoclonal antibodies F1199-6 and F1232-37-2, which were prepared by the same method as that of EXAMPLE 2, competed with the anti-GPVI antibody included in the blood of GPVI-deficient patient. The result is shown in FIG. 2.

Example 13

Preparation of Domain 2 (L9 Loop)-Specific Anti-Human GPVI Antibody 13-1 Preparation of Mouse Anti-Human GPVI Monoclonal Antibody By mixing 20 µg of purified hGPVI-mFc fusion protein, which was prepared in EXAMPLE 1, Alum (PIERCE), and oligo CpG, an antigen to be administered was prepared. To ddY mouse (female, 8-week old, SLC) the antigen was administered and further additional 20 µg of antigen was administered. After three days, a lymphocyte was isolated from lymph node or spleen. Then a cell fusion was done using the same method as that of EXAMPLE 2 to select a hybridoma.

After one week, hybridoma, which produces a desired antibody was screened using the binding property to hGPVI-hFc and hGPVI-mL9-hFc prepared in EXAMPLE 7 as an index. That is, the purified hGPVI-hFc or hGPVI-mL9-hFc, which was prepared in EXAMPLE 1, was diluted with D-PBS (pH7.4) to 1 µg/mL, and was added to Immunoplate (Maxisorb, NUNC) with 50 µg/well to make a solid phase using the same method as that of EXAMPLE 2. Next, a culture supernatant was added to each well, and after incubation at room temperature for one hour, by the same method as that of EXAMPLE 2, using peroxidase-labeled anti-mouse immunoglobulin antibody (DAKO, P260) a reaction was performed to measure an absorbance. As a result, the cell producing an antibody that binds to the purified hGPVI-hFc (absorbance: equal to or more than one), but not hGPVI-mL9-hFc (absorbance: equal to or less than 0.5) was selected and cloned by the method described in EXAMPLE 2. Eight through ten days later, a screening was done as with the similar way to obtain a hybridoma producing an L9-specific mouse anti-human GPVI antibody. As with EXAMPLE 2B (3), the obtained hybridoma was cultured and a monoclonal antibody was purified. The sub-type of each antibody was determined using IsoStrip Mouse Monoclonal antibody Isotyping Kit (Roche).

13-2 Preparation of Rat Anti-Human GPVI Monoclonal Antibody

The purified hGPVI-mFc fusion protein or the rat GPVI-mFc fusion protein, wherein L9 or L11 loop is replaced with the loop derived from human (ratGPVI-hL9/h11-mFc) (SEQ ID NO: 288) was used as an antigen to be administered. In addition, after synthesizing cDNA by reverse transcription using a rat bone marrow RNA as a template and oligo-dT primer, whole length gene of rat GPVI was cloned by PCR using the abovementioned cDNA as a template. Primer pair used for PCR is mGPVI-a: CCACATAGCTCAGGACTGGG (SEQ ID NO: 289) and mGPVI-d: CCAAGTTATTTCTAG-GCCAGTGG (SEQ ID NO: 290). Equal amount of antigen to be administered, 20 µg, and Freund's complete adjuvant (DIFCO) was mixed and administered to Wistar rat (female, 8-week old, SLC). After two weeks, a lymphocyte was isolated from lymph node. After mixing with SP2/O—Ag14 (ATTC), a cell fusion was performed using the same method as that of EXAMPLE 2 to select hybridoma.

After one week, hybridoma which produces a desired antibody was screened by the method described in the EXAMPLE 14-1. As a result, the cell producing an antibody that binds to the purified human GPVI-hFc (absorbance: equal to or more than one), but not the purified human GPVI-hFc, wherein L9 is replaced with mouse L9 (absorbance: equal to or less than 0.5) was selected and cloned by the method described in EXAMPLE 2 to obtain a hybridoma producing rat anti-human GPVI antibody. As with EXAMPLE 2B (3), the obtained hybridoma was cultured and a monoclonal antibody was purified. The sub-type of each antibody was determined using Rat MonoAB ID/SP Kit (ZYMED).

Example 14

Characterization of Anti-GPVI Monoclonal Antibody 14-1 Binding Property for Antigen To analyze a property for each antibody obtained in EXAMPLE 13, binding to human GPVI-hFc, competition with F1232-37-2 described in EXAMPLE 4 and specificity for L9 loop were investigated. That is, as for the binding to human GPVI, according to the method of EXAMPLE 2, a binding activity to immobilized antigen was measured. For the binding activity, the range of absorbance from 0.5 to 1.0 is represented by "+", from 1.0 to 2.0 by "++", the range more than 2.0 by "+++". The competitive test with F1232-37-2 was performed as follows. That is, according to the method by Nakane et al. (J. Histochem. Cytochem., 22, 1084, 1974), peroxidase (TOYOBO)-labeled F1232-37-2 antibody was prepared and an antibody concentration was calculated from the amount of the antibody used.

Next, by using the peroxidase-labeled antibody, the competitive test for a variety of purified antibody was performed. That is, 25 µL of the above labeled antibody and 25 µL of each purified antibody were added to well of hGPVI-hFc-immobilized plate. After incubation at 37° C. for one hour, the well was washed five times with the saline containing 0.05% TWEEN®20, and the reaction mixture was developed with TMB solution (BioFix). After incubation at room temperature for 10 minutes, the reaction was terminated with 0.5 M sulfuric acid solution and an absorbance at 450 nm was measured with the plate spectrophotometer (Multi-Scan JX, Dainippon Pharmaceutical). The result is shown in Table 11. For inhibiting activity, the case where more than 50% inhibition to the absorbance without inhibition antibody is represented by "+++", the case of 30% to 50% inhibition by "++" and the case of 10% to 30% inhibition by "+".

Specificity for L9 loop was measured according to the method described in EXAMPLE 13, 13-1. As a result, it is concluded that the case where the reactivity decline of more than 50% is exhibited is designated "+", that is, L9 loop is recognized.

TABLE 11 anti-human GPVI monoclonal antibodies prepared as the experimental example. 11

| Clone | Species | Binding to hGPVI-Fc | Inhibition on binding of Collagen to hGPVI-Fc | Competition with F1232-37-2 for hGPVI-hFc | KD (Relative value) |
|---|---|---|---|---|---|
| F1249-18-2 | Mouse | +++ | +++ | ++ | 1.03 × 10-3 |
| F1245-7-1 | Mouse | ++ | − | + | 2.93 × 10-3 |
| F1246-1-1 | Mouse | ++ | − | + | 8.84 × 10-1 |
| F1249-5-1 | Mouse | ++ | + | ++ | 2.85 × 10-3 |
| F1249-20-1 | Mouse | +++ | − | ++ | 2.05 × 10-3 |
| F1249-24-1 | Mouse | +++ | + | +++ | 8.21 × 10-3 |
| F1249-30-1 | Mouse | +++ | − | +++ | 3.47 × 10-1 |
| F1245-5-1 | Mouse | ++ | + | ++ | 1.43 |
| F1245-6-2 | Mouse | ++ | + | +++ | 1.22 × 10-1 |
| F1249-3-2 | Mouse | + | + | ++ | 1.59 |
| F1245-4-1 | Mouse | +++ | + | ++ | 4.27 × 10-3 |
| F1249-22-1 | Mouse | + | ++ | + | 2.06 |
| F1251-1-1 | rat | + | + | + | 7.90 |
| F1257-3-1 | rat | +++ | − | − | 2.98 × 10-3 |
| F1232-37-2 | Mouse | ++ | ++ | | 1 |

14-2 Inhibitory Activity on GPVI-Collagen Binding

Inhibitory activity on GPVI-collagen binding of each antibody obtained in EXAMPLE 13 was studied by the same method as that of EXAMPLE 2. The case where more than 50% inhibition to the absorbance without inhibition antibody is represented by "+++", the case of 30% to 50% inhibition by "++" and the case of 10% to 30% inhibition by "+" (Table 11).

14-3 Determination of Dissociation Constant

Dissociation constant of each antibody obtained in EXAMPLE 14 was determined by the same method as that of EXAMPLE 5. The result was shown in Table 11 as the relative value to the dissociation-constant of F1232-37-2.

Example 15

Identification of Amino Acid of Anti GPVI Antibody Variable Region (2)

An amino acid sequence of anti-human GPVI antibody variable region prepared in EXAMPLE 13 was determined by the same method as that of EXAMPLE 9. For the clone, wherein the base sequence for antibody variable region was determined, base sequence in CDR and variable regions and deduced amino acid sequence were shown in Tables 12 and 13 and the sequence listing (see Table 14). From the result of analyzing the gene sequence of antibody variable region, it is assumed that the sequences of these antibodies are derived from several kinds of certain genes for antibody. Further, it is recognized that repertoire selection of the antibody that recognizes loop 9 of human GPVI is characterized.

TABLE 12

Amino acid sequence of the CDR for anti-GPVI antibody heavy chain

| Clone No. | Heavy chain | | |
|---|---|---|---|
| | CDR1 | CDR2 | CDR3 |
| F1245-4-1 | SYWMH (SEQ ID NO: 335) | MIHPNSDNT NYNEKFKS (SEQ ID NO: 336) | HYYDYVDY (SEQ ID NO: 337) |
| F1245-5-1 | SYWMH (SEQ ID NO: 338) | MIHPNSGST HYNEKFKS (SEQ ID NO: 339) | GGVTPVAY (SEQ ID NO: 340) |
| F1245-6-2 | SYWMH (SEQ ID NO: 341) | MIHPNSGST NYNEKFKS (SEQ ID NO: 342) | GGVTPVAY (SEQ ID NO: 343) |
| F1245-7-1 | SYWMH (SEQ ID NO: 344) | MIHPNSGST NYNEKFKS (SEQ ID NO: 345) | PVTAVVEY YFDY (SEQ ID NO: 346) |
| F1246-1-1 | SYGMS (SEQ ID NO: 347) | TISNGGTYT YYPDSVKG (SEQ ID NO: 348) | LRDYYAMDY (SEQ ID NO: 349) |
| F1249-3-2 | SYGMS (SEQ ID NO: 350) | TISSGGSYT YYSDSVKG (SEQ ID NO: 351) | DSGYFDY (SEQ ID NO: 352) |
| F1249-5-1 | SYWMH (SEQ ID NO: 353) | MIHPNSDIT NYNEKFKN (SEQ ID NO: 354) | LGDYYAMDY (SEQ ID NO: 355) |
| F1249-18-2 | SYWMH (SEQ ID NO: 356) | MIHPNSDIT NYNEKFKN (SEQ ID NO: 357) | SGDYYAMDY (SEQ ID NO: 358) |
| F1249-20-1 | DYAMH (SEQ ID NO: 359) | VISTYYGDT SYNQKFKG (SEQ ID NO: 360) | AEDYDPWFAY (SEQ ID NO: 361) |
| F1249-22-1 | SYWMQ (SEQ ID NO: 362) | EIDPSDSYT NYNQKFKG (SEQ ID NO: 363) | GAITTATLDY (SEQ ID NO: 364) |

TABLE 12-continued

Amino acid sequence of the CDR for anti-GPVI antibody heavy chain

| Clone No. | Heavy chain CDR1 | CDR2 | CDR3 |
|---|---|---|---|
| F1249-24-1 | DYAMH (SEQ ID NO: 365) | VISTYYGDT SYNQKFKG (SEQ ID NO: 366) | AEDYDPWFAY (SEQ ID NO: 367) |
| F1249-30-1 | DYAMH (SEQ ID NO: 368) | VISTYYGDT SYNQKFKG (SEQ ID NO: 369) | AEDYDPWFAY (SEQ ID NO: 370) |
| F1251-1-1 | DYYIH (SEQ ID NO: 371) | YINPNSGYT NYNEKFKS (SEQ ID NO: 372) | CNSGYGDWFAY (SEQ ID NO: 373) |
| F1257-3-1 | TSGMVVS (SEQ ID NO: 374) | AIDWDGDKY YNPSLKS (SEQ ID NO: 375) | TPYYGYKEAYYFDY (SEQ ID NO: 376) |

TABLE 13

Amino acid sequence of the CDR for anti-GPVI antibody light chain

| Clone No. | Light chain CDR1 | CDR2 | CDR3 |
|---|---|---|---|
| F1245-4-1 | KASQSVSN DVA (SEQ ID NO: 377) | YASNRYT (SEQ ID NO: 378) | QQDYSSPWT (SEQ ID NO: 379) |
| F1245-5-1 | KASQSVSN DVA (SEQ ID NO: 380) | YASNRYT (SEQ ID NO: 381) | QQDYSSPWT (SEQ ID NO: 382) |
| F1245-6-2 | KASQSVSN DVA (SEQ ID NO: 383) | YASNRYT (SEQ ID NO: 384) | QQDYSSPWT (SEQ ID NO: 385) |
| F1245-7-1 | KASQSVSN DVA (SEQ ID NO: 386) | YASNRYT (SEQ ID NO: 387) | QQDYSSLT (SEQ ID NO: 388) |
| F1246-1-1 | RASESVDS YGNSFMH (SEQ ID NO: 389) | RASNLES (SEQ ID NO: 390) | QQSNEDPWT (SEQ ID NO: 391) |
| F1249-3-2 | RASESVDS YGNSFMH (SEQ ID NO: 392) | LASNLES (SEQ ID NO: 393) | QQSNNEDPRT (SEQ ID NO: 394) |
| F1249-5-1 | KASQSVSN DVT (SEQ ID NO: 395) | YASNRYT (SEQ ID NO: 396) | QQDYSSPPT (SEQ ID NO: 397) |
| F1249-18-2 | KASQSVSN DVA (SEQ ID NO: 398) | YASNRYT (SEQ ID NO: 399) | QQDYSSPPT (SEQ ID NO: 400) |
| F1249-20-1 | RASESVDS YGNSFMY (SEQ ID NO: 401) | RASNLES (SEQ ID NO: 402) | QQSDEDPLT (SEQ ID NO: 403) |
| F1249-22-1 | KSSQSLLNS NNQKNYLA (SEQ ID NO: 404) | FASTRES (SEQ ID NO: 405) | QQHYITPLT (SEQ ID NO: 406) |
| F1249-24-1 | RASESVDS YGNSFMH (SEQ ID NO: 407) | RASNLES (SEQ ID NO: 408) | QQSDEDPLT (SEQ ID NO: 409) |
| F1249-30-1 | RASESVDS YGNSFMH (SEQ ID NO: 410) | RASNLES (SEQ ID NO: 411) | QQSDEDPLT (SEQ ID NO: 412) |
| F1251-1-1 | KASQNINK NLD (SEQ ID NO: 413) | YTNNLQT (SEQ ID NO: 414) | YQYNSGPGT (SEQ ID NO: 415) |
| F1257-3-1 | KASRAIDD YLS (SEQ ID NO: 416) | DATSLAD (SEQ ID NO: 417) | LQSYSTPWT (SEQ ID NO: 418) |

TABLE 14

Nucleotide sequence and amino acid sequence of the variable region of anti-GPVI monoclonal antibody

| Clone No. | Nucleotide sequence Heavy chain | Nucleotide sequence Light chain | Amino acid sequence Heavy chain | Amino acid sequence Light chain |
|---|---|---|---|---|
| F1245-4-1 | Seq. ID224 | Seq. ID226 | Seq. ID225 | Seq. ID227 |
| F1245-5-1 | Seq. ID228 | Seq. ID230 | Seq. ID229 | Seq. ID231 |
| F1245-6-2 | Seq. ID232 | Seq. ID234 | Seq. ID233 | Seq. ID235 |
| F1245-7-1 | Seq. ID236 | Seq. ID238 | Seq. ID237 | Seq. ID239 |
| F1246-1-1 | Seq. ID240 | Seq. ID242 | Seq, ID241 | Seq, ID243 |
| F1249-3-2 | Seq. ID244 | Seq. ID246 | Seq. ID245 | Seq. ID247 |
| F1249-5-1 | Seq. ID248 | Seq. ID250 | Seq. ID249 | Seq. ID251 |
| F1249-18-2 | Seq. ID252 | Seq. ID254 | Seq. ID253 | Seq. ID255 |
| F1249-20-1 | Seq. ID256 | Seq. ID258 | Seq. ID257 | Seq. ID259 |
| F1249-22-1 | Seq. ID260 | Seq. ID262 | Seq. ID261 | Seq. ID263 |
| F1249-24-1 | Seq. ID264 | Seq. ID266 | Seq. ID265 | Seq. ID267 |
| F1249-30-1 | Seq. ID268 | Seq. ID270 | Seq. ID269 | Seq. ID271 |
| F1251-1-1 | Seq. ID272 | Seq. ID274 | Seq. ID273 | Seq. ID275 |
| F1257-3-1 | Seq. ID276 | Seq. ID278 | Seq. ID277 | Seq. ID279 |
| NEW-HAN | Seq. ID280 | — | Seq. ID281 | — |
| Eu-HC | Seq. ID282 | — | Seq. ID283 | — |
| REI-KA | — | Seq. ID284 | — | Seq. ID285 |
| Eu-KA | — | Seq. ID286 | — | Seq. ID287 |

Example 16

Production of Mouse/Human Chimeric Anti-GPVI Antibody (2)

16-1 Production of Mouse/Human Chimeric Antibody

The expression plasmid prepared by the same method as that of EXAMPLE 10 was introduced into COS-1 cells with the method below to develop a transient expression of chimeric antibody. In addition, when expressing cF1232-18-3

(Mouse/human chimeric antibody of mouse monoclonal antibody F1232-18-3 is referred to as cF1232-18-3. Hereinafter, other mouse monoclonal antibodies are referred to in a similar manner), co-transfection of the heavy chain expression plasmid pTK-2471 and the light chain expression plasmid pTK-2475 was done. For cF1232-43-3, cF1232-10-1 or cF1232-37-2, pTK-2504 and pTK-2514, pTK-2509 and pTK-2517, or pTK-2510 and pTK-2511 were co-transfected, respectively.

COS-1 cells were inoculated to CELLSTACK® (culture chambers) 10 Chamber (CORNING) at $2.1 \times 10^6$ cells/vessel and cultivated at 37° C. for four days. After discarding culture fluid, cells were washed twice with D-MEM. Then the following mixture with FUGENE®6/DNA/production medium was added with about 1.3 L/chamber. After mixing 2.12 ml of FUGENE®6 (Roche Diagnostics), 530 µg each of heavy chain expression plasmid and light chain expression plasmids according to the protocol attached, the mixture was added to 1.3 L of Hybridoma-SFM (Invitrogen). After addition of mixture with FUGENE®/DNA/production medium, cultivation was performed under the conditions of 37° C. for 3-4 days to collect the supernatant. Hybridoma-SFM medium, 1.3 L was newly added to CELLSTACK® 10 Chamber, and further cultivation was done for 3-4 days to collect the supernatant again. The mouse/human chimeric antibody expressed in the supernatant was purified as described below.

16-2 Purification of Mouse/Human Chimeric Antibody

Purification procedure was done at 4° C. if not otherwise specified. The cF1232-37-2/COS culture fluid prepared in 16-1 was clarified at room temperature using a capsule cartridge filter (Toyo Roshi Kaisha, Ltd.) having a one micrometer pore size as a prefilter and FLUORODYNE® (water and chemical filter cartridge) filter (PALL) having a 0.22 µm pore size as a real filter to obtain a culture supernatant. The culture supernatant was loaded onto rpm Protein A SEPHAROSE® (a crosslinked, beaded-form of agarose) Fast Flow (Amersham Biosciences) previously equilibrated with PBS- (Sigma). After washing non-absorbed proteins with PBS-, proteins non-specifically bound was eluted with 100 mM phosphate buffer containing 1.5 M NaCl. Thereafter the antibody specifically bound was eluted with 100 mM glycine-HCl buffer (pH 3.0). The volume of eluate was measured and by adding a 1/10 volume of 1 M Tris-HCl (pH 7.0) pH was immediately neutralized. The preparation obtained was dialyzed against 0.9% NaCl aqueous solution to obtain a purified preparation. Using a similar manner, cF1232-43-3, cF1232-10-1 or cF1232-18-3 was purified.

In addition, among monoclonal antibodies cloned in EXAMPLE 13, as for F1249-18-2, F1245-7-1, F1246-1-1, F1249-24-1, F1245-4-1, F1249-22-1 and F1251-1-1, using the similar methods, preparation of chimeric antibody expression plasmid, expression of the antibody in COS-1 cells and purification of the antibody were performed.

Example 17

Binding Property of Mouse/Human Chimeric Antibody to Antigen 17-1 Binding Property of Mouse/Human Chimeric Antibody to Antigen Dissociation constant of each chimeric antibody prepared in 16-2 was measured using the protein interaction analyzer BIACORE® 3000 (BIACORE) in a similar way to EXAMPLE 5. It was exhibited that the chimeric antibodies prepared have a sufficient affinity to hGPVI-hFc.

Figure 4:
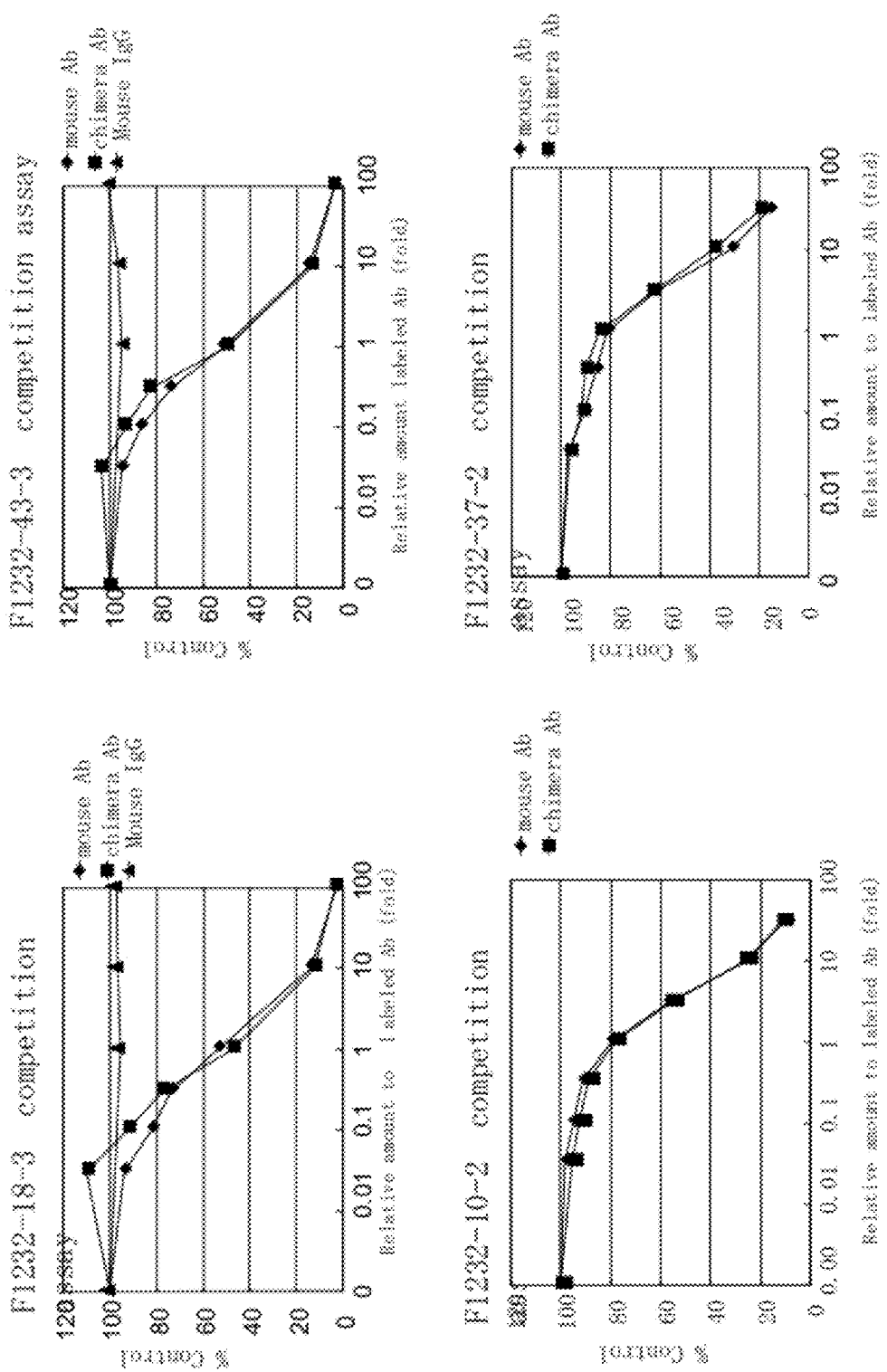
FIG. 4 shows the results of reactivity for mouse hybridoma antibody and chimeric antibody.
Figure 5:
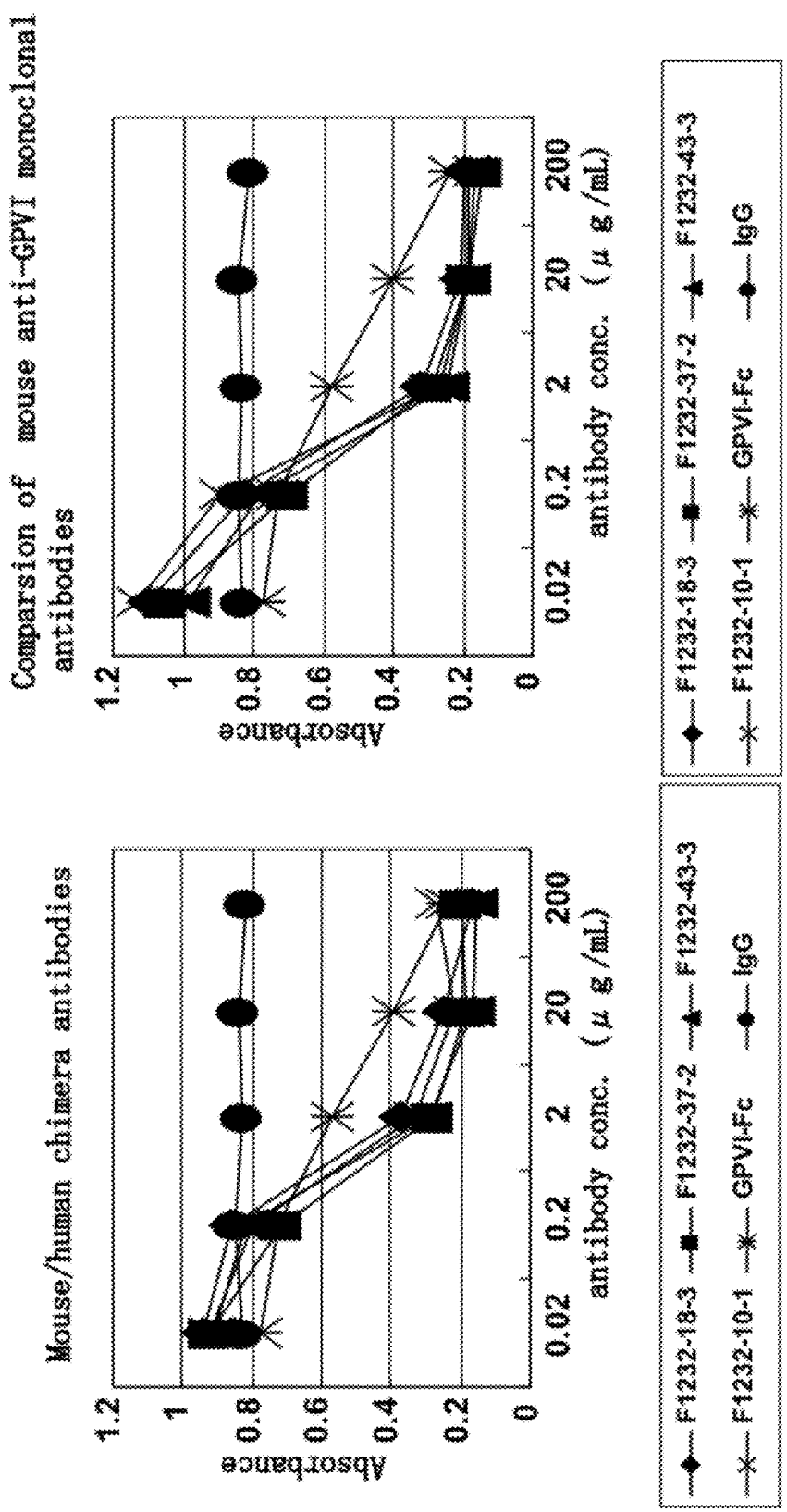
FIG. 5 shows the inhibition of binding between GPVI and collagen by the chimeric antibody and the mouse hybridoma antibody.

17-2 Comparison of Antigen Binding Property Between Mouse/Human Chimeric Antibody and Corresponding Mouse Monoclonal Antibody To compare an antigen binding property of mouse/human chimeric antibody with that of the corresponding mouse monoclonal antibody, in the same method as that of EXAMPLE 14, peroxidase-labeled F1232-37-2, F1232-18-3, F1232-43-3 and F1232-10-1 were prepared. By the competitive method (the method described in EXAMPLE 14, 14-1), wherein to the binding reaction system with these labeled antibody and immobilized hGPVI-hFc, the corresponding non-labeled mouse/human chimeric antibody is added, a binding activity of mouse monoclonal antibody to human GPVI was compared with that of the corresponding mouse/human chimeric antibody. As a result, as shown in FIG. 4, there was no difference in both. Further, an inhibiting activity of each antibody for binding of GPVI to collagen was measured according to the method described in EXAMPLE 2 or EXAMPLE 14. From a result of this experiment, as shown in FIG. 5, the inhibiting activity for binding of GPVI to collagen by each antibody to be tested was confirmed. The inhibiting activity for binding of GPVI to collagen by the chimeric antibody was equivalent to that by mouse hybridoma antibody.

17-3 Binding Property of Anti-Human GPVI Antibody to GPVI Mutant

To the plate, wherein hGPVI-hFc has been immobilized at 4 µg/mL, a mixture of peroxidase-labeled F1232-37-2 or cF1232-37-2 by the method described in EXAMPLE 14, and hGPVI-hFc, mGPVI-hFc, hGPVI-mL3-hFc, wherein these were prepared in EXAMPLE 7, or hGPVI-K59E-hFc (a fusion protein consisting of one amino acid mutated human GPVI extracellular region, wherein lysine at 59 of human GPVI is substituted for glutamic acid, and human Fc), which has been prepared by the same method as that of EXAMPLE 1 and diluted with 0.1% BSA/PBS was added, and the plate was incubated at 37° C. for one hour. After incubation, the mixture was developed using TMB solution, and absorbance at 450 nm was measured.

Figure 6:
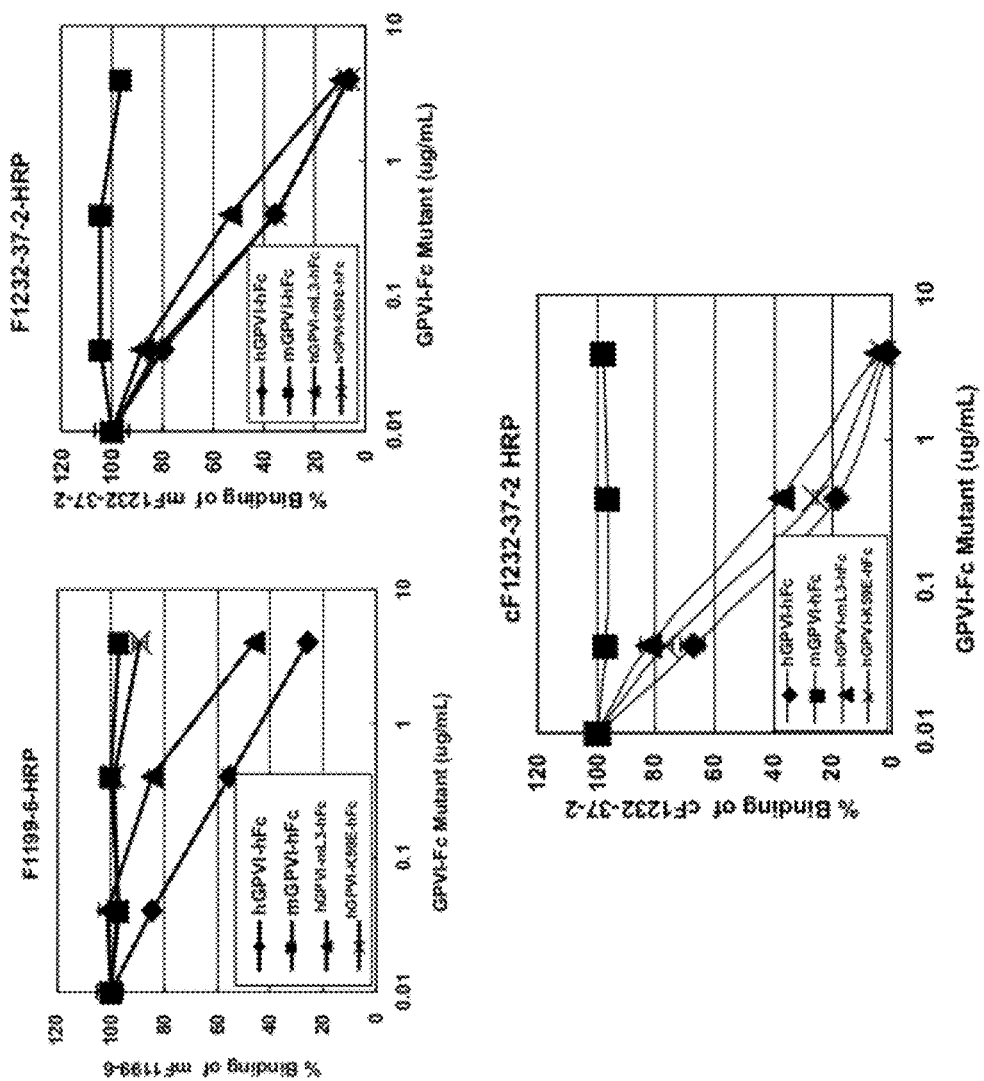
FIG. 6 presents the results of a binding property of anti-human GPVI antibody to GPVI mutant.

The experiment revealed that the binding of peroxidase-labeled F1232-37-2 or cF1232-37-2 to hGPVI-hFc is inhibited by hGPVI-hFc, hGPVI-mL3-hFc and hGPVI-K59E-hFc, but not by mGPVI-hFc. For this result, F1232-37-2 was equivalent to cF1232-37-2. On the other hand, mouse monoclonal antibody F1199-6 prepared by the same method as that of EXAMPLE 2 indicated a different event. That is, the binding of peroxidase-labeled F1199-6 antibody to hGPVI-hFc was inhibited by hGPVI-hFc and hGPVI-mL3-hFc, but not by hGPVI-mFc and GPVI-K59E-hFc. The result was shown in FIG. 6.

17-4 Analysis for Epitope of Mouse/Human Chimeric F1232-37-2 Antibody

To confirm an antigen recognition site for cF1232-37-2 antibody, a binding activity of GPVI-HHH-hFc, GPVI-MMM-hFc, hGPVI-mL2-hFc, hGPVI-mL3-hFc, hGPVI-mL4-hFc, hGPVI-mL5-hFc, hGPVI-mL6-hFc, hGPVI-mL7-hFc, hGPVI-mL8-hFc, hGPVI-mL9-hFc, hGPVI-mL10-hFc, hGPVI-mL11-hFc, hGPVI-mL13-hFc, and hGPVI-mL14-hFc, wherein these were prepared in EXAMPLE 7, to cF1232-37-2 antibody was measured.

That is, when by replacing a human GPVI loop region with a corresponding mouse loop region, the binding activity of the antibody reduces relative to the binding activity to human GPVI prior to replacement, it is speculated that the loop region replaced has an antibody's recognition region. Further, when in the substitution mutant in which a mouse GPVI loop region is replaced with a corresponding human loop region, the binding activity of the antibody is restored, it can be assumed that the loop region replaced is an antibody's recognition region. Accordingly, from both experiments, it is possible to identify the reaction region of the antibody.

The measurement method was according to the method of 17-3.

Figure 7:
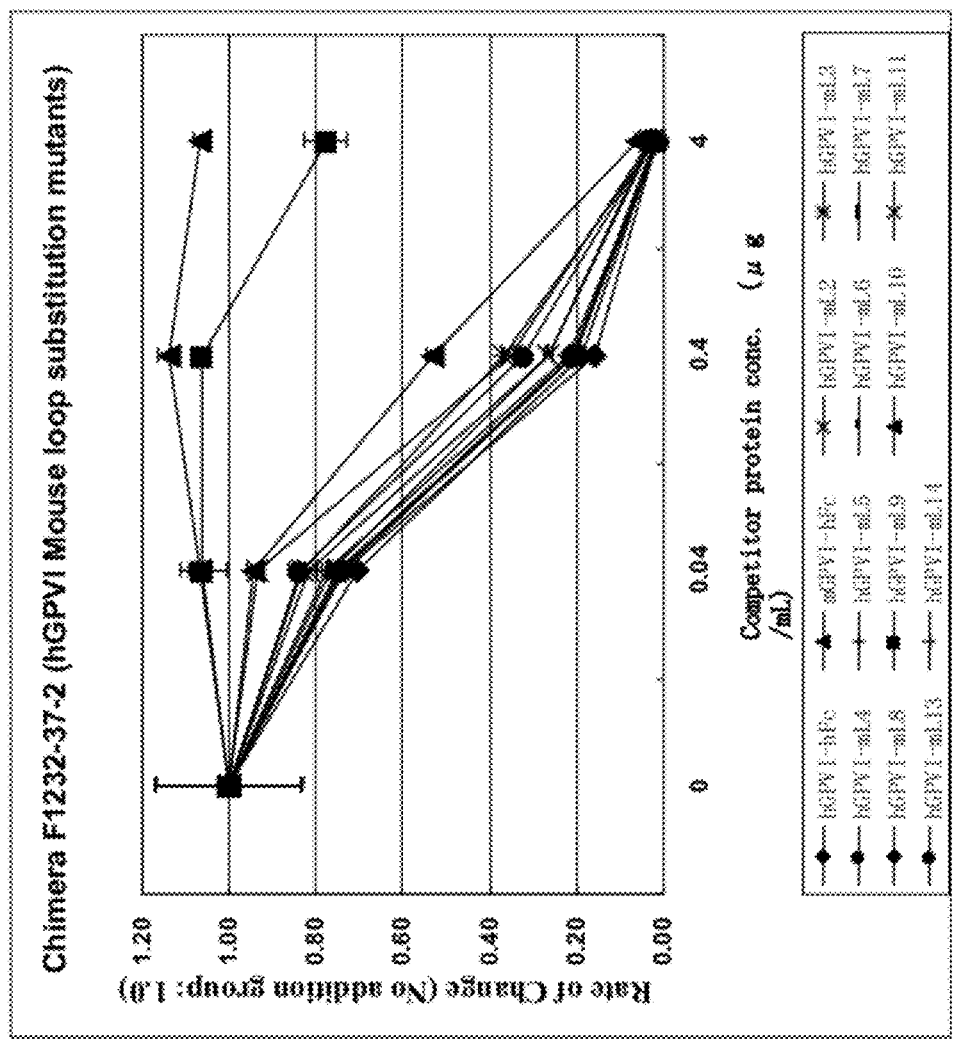
FIG. 7 shows the results of a reactivity of cF1232-37-2 with various hGPVI mouse loop substitution mutants.

The results analyzed revealed, as shown in FIG. 7, in the case of cF1232-37-2 the activity significantly reduced when using hGPVI-mL9-hFc. From this result, it is speculated that cF1232-37-2 recognizes loop 9 region.

Example 18

Effects of Mouse Anti-GPVI Monoclonal Antibody and Mouse/Human Chimeric Anti-GPVI Monoclonal Antibody to Platelet 18-1 Activation of Human Platelet and Cynomolgus Platelet Citrate-added blood collected from normal human or cynomolgus monkey was provided to SYSMEX® (semi-automated hematology analyzer) F-820 to count platelets. Then, by centrifugation at 170×g at 25° C. for 15 minutes in the case of human, or at 115×g at 25° C. for 20 minutes in the case of monkey, platelet rich plasma (PRP) was obtained; then by 1300×g at 25° C. for 15 minutes, platelet poor plasma (PPP) was obtained.

Subsequently, the obtained PRP was diluted with PPP to make a concentration of platelet $3.33 \times 10^8$ cells/mL. The antibody, which final concentration was 1-10 µg/mL, was added thereto, and the mixture was incubated at 37° C. for 30 minutes. After incubation, para-formaldehyde (final concentration: 1%) was added for fixation at 4° C. for one hour. After washing the platelet with PBS containing 0.5% heat-inactivated FBS (hereinafter referred to as FBS buffer), anti-human CD62P-PE (BECKMAN COULTER) was added thereto and stood at room temperature under the condition of light shielding for 30 minutes. After 30 minutes, the platelet was washed with FBS buffer. Then by measuring a fluorescent intensity of platelet with Flow cytometer CYTMICS FC500 (BECKMAN COULTER), CD62P expression was analyzed.

Figure 8:
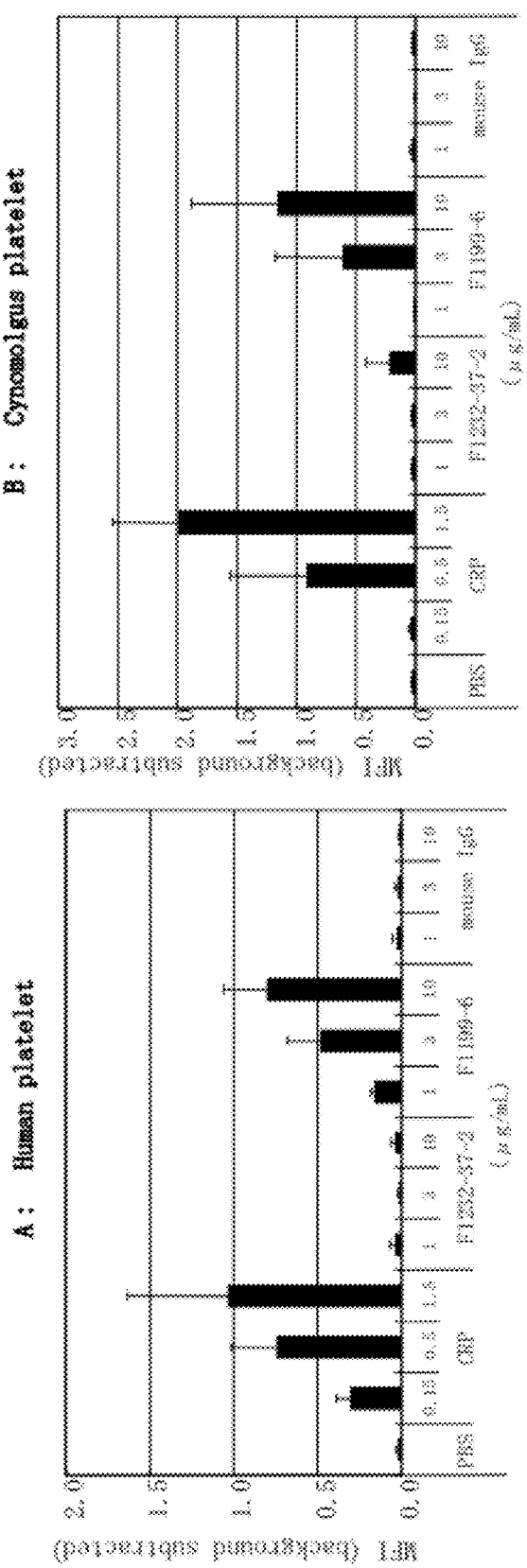
FIG. 8 shows the activating action on human and cynomolgus platelets. Expression level of CD62P (P-selectin) on human platelet (A) and cynomolgus monkey platelet (B) was assayed by FACS and the results were shown by mean fluorescent intensity (MFI).

As shown in FIG. 8, F1199-6 antibody activated human platelet or cynomolgus monkey platelet depending on the concentration, meanwhile platelet activating action could hardly be recognized in F1232-37-2 antibody. Further, the action of cF1232-37-2 on human or cynomolgus platelet was the same as the above. In addition, when as for the chimeric antibodies prepared in EXAMPLE 16, that is, cF1249-18-2, cF1245-7-1, cF1246-1-1, cF1249-24-1, cF1245-4-1, cF1249-22-1 and cF1251-1-1, their activating action on monkey platelet was studied, any activating action was not observed. In some clones, there were mouse non-chimeric antibodies which exhibited the activating action on monkey platelet. However, by chimerization the action disappeared. In addition, as for mouse monoclonal antibodies prepared in EXAMPLE 2, the same experiment was performed. As a result, it could not be detected that each antibody possessed a human platelet activating function.

18-2 Induction of Human Platelet Aggregation by Anti-GPVI Antibody

The PRP prepared by the method described in 19-1 was diluted with PPP to make a concentration of platelet $3.33 \times 10^8$ cells/mL. The antibody, which final concentration was 1-10 µg/mL, was added thereto, and the mixture was incubated at 37° C. for 5 minutes. Hereto CaCl$_2$ solution was added at the final concentration of 1 mM, and during incubation at 37° C. for 12 minutes, a light transmission of PRP was measured with MCM Hema Tracer 313M (MCMEDICAL) to investigate a platelet aggregation.

Figure 9:
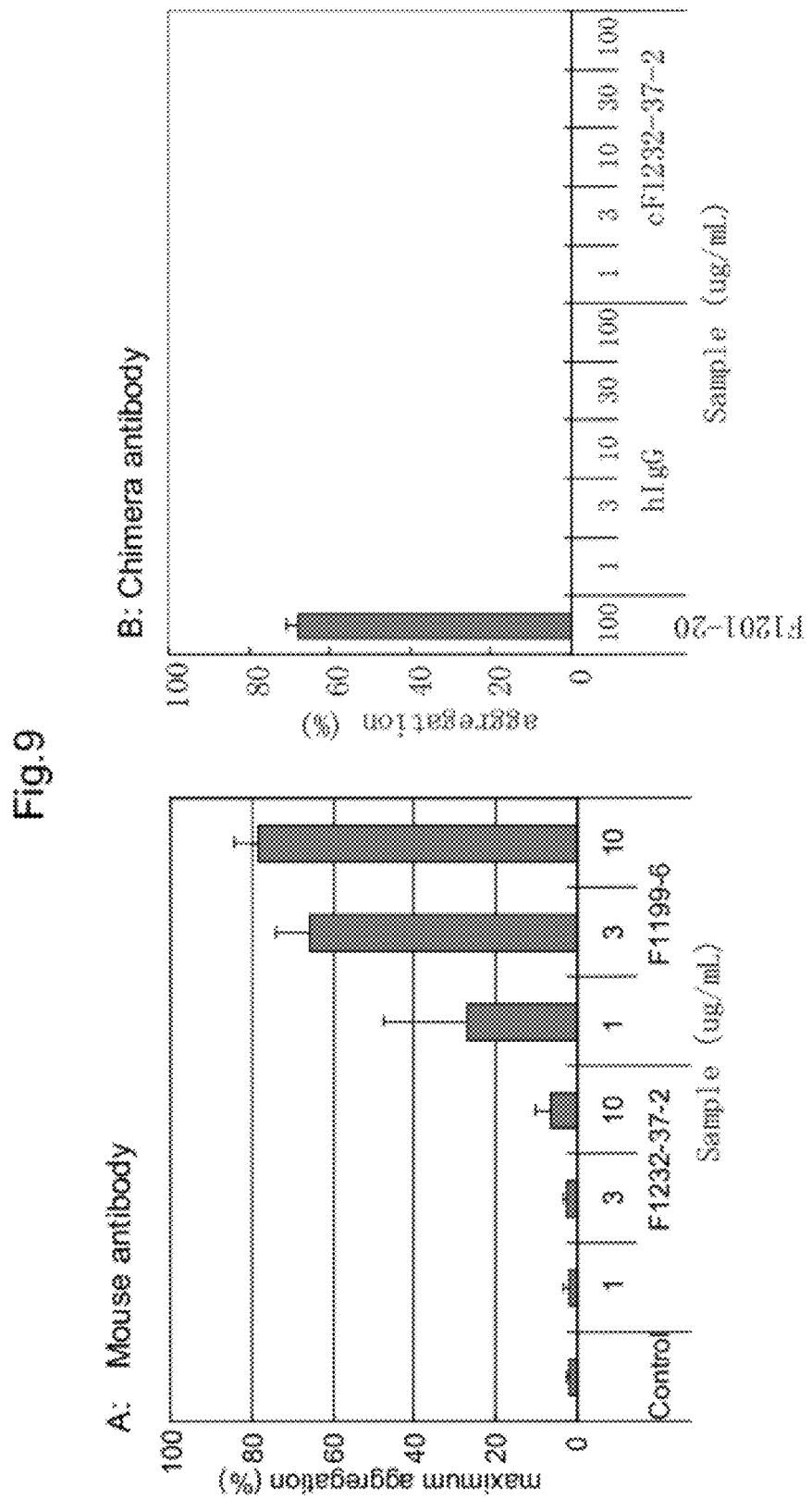
FIG. 9 shows the aggregation-inducting action on human platelet.

As shown in FIG. 9, F1199-6 induced human platelet aggregation depending on the concentration; meanwhile, the platelet aggregation action of F1232-37-2 and cF1232-37-2 could hardly be detected.

18-3 Inhibitory Effect of Anti-GPVI Antibody on Collagen-Induced Human Platelet Aggregation The PRP prepared by the method described in 18-1 was diluted with PPP to make a concentration of platelet $3.33 \times 10^8$ cells/mL. The antibody, which final concentration was 1-10 µg/mL, was added thereto, and the mixture was incubated at 37° C. for 5 minutes. Hereto CaCl$_2$ solution was added at the final concentration of 1 mM, and after additional incubation at 37° C. for three minutes, collagen solution was added at the final concentration of 1 µg/mL. During incubation at 37° C. for 12 minutes, a light transmission of PRP was measured with MCM Hema Tracer 313M (MCMEDICAL) to investigate a platelet aggregation induced by collagen.

Figure 10:
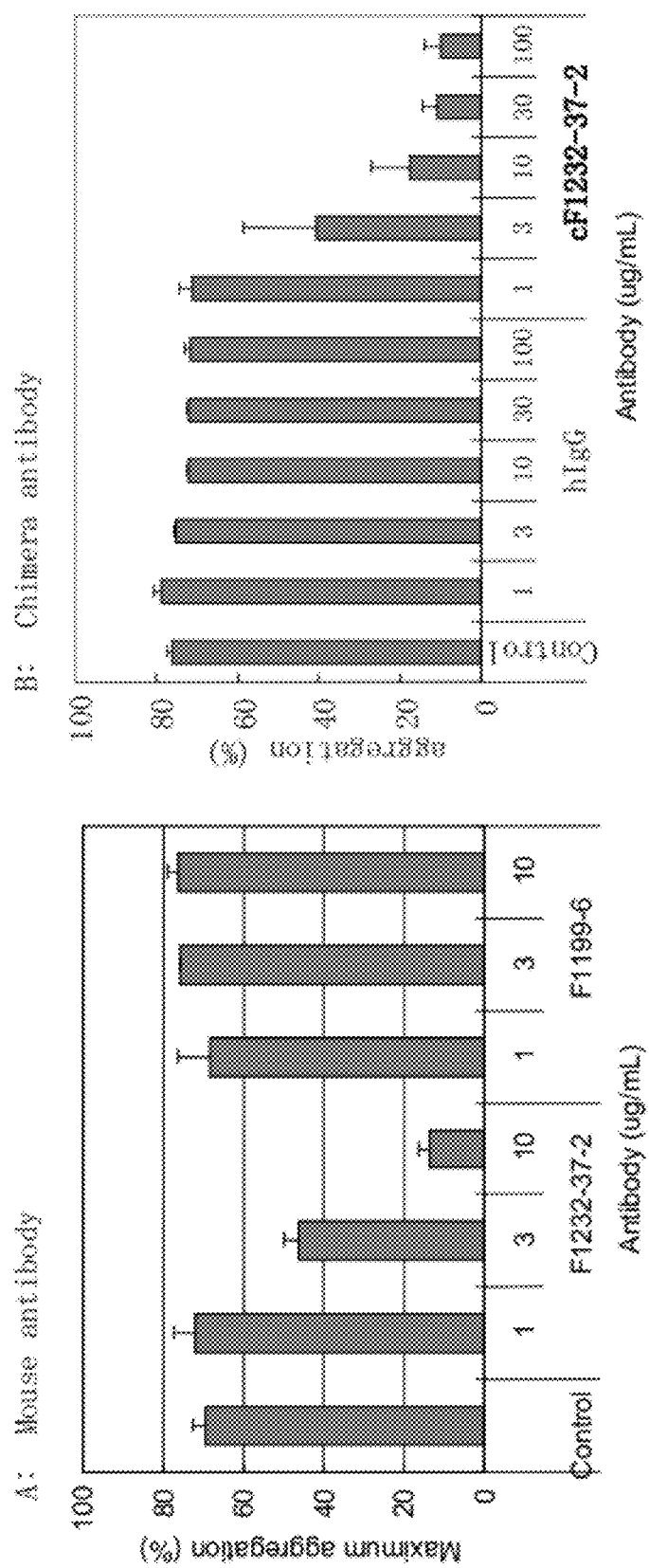
FIG. 10 shows the action of F1232-37-2 on collagen-induced human platelet aggregation.

As shown in FIG. 10, F1232-37-2 and cF1232-37-2 inhibited collagen-induced human platelet aggregation depending on the concentration.

Figure 11:
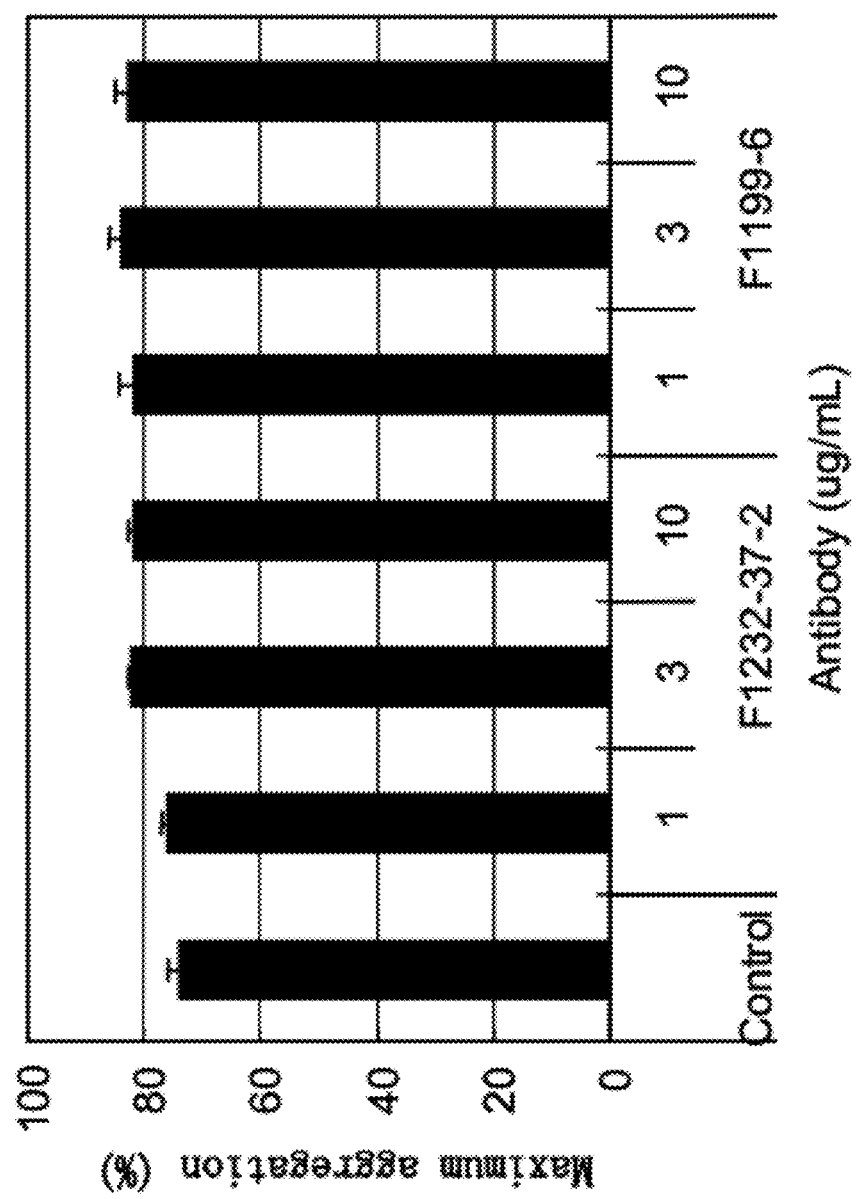
FIG. 11 shows the action of F1232-37-2 on ADP-induced human platelet aggregation.

18-4 Non-Inhibitory Effect of Anti-GPVI Antibody on ADP-Induced Human Platelet Aggregation The PRP prepared by the method described in 18-1 was diluted with PPP to make a concentration of platelet $3.33 \times 10^8$ cells/mL. The antibody, which final concentration was 1-10 µg/mL, was added thereto, and the mixture was incubated at 37° C. for 5 minutes. Hereto CaCl$_2$ solution was added at the final concentration of 1 mM, and after additional incubation at 37° C. for three minutes, ADP solution was added at the final concentration of 5 µM. During incubation at 37° C. for 12 minutes, a light transmission of PRP was measured with MCM Hema Tracer 313M (MCMEDICAL) to investigate a platelet aggregation induced by ADP. The result is shown in FIG. 11.

ADP-induced human platelet aggregation inhibiting action was not detected in F1232-37-2 and cF1232-37-2.

Example 19

Measurement System for Anti-GPVI Antibody (EIA)

By the sandwich EIA method, concentration of anti-GPVI antibody was measured. That is, the sandwich EIA system using hGPVI-hFc having a sequence of human GPVI, which has been prepared as a immobilized protein by the same method as that of EXAMPLE 1, and Anti Human Kappa Light Chain HRP (DAKO) as a labeled antibody was constructed.

As a standard preparation, anti-GPVI antibody prepared in EXAMPLE 16 was used. The hGPVI-hFc was diluted to 4 µg/mL with PBS (pH 7.4) and 50 µL of the solution was added to each well of NUNC-Immunoplate Maxisorp (NUNC). After incubation at 4° C. for overnight, the plate was washed five times with ice cold water, and 100 µL of PBS (pH 7.4) containing 2% STABILGUARD® (SurModics, Inc.) was added to each well for blocking. Then diluted samples to be measured and standard preparation were prepared using PBS (pH 7.4) containing 0.1% BSA as diluent. Blocking agent was discarded from the plate, 50 µL of the diluted sample was added to each well, and the sample was incubated at 37° C. for one hour. After the incubation, each well was washed three times with 0.05% TWEEN® 20/0.9% NaCl solution. Next, 50 µL of the labeled antibody diluted with PBS (pH 7.4) containing 10% rabbit serum were added to each well and incubated at 37° C. for one hour. After completion of the incubation, each well was washed three times with 0.05% TWEEN® 20/0.9% NaCl solution. Further, 50 µL/well of tetramethylbenzidine solution (BIOFX®) was added. After incubation at room temperature for about ten minutes, the reaction was terminated with 50 μL of 1 mol/L hydrochloride solution, and an absorbance at 450 nm was measured with plate photometer.

In addition, when the concentration of GPVI antibody in monkey blood plasma was measured, PBS (pH 7.4) containing 10% monkey plasma and 10% rabbit plasma was used, and measurement was done in a similar manner.

Example 20

Evaluation of Anti-GPVI Monoclonal Antibody by Cynomolgus Monkey Ex Vivo Test (2)

At the start of test, measurement of body weight and blood drawing of the cynomolgus monkey to be tested prior to drug administration were performed. Blood collected was done at 0.5 hours to two weeks after administration of anti-GPVI antibody. To evaluate each antibody, 1) platelet count, 2) expression of platelet membrane protein (GPIIb/GPIIIa (CD41a), GPIX (CD42a)), 3) expression of platelet GPVI, and 4) platelet aggregation (the response to collagen and ADP) were determined.

That is, citrate-added blood collected from leg vein of cynomolgus monkey (male, about 5 kg) was subjected to SYSMEX® F-820 to count platelets. Then, by centrifugation at 115×g at 25° C. for 15 minutes, platelet rich plasma (PRP) was obtained; then by 830×g at 25° C. for 20 minutes, platelet poor plasma (PPP) was obtained. Subsequently, the obtained PRP was diluted with PBS containing 0.5% heat-inactivated FBS and 2.5 mM EDTA (hereinafter referred to as FACS buffer). The anti-human CD41a-FITC (BD Biosciences Pharmingen) for CD41a expression, anti-human CD42a-FITC (BD Biosciences Pharmingen) for CD42a expression, rabbit anti-GPVI-mFc polyclonal antibody and mouse anti-GPVI-mFc monoclonal antibody, wherein both were labeled with fluorescent dye Af488, for GPVI expression were respectively added thereto, and the mixture was stood at room temperature for 30 minutes under the condition of light shielding. After 30 minutes, the platelet was washed with FACS buffer. Then by measuring a fluorescent intensity of platelet with Flow cytometer CYTOMICS FC500 (BECKMAN COULTER), expression of each membrane protein was analyzed. In addition, using the obtained PRP, by Western blotting, expression of each membrane protein was also analyzed. The method was as follows. Various PRPs obtained from the monkey ex vivo test were washed twice with 2.5 mM EDTA/PBS. The 1× Sample buffer (+β-mercaptoethanol, Protease inhibitor cocktail (Roche) and Phosphatase inhibitor cocktail (PIERCE) was added to the platelet to make $0.5 \times 10^6$ platelets/μL. The sample was heat-treated at 99° C. for five minutes. The treated sample was frozen by liquid nitrogen to store at −30° C. until use.

To analyze respective proteins in the monkey PRP by Western blotting, firstly protein isolation by SDS-PAGE was performed. Using a 5-20% gradient polyacrylamide gel (ATTO), the sample was loaded at 2.5×106 platelets/lane to run at 30 mA/gel. Blotting was carried out according to a conventional method, that is, by the semi-dry method, the proteins was transferred to a low fluorescent membrane (IMMOBILON® (transfer membranes for protein and nucleic acids)-FL PVDF, MILLIPORE). After blotting, the membrane was lightly rinsed with 0.1% TWEEN® 20/PBS (TPBS) and was blocked with BlockAce (Dainippon Pharmaceutical Co., Ltd.) at 4° C. for overnight. After blocking, a first antibody diluted with 10% BlockAce/TPBS was added thereto and incubated at room temperature for one hour with rotary shaking. The first antibody used was anti-GPIIIa antibody (Anti-Integrin β3, Santa Cruz), anti-GPVI antibody (a polyclonal antibody to human GPVI synthetic peptide as an antigen), and anti-GPIX antibody (Anti-CD42a, Santa Cruz). After incubation with the first antibody, the membrane was extensively rinsed with TPBS and washed with TPBS. After washing, a second antibody diluted with 10% BlockAce/TPBS was added thereto and incubated at room temperature for 30 minutes with rotary shaking. The second antibody used was Anti-Rabbit Igs HRP for GPIIIa and GPVI, and Anti-Goat Igs HRP for GPIX (both are from DakoCytomation). After incubation with the second antibody, the membrane was extensively washed with TPBS, and the protein was detected with ECL™ (kits for detecting nucleic acids and proteins) Plus (Amersham Biosciences). After incubation, luminescence was detected with TYPHOON® (fluorescent sample readers and scanners) 9410 (Amersham Biosciences) in Fluorescence mode. In this mode, ECL™ Plus luminescent intermediate was detected. From the detected band, using the analysis software IMAGEQUANT® (computer software for image analysis) 5.2, proteins expressed were quantified.

Meanwhile, the response of platelet to collagen and ADP was studied as follows. Firstly, the PRP was diluted with PPP to make a concentration of platelet $3 \times 10^8$ cells/mL. Then $CaCl_2$ solution was added at the final concentration of 1 mM, and the mixture was incubated at 37° C. for three minutes. Further, collagen solution at the final concentration of 2 μg/mL or ADP solution at the final concentration of 20 μM was added. During incubation at 37° C. for 12 minutes, a light transmission of PRP was measured with MCM Hema Tracer 313M (MCMEDICAL) to investigate a platelet aggregation responsive to collagen or ADP.

20-1 Cynomolgus Monkey Ex Vivo Test for Mouse Anti-Human GPVI Monoclonal Antibody When mouse monoclonal antibodies F1232-37-2 and F1199-6 were intravenously administered at 0.3 mg/kg, one day after administration, reduction of response of platelet to collagen as well as decrease in platelet GPVI level was observed. This action was continued for more than two days in mouse monoclonal antibody F1232-37-2.

In cynomolgus monkey administered with F1199-6, the reduction of platelet number was detected after administration. However, in cynomolgus monkey administered with F1237-2, no significant change in platelet number was observed.

Figure 12:
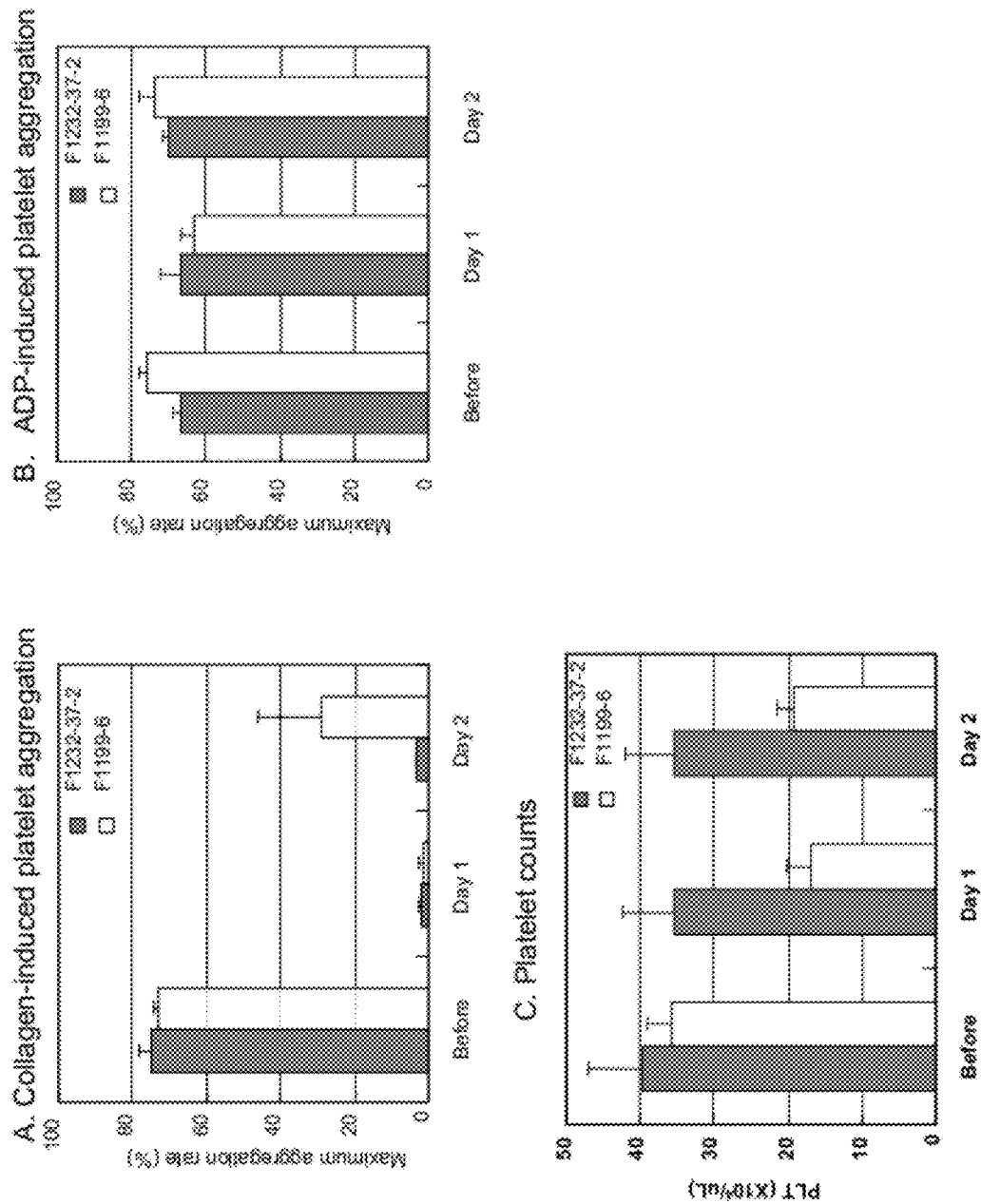
FIG. 12 shows the results of the test of intravenous administration of mouse anti-human GPVI monoclonal antibodies F1232-37-2 and F1199-6 into cynomolgus.

The results are shown in FIG. 12.

20-2 Cynomolgus Monkey Ex Vivo Test for Mouse/Human Chimeric Anti-Human GPVI Antibody (1) Single Intravenous Test The antibody cF1232-37-2 was intravenously administered to cynomolgus monkey (male) at 0.1, 0.3 and 1 mg/kg.

Figure 13:
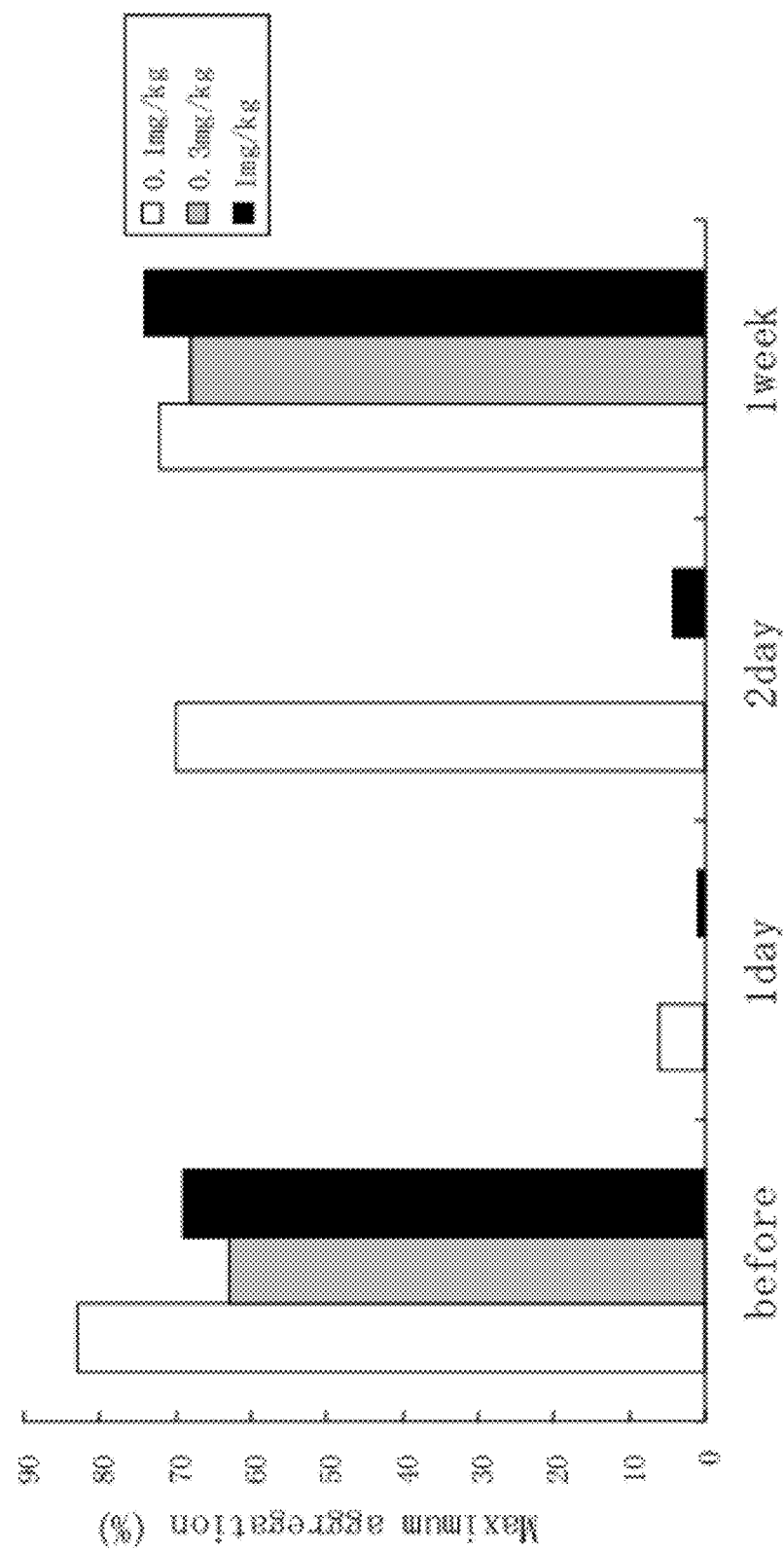
FIG. 13 shows the results of ex vivo test of single intravenous administration of mouse/human chimeric anti-human GPVI antibody (cF1232-37-2) in cynomolgus.

As shown in FIG. 13, in the animal administered with cF1232-37-2 at 0.1, 0.3 and 1 mg/kg, response of platelet to collagen rapidly decreased after administration. This action was continued for more than two days in the animal administered at 0.3 and 1 mg/kg. In addition, in the animal administered with cF1232-37-2 at 0.1 mg/kg, the response to collagen reduced over two hours after administration, and the action was continued for one day.

20-3 Cynomolgus Monkey Ex Vivo Test for Mouse/Human Chimeric Anti-Human GPVI Antibody (2) Repetitive Intravenous Administration Test The antibody cF1232-37-2 was administered to cynomolgus monkey (male) every other day four times. Blood drawing was scheduled prior to administration, at the day after administration, and at the day after final administration through 17 days after. In addition, regarding the blood collected, 1) platelet count, 2) expression of platelet membrane proteins GPIIb/GPIIIa (CD41a), GPIX (CD42a), and GPIIIa (CD61), 3) expression of platelet GPVI, and 4) the platelet aggregation response to collagen and ADP were determined, respectively.

Figure 14:
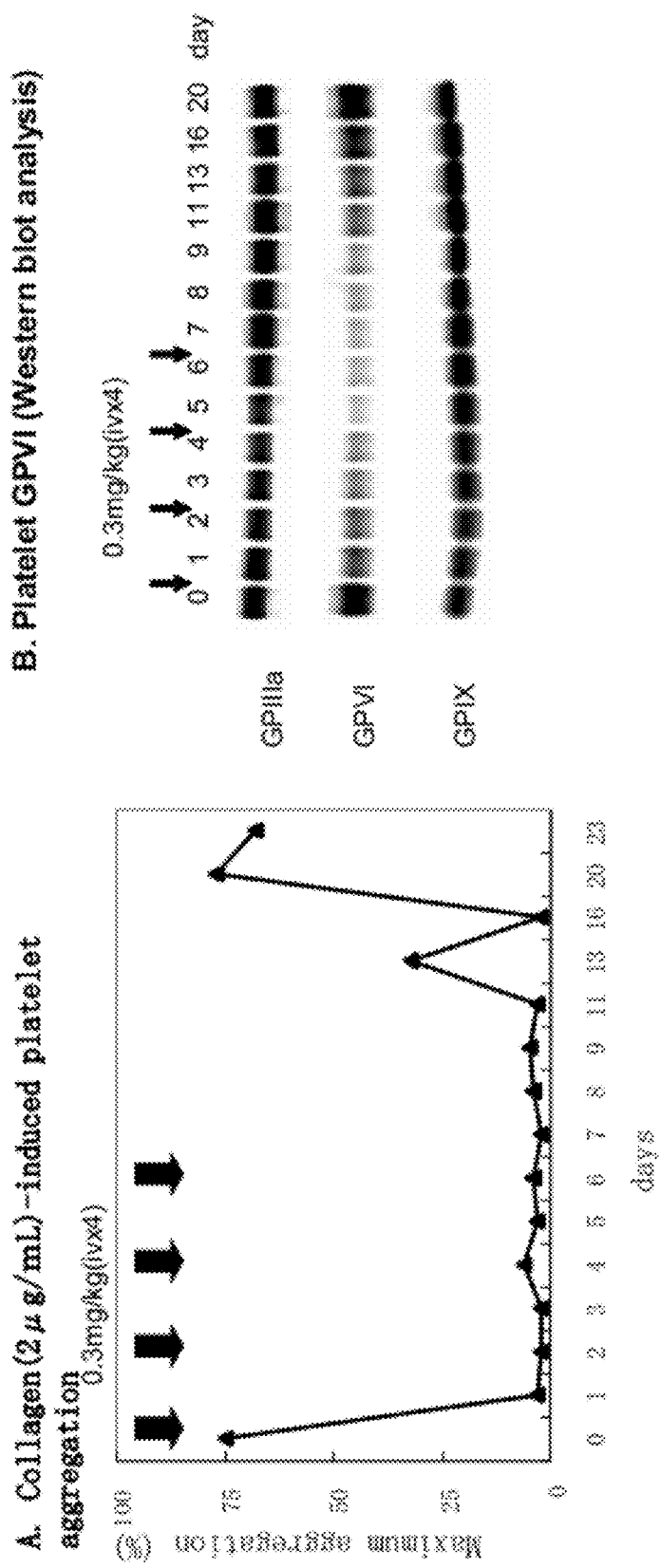
FIG. 14 shows the results of ex vivo test of repetitive intravenous administrations of mouse/human chimeric anti-human GPVI antibody in cynomolgus. When 0.3 mg/kg of cF1232-37-2 was administered four times to cynomolgus monkey every other day, collagen-induced platelet aggregation (A) and platelet GPVI level (B) were measured.
Figure 15:
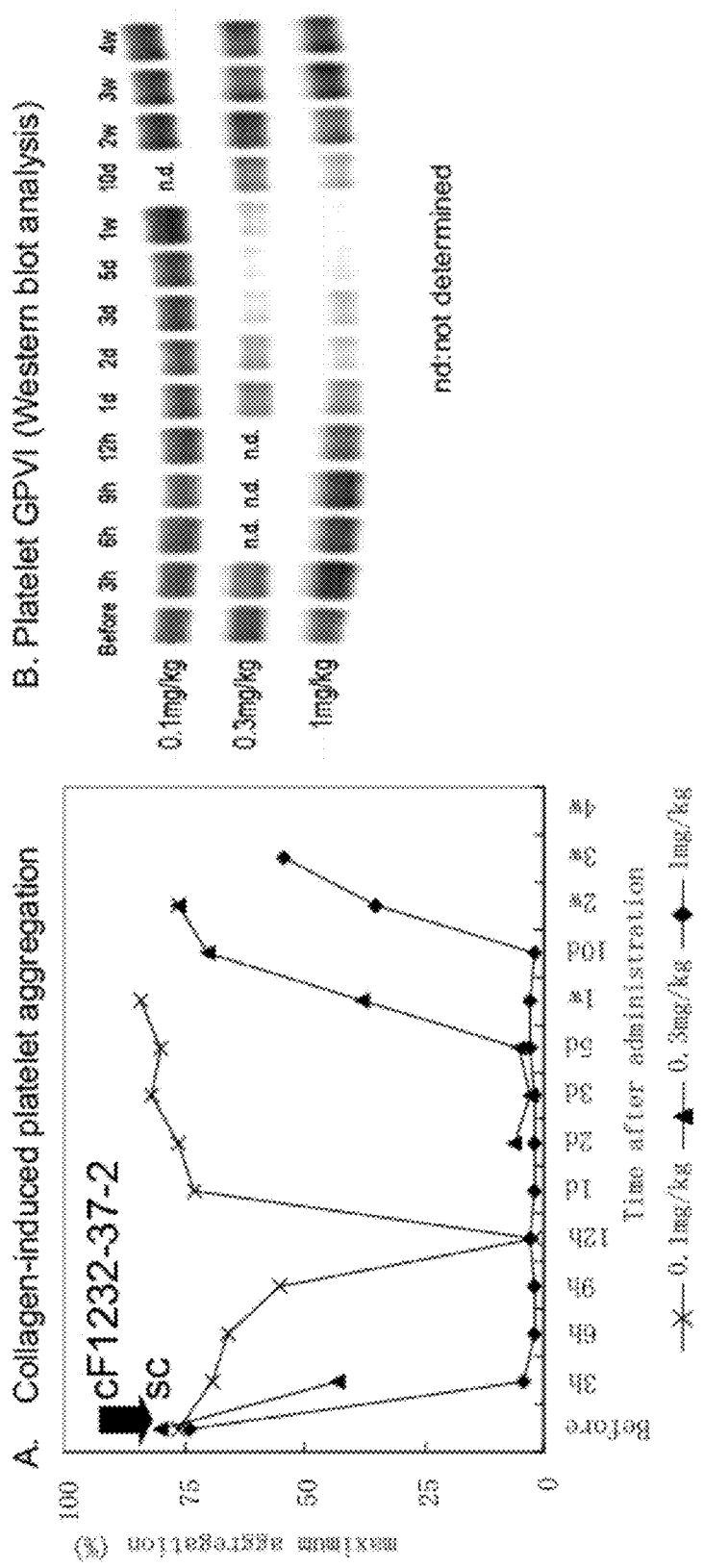
FIG. 15 shows the results of ex vivo test of subcutaneous administration of mouse/human chimeric anti-human GPVI antibody in cynomolgus. After cF1232-37-2 was subcutaneously administered to cynomolgus monkey, the blood was collected with time, and platelet aggregation (A) induced by 2 μg/mL of collagen and platelet GPVI level (B) were measured.

From the day after the first administration, decrease in the platelet GPVI level and reduction of response of platelet to collagen was observed. The reduction of response of platelet to collagen was continued for two days after the final administration in the animal at 0.1 mg/kg administration and for more than ten days after the final administration in the animal at 0.3 mg/kg administration. In FIG. 14, collagen-induced platelet aggregation of cynomolgus monkey and level of platelet GPVI, GPIIIa and GPIX in 0.3 mg/kg repetitive administration test were shown. In addition, in the test, expression level of the platelet membrane proteins GPIX (CD42a) and GPIIIa (CD61) was not significantly changed.
20-4 Cynomolgus Monkey Ex Vivo Test for Mouse/Human Chimeric Anti-Human GPVI Antibody
(3) Single Subcutaneous Administration Test The antibody cF1232-37-2 was subcutaneously administered to cynomolgus monkey (male) at 0.1, 0.3 and 1 mg/kg. Using the blood obtained from the successive blood drawing prior to and after administration as a sample, 1) platelet count, 2) expression of platelet membrane proteins (GPIIb/GPIIIa (CD41a), GPIX (CD42a)), and GPIIIa (CD61)), 3) expression of platelet GPVI, and 4) platelet aggregation (the reactivity to collagen and ADP) were determined. The results are shown in FIG. 15.

In the animal subcutaneously administrated at 1 mg/kg and 0.3 mg/kg, from three hours after the administration, reduction of response of platelet to collagen was observed. The day after administration, decrease in the platelet GPVI level was detected. The reduction of response of platelet to collagen was continued for more than one week after administration in the animal at 0.3 mg/kg administration and for more than two weeks in the animal at 1 mg/kg administration. Further, in the animal administered at 0.1 mg/kg, the reduction of response to collagen was observed on the day of administration. In addition, expression level of the platelet membrane proteins (GPIIb/GPIIIa (CD41a), GPIX (CD42a), GPIIIa (CD61)) was not significantly changed.

Example 21

Preparation of Anti-GPVI Monoclonal Antibody Fab and F(ab')$_2$
21-1 Preparation of Mouse Monoclonal Antibody F1232-37-2 F(ab')$_2$ To prepare mouse monoclonal antibody F1232-37-2 F(ab')$_2$, the mouse monoclonal antibody F1232-37-2 obtained in EXAMPLE 2 was treated with LysylEndopeptidase. That is, to the purified mouse monoclonal antibody F1232-37-2 1/10 volume of 1 M Tris buffer (pH 8.5) was added, and further Lysyl Endopeptidase (Wako) was added thereto at the ratio of 30:1 for antibody:enzyme (molar ratio) to incubate at 37° C. for three hours. At the end of incubation, TLCK (SIGMA) was added to the reaction mixture at the final concentration of 30 mM.

Subsequently, F(ab')$_2$ was purified. At first, to remove undigested antibody and Fc region, the antibody treated with LysylEndopeptidase was loaded to PROSEP® rA (Millipore). Further, for removal of LysylEndopeptidase, non-absorbed fraction on PROSEP® rA was loaded to SUPERDEX® (filtration material for chromatographic separation of mixtures) 75 (Amersham) to obtain F1232-37-2 F(ab')$_2$. Then the obtained F(ab')$_2$ was dialyzed against saline (Ohtsuka) and evaluated for purity of the antibody by analysis on acrylamide gel. In addition, concentration of the antibody was determined by Bradford method using bovine IgG as a standard.

21-2 Preparation of F1232-37-2 Fab

To prepare F1232-37-2 Fab, the purified mouse monoclonal antibody F1232-37-2 obtained in EXAMPLE 2 was treated with Papain (Wako). That is, the purified mouse monoclonal antibody F1232-37-2 was placed in 1 mM cysteine, 20 mM EDTA/D-PBS-(pH 7.4) buffer, and further Papain (Wako) was added thereto at the ratio of 30:1 for antibody:enzyme (weight ratio) to incubate at 25° C. for 16 hours. At the end of incubation, Iodoacetamide (Wako) was added to the reaction mixture at the final concentration of 30 mM.

Subsequently, Fab was purified. At first, to remove undigested antibody and Fc region, the antibody treated with Papain was loaded to PROSEP® rA (Millipore). Further, for removal of Papain, non-absorbed fraction on PROSEP® rA was loaded to SUPERDEX® 75 (Amersham) to obtain F1232-37-2 Fab. Then the obtained Fab was dialyzed against saline (Ohtsuka) and evaluated for purity of the antibody by analysis on acrylamide gel. In addition, concentration of the antibody was determined by Bradford method using bovine IgG as a standard.
21-3 Reactivity for Antigen Binding of F1232-37-2 Antibody F(ab')$_2$ and Fab Dissociation constant for F1232-37-2 (whole antibody) prepared in EXAMPLE 2, and F(ab')2 and Fab prepared in 22-1 and 21-2 was measured with Protein Interaction Analyzer BIACORE® 3000 (BIACORE). That is, hGPVI-hFc prepared in EXAMPLE 1 was coupled to sensorchip CM5 (BIACORE) according to the manual. Then a series of dilution from 0 to 800 nM of each antibody was prepared with HBS-EP buffer (BIACORE) and analyzed with BIACORE® 3000. After completion of antibody binding, chip was regenerated with glycine buffer (pH 1.5) (BIACORE). Regarding the results of whole antibody and F(ab')$_2$, evaluation software Bivalent analyte (BIACORE) was used for analysis; 1:1 Binding for Fab analysis. Then the dissociation constant was calculated. As a result, dissociation constant of F1232-37-2 F(ab')2 and Fab was about 0.7 and 0.6, respectively, when that of whole antibody defined as one. It was found that both have an equivalent affinity in comparison with whole antibody.

Example 22

Cynomolgus Monkey In Vitro Test for Anti-GPVI Antibody Fab

Figure 16:
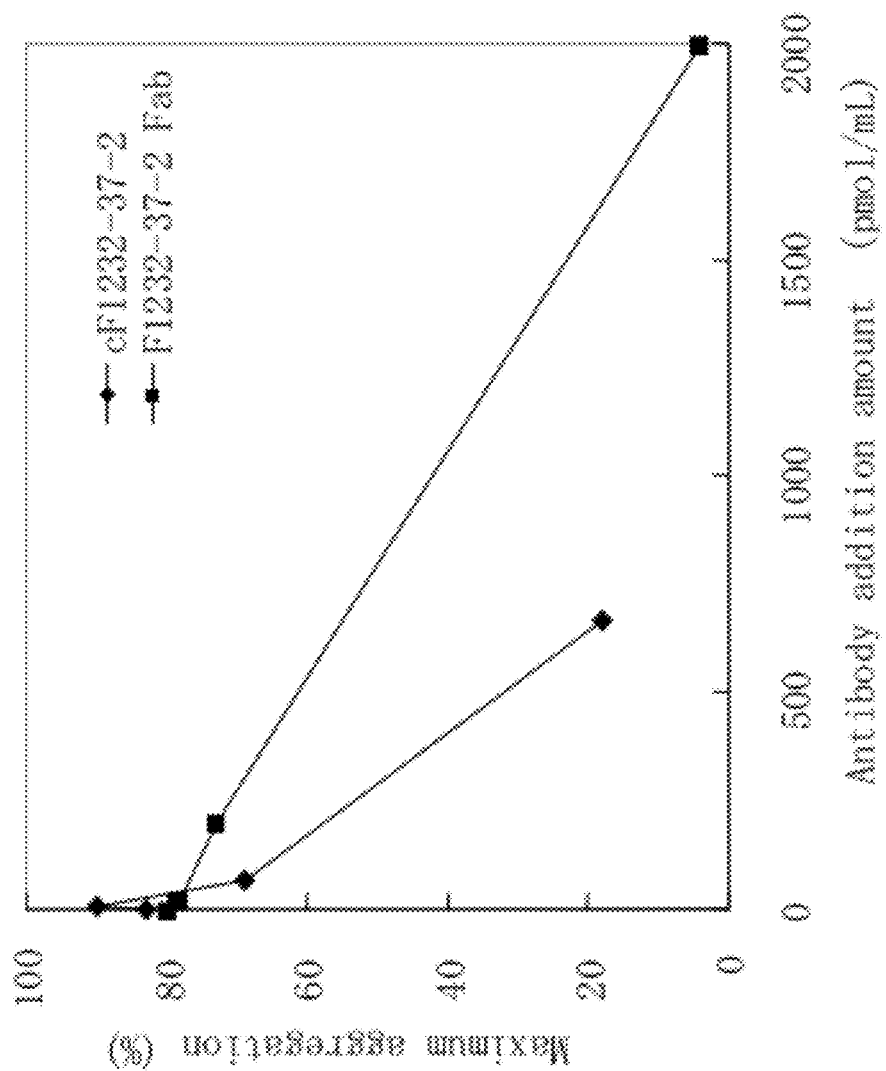
FIG. 16 shows an inhibiting action of F1232-37-2 Fab on collagen-induced platelet aggregation.

From cynomolgus monkey, by the method described in EXAMPLE 20, blood was collected. The PRP prepared was diluted with PPP to make a concentration of platelet $3.33 \times 10^8$ cells/mL. The F1232-37-2 Fab, of which final concentration was 1-100 µg/mL, was added thereto, and the mixture was incubated at 37° C. for five minutes. Hereto CaCl$_2$ solution was added at the final concentration of 1 mM, and the mixture was incubated at 37° C. for three minutes. Hereto, collagen solution was added at final concentration of 2 µg/ml. Then, during incubation at 37° C. for 12 minutes, a light transmission of PRP was measured with MCM Hema Tracer 313M (MCMEDICAL) to investigate a platelet aggregation responsive to collagen. The results are shown in FIG. 16.

Collagen-induced platelet aggregation inhibiting action of F1232-37-2 Fab was weaker than that of cF1232-37-2.

Example 23

Cynomolgus Monkey Ex Vivo Test for Anti-GPVI Antibody F(ab')$_2$

F1232-37-2 F(ab')$_2$ prepared in EXAMPLE 21 was subcutaneously administered to cynomolgus monkey at 1 mg/kg. Using the blood prior to and after administration as a sample, expression of platelet GPVI and platelet aggregation (the reactivity to collagen and ADP) were measured.

Figure 17:
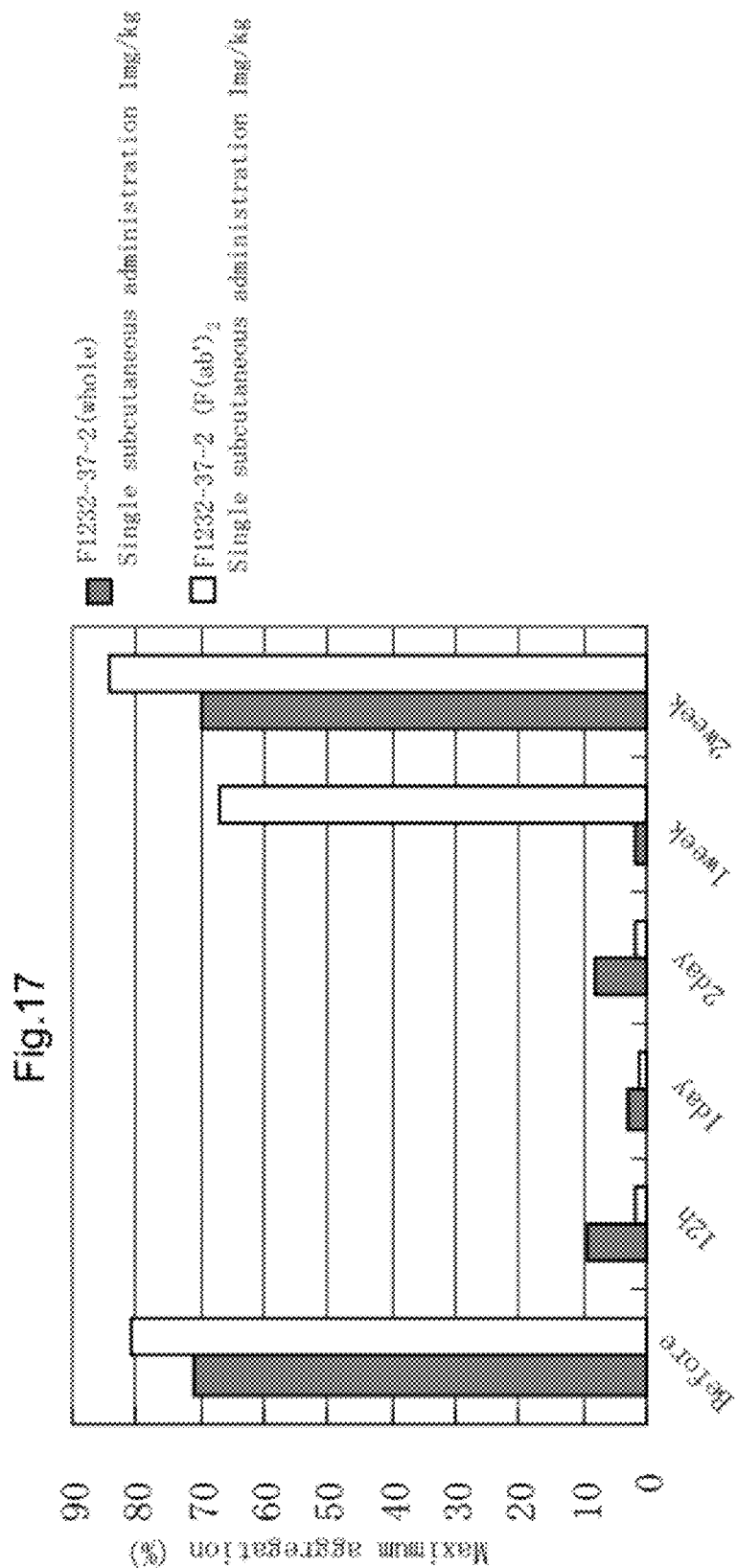
FIG. 17 shows the results of ex vivo test of F1232-37-2 F(ab')$_2$ in cynomolgus.

As shown in FIG. 17, in the animal administrated with F1232-37-2 F(ab')$_2$, from 12 hours after the administration, reduction of response to collagen was observed. The day after administration, decrease in the platelet GPVI expression level was detected. The reduction of response to collagen was continued for more than two days. In addition, expression level of the platelet membrane proteins (Fc γ RII (CD32), GPIX (CD42a), and GPIIIa (CD61)) was not significantly changed.

Example 24

Measurement of Bleeding Time of Monkey

In advance of bleeding test, weight of cynomolgus monkey is weighed and no abnormality concerning hematological parameter, hemostatic parameter and platelet function is confirmed. At 1 mg/kg, cF1232-37-2 is subcutaneously administered and the bleeding time is measured at three hours and 48 hours after administration.

An injection needle is inserted to flank tail vein of cynomolgus monkey (male, 2.5 to 5 kg), and then the measurement of bleeding time is started.

In the animal administered with cF1232-37-2, no significant prolongation of bleeding time in comparison with the time prior to administration is detected.

Example 25

Preparation of Mouse/Human Chimeric Antibody-Expressing CHO Cells 25-1 Preparation of the Expression Plasmid for Mouse/Human Chimeric F1232-37-2

To enhance a expression efficiency, cF1232-37-2 heavy chain-expressing plasmid (pTK-2510) was digested with EcoRI and NcoI so that a fragment having Kozak sequence (Kozak, M. et al., J. Mol. Biol., 196, 947-950, 1987) consisting of sense strand: 5'-AATTCGCCGCCACC-3' (SEQ ID NO: 291) and antisense strand: 5'-CATGGTGGCGGCG-3' (SEQ ID NO: 292) was inserted to the site between promoter and initiation codon for construction of pTK-2571. In a similar manner, Kozak sequence was inserted into cF1232-37-2 light chain-expressing plasmid (pTK-2511) for construction of pTK-2572.

Figure 18:
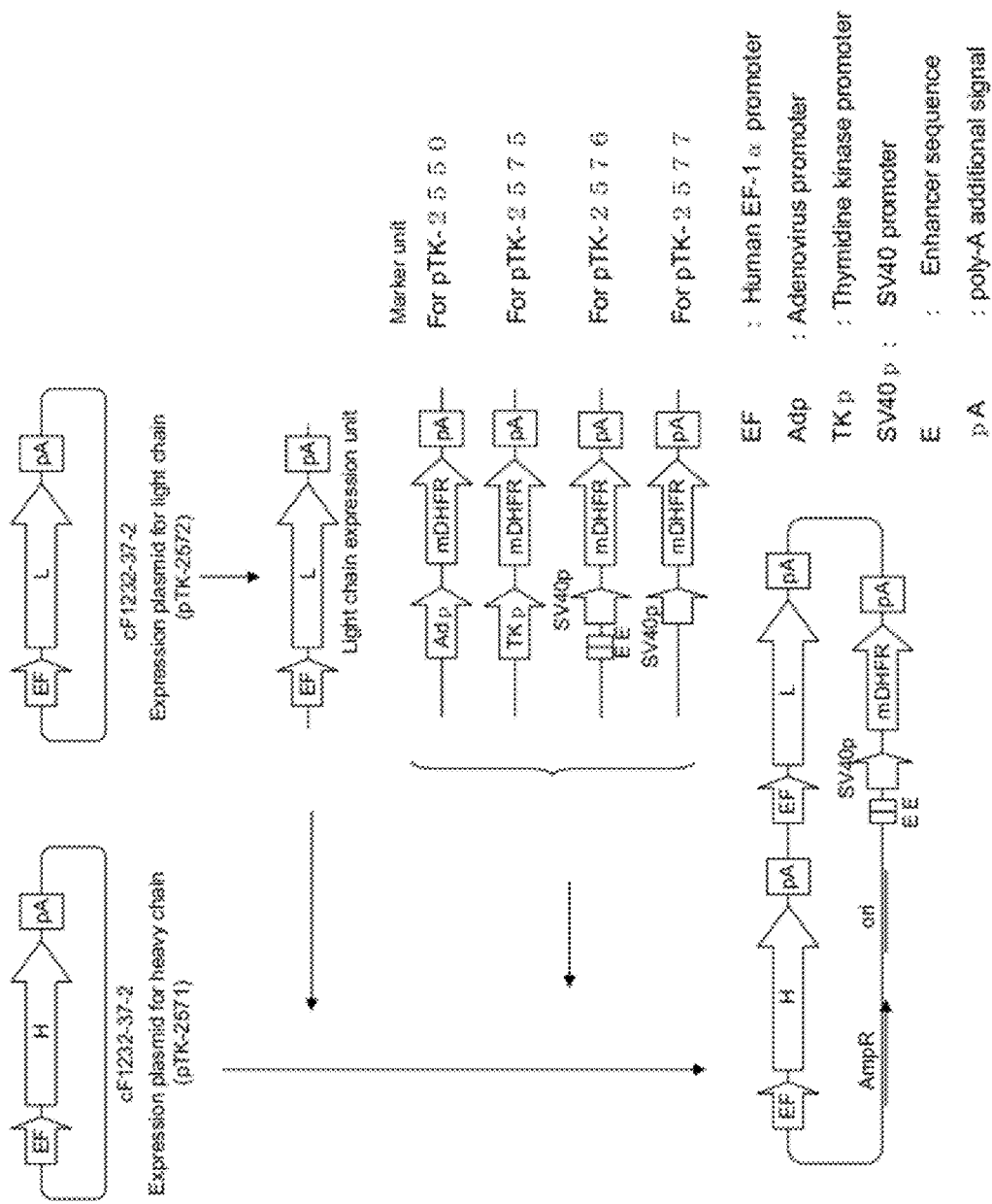
FIG. 18 shows the construction of a stable co-expression plasmid for both chains of cF1232-37-2.

Next, by cleaving pTK-2572 with restriction enzymes SspI and Sse8387I and blunting termini of the obtained fragment, the light chain expressing unit (EF promoter, gene encoding antibody light chain and polyA signal sequence) was prepared. Meanwhile, by cleaving TK-2571 with restriction enzymes Sse8387I, which cannot digest a heavy chain expressing unit, blunting and inserting the light chain expressing unit and marker unit to the above site, both chain stably coexpressing plasmid, in which three units are present on one vector, was constructed. Herein, marker unit is a gene fragment wherein an appropriate promoter/enhancer and polyA signal sequence is added to mouse dihydrofolate reductase (mDHFR) for gene amplification. Using four kinds of synthetic promoter/enhancer sequence (derived from adenovirus promoter, thymidine kinase promoter, SV40 promoter/enhancer and SV40 promoter), four kinds of both chain stably co-expressing plasmids (pTK-2550, pTK-2575, pTK-2576 and pTK-2577, respectively) were constructed (see FIG. 18).

25-2 Preparation of Transformant of CHO Cells Expressing Mouse/Human Chimeric F1232-37-2

The expression plasmid pTK-2577 constructed in EXAMPLE 25-1 was transfected to DHFR gene-deficient CHO cells to establish CHO transformant producing chimeric antibody. That is, CHO DXB11, which had been adapted in EX-CELL® (serum-free media for growth of cells in culture) 325 PF CHO (JRH Bioscience) containing HT media Supplement (50×) Hybri-Max (Sigma; used at the final concentration of 1×) and 200 mM L-glutamine (Sigma; used at the final concentration of 4 mM), was centrifuged on the day of transfection to inoculate into flask at the density of 8×106 cells/150 cm2 Roux. Using 125 μl of FUGENE®6 (Roche Diagnostics), 12.5 μg of expression plasmid pTK-2577 was prepared in accordance with FUGENE® 6-attached protocol and introduced into the above CHO DXB11. Under the condition of 5% CO2, the cells were cultured at 37° C. for two days and harvested. The cells were washed twice with EX-CELL® 325 PF CHO medium without HT and with 4 mM L-glutamine (hereinafter referred to as EX-CELL® (HT-) and resuspended in EX-CELL® (HT-). Then at the density of 12,500-50,000 cells/well the cells were inoculated to 96 well plate and continued to culture under the condition of 5% CO2 at 37° C. During the culture, every three or four days half of medium was replaced with fresh EX-CELL® (HT-). After about one month cultivation, growing cells in the well were transferred to a new vessel, and cF1232-37-2 expressed by CHO cells as a host in culture supernatant was measured by EIA method described in EXAMPLE 19. The cells wherein the cF1232-37-2 expression had been found in the supernatant were screened as a cF1232-37-2/CHO producing transformant.

In a similar manner, CHO DXB11 was transformed with cF1232-37-2 expressing plasmids pTK-2550, pTK-2575 and pTK-2576, and cF1232-37-2/CHO produced by the obtained recombinant cells was determined by EIA method described in EXAMPLE 19. As shown in Table 15, it was confirmed that the productivity of cF1232-37-2/CHO is different depending on a kind of promoter for mDHFR promoters used as a selection marker, and by utilizing a relatively weak promoter as an expression promoter of selection marker highly expressing clone is obtained.

TABLE 15

Result of transfection experiment using each cF1232-37-2/CHO expression plasmid

| Expression plasmid | Number of clones having productivity of 1.8 mg/L or more/Number of clones evaluated |
|---|---|
| pTK-2550 | 0/552 |
| pTK-2576 | 1/352 |
| pTK-2577 | 40/352 |
| pTK-2575 | 19/352 |

25-3 Gene Amplification Using Methotrexate

The chimeric antibody expressing CHO transformant obtained in 26-2 was cultured in EX-CELL® (HT-) containing methotrexate (hereinafter referred to as MTX) to select clones, in which the production level of chimeric antibody is increased, by gene amplification.

That is, the transformant obtained in EXAMPLE 25-2 was suspended in EX-CELL® (HT-) containing 30 or 100 nM MTX and inoculated to 96-well plate. During the culture, every three or four days half of medium was replaced with fresh EX-CELL® (HT-) containing 30 or 100 nM MTX. The culture was continued in 5% $CO_2$ at 37° C. until colony was emerged. Expression level of the obtained colony into the culture supernatant was confirmed by EIA method and the clone increasing the productivity was selected. As a result, the transformants wherein its productivity is increased at about two to ten fold were obtained. In addition, by repeating selective culture of the gene-amplified transformants in medium containing three to ten-folded concentration of MTX, the clone, in which the productivity is further increased, can be obtained.

25-4 Production of cF1232-37-2 by cF1232-37-2 Expressing CHO Cells

The clone CHO-G32DS25H8 cells obtained in 25-3 was inoculated to EX-CELL® (HT-) containing 100 nM MTX at the density of $1.5 \times 10^5$ cells/ml and cultured at 37° C. for seven days. The obtained culture supernatant was used for the following purification.

25-5 Purification of cF1232-37-2/CHO

The procedures described below were performed at 4° C. if not otherwise specified.

The CHO cell culture supernatant prepared in 25-4 was clarified at room temperature using a capsule cartridge filter (Toyo Roshi Kaisha, Ltd.) having a one micrometer pore size as a prefilter and FLUORODYNE® filter (PALL) having a 0.22 μm pore size as a real filter. The clarified culture supernatant was loaded onto Protein A (rmp Protein A SEPHAROSE® Fast Flow; GE Healthcare/Amersham Biosciences) previously equilibrated with PBS- (Sigma). After washing non-absorbed proteins with PBS-, proteins non-specifically bound was eluted with 10×PBS- (Sigma). Thereafter the antibody specifically bound to Protein A was eluted with 100 mM glycine-HCl buffer (pH 3.0). The volume of eluate was measured and by adding a 1/10 volume of 2 M Tris-HCl (pH 8.5), pH was immediately neutralized to obtain an eluate containing purified antibody. The eluate was concentrated by ultrafiltration with AMICON® (media for performing chromatographic separations) PM10 ultrafiltration disc (MILLIPORE), and dialyzed against saline (OHTSUKA) to obtain a final purified preparation.

25-6 The Reactivity for Antigen Binding of cF1232-37-2/CHO

In the same method as that of EXAMPLE 5, dissociation constant of cF1232-37-2/CHO for hGPVI-hFc was measured. As a result, it was exhibited that cF1232-37-2/CHO has a sufficient affinity to hGPVI-hFc and is equivalent to that of cF1232-37-2 transiently expressed in COS cells and prepared (sometimes abbreviated as cF1232-37-2/COS).

25-7 Confirmation of the Reactivity for cF1232-37-2/CHO

To confirm the reactivity of cF1232-37-2/CHO, using binding ability to hGPVI-hFc as an index, the competitive test with cF1232-37-2 prepared by transient gene expression system with COS cells was performed. The measurement method was in accordance with the method described in 17-3 of EXAMPLE 17. Using hGPVI-hFc as an immobilized protein, a competitive activity to labeled cF1232-37-2/COS was confirmed when unlabeled cF1232-37-2/CHO or cF1232-37-2/COS was added at a variety of concentration. The results are shown in FIG. 19. It was confirmed that the reactivity of cF1232-37-2/CHO is equivalent to that of cF1232-37-2/COS.

Example 26

Preparation of Humanized Anti-Human GPVI Monoclonal Antibody

Among four kinds of mouse anti-GPVI antibodies, as the first choice for designing and preparing reconstituted human antibody, F1232-37-2 could be selected. Design of humanized antibody was performed by replacing three CDR of respective variable regions of this antibody with CDRs of the known antibody derived from human myeloma. As a heavy chain, NEW (Saul, F. et al., J. Biol. Chem. 253, 585-597) and Eu (Cunningham B. et al., Biochemistry 9, 3161) were selected; as a light chain (κ chain), REI (Epp, O. et al., Eur. J. Biochem. 45, 513-524) and framework of Eu (hereinafter referred to as FR) was used as a receptor. As NEW-HA, Eu-HA, REI-KA and Eu-KA, the first amino acid sequences (version A; FIGS. 20 and 21) were designed, respectively. However, since Eu-HA possesses extremely rare sequences in FR3 and FR4, Eu-HC (version C) having a more general sequence was re-designed. Next, from these amino acid sequences, gene sequences enable to express the above sequences were constructed. Entire sequence was divided into several fragments, and DNA fragments were synthesized. By ligating with each DNA fragment, a gene fragment encoding variable region was obtained. This gene fragment was amplified with primers having appropriate restriction enzyme cleavage sites (see EXAMPLE 10). As a result, it could be bound to human antibody constant region (IgG4 as a heavy chain, and κ chain as a light chain) to obtain an entire gene encoding humanized antibody. Further, by integrating this gene downstream of EF promoter in the expression vector pEF2cew, plasmids enable to express respective humanized antibodies were constructed. These plasmids were designated pTK-2560 (NEW-HA), pTK-2632 (Eu-HC), pTK-2561 (REI-KA) and pTK-2631 (Eu-KA), respectively.

These humanized antibody-expressing plasmids were expressed in combination with the chimeric antibody-expressing plasmid (heavy chain: pTK-2571; light chain: pTK-2572). Then it was investigated whether the antibodies produced maintain the binding property to antigen. As a result, in Eu-HC, REI-KA and Eu-KA, expression and the binding activity to antigen could be recognized in any combination of chimeric antibody or humanized antibody. On the other hand, NEW-HA shows neither expression nor the binding activity in any combination. Consequently, a number of mutants were prepared by introducing mutation into the amino acid sequence of each FR of NEW-HA (replacing human sequence with mouse sequence), and the binding activity to antigen was comparatively studied. As a result, in NEW-HAN, a version wherein four mutations are finally introduced into FR1, expression of humanized antibody molecule and restoration of the binding activity to antigen were confirmed.

Figure 22:
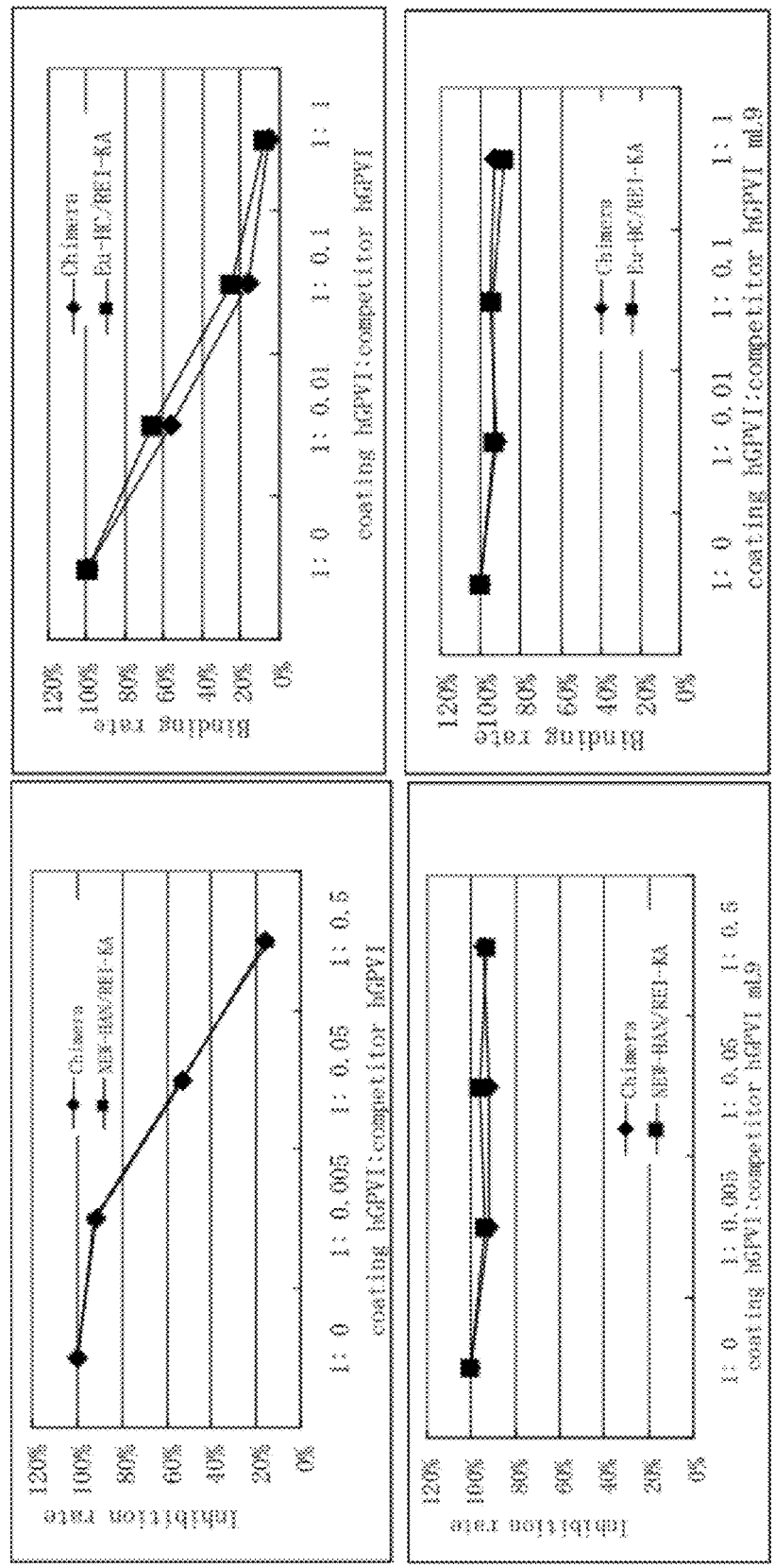
FIG. 22 shows a binding specificity of humanized antibody to GPVI.

Further, it was perceived that each humanized antibody exhibited the same binding specificity as that of original chimeric antibody by the competitive assay using loop-substituted GPVI-Fc (FIG. 22).

Example 27

Evaluation of Anti-GPVI Monoclonal Antibody by Cynomolgus Monkey Ex Vivo Test (2)

27-1 Cynomolgus Monkey Ex Vivo Test for Mouse/Human Chimeric Anti-GPVI Antibody (2)

(Single Intravenous Administration Test 2)

Figure 23:
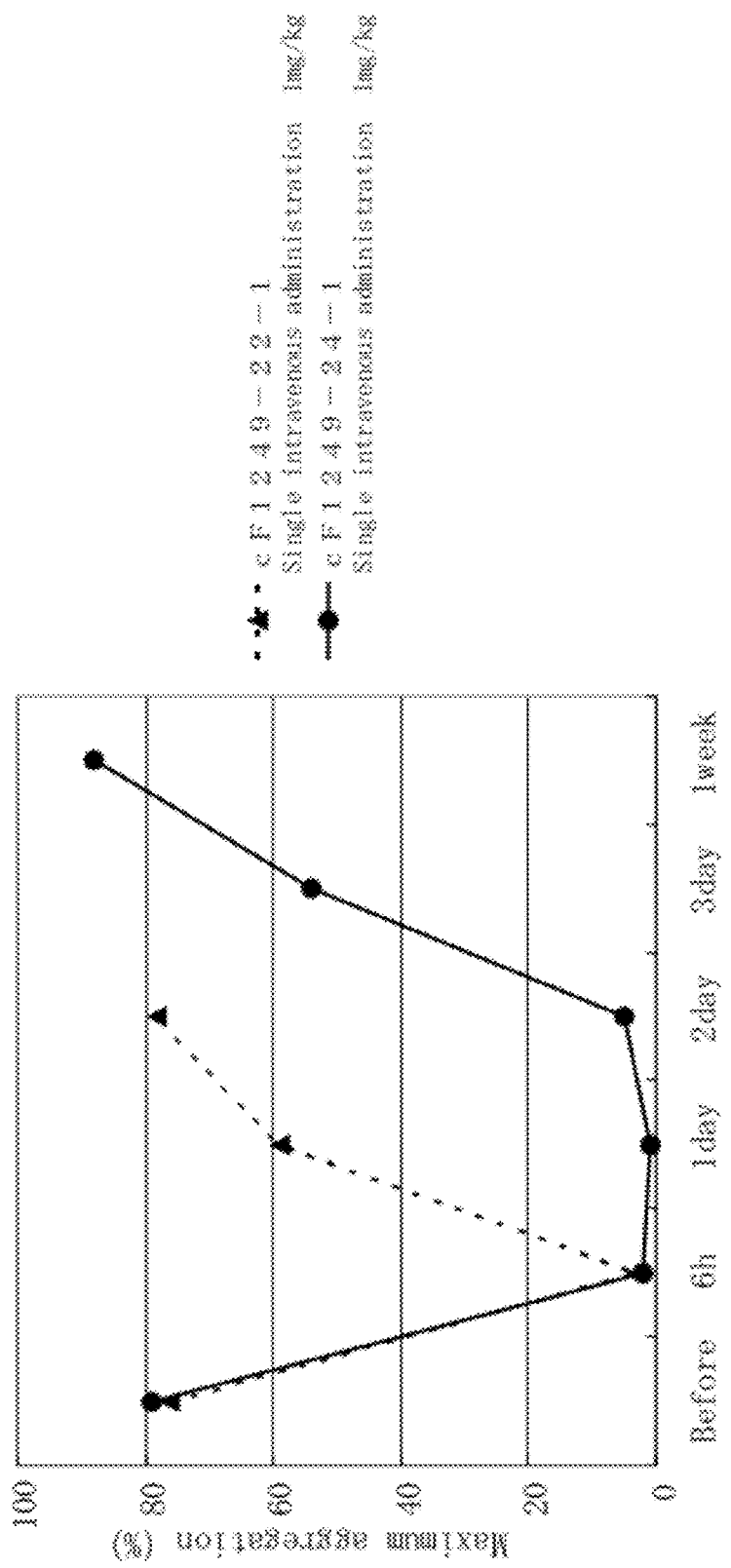
FIG. 23 presents a result of collagen-induced aggregation test of platelet from cynomolgus monkey administered with chimeric anti-GPVI antibody.

To cynomolgus monkey (male) the chimeric antibody cF1249-24-1 or cF1249-22-1 prepared in EXAMPLE 16 was intravenously administered at 1 mg/kg. Using the method shown in EXAMPLE 20, various analyses were performed. As a result, after administration, both antibodies caused decrease in platelet GPVI level. At the same time, both reduced response of platelet against collagen. As shown in FIG. 23, the effects were maintained over two days for cF1249-24-1 and for six hours for cF1249-22-1. Further, both antibodies had no effect on expression level of the platelet membrane protein (GPIIIa (CD61)).

Example 28

Measurement of Bleeding Time of Cynomolgus Monkey (2)

Firstly, weight of cynomolgus monkey (male, 2.5 to 5 kg) was measured. Then no abnormality concerning hematological parameter, hemostatic parameter and platelet function was confirmed. At 1 mg/kg, cF1232-37-2 was subcutaneously administered. The bleeding time was measured prior to administration and at three hours and 48 hours after administration. For comparison, eptifibatide was intravenously administered at 0.03, 0.1 and 0.3 mg/kg, and the bleeding time was measured at five minutes after administration in a similar manner. In addition, a collagen-induced platelet aggregation at the time when the bleeding time was measured was assayed by the method described in EXAMPLE 20.

After inserting an injection needle to the vein of both sides of tail of the cynomolgus monkey, a chronograph was activated and at the same time the needle was pulled out. The blood from the vein was suck up to filter paper (Advantec, filter paper for quantification No. 2, 150 mm) every five seconds. This operation was repeated during the blood adhered to the filter paper, and by quintupling the number of the filter paper with the bloodstain, it made a bleeding-time (seconds).

Figure 24:
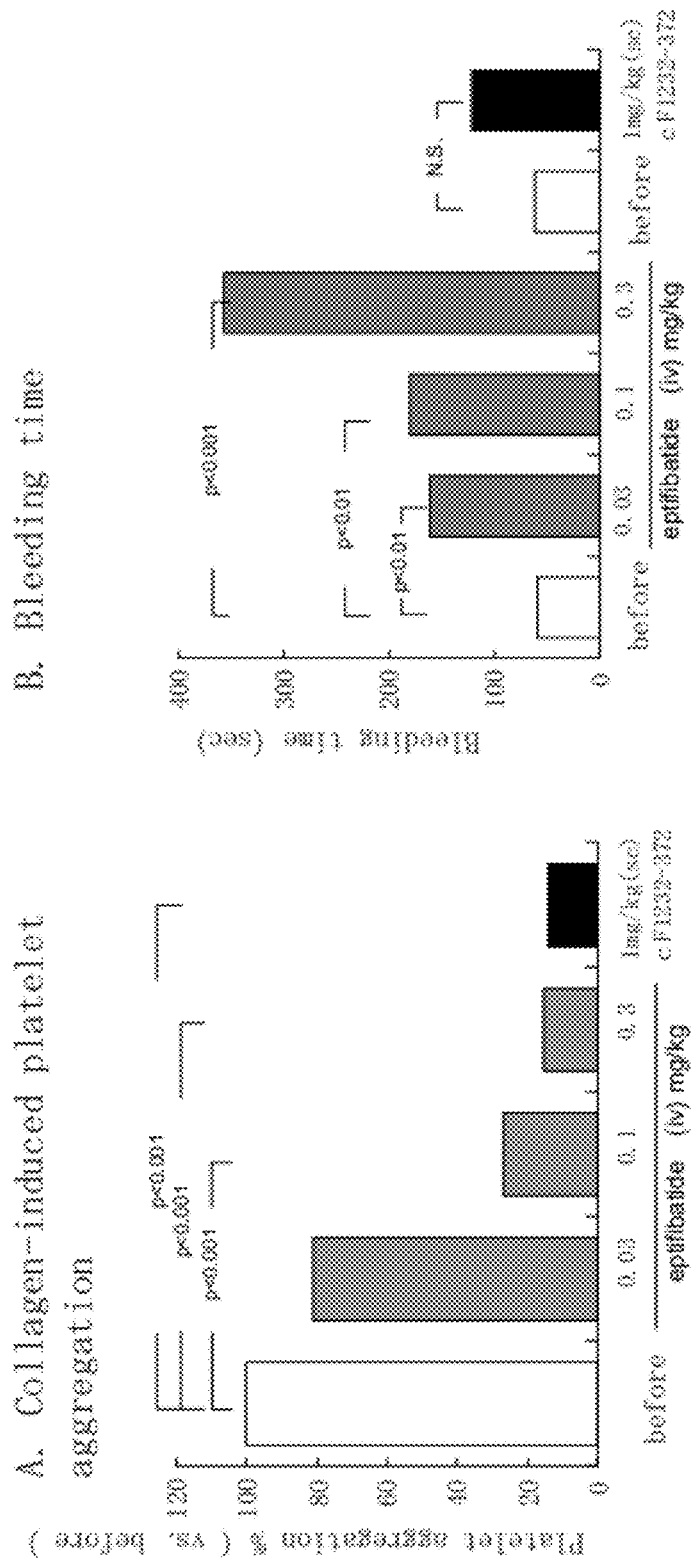
FIG. 24 presents a result of the bleeding time test in cynomolgus monkey. A: shows the collagen-induced platelet aggregation at five minutes after intravenous administration of eptifibatide and at 48 hours after administration of anti-GPVI antibody cF1232-37-2. B: shows a result of the bleeding time at five minutes after intravenous administration of eptifibatide and at 48 hours after administration of anti-GPVI antibody cF1232-37-2 compared with the bleeding time prior to administration.

As a result, in the group administered eptifibatide, under the condition of inhibiting a collagen-induced platelet aggregation, a significant prolongation of the bleeding time was detected. However, in the group subcutaneously administered 1 mg/kg of cF1232-37-2, under the condition of inhibiting a collagen-induced platelet aggregation, no significant prolongation of the bleeding time was detected in comparison with that prior to the administration (FIG. 24).

Example 29

Preparation of Polyvalent Anti-GPVI Antibody, and Antigen Binding Activity 29-1 Preparation of NM-Type Anti-GPVI Antibody-Expressing Plasmid 1) Cloning of Human μ-Chain Constant Region Gene Using HeLa genomic DNA as a template, C μ1 region was amplified with a primer pair (IgM-b and IgM-c); C μ2 region with a primer pair (IgM-d and IgM-e); C μ3 region with a primer pair (IgM-f and IgM-g); and C μ4 region with a primer pair (IgM-h and IgM-j), respectively. Using a mixture of the amplified product as a template, PCR with a primer pair (Nae-IgM and IgM-j) was performed again. As a result, the gene fragment, wherein each region was connected, was amplified. The amplified product was cloned into pT7-Blue (T) vector (TA cloning). By analyzing the sequence, it was confirmed that it was the gene sequence coding for human μ-chain constant region. The plasmid was designated pT7-IgM(Nae I).

```
                            (SEQ ID NO: 293)
IgM-b  GGAGTGCATCCGCCCCAACCCTT (SEQ ID NO: 294)
IgM-c  GCAGCTCGGCAATCACTGGAAGAGGCACGT (SEQ ID NO: 295)
IgM-d  ACGTGCCTCTTCCAGTGATTGCCGAGCTGC (SEQ ID NO: 296)
IgM-e  TGGCTGTGTCTTGATCGGGGCCACACATGG (SEQ ID NO: 297)
IgM-f  CCATGTGTGGCCCCGATCAAGACACAGCCA (SEQ ID NO: 298)
IgM-g  TGTGCAGGGCCACCCCCTTGGGCCGGGAGA (SEQ ID NO: 299)
IgM-h  TCTCCCGGCCCAAGGGGGTGGCCCTGCACA
```

```
                            (SEQ ID NO: 300)
IgM-j    GTTGACACGGTTAGTTTGCATGCA (SEQ ID NO: 301)
Nae-IgM  GCCGGCAGTGCATCCGCCCCAACC
```

2) Construction of Chimeric IgM-type F1232-37-2 Expressing Plasmid

Firstly, by cleaving pTK-2510 (the IgG4-type cF1232-37-2 heavy chain expressing plasmid described in EXAMPLE 16) with BamHI and Aor51HI, a gene fragment encoding γ 4-chain region was removed to obtain a remaining segment of the vector (including EF-1α promoter for expression and variable region of cF1232-37-2). To the vector segment, the gene fragment encoding μ-chain constant region obtained by cleaving pT7-IgM(Nae I) with BamHI and NaeI was inserted to construct a chimeric IgM-type F1232-37-2 expressing plasmid (pTK-2820), in which γ 4-chain of the constant region of cF1232-37-2 was replaced with μ-chain. In addition, in the similar way, from the IgG4-type cF1232-43-3 heavy chain expressing plasmid (pTK-2504), a chimeric IgM-type F1232-43-3 expressing plasmid (pTK-2822) was constructed.

3) Cloning of Human J Chain and Construction of Expression Plasmid

Using HeLa genomic DNA as a template, the first exon fragment was amplified with a primer pair (IgJ-a and IgJ-d); the second exon fragment with a primer pair (IgJ-c and IgJ-f); the third exon fragment with a primer pair (IgJ-e and IgJ-h); and the fourth exon fragment with a primer pair (IgJ-g and IgJ-j), respectively. Using a mixture of the amplified product as a template, PCR with a primer pair (IgJ-b and IgJ-i) was performed again. As a result, the gene fragment, wherein each region was connected, was amplified. The amplified product was cloned into pT7-Blue(T) vector (TA cloning). By analyzing the sequence, it was confirmed that it was the gene sequence coding for human J-chain constant region. The plasmid was designated pT7-IgJ. By cleaving pT7-IgJ with XbaI and BamHI, a gene fragment encoding the J-chain was obtained. Then by inserting the fragment into the XbaI/BamHI site where is present downstream the EF-1α promoter of expression vector (pEF2cew), human J-chain expressing plasmid (pTK-2393) was constructed.

```
                          (SEQ ID NO: 302)
IgJ-a  CACTCCTTATAGATCACACACCT (SEQ ID NO: 303)
IgJ-b  AAGTGAAGTCAAGATGAAGAACC (SEQ ID NO: 304)
IgJ-c  CTGTTCATGTGAAAGCCCAAGAAGATGAAA (SEQ ID NO: 305)
IgJ-d  TTTCATCTTCTTTGGGCTTTCACATGAACAG (SEQ ID NO: 306)
IgJ-e  AAACATCCGAATTATTGTTCCTCTGAACAA (SEQ ID NO: 307)
IgJ-f  TTGTTCAGAGGAACAATAATTCGGATGTTT (SEQ ID NO: 308)
IgJ-g  CCATTTGTCTGACCTCTGTAAAAAATGTGA (SEQ ID NO: 309)
IgJ-h  TCACATTTTTTACAGAGGTCAGACAAATGG
```

```
IgJ-I  TTAGTCAGGATAGCAGGCATCTG                    (SEQ ID NO: 310)

IgJ-j  AGAGCTATGCAGTCAGC                          (SEQ ID NO: 311)
```

29-2 Preparation of IgM-Type Mouse/Human Chimeric Anti-GPVI Antibody

After mixing an appropriate amount of the expression plasmid prepared in 29-1 above with the transfection reagent (FUGENE® 6, Roche Diagnostics), the mixture was dropped into COS cell culture system to perform transfection. Then a chimeric antibody was transiently expressed. For expression of mouse/human chimeric IgM-type F1232-37-2 (hereinafter abbreviated as cF1232-37-2 (IgM)), a heavy chain-expressing plasmid pTK-2820, a light chain-expressing plasmid pTK-2474 and J-chain plasmid pTK-2393 were co-transfected. Also, for expression of mouse/human chimeric IgM-type F1232-43-3 (hereinafter abbreviated as cF1232-43-3 (IgM)), a heavy chain-expressing plasmid pTK-2822, a light chain-expressing plasmid pTK-2514 and J-chain plasmid pTK-2393 were co-transfected.

After transfection, the cells were cultivated for 3 days at 37° C. under 5% $CO_2$-95% air. The culture supernatant was salted out by 60% ammonium sulfate and concentrated to purify it by an affinity chromatography with protein L column (IMMUNOPURE® (immobilized substances for purification of chemical and biological substances) Immobilized ProteinL, PIERCE).

29-3 Confirmation of Antigen Binding Activity of IgM-Type Mouse/Human Chimeric Anti-GPVI Antibody To each well of immunoplate coated with hGPVI-hFc (prepared by the method described in EXAMPLE 2 and the like), cF1232-37-2 (IgM) and cF1232-43-3 (IgM) was added and incubated at 37° C. for one hour. After washing the well with saline containing 0.05% TWEEN®20, 50 μL of peroxidase-labeled anti-human μ-chain antibody (DAKO, P0322), which had been diluted by 2000-fold with 10% rabbit serum-containing D-PBS, was added to each well. After incubation at 37° C. for one hour, coloring reaction by the TMB substrate was done to measure an absorbance at 450 nm with plate spectro-photometer (Molecular Devices, Wako). As a result, it was confirmed that both cF1232-37-2 (IgM) and cF1232-43-3 (IgM) bind to hGPVI-hFc.

Cynomolgus monkey and human PRPs prepared by the method described in 18-1 of EXAMPLE 18 were diluted with FACS buffer to make the platelet concentration $3.75 \times 10^8$ cells/mL. To the diluted PRP, cF1232-37-2 (IgM) or cF1232-43-3 (IgM) prepared in the above 29-2 was added at the final concentration of 3-4 μg/mL, and stood at 25° C. for 30 minutes. After incubation, the platelet was washed with FACS buffer. Subsequently, after adding anti-human IgM-FITC (BD Biosciences Pharmingen) and standing at room temperature for 30 minutes, the platelet was washed with FACS buffer and the fluorescence intensity of the platelet was measured with flow cytometer CYTOMICS FC500 (BECKMAN COULTER). As a result, it was confirmed that both antibodies of cF1232-37-2 (IgM) and cF1232-43-3 (IgM) bind to the monkey and the human platelet.

Example 30

Confirmation of an Activity of Anti-GPVI Antibody for Inducing Disappearance of Platelet GPVI Antigen (In Vitro)

By the method according to 18-1 of EXAMPLE 18, platelet rich plasma (PRP) was prepared from the monkey whole blood. To the prepared PRP, ACD-A (acid-citrate-dextrose) was added to adjust to pH6.5. After preparation, by centrifugation at 2000 rpm a platelet was precipitated. Then the platelet was washed with HEPES Buffer (adjusting to pH6.5 with ACD-A). After that, an appropriate volume of HEPES Buffer (pH7.4) was added to make the platelet suspend. With Sysmex the count of washed platelets prepared was measured.

The washed platelet was fractionated to microtube to make the platelet concentration $1.5 \times 10^7$ PLT/tube. Thereto 2 μL each of 10 mM $CaCl_2$ and 10 mM $MgCl_2$ was added and the volume was filled up to 18 μL with PBS. 5.0 μg/mL of Convulxin, cF1232-37-2, cF1249-22-1, cF1249-24-1, or cF1249-18-2 (each concentration 1 mg/mL) was added at 2 μL and mixed, and the mixture was incubated at room temperature for one hour. After incubation, by addition of 10 μL of 10 mM EDTA, the reaction was terminated. Then by centrifugation at 15000 rpm at room temperature for one minute, supernatant was isolated to precipitate. To each fraction, Sample Buffer was added, and the mixture was heated at 99° C. for 5 minutes. This sample was preserved at −30° C., until just before testings.

Figure 25:
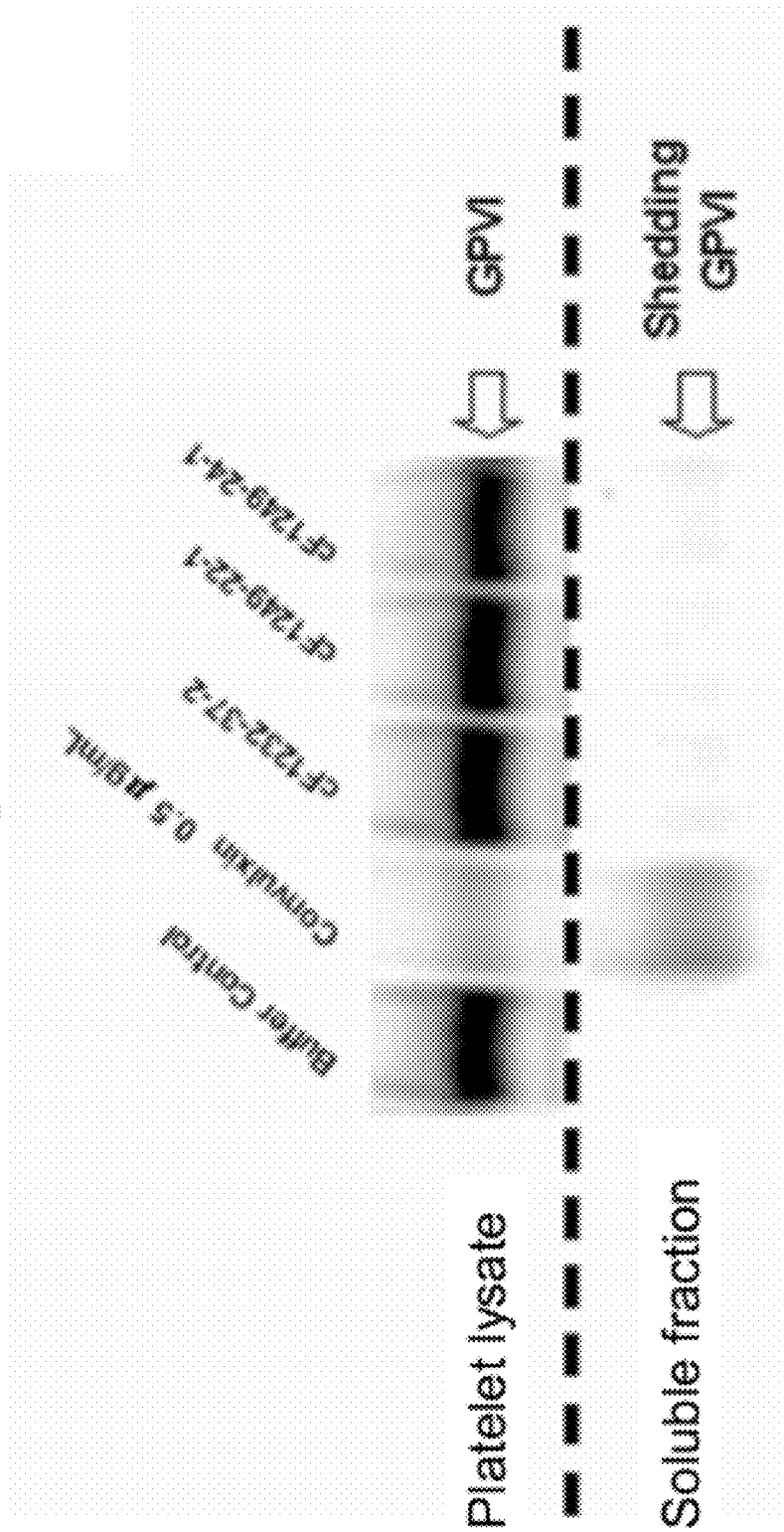
FIG. 25 shows a result of confirmation test for platelet GPVI antigen shedding by anti-GPVI antibodies.

According to the method of EXAMPLE 20, by performing SDS-PAGE and Western blotting, GPVI in each sample was detected. As a result shown in FIG. 25, for the Convulxin addition, GPVI antigen was detected in the supernatant after incubation, but GPVI antigen was not detected by addition of cF1232-37-2, cF1249-22-1, cF1249-24-1 and the cF1249-18-2, and no shedding of the GPVI antigen was induced by the anti-GPVI antibodies tested.

Example 31

Preparation of PEGylated Anti-GPVI Antibody and the Antigen Binding Activity 31-1 PEGylation of F1232-37-2 Antibody To prepare a PEGylated F1232-37-2 antibody, a purified F1232-37-2 was reacted with linear PEG (NEKTAR) with 20 KD having succiimide group. That is, the purified F1232-37-2 was placed into PBS (pH7.4) buffer and PEG was added to make the ratio of antibody to PEG 1:10 (the molar-ratio) and incubated at 37° C. for one hour.

Figure 26:
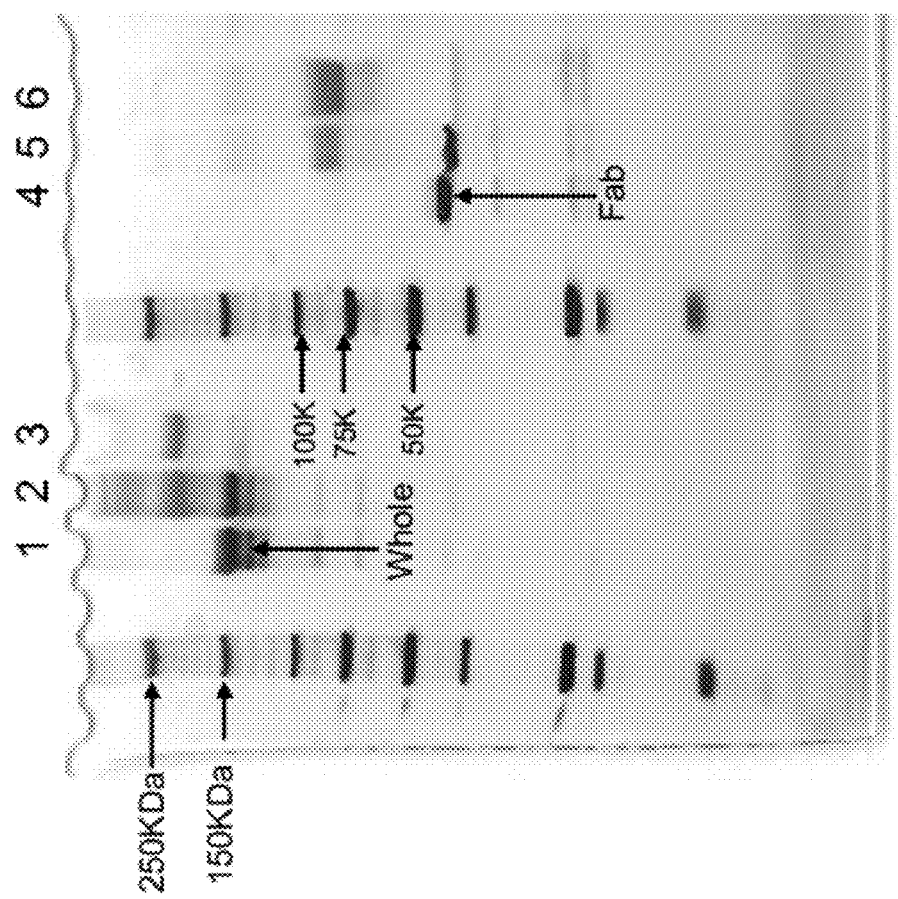
FIG. 26 presents a result of PEGylation of anti-GPVI whole antibody and Fab antibody. Lanes shows 1: F1232-37-2 whole antibody; 2: PEGylated product of F1232-37-2; 3: PEGylated purified product of F1232-37-2; 4: F1232-37-2 Fab antibody; 5: PEGylated product of F1232-37-2 Fab; and 6: PEGylated purified product of F1232-37-2 Fab, respectively.

Next, PEGylated antibody was purified. In order to isolate unmodified antibody from PEGylated antibody, the reaction mixture was loaded to anion exchange column Q Sepharose® HP (Amersham). The purity was evaluated by analyzing the acrylamide gel (FIG. 26). Further, the concentration of the antibody was calculated with Bradford method (Bio-Rad) using Bovine IgG as a standard.

31-2 PEGylated F1232-37-2 Fab Antibody

To prepare PEGylated F1232-37-2 Fab antibody, F1232-37-2 Fab antibody prepared in 21-2 of EXAMPLE 21 was used for PEGylation in the same method as the above-mentioned method.

Next, PEGylated Fab antibody was purified using SUPERDEX® 75 (Amersham). The purity was evaluated by analyzing the acrylamide gel (FIG. 26). Further, the concentration of the antibody was calculated with Bradford method (Bio-Rad) using Bovine IgG as a standard.

31-3 Antigen Binding Activity of F1232-37-2 Antibody

Binding activity to the antigen was detected by ELISA. To each well of immunoplate coated with hGPVI-hFc (prepared by the method described in EXAMPLE 2 and the like), F1232-37-2 antibody and PEGylated F1232-37-2 antibody, wherein both antibodies had been adjusted to the same concentration, was added and the plate was incubated at 37° C. for one hour. The well was washed with saline containing 0.05% TWEEN®20. Then 50 μL of peroxidase-labeled anti-mouse immunoglobulin antibody (DAKO, P260), which had been diluted by 1000-fold with 10% rabbit serum-containing D-PBS, was added to each well. After incubation at 37° C. for one hour, the TMB substrate was added, and an absorbance at 450 nm was measured with plate spectro-photometer (Molecular Devices, Wako). As a result, it was confirmed that both F1232-37-2 antibody and PEGylated F1232-43-3 antibody have almost equivalent binding activity (FIG. 27).

Example 32

Genetic Analysis for Repertoire of Anti-GPVI Antibody

It is thought that the sequences of the anti-GPVI monoclonal antibody described in EXAMPLES 9 and 15 are derived from several kinds of certain antibody gene. In particular, it was recognized that the repertoire selection of the antibody that recognizes loop 9 of human GPVI is characteristic. An antibody gene is composed by the combination in the germ-line antibody gene segment (H, D, and J of the heavy chain, V and J of the light-chain) and moreover in many cases, is formed accompanied with the somatic mutation (see Immunoglobulin Genes 2nd eds. T. Honjo and F. W. Alt, Academic Press, 1995). Therefore, using the nucleic acid base sequences of heavy chain variable region and the nucleic acid base sequences of light-chain variable region of these antibodies as a query sequence, and database for Ig germ-line V gene of NCBI (National Center for Biotechnology Information) as a subject, Ig-BLAST search was done. As a result shown in Table 16, the variable region nucleic acid base sequence of each antibody showed a high identity % (Identity %) to the mouse germ-line antibody heavy-chain-gene H segment, D segment, J segment ($V_H$, $D_H$ and $J_H$ segments), and an antibody light-chain gene V segment and J segment ($V_L$ and $J_L$). In addition, in Table 16, three segments having highest score to each clone were disclosed. It is estimated that any segment is the one, which composes the germ-line antibody gene, from which each antibody gene is originated. However, among them, it is thought to have the highest possibility that each clone is derived from a gene composed of a combination of the first line segment.

TABLE 16

| | | | | | | Heavy | | | | | |
|---|---|---|---|---|---|---|---|---|---|---|---|
| | | V | | | | D | | | | J | |
| Antibody | VH family | ID | % | idnt | total | ID | % | idnt | total | ID | % |
| F1246-1-1 | 7183(VH5) | 3:3.9 | 99 | 286 | 289 | DSP2.7 | 90 | 11 | 12 | JH4 | 100 |
| | 7183(VH5) | VH7183.7b | 98.9 | 279 | 282 | DSP2.5 | 90 | 11 | 12 | JH2 | 85 |
| | 7183(VH5) | VH7183.27b | 98.6 | 278 | 282 | DFL16.2 | 100 | 8 | 8 | | |
| F1249-3-2 | 7183(VH5) | VH7183.27b | 98 | 288 | 294 | DSP2.9 | 100 | 8 | 8 | JH2 | 100 |
| | 7183(VH5) | 3:3.9 | 97.9 | 285 | 291 | DSP2.6 | 100 | 7 | 7 | JH4 | 85 |
| | 7183(VH5) | VH7183.7b | 97.6 | 287 | 294 | DSP2.4 | 100 | 7 | 7 | JH3 | 100 |
| F1232-17-1 | 7183(VH5) | 3:3.9 | 99 | 288 | 291 | DFL16.1 | 86 | 20 | 23 | JH2 | 100 |
| | 7183(VH5) | VH7183.7b | 99.3 | 284 | 286 | DFL16.1j | 78 | 18 | 23 | JH4 | 85 |
| | 7183(VH5) | VH7183.27b | 99 | 283 | 286 | | | | | JH3 | 100 |
| F1232-18-3 | 7183(VH5) | VH7183.9 | 99.7 | 289 | 290 | DFL16.2 | 100 | 9 | 9 | JH2 | 100 |
| | 7183(VH5) | VH37.1 | 97.9 | 284 | 290 | DSP2.2 | 100 | 7 | 7 | JH4 | 85 |
| | 7183(VH5) | VH76-1BG | 99.6 | 265 | 266 | DSP2.13 | 100 | 7 | 7 | JH3 | 100 |
| F1232-19-1 | 7183(VH5) | 3:3.9 | 100 | 291 | 291 | DFL16.1 | 95 | 21 | 23 | JH2 | 100 |
| | 7183(VH5) | VH7183.7b | 100 | 288 | 288 | DFL16.1j | 86 | 20 | 23 | JH4 | 85 |
| | 7183(VH5) | VH7183.27b | 99.7 | 287 | 288 | DFL16.2 | 92 | 12 | 13 | JH3 | 100 |
| F1201-18 | 7183(VH5) | VH7183.9 | 99 | 285 | 288 | DSP2.9 | 100 | 7 | 7 | JH2 | 100 |
| | 7183(VH5) | VH7183.3b | 97.9 | 282 | 288 | DSP2.13 | 100 | 7 | 7 | JH4 | 85 |
| | 7183(VH5) | VH7183.14 | 97.6 | 282 | 289 | | | | | JH3 | 100 |
| F1245-4-1 | J558(VH1) | V186.2 | 94.5 | 276 | 292 | DSP2.2 | 100 | 14 | 14 | JH2 | 100 |
| | J558(VH1) | V145 | 94.5 | 276 | 292 | DSP2.6 | 92 | 13 | 14 | JH4 | 84 |
| | J558(VH1) | J558.33 | 94.2 | 275 | 292 | DSP2.4 | 92 | 13 | 14 | JH3 | 100 |
| F1245-7-1 | J558(VH1) | V186.2 | 95.9 | 281 | 293 | DFL16.1 | 93 | 14 | 15 | JH2 | 100 |
| | J558(VH1) | V145 | 95.9 | 281 | 293 | DSP2.13 | 80 | 12 | 15 | JH4 | 85 |
| | J558(VH1) | J558.33 | 95.9 | 281 | 293 | | | | | JH3 | 100 |
| F1245-5-1 | J558(VH1) | V186.2 | 95.2 | 280 | 294 | DSP2.9 | 100 | 7 | 7 | JH3 | 100 |
| | J558(VH1) | V145 | 95.2 | 280 | 294 | | | | | JH2 | 100 |
| | J558(VH1) | J558.33 | 95.2 | 280 | 294 | | | | | | |
| F1245-6-2 | J558(VH1) | V186.2 | 95.6 | 281 | 294 | DSP2.9 | 100 | 7 | 7 | JH3 | 100 |
| | J558(VH1) | V145 | 95.6 | 281 | 294 | | | | | JH2 | 100 |
| | J558(VH1) | J558.33 | 95.6 | 281 | 294 | | | | | | |
| F1249-18-2 | J558(VH1) | V186.2 | 94.6 | 278 | 294 | DFL16.1 | 83 | 10 | 12 | JH4 | 100 |
| | J558(VH1) | V145 | 94.6 | 278 | 294 | DSP2.5 | 90 | 9 | 10 | JH2 | 85 |
| | J558(VH1) | J558.33 | 94.6 | 278 | 294 | DSP2.7 | 90 | 9 | 10 | | |
| F1249-5-1 | J558(VH1) | V186.2 | 94.2 | 277 | 294 | DSP2.5 | 90 | 11 | 12 | JH4 | 100 |
| | J558(VH1) | V145 | 94.2 | 277 | 294 | DSP2.6 | 100 | 9 | 9 | JH2 | 85 |
| | J558(VH1) | J558.33 | 94.2 | 277 | 294 | DSP2.7 | 90 | 9 | 10 | | |
| F1249-22-1 | J558(VH1) | V303 | 99.3 | 292 | 294 | DFL16.2 | 100 | 14 | 14 | JH2 | 100 |
| | J558(VH1) | VH124 | 97.3 | 286 | 294 | DFL16.1 | 100 | 10 | 10 | JH4 | 85 |
| | J558(VH1) | V304 | 96.1 | 271 | 282 | DFL16.1j | 100 | 9 | 9 | JH3 | 100 |
| F1249-20-1 | J558(VH1) | J558.n | 98 | 288 | 294 | DSP2.2 | 100 | 9 | 9 | JH3 | 98 |
| | J558(VH1) | J558.n1 | 97 | 225 | 232 | DSP2.6 | 100 | 7 | 7 | JH2 | 100 |
| | J558(VH1) | J558.5 | 88.1 | 258 | 293 | DSP2.4 | 100 | 7 | 7 | JH4 | 100 |
| F1249-24-1 | J558(VH1) | J558.n | 98.3 | 289 | 294 | DSP2.2 | 100 | 9 | 9 | JH3 | 100 |
| | J558(VH1) | J558.n1 | 97.4 | 226 | 232 | DSP2.6 | 100 | 7 | 7 | JH2 | 100 |
| | J558(VH1) | J558.5 | 88.4 | 259 | 293 | DSP2.4 | 100 | 7 | 7 | | |
| F1249-30-1 | J558(VH1) | J558.n | 97.6 | 287 | 294 | DSP2.2 | 100 | 9 | 9 | JH3 | 100 |
| | J558(VH1) | J558.n1 | 96.6 | 224 | 232 | DSP2.6 | 100 | 7 | 7 | JH2 | 100 |
| | J558(VH1) | J558.5 | 87.7 | 257 | 293 | DSP2.4 | 100 | 7 | 7 | | |

TABLE 16-continued

| | | | | | | | | | | | | |
|---|---|---|---|---|---|---|---|---|---|---|---|---|
| F1232-24-1 | J558(VH1) | J558.n | 98.3 | 286 | 291 | DSP2.2 | | 100 | 13 | 13 | JH3 | 100 |
| | J558(VH1) | J558.n1 | 97.4 | 226 | 232 | DSP2.6 | | 92 | 12 | 13 | JH2 | 100 |
| | J558(VH1) | J558.5 | 88.3 | 257 | 291 | DSP2.4 | | 92 | 12 | 13 | | |
| F1232-7-1 | J558(VH1) | J558.n | 94.8 | 276 | 291 | DST4.2 | | 92 | 12 | 13 | JH4 | 100 |
| | J558(VH1) | J558.n1 | 94.4 | 219 | 232 | DST4-BALB/c | | 100 | 11 | 11 | JH2 | 85 |
| | J558(VH1) | J558.5 | 85.6 | 249 | 291 | DST4-C57BL/6 | | 90 | 10 | 11 | | |
| F1232-37-2 | J558(VH1) | J558.n | 94.5 | 275 | 291 | DST4.2 | | 92 | 12 | 13 | JH4 | 100 |
| | J558(VH1) | J558.n1 | 94 | 218 | 232 | DST4-BALB/c | | 100 | 11 | 11 | JH2 | 85 |
| | J558(VH1) | J558.5 | 85.2 | 248 | 291 | DST4-C57BL/6 | | 90 | 10 | 11 | | |
| F1232-21-1 | J558(VH1) | J558.13 | 98.6 | 286 | 290 | DFL16.1 | | 100 | 11 | 11 | JH2 | 100 |
| | J558(VH1) | J558.i | 98.3 | 286 | 291 | DFL16.2 | | 100 | 9 | 9 | JH4 | 85 |
| | J558(VH1) | J558.14 | 97.3 | 283 | 291 | DFL16.1j | | 100 | 8 | 8 | JH3 | 100 |
| F1201-20 | J558(VH1) | J558.23 | 98.6 | 281 | 285 | DSP2.2 | | 100 | 17 | 17 | JH3 | 100 |
| | J558(VH1) | J558.24 | 94.8 | 271 | 286 | DSP2.4 | | 94 | 16 | 17 | JH2 | 100 |
| | J558(VH1) | J558.22 | 93.4 | 270 | 289 | DSP2.3 | | 94 | 16 | 17 | | |
| F1232-10-1 | 3609(VH8) | CB17H-3 | 96.1 | 271 | 282 | DFL16.1 | | 100 | 19 | 19 | JH2 | 100 |
| | 3609(VH8) | CB17H-10 | 95.7 | 270 | 282 | DFL16.1j | | 100 | 12 | 12 | JH4 | 85 |
| | 3609(VH8) | CB17H-1 | 93.3 | 263 | 282 | | | | | | JH3 | 100 |
| F1232-43-3 | 3609(VH8) | CB17H-3 | 96.5 | 272 | 282 | DFL16.1 | | 100 | 17 | 17 | JH2 | 100 |
| | 3609(VH8) | CB17H-10 | 95.4 | 269 | 282 | DFL16.2 | | 100 | 11 | 11 | JH4 | 85 |
| | 3609(VH8) | CB17H-1 | 93.6 | 264 | 282 | | | | | | JH3 | 100 |

| | Heavy | | Light | | | | | |
|---|---|---|---|---|---|---|---|---|
| | J | | V | | | J | | |
| Antibody | idnt | total | ID | % | idnt | total | ID | % | idnt | total |
| F1246-1-1 | 53 | 53 | 21-5 | 100 | 296 | 296 | JK1 | 100 | 38 | 38 |
| | 33 | 39 | 21-10 | 98.3 | 290 | 295 | JK2 | 89 | 31 | 35 |
| | | | 21-4 | 91.2 | 270 | 296 | JK5 | 89 | 23 | 26 |
| F1249-3-2 | 45 | 45 | 21-10 | 100 | 298 | 298 | JK1 | 100 | 37 | 37 |
| | 33 | 39 | 21-5 | 98.3 | 292 | 297 | JK2 | 89 | 31 | 35 |
| | 14 | 14 | 21-4 | 90.9 | 269 | 296 | JK5 | 89 | 23 | 26 |
| F1232-17-1 | 39 | 39 | 21-5 | 98 | 290 | 296 | JK1 | 100 | 38 | 38 |
| | 33 | 39 | 21-10 | 96.3 | 284 | 295 | JK2 | 89 | 31 | 35 |
| | 14 | 14 | 21-4 | 91.2 | 270 | 296 | JK5 | 89 | 23 | 26 |
| F1232-18-3 | 45 | 45 | 21-5 | 97 | 289 | 298 | JK1 | 97 | 36 | 37 |
| | 33 | 39 | 21-10 | 95.3 | 283 | 297 | JK2 | 91 | 32 | 35 |
| | 14 | 14 | 21-2 | 90.9 | 261 | 287 | JK5 | 89 | 23 | 26 |
| F1232-19-1 | 39 | 39 | 21-5 | 98 | 290 | 296 | JK1 | 100 | 38 | 38 |
| | 33 | 39 | 21-10 | 96.3 | 284 | 295 | JK2 | 89 | 31 | 35 |
| | 14 | 14 | 21-4 | 91.2 | 270 | 296 | JK5 | 89 | 23 | 26 |
| F1201-18 | 45 | 45 | 21-5 | 99.7 | 297 | 298 | JK5 | 100 | 35 | 35 |
| | 33 | 39 | 21-10 | 98 | 291 | 297 | JK2 | 100 | 14 | 14 |
| | 14 | 14 | 21-4 | 90.9 | 270 | 297 | JK1 | 89 | 23 | 26 |
| F1245-4-1 | 38 | 38 | 19-32 | 100 | 282 | 282 | JK1 | 100 | 38 | 38 |
| | 32 | 38 | 19-17 | 88 | 242 | 275 | JK2 | 89 | 31 | 35 |
| | 14 | 14 | 19-13 | 88.3 | 204 | 231 | JK5 | 89 | 23 | 26 |
| F1245-7-1 | 45 | 45 | 19-32 | 100 | 283 | 283 | JK4 | 97 | 36 | 37 |
| | 33 | 39 | 19-17 | 88 | 242 | 275 | JK2 | 100 | 13 | 13 |
| | 14 | 14 | 19-13 | 88.3 | 204 | 231 | JK3 | 100 | 12 | 12 |
| F1245-5-1 | 41 | 41 | 19-32 | 100 | 284 | 284 | JK1 | 100 | 38 | 38 |
| | | | 19-17 | 88 | 242 | 275 | JK2 | 89 | 31 | 35 |
| | 14 | 14 | 19-13 | 88.3 | 204 | 231 | JK5 | 89 | 23 | 26 |
| F1245-6-2 | 41 | 41 | 19-32 | 99.6 | 283 | 284 | JK1 | 100 | 38 | 38 |
| | | | 19-17 | 87.6 | 241 | 275 | JK2 | 89 | 31 | 35 |
| | 14 | 14 | 19-13 | 87.9 | 203 | 231 | JK5 | 89 | 23 | 26 |
| F1249-18-2 | 53 | 53 | 19-32 | 100 | 285 | 285 | JK1 | 100 | 36 | 36 |
| | 33 | 39 | 19-17 | 88 | 242 | 275 | JK2 | 89 | 31 | 35 |
| | | | 19-13 | 88.3 | 204 | 231 | JK5 | 89 | 23 | 26 |
| F1249-5-1 | 51 | 51 | 19-32 | 99.6 | 284 | 285 | JK1 | 100 | 36 | 36 |
| | 33 | 39 | 19-17 | 87.6 | 241 | 275 | JK2 | 89 | 31 | 35 |
| | | | 19-13 | 87.9 | 203 | 231 | JK5 | 89 | 23 | 26 |
| F1249-22-1 | 41 | 41 | 8-24 | 99.3 | 300 | 302 | JK5 | 97 | 37 | 38 |
| | 33 | 39 | 8-30 | 92.5 | 273 | 295 | JK2 | 89 | 25 | 28 |
| | 14 | 14 | 8-28 | 90.5 | 258 | 285 | JK1 | 89 | 24 | 27 |
| F1249-20-1 | 46 | 47 | 21-5 | 98.3 | 291 | 296 | JK5 | 100 | 38 | 38 |
| | 14 | 14 | 21-10 | 96.6 | 285 | 295 | JK2 | 89 | 24 | 27 |
| | 11 | 11 | 21-4 | 89.9 | 266 | 296 | JK1 | 89 | 23 | 26 |
| F1249-24-1 | 47 | 47 | 21-5 | 99.7 | 295 | 296 | JK5 | 100 | 38 | 38 |
| | 14 | 14 | 21-10 | 98 | 289 | 295 | JK2 | 89 | 24 | 27 |
| | | | 21-4 | 90.9 | 269 | 296 | JK1 | 89 | 23 | 26 |
| F1249-30-1 | 47 | 47 | 21-5 | 99.7 | 295 | 296 | JK5 | 100 | 38 | 38 |
| | 14 | 14 | 21-10 | 98 | 289 | 295 | JK2 | 89 | 24 | 27 |
| | | | 21-4 | 90.9 | 269 | 296 | JK1 | 89 | 23 | 26 |
| F1232-24-1 | 47 | 47 | 21-5 | 98 | 290 | 296 | JK5 | 100 | 38 | 38 |
| | 14 | 14 | 21-10 | 96.3 | 284 | 295 | JK2 | 89 | 24 | 27 |
| | | | 21-4 | 91.2 | 270 | 296 | JK1 | 89 | 23 | 26 |

TABLE 16-continued

| | | | | | | | | | |
|---|---|---|---|---|---|---|---|---|---|
| F1232-7-1 | 49 | 49 | 21-5 | 100 | 296 | 296 | JK2 | 100 | 38 | 38 |
| | 33 | 39 | 21-10 | 98.3 | 290 | 295 | JK1 | 89 | 31 | 35 |
| | | | 21-4 | 91.2 | 270 | 296 | JK4 | 92 | 22 | 24 |
| F1232-37-2 | 49 | 49 | 21-5 | 100 | 296 | 296 | JK2 | 100 | 38 | 38 |
| | 33 | 39 | 21-10 | 98.3 | 290 | 295 | JK1 | 89 | 31 | 35 |
| | | | 21-4 | 91.2 | 270 | 296 | JK4 | 92 | 22 | 24 |
| F1232-21-1 | 41 | 41 | ce9 | 97.9 | 278 | 284 | JK2 | 100 | 38 | 38 |
| | 33 | 39 | cp9 | 94.4 | 268 | 284 | JK1 | 89 | 31 | 35 |
| | 14 | 14 | cy9 | 84.5 | 191 | 226 | JK4 | 92 | 22 | 24 |
| F1201-20 | 43 | 43 | cw9 | 95.8 | 272 | 284 | JK2 | 100 | 38 | 38 |
| | 14 | 14 | bv9 | 96.1 | 269 | 280 | JK1 | 89 | 31 | 35 |
| | | | cj9 | 93.2 | 261 | 280 | JK4 | 92 | 22 | 24 |
| F1232-10-1 | 42 | 42 | 12-46 | 96.1 | 273 | 284 | JK1 | 100 | 38 | 38 |
| | 33 | 39 | 12-44 | 95.8 | 272 | 284 | JK2 | 89 | 31 | 35 |
| | 14 | 14 | 12-41 | 94.2 | 258 | 274 | JK5 | 89 | 23 | 26 |
| F1232-43-3 | 41 | 41 | 12-44 | 96.8 | 275 | 284 | JK1 | 100 | 38 | 38 |
| | 33 | 39 | 12-46 | 96.5 | 274 | 284 | JK2 | 89 | 31 | 35 |
| | 14 | 14 | 12-41 | 95.3 | 261 | 274 | JK5 | 89 | 23 | 26 |

Example 33

Cloning of Rat GPVI Gene

To clone rat GPVI gene, PCR primers (six pairs) were designed to amplify all exons based on mouse GPVI gene which is well known to those skilled in the art. The gene fragments were specifically amplified by PCR using rat genomic DNA as a template with these primers. The resulting PCR fragments were sequenced and then ligated to estimate rat GPVI gene sequence. Next, based on the obtained sequence information, PCR primers for rat GPVI (rat GPVI#a, mGPVI-m) were re-designed and generated, and the full-length GVPI was amplified by PCR using rat bone marrow-derived cDNA (which was prepared by reverse transcription of rat bone marrow-derived RNA using an oligo dT primer) as a template. The amplified product extracted from the gel was cloned into pT7-Blue(T) vector (TAKARA BIO INC.) using TA cloning kit and sequenced. The plasmid harboring this sequence was designated as pTK-2478. FIG. 28 shows the nucleotide sequence (SEQ. ID. NO.: 312) and the encoded amino acid sequence (SEQ. ID. NO.: 313) of rat GPVI gene.

Example 34

Preparation of Rat GPVI(D1D2) Mouse GPVI(D3)-Mouse Fc Fusion Protein (rGPVI-mFc), etc.

Construction of the Expression Plasmid for rGPVI-hFc Fusion Protein

The gene fragment A, which encodes rat GPVI D1 and D2 (GPVI extracellular domain 1 and domain 2), was generated by PCR using pTK-2478 as a template with a pair of primers (rat GPVI-#a and rat GPVI-#t). In a similar manner, the gene fragment B, which encodes mouse GPVI D3 (GPVI extracellular domain excluding D1 and D2), was generated by PCR using pTK-2440 (described in MD075JP, P05-028, Patent Application No. 2005-348534) as a template with a pair of primers (rat GPVI-#s and IgG1-i). Next, we repeated PCR using the mixture of the fragments A and B as templates and a pair of primers (rat GPVI-#a and IgG1-i) to generate the gene fragment C, a fragment that the rat GPVI (D1 and D2) and the mouse GPVI (D3) were ligated. The fragment C was digested with EcoRI and BamHI at 5'- and 3'-termini, respec-

TABLE 17

| | |
|---|---|
| exon 1 rat GPVI-aCCCTCAGCGCATCCTGTTCCTAT | (SEQ. ID. NO.: 314) |
| rat GPVI-cTTTCCCAGGTCACCTTCAGGACT | (SEQ. ID. NO.: 315) |
| exons 2, 3 rat GPVI-fTTAAGGGAGTCTCTAGCCTCTG | (SEQ. ID. NO.: 316) |
| mGPVI-gGTTTAGCATACACACCTGTAGCAATTAGCT | (SEQ. ID. NO.: 317) |
| exon 4rat GPVI-jCCTGTTTCCTGTCTTTAATAGAG | (SEQ. ID. NO.: 318) |
| rat GPVI-lCCTTGCCCACACCTCTGACTCC | (SEQ. ID. NO.: 319) |
| exon 5rat GPVI-mGTGAGAAAATCAAGTCACAGAAATG | (SEQ. ID. NO.: 320) |
| rat GPVI-oTTCAGACACATTTGTAGTAGAAC | (SEQ. ID. NO.: 321) |
| exon 6rat GPVI-rGGAGCACTTGGGATGAACTGTCA | (SEQ. ID. NO.: 322) |
| rat GPVI-sGAGAAACCCATCCTCTTGCCAC | (SEQ. ID. NO.: 323) |
| exon 7rat GPVI-vGCTTCACAAGCATATGAGCACGTG | (SEQ. ID. NO.: 324) |
| rat GPVI-wATTATAGCTCTATAGATTCCATG | (SEQ. ID. NO.: 325) |
| full-lengthrat GPVI-#aGGGAATTCCATGTCTCCAGCCTCACTC | (SEQ. ID. NO.: 326) |
| mGPVI-dCCAAGTTATTTCTAGGCCAGTGG | (SEQ. ID. NO.: 327) | tively, and cloned into a EcoRI-BamHI site of the plasmid which contains mouse Fc domain (mFc) in the downstream of EF promoter (pTK-2299: described in MD0754JP, P05-028, Patent Application No. 2005-348534), thereby constructing pTK-2483, a plasmid designed to express rGPVI-mFc fusion protein.

TABLE 18

| | | |
|---|---|---|
| IgG1-i | CCAGGAGTTCAGGTGCTGGGCACGGTGGGC | (SEQ. ID. NO.: 328) |
| rat GPVI-#s | GTGGTTACTGGACCCTCTGCCACTCCCAGC | (SEQ. ID. NO.: 329) |
| rat GPVI-#t | GCTGGGAGTGGCAGAGGGTCCAGTAACCAC | (SEQ. ID. NO.: 330) |

Figure 3:
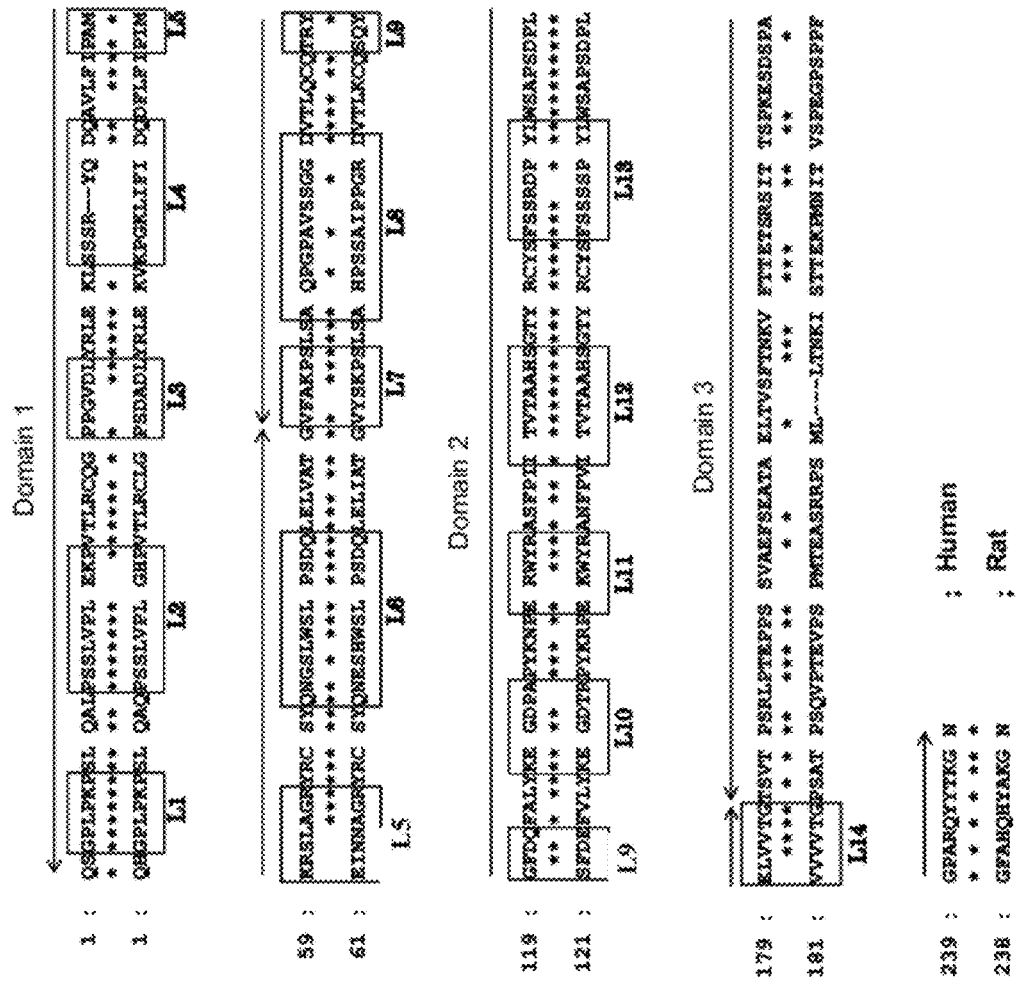
FIG. 3 is the alignment of the amino acid sequence of human soluble GPVI (SEQ ID NO: 419) and rat soluble GPVI (SEQ ID NO: 421). The squares show the positions of each domain region of GPVI and the loop region deduced by the modeling (L1-L14).

Based on the human GPVI and mouse GPVI sequences which are well known to those skilled in the art, rat GPVI sequence (FIG. 1) and amino acid sequence alignments of rat and human GPVIs (FIG. 3), or amino acid sequence of each loop shown in the amino acid alignment of human and mouse GPVIs (FIG. 1) and according to the method similar to those described in EXAMPLE 1 and EXAMPLE 33 in reference with the methods well known to those skilled in the art (see WO01/810, WO03/54020, WO02005/7800, etc.), the following expression plasmids were constructed: rat GPVI-human Fc (rGPVI-hFc) where mFc was replaced with hFc; mouse GPVI-hFc (mGPVI-hFc); human GPVI-human Fc (hGPVI-hFc); rGPVI-hL2, 5-hFc (mutant GPVI protein of which loops 2, 5 of rGPVI-hFc were replaced with the corresponding hGPVI sequences); rGPVI-hL9, 11-hFc (mutant GPVI protein of which loops 9, 11 of rGPVI-hFc were replaced with the corresponding hGPVI sequences); and hGPVI-mL9-hFc (mutant GPVI protein of which loop 9 of hGPVI-hFc was replaced with that of the corresponding mouse GPVI protein).

Example 35

Expression and Purification of rGPVI-mFc Fusion Protein

COS-1 cells were transfected with pTK-2483, an expression plasmid for rGPVI-mFc fusion protein, in the method similar to that described in EXAMPLE 1. The supernatant was collected after three days of culture, and rGPVI-mFc fusion protein was purified using Protein A column chromatography (Prosp-vA, Millipore). The resulting rGPVI-mFc was analyzed by standard SDS-PAGE (FIG. 29).

In addition, rGPVI-hFc, mGPVI-hFc, hGPVI-hFc, rGPVI-hL2, 5-hFc, rGPVI-hL9, 11-hFc and hGPVI-mL9-hFc were expressed and purified in a similar manner.

Example 36

Preparation of Anti-Rat GPVI Monoclonal Antibodies

To prepare antigen solution, 20 μg purified rat GPVI-mFc fusion protein was mixed with 12.5 μA Alum (Pierce) and 1 mg CpG adjuvant to a final volume of 100 μL. 25 μL antigen solution was administered to each footpad of ddy mouse (female, 8-week-old, SLC). Three days after immunization, lymphocytes were isolated from iliac lymph nodes, and subjected to cell fusion and hybridoma screening according to the method similar to that described EXAMPLE 2. Furthermore, the cells that were reacted with the purified rat GPVI-hFc protein were selected, then, cloned by limiting dilution culture method. The same screening was conducted 11 days after immunization, then 17 clones that generated antibodies against purified rat CPVI-hFc protein were obtained (Table 19).

These anti-rat GPVI antibodies produced by hybridoma clones were purified according to the method similar to that described in EXAMPLE 2.

TABLE 19

| | | Immobilized antigen | |
|---|---|---|---|
| | Sample | Rat GPVI | Human GPVI |
| Sample | F1239-1-3 | 2.288 | 0.019 |
| | F1239-2-3 | 2.953 | 0.015 |
| | F1239-4-2 | 0.843 | 0.026 |
| | F1239-5-3 | 2.259 | 0.021 |
| | F1239-6-1 | 2.272 | 0.032 |
| | F1239-7-1 | 2.872 | 0.013 |
| | F1239-8-1 | 1.344 | 0.013 |
| | F1239-9-1 | 2.284 | 0.028 |
| | F1239-10-2 | 2.061 | 0.021 |
| | F1239-11-1 | 1.372 | 0.014 |
| | F1239-15-3 | 1.552 | 0.023 |
| | F1239-16-3 | 1.224 | 0.017 |
| | F1239-17-2 | 1.502 | 0.014 |
| | F1237-18-1 | 1.098 | 0.015 |
| | F1239-19-1 | 2.93 | 0.017 |
| | F1239-22-3 | 1.956 | 0.024 |
| | F1239-23-1 | 2.668 | 0.021 |
| Control | Anti IgG | 2.944 | 2.84 |
| | Normal Mouse IgG | 0.123 | 0.026 |
| | F1232-37-2 | 0.137 | 2.757 |

Example 37

Analysis of the Anti-Rat GPVI Antibody Recognition Site

We analyzed the domain recognized by the anti-rat GPVI monoclonal antibodies, which were obtained in EXAMPLE 36, according to the method similar to that described in EXAMPLE 7. Namely, purified monoclonal antibodies prepared in EXAMPLE 36 were respectively mixed with rGPVI-hFc, hGPVI-hFc, rGPVI-hL2, 5-hFc (GPVI protein of which loops 2, 5 of rGPVI-hFc were replaced with the corresponding hGPVI sequences), or rGPVI-hL9, 11-hFc (GPVI protein of which loops 9, 11 were replaced with the corresponding hGPVI sequences). Each mixture was added to the immunoplate coated with rGPVI-hFc (solid phase) to examine the immunoreactivity. As a result, one type of the antibodies (F1239-11-1) did not exhibit the decrease in absorbance when rGPVI-hL2, 5-hFc was added, suggesting that this antibody recognizes loop 2 and/or loop 5. On the other hand, three types of the antibodies (F1239-4-2, F1239-6-1, F1239-22-2) showed no decrease in absorbance when rGPVI-9,11-hFc was added, suggesting that these antibodies recognize loop 9 and/or loop 11 (FIG. 30).

Moreover, the examination by the similar assay revealed that the above-described three types of the antibodies (F1239-4-2, F1239-6-1, F1239-22-2) did not bind to the mouse GPVI-Fc. Because the amino acid sequence of loop 11 of rat GPVI is homologous to that of mouse GPVI, it is thought that the loop 11 may not be a key recognition site. Therefore, we assume that these antibodies may at least recognize the structure comprising a part of the loop 9 of rat GPVI.

Example 38

Binding Capacity of Anti-Rat GPVI Antibodies to Rat Platelets

Blood was drawn from rat's ventral aorta into the tube with sodium citrate and the citrated blood was centrifuged at 110×g for 10 min at 25° C. to collect platelet rich plasma (PRP). Then anti-rat GPVI monoclonal antibodies (F1239-6-1) prepared in EXAMPLE 36 was added to the above-described PRP, which was diluted in PBS (hereafter referred to as FACS buffer) containing 0.5% inactivated FBS and 2.5 mM EDTA and the mixture was incubated at 25° C. for 30 min under stationary condition. After 30-min incubation, the platelets were washed with FACS buffer, to which anti-mouse IgG-FITC antibodies (DAKO) were added. The mixture was incubated at 25° C. for 30 min in the light-shielded stationary condition. After 30-min incubation, the platelets were washed with FACS buffer. To analyze the binding capacity of anti-rat GPVI monoclonal antibodies, we measured the fluorescence intensity of the platelets using CYTOMICS FC500 flow cytometer (BECKMAN COULTER). The results demonstrated that F1239-6-1 binds to rat platelets (FIG. 31).

Example 39

Reactivity of Anti-Rat GPVI Antibodies Against Platelets

PRP was prepared from blood drawn from normal Wistar rats. In order to evaluate if anti-rat GPVI antibody (F1239-6-1) activates rat platelets, we used CD62P expression as an indicator and measured its expression level when F1239-6-1 was added to PRP to a final concentration of 1-100 µg/mL by using FACS analysis according to the method similar to that described in EXAMPLE 18. Furthermore, anti-rat CD62P-PE (Biocytex) was used to detect rat CD62P. F1239-6-1 did not activate rat platelets at any concentration.

Example 40

Reactivity of Anti-Rat GPVI Antibodies on Inhibition of Platelet Aggregation and Induction of GPVI Depletion Anti-rat GPVI monoclonal antibodies, which were prepared in EXAMPLE 36, were subcutaneously administered to male SD rats at a dose of 0.01-1 mg/kg. Six days after administration, the blood was drawn and centrifuged at 730 rpm to prepare platelet rich plasma (PRP). Platelet aggregation (response to collagen and ADP) was measured using a platelet aggregometer (MCM HEMA TRACER 313M, MC Medical). Namely, PRP was diluted with plasma obtained from the same rat to platelet count at $3 \times 10^5$ cells/µL followed by adding $CaCl_2$ solution at a final concentration of 1 mM, and then the mixture was incubated at 37° C. for 3 min. To the mixture, collagen solution (final concentration of 10 µg/mL) or ADP solution (final concentration of 20 µM) was added and further incubated at 37° C. for 12 min. Platelet aggregation rate was determined by light transmittance. As a result, PRP prepared from the blood of the rats administered F1239-6-1 (0.3 mg/kg) exhibited a significant decrease in collagen-induced platelet aggregation, whereas no effect was detected on ADP-induced platelet aggregation (FIG. 32).

In addition, Western blot analysis revealed that the GPVI expression in platelets was significantly decreased at 3, 6, and 9 days after administration of anti-rat GPVI monoclonal antibodies, thus confirmed that said antibodies play a role in eliminating GPVI from platelets (FIG. 33).

Example 41

Reactivity of Anti-Rat GPVI Antibodies in the Collagen-Induced Lethal Model

Figure 34:
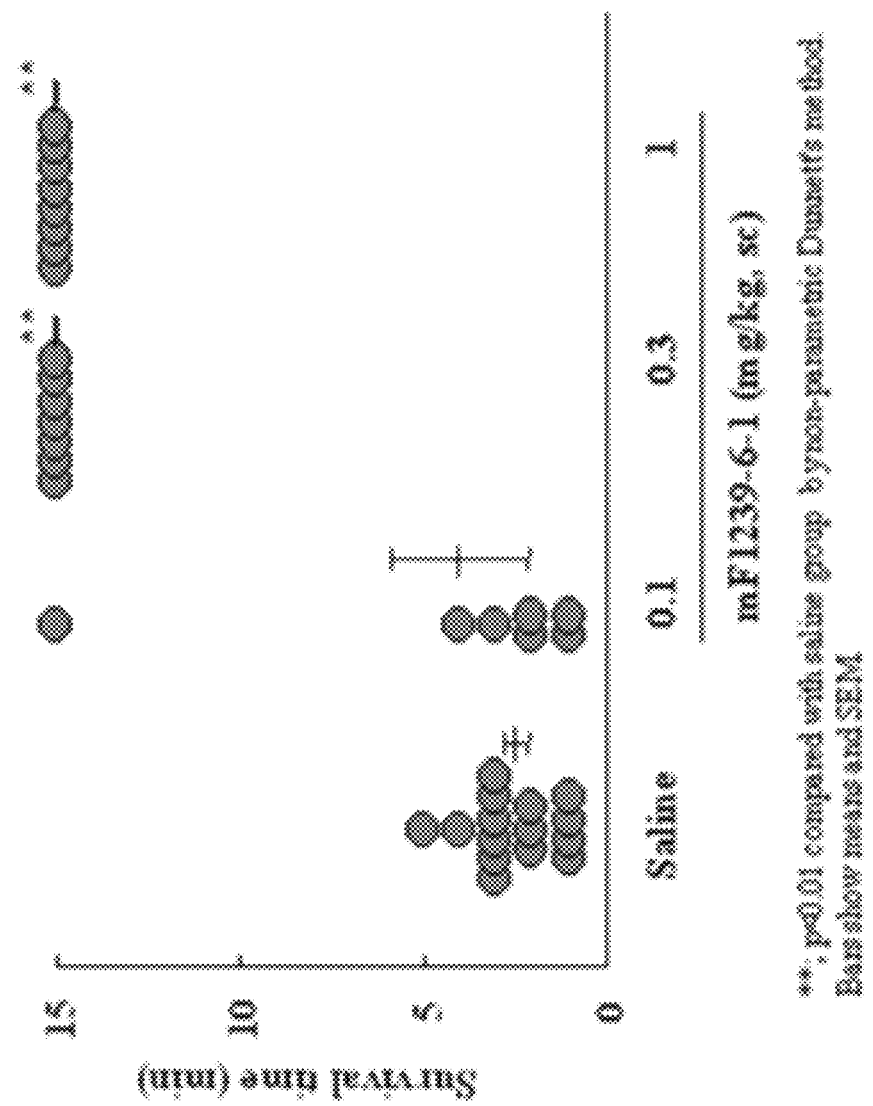
FIG. 34 shows a result of assay for effects of anti-GPVI antibody to collagen-induced lethal model.

Anti-rat GPVI monoclonal antibody F1239-6-1, which was prepared in EXAMPLE 36, was subcutaneously administered to male SD rats at a dose of 0.1, 0.3, or 1 mg/kg. As for a negative control, the saline was administered at the same volume. Six days after administering the test solutions, rats received rapid i.v. injection of collagen solution (collagen reagent "HORM" NYCOMED) at a dose of 0.8 mg/kg, then general conditions were observed up to 15 min. Death was determined by complete respiratory arrest. Survival time was defined as an elapsed time (in minutes) from the time point the animal received an injection until its death. When the animal survived more than 15 min, the survival time of the animal was recorded to be 15 min. The number of deaths per number of animals for each group was recorded. The statistical significance of differences between the treated groups and the control group (saline) was examined using the Chi-square test (Yukum's stat light). In addition, the survival time (mean±SEM) was calculated for each group, and the statistical significance of differences in the mean survival time between the treated groups and the control group (saline) was examined using the Dunnett's method (non-parametric, Yukum's stat light). The result showed that F1239-6-1 was effective at a dose of 0.3 mg/kg or greater in the collagen lethal model (FIG. 34).

Example 42

Figure 35:
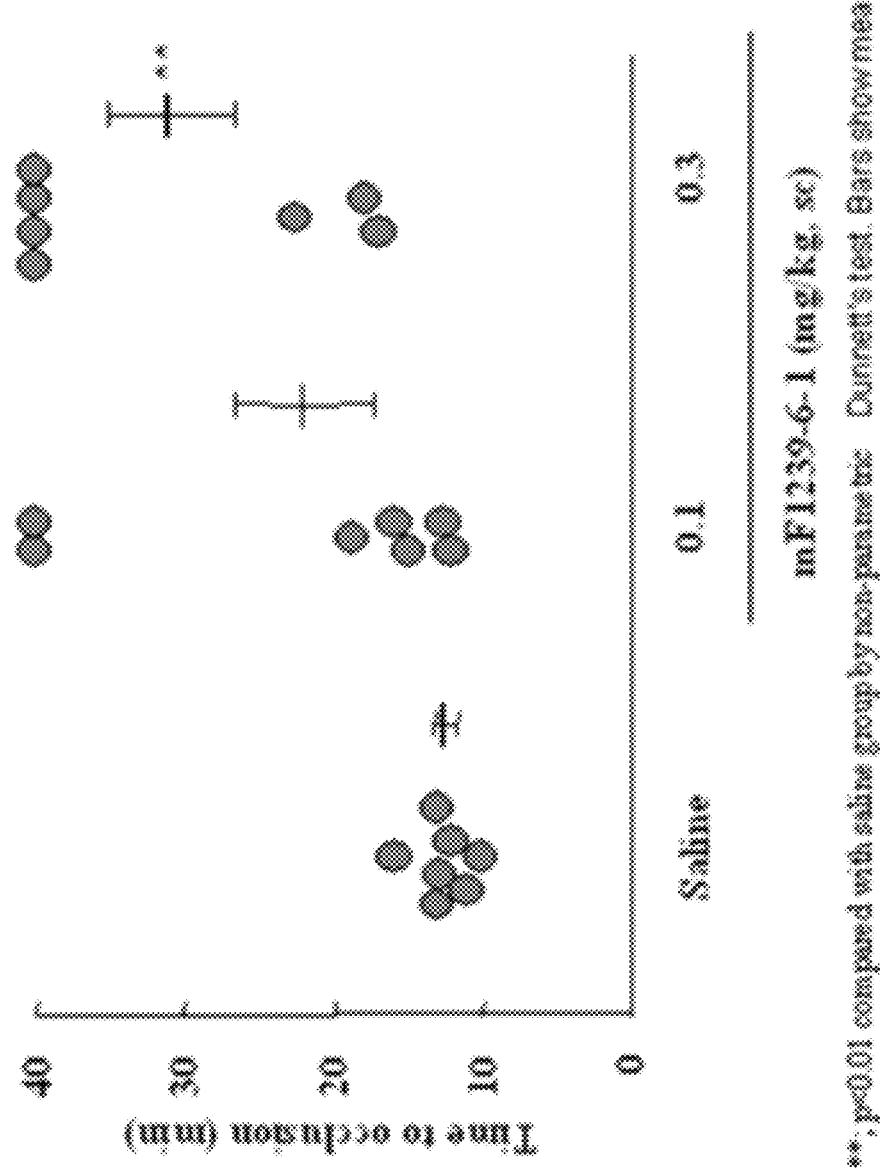
FIG. 35 shows a result of assay for effects of anti-GPVI antibody to electric stimulus-induced arterial thrombosis model.

Effect of Anti-Rat GPVI Antibodies on Rat an Arterial Thrombosis Model Under Anesthesia Anti-rat GPVI monoclonal antibody F1239-6-1, which was prepared in EXAMPLE 36, was subcutaneously administered to male SD rats at a dose of 0.1 or 0.3 mg/kg. As for a negative control, saline was administered at the same volume. Six days after administering the test solutions, rats were anesthetized with urethane, and fixed on the temperature control equipment (BWT-100, Bioresearch Center) in dorsal position. An midline incision was made in the rat's cervical region to expose approximately 1 cm of the right carotid artery. The pulse Doppler blood flow meter probe (Module: PD-20, System: VF-1, CRYSTAL BIOTEC, Primetech) was attached to the exposed carotid artery and the blood flow velocity was monitored with a polygraph system (365, NEC Sanei) and recorded on a chart. A hook-shaped bipolar electrode was hanged on the exposed carotid artery at the periphery of the probe and 0.3 mA direct current was passed through using an electric stimulator (SEN-7103, Nihon Koden) for 3 min. The elapsed time from the time point when electric stimulation was applied until when the blood flow arrested was measured using a stop watch (maximum 40 min). In addition, the surface temperature of the carotid artery at downstream of the stimulating electrode was measured every 5 min using a digital thermometer and recorded. In addition, the elapsed time until the blood flow arrest (mean±SEM) was calculated for each group, and the statistical significance of differences in the mean values between the treated groups and the control group (saline) was examined using the Dunnett's method (non-parametric, Yukum's stat light). Furthermore, the difference between the surface temperature of the carotid artery and the rectal temperature was calculated for each treated group, and all data was represented as mean±SE. The statistical significance of difference between the surface temperature of the carotid artery and the rectal temperature at each time point was examined using Dunnett's method (parametric, as above). The antibody-treated group delayed the time starting arterial obstruction in a dose dependent manner, and there was significant difference between 0.3 mg/kg dose group and the control group (FIG. 35). The significant difference in the surface temperature of the carotid artery was observed between the antibody-treated groups and the control group 15 min after the electrical stimulation. Furthermore, after 20, 25, and 35 min of electrical stimulation, the significant difference in the surface temperature was detected between the 0.3 mg/kg dose group and the control group. Taken together, we concluded that F1239-6-1 was effective at a dose of 0.3 mg/kg in this model.

Example 43

Analysis Using CYPHER®5E-Labeled Anti-GPVI Antibodies cF1232-37-2/CHO and human IgG4 (for control, Calbiochem) were labeled using pH-sensitive fluorescent reagent, CYPHER®5E Mono NHS Ester (GE Healthcare Bioscience), according to the manufacturers instruction. F1239-6-1 and mouse IgG (for control), which was purified from normal mouse plasma using PROSEP®-rA (Millipore), were labeled with CYPHER®5E in a similar manner. Each CYPHER®5E-labeled antibody titer was calculated from the measurements of absorbance.

43-1 Antigen-Binding Activity of CYPHER®5E-Labeled cF1232-37-2/CHO

Figure 36:
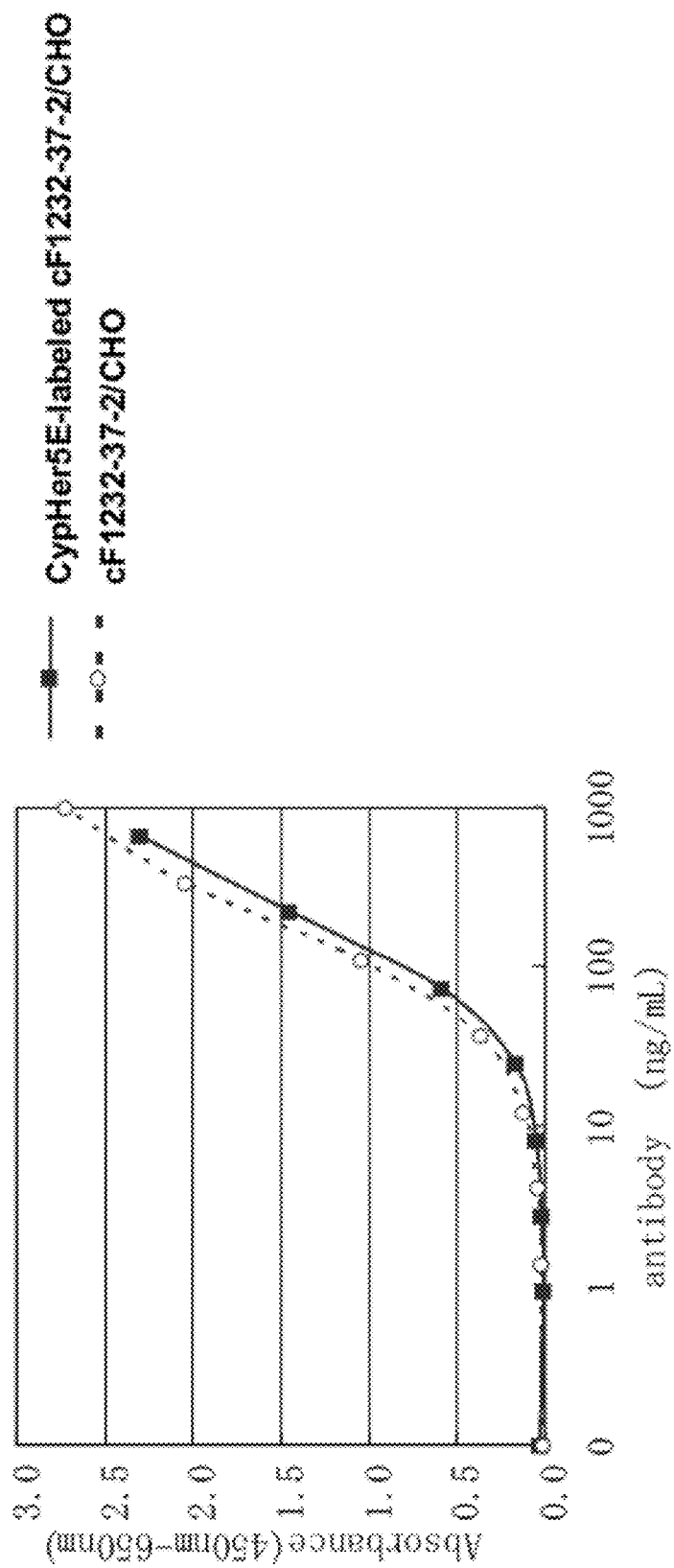
FIG. 36 shows an assessment of antigen binding for CYPHER® (fluorescent dyes for labeling nucleotides and proteins)5E-labeled cF1232-37-2/CHO.

We examined the binding activity of CYPHER®5E-labeled and non-labeled cF1232-37-2/CHOs, which were immunoreactive to hGPVI-hFc, against human GPVI according to the method similar to that described in EXAMPLE 31-3. Human immunoglobulin κ-chain antibody (Dako), which was diluted to 1:2,000 with D-PBS containing 0.1% BSA, was used to detect the binding to antigen. The results showed that both CYPHER®5E-labeled and non-labeled cF1232-37-2/CHOs had almost an equivalent binding activity (FIG. 36).

Figure 37:
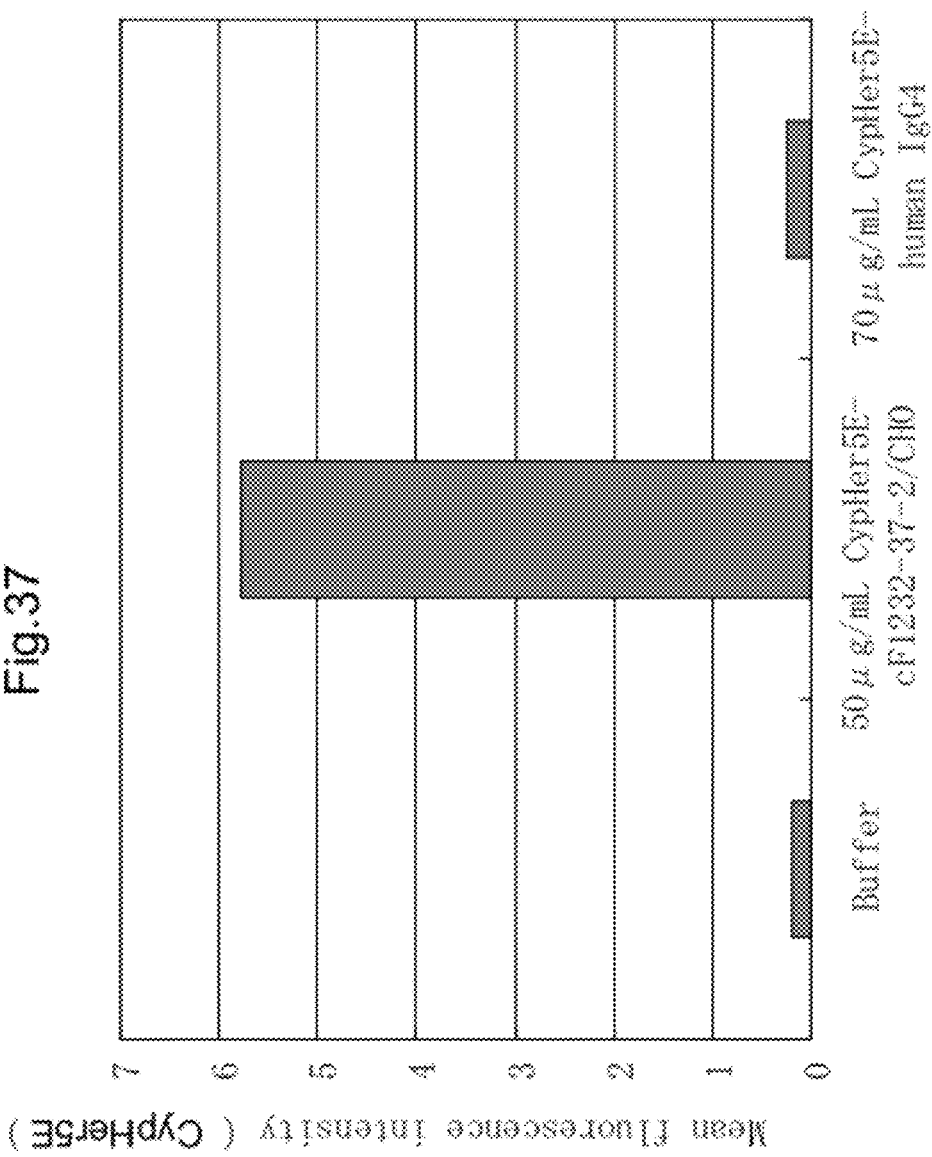
FIG. 37 presents a result of in vitro internalization of CYPHER®5E-labeled cF1232-37-2/CHO.

43-2 Examination of In Vitro Internalization Using CYPHER®5E-Labeled cF1232-37-2/CHO Cynomolgus PRP, which was prepared according to the method described in EXAMPLE 18-1, was diluted with platelet poor plasma (PPP) to platelet count at $3.7 \times 10^8$ cells/mL. To the diluted PRP, CYPHER®5E-labeled cF1232-37-2/CHO or CYPHER®5E-labeled human IgG4 was added to achieve a final concentration of 50 to 70 μg/mL, and the mixture was incubated for one hour at room temperature in the light-shielded condition. Immediately after incubation, the samples were analyzed with CYTOMICS FC500 flow cytometer (BECKMAN COULTER) to measure the fluorescence intensity originated from CYPHER®5E antibodies that were internalized in platelets. While in the platelets mixed with CYPHER®5E-labeled cF1232-37-2/CHO the fluorescence originated from the labeled antibodies was clearly observed, the platelets mixed with CYPHER®5E-labeled human IgG4 exhibited the fluorescence intensity similar to those with buffer alone. Therefore, we concluded that CYPHER®5E-labeled cF1232-37-2/CHO was internalized in platelets (FIG. 37).

43-3 Examination of Antigen Binding Activity of CYPHER®5E-Labeled F1239-6-1

Peroxidase-labeled F1239-6-1 was prepared according to the method similar to that described in EXAMPLE 3. The examination was carried out using a competitive binding assay (described in EXAMPLE 3). Subject antibody as competitor was added to a system where labeled antibody was bound to immobilized antigen. The binding activity of CYPHER®5E-labeled F1239-6-1 to rat GPVI was compared to that of non-labeled F1239-6-1.

Figure 38:
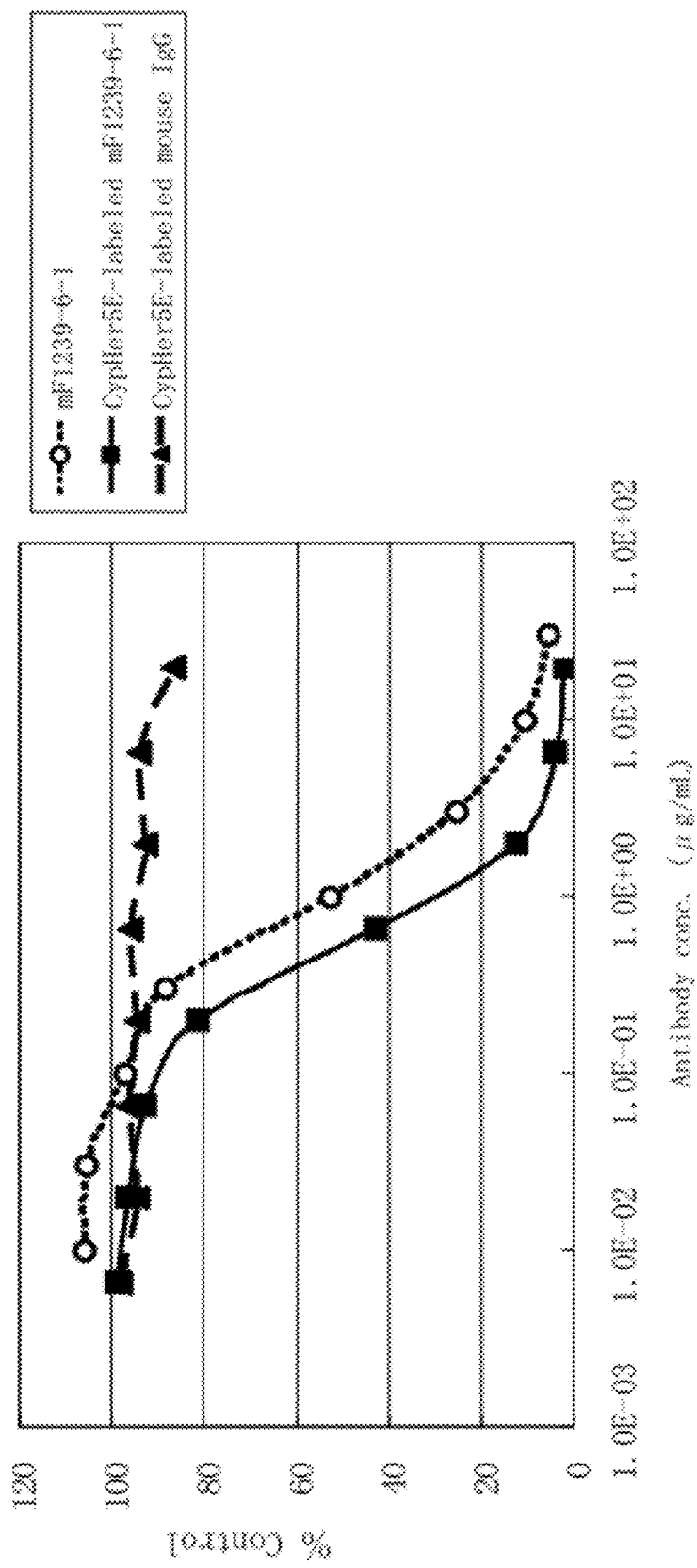
FIG. 38 shows an assessment for antigen binding of CYPHER®5E-labeled F1239-6-1.

The results showed that both CYPHER®5E-labeled and non-labeled F1239-6-1 had approximately an equivalent binding activity (FIG. 38).

43-4 Examination of In Vitro Internalization Using CYPHER®5E-Labeled F1239-6-1

Figure 39:
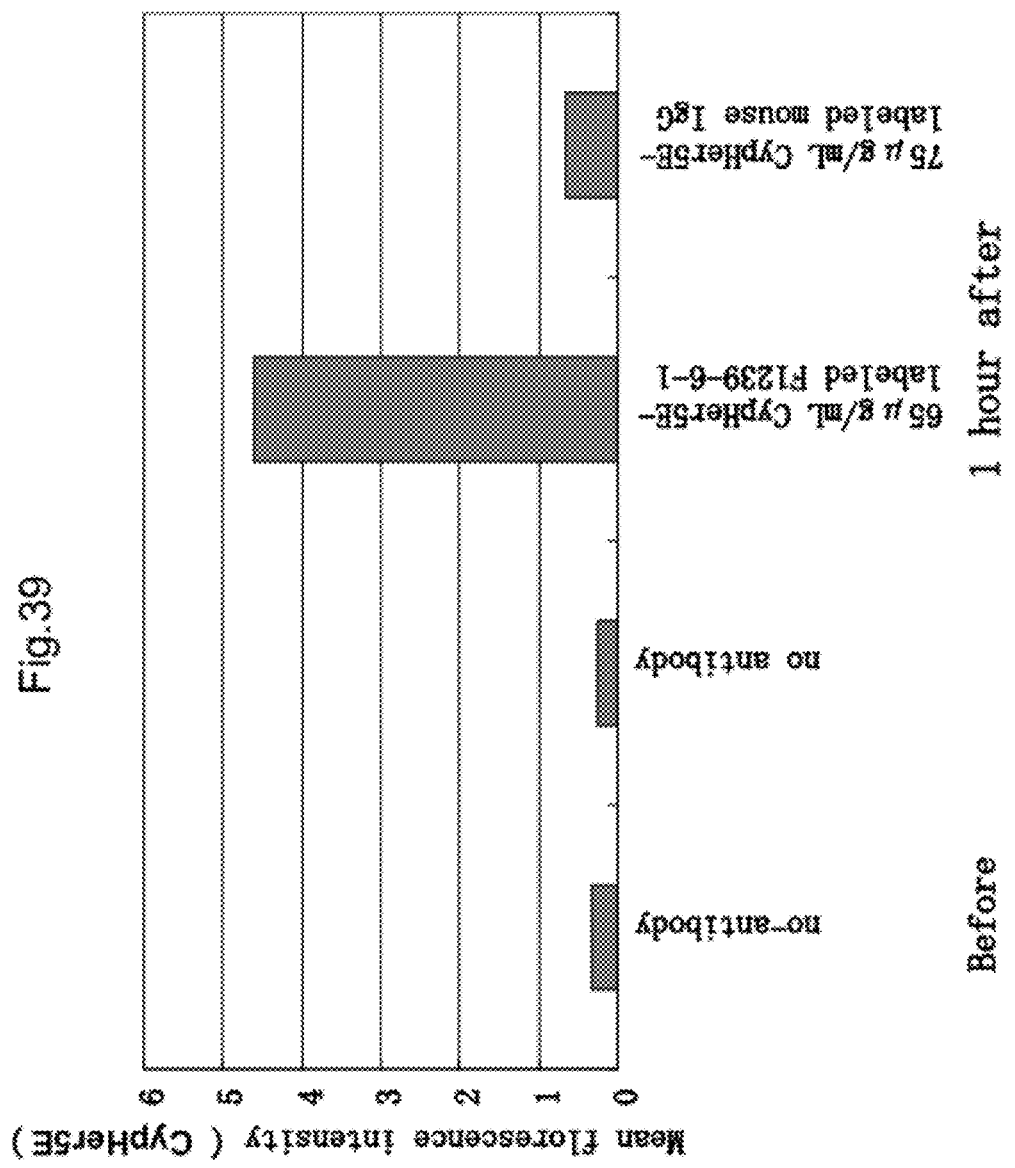
FIG. 39 presents a result of in vitro internalization of CYPHER®5E-labeled F1239-6-1.

Rat PRP was diluted with PPP to platelet count at $3.7 \times 10^8$ cells/mL. To the diluted PRP, CYPHER®5E-labeled F1239-6-1 or CYPHER®5E-labeled mouse IgG was added at a final concentration of 65 or 75 μg/mL, and the mixture was incubated for one hour at room temperature in the light-shielded condition. Immediately after culture, the samples were analyzed with CYTOMICS FC500 flow cytometer (BECKMAN COULTER) to measure the fluorescence intensity originated from CYPHER®5E-labeled antibodies that were internalized in platelets. While in the platelets mixed with CYPHER®5E-labeled F1239-6-1 the fluorescence originated from the antibodies was clearly observed, the platelets mixed with CYPHER®5E-labeled mouse IgG exhibited the fluorescence intensity similar to those with buffer alone. Therefore, we concluded that CYPHER®5E-labeled F1239-6-1 was internalized in platelets (FIG. 39).

43-5 Examination of In Vivo Internalization Using CYPHER®5E-Labeled F1239-6-1

Figure 40:
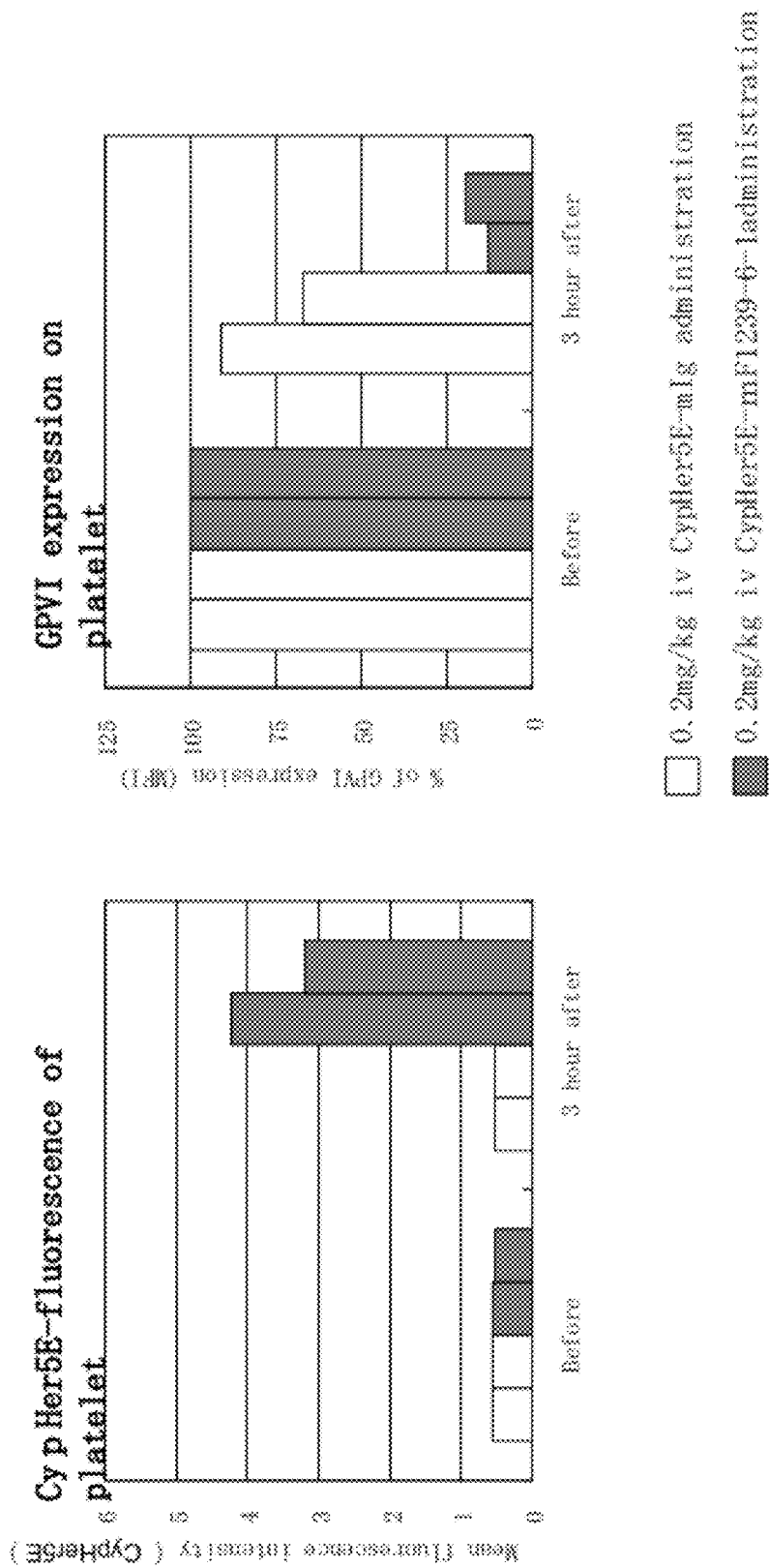
FIG. 40 presents a result of in vivo internalization of CYPHER®5E-labeled F1239-6-1.

CYPHER®5E-labeled F1239-6-1 or CYPHER®5E-labeled mouse IgG was i.v. administered to Wistar rats at a dose of 0.2 mg/kg. Citrated blood samples (100 μL) were collected before and 3 hours after administration. The blood samples were diluted with 2.5 mM EDTA/PBS, and analyzed using CYTOMIC FC500 flow cytometer (BECKMAN COULTER) to measure the fluorescence intensity originated from CYPHER®5E-labeled antibodies that were internalized in platelets. In addition, 0.8 μg PE-labeled F1239-11-1 was added to 1 μL blood sample, and the mixture was incubated at room temperature for 30 min in the light-shielded stationary condition. In a similar manner, we prepared PE-labeled mouse IgG2aκ as isotype control for PE-labeled F1239-11-1. Thirty minutes after culture, the sample was diluted with 2.5 mM EDTA/PBS and the fluorescence intensity of the sample was measured using CYTOMICS FC500 flow cytometer (BECKMAN COULTER) to quantitatively analyze the GPVI expression on the platelet membrane. Moreover, platelet fraction was gated on the forward/side scattering plot diagrams. Considering the fluorescence intensity obtained for the PE-labeled mouse IgG2aκ as that for non-specific binding, the difference in GPVI expression was calculated by subtracting the value obtained for the PE-labeled mouse IgG2aκ from that obtained for PE-labeled F1239-11-1. While in the platelets obtained from rats received CYPHER®5E-labeled F1239-6-1 the fluorescence originated from the antibodies was clearly observed, the platelets obtained from rats administered CYPHER®5E-labeled mouse IgG exhibited no increase in fluorescence intensity. Furthermore, GPVI expression level on the platelet membrane decreased significantly in the platelets obtained from the animals received CYPHER®5E-labeled F1239-6-1 in comparison to the level measured prior to the administration. However, in the platelets obtained from the animals administered CYPHER®5E-labeled mouse IgG, the GPVI expression on the platelet membrane decreased only slightly. Therefore, we concluded that CYPHER®5E-labeled F1239-6-1 was internalized with the GPVI on the platelet membrane in platelets (FIG. 40).

Example 44

Construction of cF1232-37-2S Expression Plasmid

In order to express cF1232-37-2, which is normally a bivalent antibody, in a form of two univalent antibodies, each of which consists of H-chain or L-chain (which can be designated as "cF1232-37-2S"), two cysteine residues at the hinge of the H-chain were replaced with two glycine residues. Specifically, PCR was performed using pTK-2571, a expression plasmid of cF1232-37-2 H-chain, as a template (described in EXAMPLE 25) with two pairs of primers, (IgG4-s, IgG4-m) and (IgG4-r, pEF2ce-27). Using small amount of each reaction products, agarose gel electrophoreses were performed to verify that the target sequences were correctly amplified. Then PCR was repeated using a mixture of both reaction products as a template with a pair of primers (IgG4-m, pEF2ce-27). Upon verifying that this reaction product was in fact the target fragment, the resulting protein was applied to a gel filtration column for demineralization, then double digested with restriction enzymes, Nhe I and Bam HI. The digested product was applied to a agarose gel electrophoresis, and the target fragment was extracted from the gel (designated as the fragment A). In a similar manner, the plasmid pTK-2571 was double digested with restriction enzymes, Nhe I and Bam HI to prepare the vector portion (designated as the fragment B). After mixing both fragments, the fragments A and B were ligated with ligase to construct cF1232-37-2S H-chain expression plasmid (designated as pTK-2828). On the other hand, the L-chain expression plasmid, pTK-2572, was used for expression assays without any alteration.

```
                                         (SEQ. ID. NO.: 331)
IgG4-s 5' GGTGCTGGGCCTGATGGGCCTGGGGACCA 3'

(SEQ. ID. NO.: 332)
IgG4-m 5' AGCGCTAGCACCAAGGGCCCATCCGTCTTC 3'

(SEQ. ID. NO.: 333)
IgG4-r 5' TGGTCCCCCAGGCCCATCAGGCCCAGCACC 3'

(SEQ. ID. NO.: 334)
pEF2ce-27 5' CATCAATGTATCTTATCATGTCT 3'
```

Example 45

Preparation of cF1232-37-2S/COS

Using CF1232-37-2S expression plasmid, pTK2828, which was prepared in EXAMPLE 44, COS cells were transfected according to the method similar to that described in EXAMPLE 1. The COS cell culture solution that contains the recombinant F1232-37-2S antibodies were pre-filtered with capsule cartridge filter (pore diameter: 0.8 µm, Toyo Roshi Kaisha Ltd.), then filtered with FLUORODYNE® filter (pore diameter: 0.22 µm, Pall), and clarified at room temperature to collect the supernatant of the culture. The resulting supernatant was passed through the column packed with rmp Protein A SEPHAROSE® Fast Flow (GE Healthcare Bioscience) which was pre-equilibrated with PBS- (Sigma). The column was washed with PBS—to eliminate proteins that did not bind, and 100 mM phosphate buffer containing 1.5 M NaCl was added to elute non-specifically bound proteins. Then specifically bound antibodies were eluted with 100 mM glycine-HCl buffer (pH 3.7). Immediately after measuring the volume of the resulting eluate, 1/10 volume of 1 M Tris-HCl (pH 8.5) was added to adjust pH to neutral. The resulting preparation was dialyzed against 0.9% aqueous NaCl solution. The final preparation was designated as purified cF1232-37-2S/COS sample.

Example 46

Binding Reactivity of cF1232-37-2S/COS Against Platelets

PRP, which was prepared from cynomolgus monkey and human blood according to the method described in EXAMPLE 18-1, was diluted with FACS buffer to platelet count at $3.75 \times 10^8$ cells/mL. To the above diluted PRP, cF1232-37-2S/COS, which was prepared in EXAMPLE 45, was added to bring a final concentration at 10 µg/mL and the mixture was incubated at 25° C. for 30 min under stationary condition. Then the platelets were washed with FACS buffer. Next, anti-human IgG-FITC (Dako) was added to the platelets and the mixture was incubated at 25° C. for 30 min in the light-shielded stationary condition. After washing the platelets with FACS buffer, the fluorescence intensity of the platelets was analyzed using CYTOMICS FC500 flow cytometer (BECKMAN COULTER). The results confirmed that cF1232-37-2S/COS binds to both simian and human platelets.

Example 47

Figure 41:
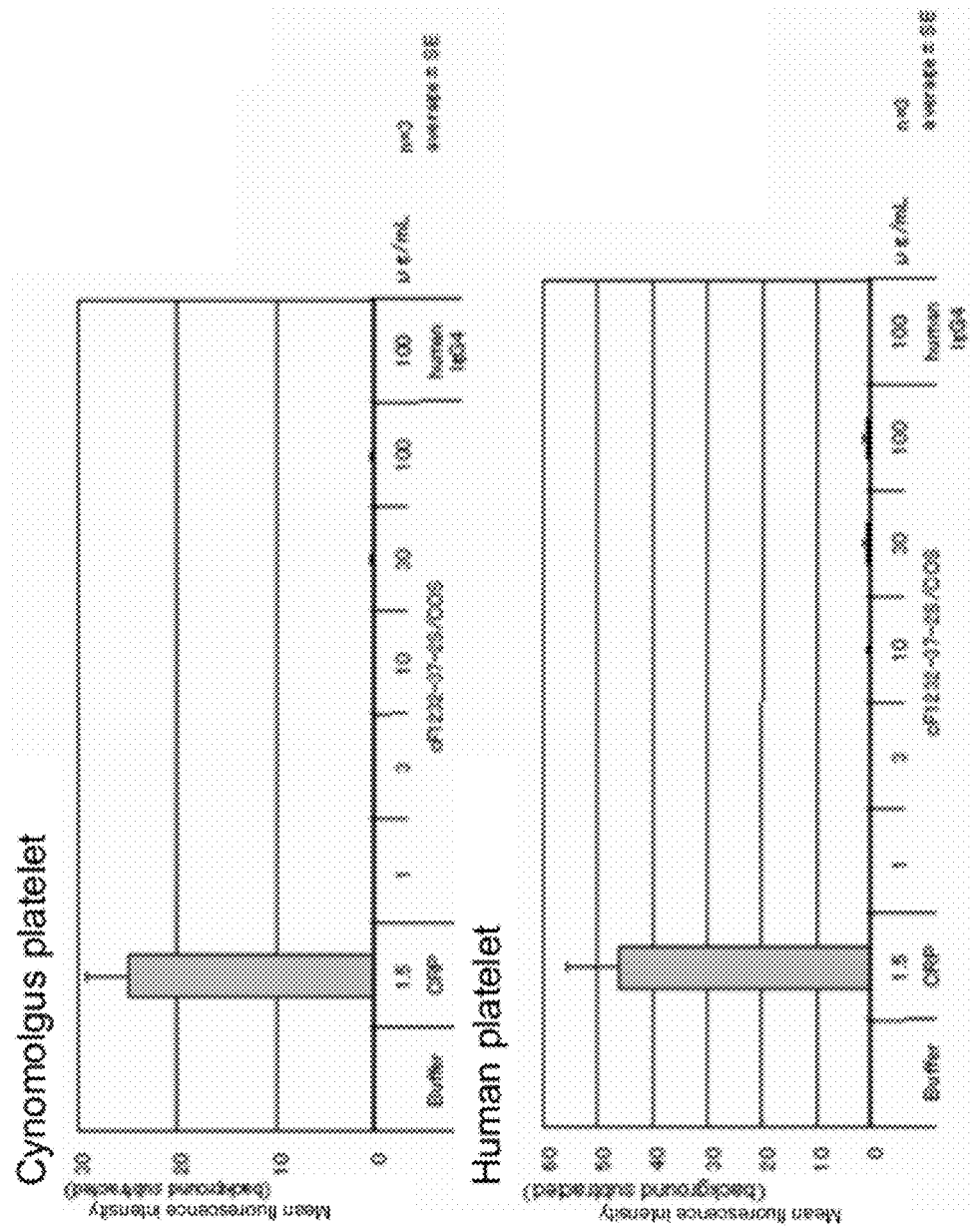
FIG. 41 shows a result of assessment for platelet activation (CD62P) of cF1232-37-2S/COS.

Action of cF1232-37-2S/COS Against Platelets
47-1 Activation of Human and Cynomolgus Monkey Platelets by cF1232-37-2S/COS To analyze if cF1232-37-2S/COS activates cynomolgus monkey and human platelets, we used CD62P expression as an indicator and measured the expression level in the condition that the reactant contained $CaCl_2$ at a final concentration of 1 mM and cF1232-37-2S/COS was added at a final concentration of 1-100 µg/mL according to the method described in EXAMPLE 18-1.

cF1232-37-2S/COS did not activate human and cynomolgus monkey platelets at any concentration (FIG. 41).
47-2 Inhibitory Effect of cF1232-37-2S on Collagen-Induced Platelet Aggregation (In Vitro)

Figure 42:
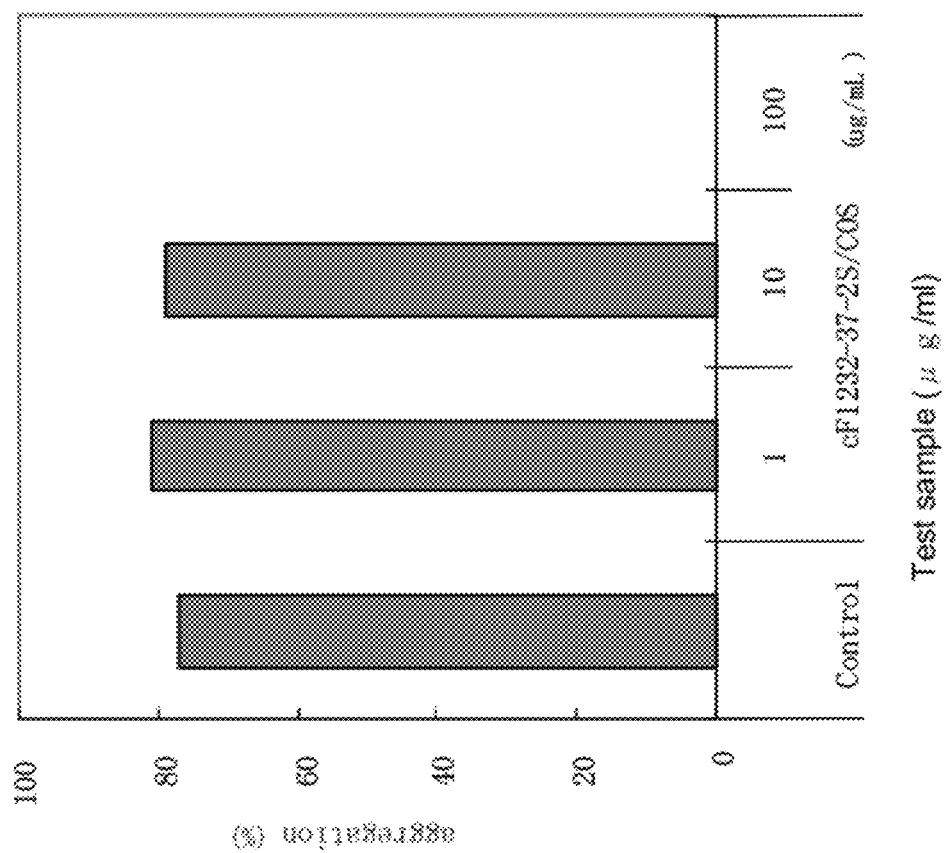
FIG. 42 shows a suppressing effect on collagen-induced platelet aggregation of cF1232-37-2S/COS.
Figure 43:
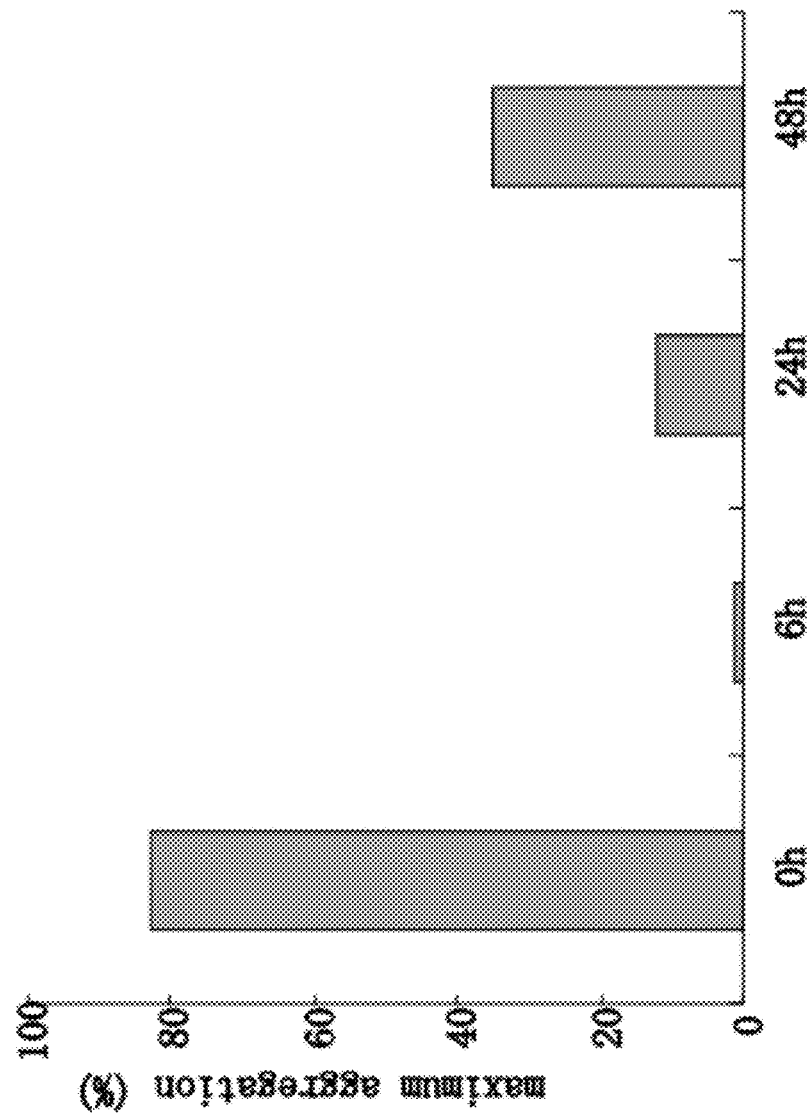
FIG. 43 presents a result of ex vivo test using cynomolgus monkey for cF1232-37-2S/COS. The result was shown by collagen-induced platelet aggregation.

Cynomolgus monkey PRP was diluted with PPP to platelet count at $3.33 \times 10^8$ cells/mL. To the diluted PRP, cF1232-37-2S was added at a final concentration of 1-100 µg/mL, and the mixture was incubated at 37° C. for 5 min. $CaCl_2$ was added to the mixture at a final concentration of 1 mM and incubated at 37° C. for 3 min, followed by adding collagen solution at a final concentration of 1 µg/mL, then, the mixture was further incubated at 37° C. for 12 min. The platelet aggregation induced by collagen was then measured.

cF1232-37-2S inhibited human platelet aggregation induced by collagen at the high concentration at 100 µg/mL (FIG. 42).
47-3 Ex Vivo Assay of cF1232-37-2S Using Cynomolgus Monkey Platelets—Collagen-Induced Platelet Aggregation Activity cF1232-37-2S/COS was intravenously administered to a cynomolgus monkey (male, approximately 4 kg) at a dose of 3 mg/kg. After administration, the platelets were collected and the platelet aggregation activity was analyzed. The animal received cF1232-37-2S at a dose of 3 mg/kg decreased the responsiveness for collagen-induced platelet aggregation within 6 hours of administration, which lasted for more than 2 days (FIG. 43).

Example 48

F1239-6-1 Fab and PEGylated F1239-6-1 Fab
48-1 Preparation of F1239-6-1 Fab Fragment To prepare F1239-6-1 Fab fragment, purified F1239-6-1 was digested with metalloendopeptidase. Namely, purified F1239-6-1 and metalloendopeptidase was mixed with the ratio of antibody:enzyme=3,000:1 (w/w) in PBS buffer (pH 7.4). Reaction was carried out at 25° C. for 4 hours. At the end of reaction EDTA was added to obtain a final concentration of 30 mM.

Then, Fab fragment was purified and analyzed according to the method similar to that described in EXAMPLE 21-2.

48-2 PEGylation of F1239-6-1 Fab Antibody Fragment

The above-described F1239-6-1 Fab fragment was used to prepare the PEGylated antibody fragment according to the method similar to that described in EXAMPLE 31-1.

Then PEGylated antibody fragment was purified. In order to separate PEGylated antibody fragment from non-modified antibodies, the PEGylated fragment was applied to a hydrophobic chromatography, the MACRO-PREP® (chemicals used in ion exchange chromatography) Methyl HIC (Bio-Rad). The purity of the resulting antibody was analyzed on an acrylamide gel, and the antibody titer was determined by the Bradford method (BioRad) using bovine IgG as standard.

48-3 Verification of the Binding Activity of PEGylated F1239-6-1 Fab

Figure 44:
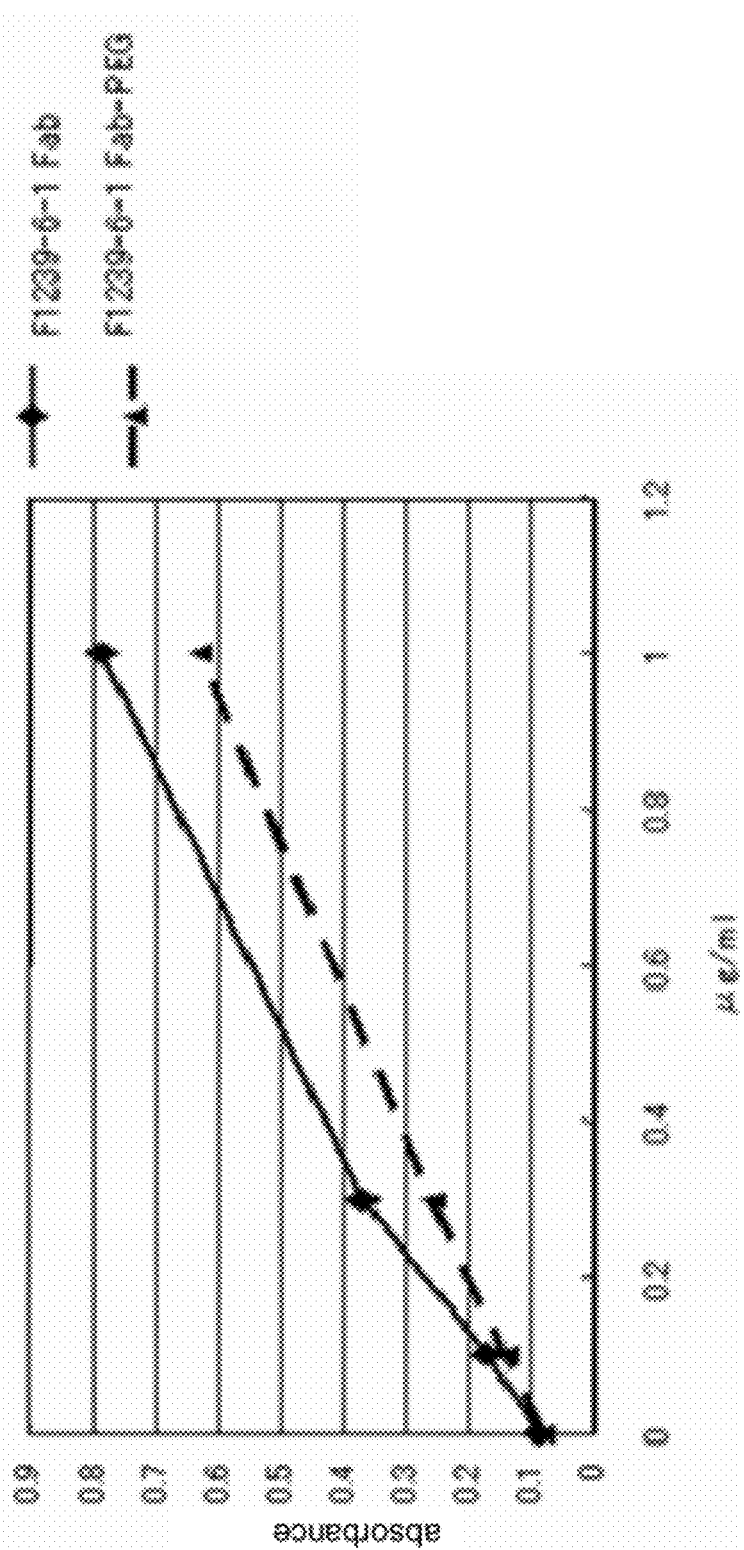
FIG. 44 shows a result of assay for antigen binding activity of PEGylated F1239-6-1 Fab.

The binding of PEGylated F1239-6-1 Fab antibody fragment to rat GPVI was analyzed using ELISA according to the method similar to that described in EXAMPLE 2. The result showed that the binding activity of the PEGylated F1239-6-1 Fab antibody fragment was approximately equal to that of F1239-6-1 Fab antibody fragment (FIG. 44).

48-4 Verification of the Binding Between PEGylated F1239-6-1 Fab and Cynomolgus Monkey and Human Platelets Rat PRPs were diluted with FACS buffer to platelet count at $2.0 \times 10^8$ cells/mL. To the PRP solution, PEGylated F1239-6-1 Fab prepared in EXAMPLE 48-1 and 48-2 was added to obtain a final concentration of 38 μg/mL. The mixture was incubated at 25° C. for 30 min under stationary condition. The platelets collected were washed with FACS buffer. Next, anti-mouse IgG-FITC (Dako) was added to the platelets and the mixture was incubated at 25° C. for 30 min in the light-shielded stationary condition. After washing the platelets with FACS buffer, the fluorescence intensity of the platelets were analyzed using CYTOMICS FC500 flow cytometer (BECKMAN COULTER). The results confirmed the binding of the PEGylated F1239-6-1 Fab to rat platelets.

Example 49

Measurement of Bleeding Time in Cynomolgus Monkey (3) at High Dosage

Before bleeding time measurement, the body weight of the cynomolgus monkey was measured. The laboratory test was performed to confirm that the animal's hematological parameters, coagulation parameters, and platelet function were within normal range. Then cF1232-37-2/CHO was subcutaneously administered at a dose of 3.0 mg/kg or 10.0 mg/kg. Forty-eight hours after administration, the bleeding time was determined according to the method similar to that described in EXAMPLE 28.

Figure 45:
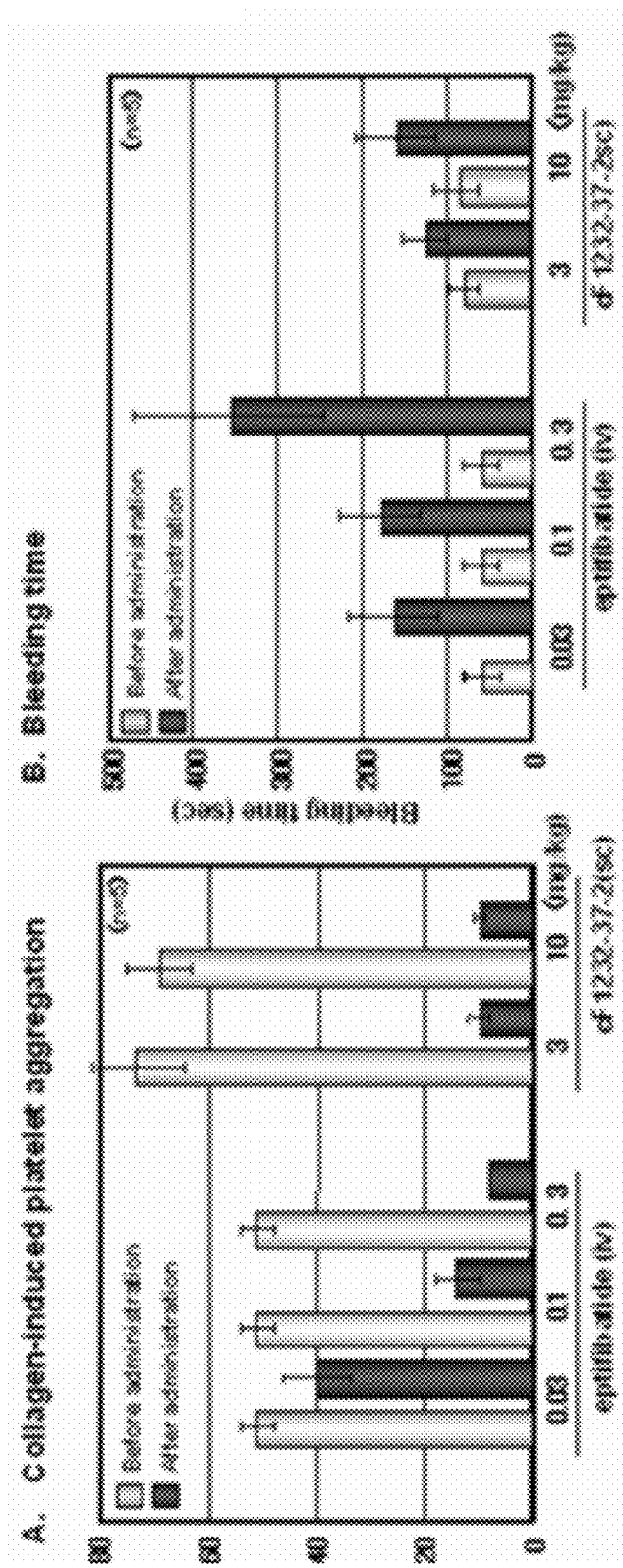
FIG. 45 indicates a bleeding time of cynomolgus monkey under high-dose administration of cF1232-37-2.

Compared with bleeding time measured before administration, the cF1232-37-2/CHO-treated animals exhibited less than 2-fold prolongation of bleeding time (FIG. 45).

Example 50

Measurement of Bleeding Time in Rats

To non-fasting SD rats (male, Crj:CD (SD) IGS, 8 weeks of age), which were divided into groups so that the mean body weight of each group does not vary, F1239-6-1 or saline was subcutaneously administered at a dose of 0.3-3 mg/kg or 1 mL/kg, respectively. Six days after administering the test solutions, rats were anesthetized by intraperitoneal injection of pentobarbital 15 min before an incised wound was made. Using scalpel, a 5-6 cm incision was made from the tip of the tail on the dorsal side of the animal, with special care not to damage arteries and veins. The tip of the tail (12 cm) was hanging down vertically, and the filter paper (ADVANTEC 1×3 cm) was placed every 30 sec to absorb the bleeding from the wound. The bleeding time was measured from the moment that the incision was made until bleeding stopped completely.

Figure 46:
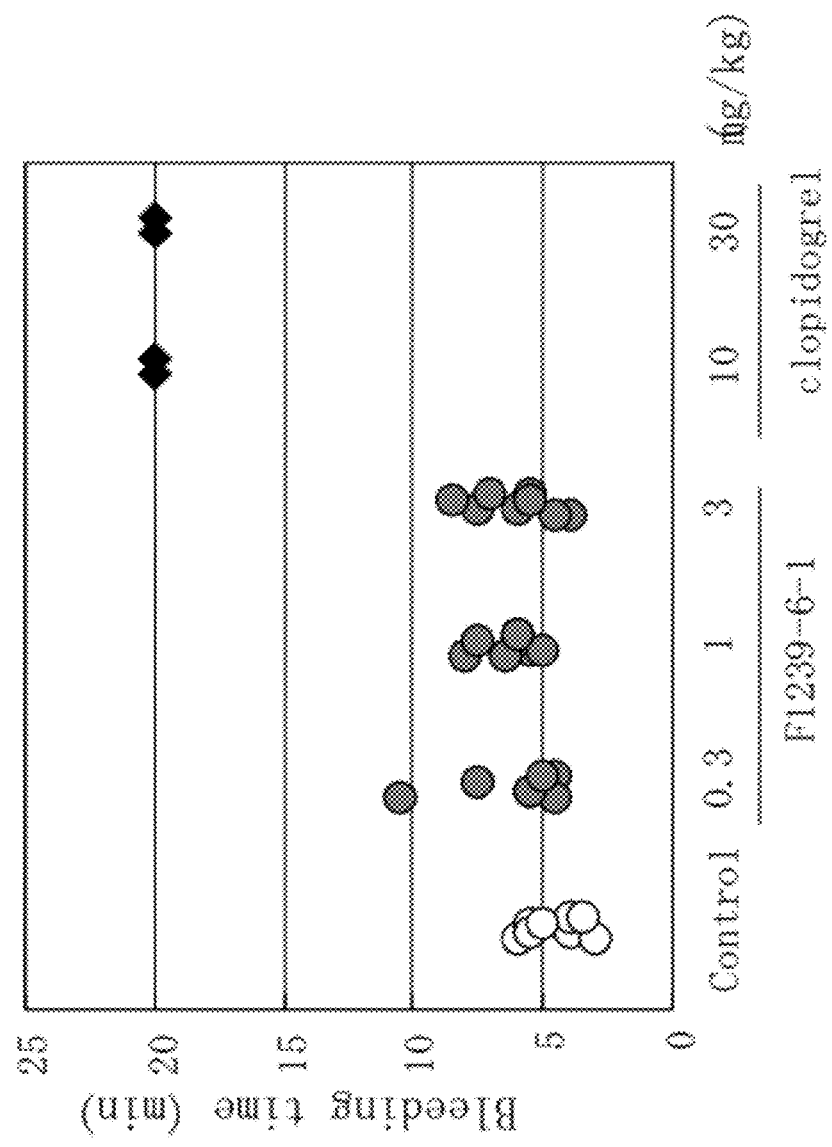
FIG. 46 shows a result of assay for the bleeding time of rat in EXAMPLE 50.

The antibody-treated animals exhibited less than 2-fold prolongation of bleeding time compared to the saline-treated group (FIG. 46). A group of animals were orally administered clopidogrel (as positive control group). At 2 hours after administration, the animals received clopidogrel at a dose greater than 10 mg/kg exhibited more than 5-fold prolongation of bleeding time compared to the negative control group. Furthermore, in the clopidogrel-treated group, the platelets collected from the animals received at a dose of 10 mg/kg or greater decreased the responsiveness to collagen-induced platelet aggregation. The platelets from animals received 30 mg/kg or greater decreased the responsiveness to both collagen and ADP; therefore, the above dosage is considered to be within the effective dose under normal conditions.

Example 51

Preparation of [$^{125}$I] Labeled cF1232-37-2/CHO

[$^{125}$I] labeled cF1232-37-2/CHO was prepared using cF1232-37-2/CHO which was prepared in EXAMPLE 25. Namely, cF1232-37-2/CHO was reacted with N-succinimidyl-3-(4-hydroxy-3-[$^{125}$I] iodophenyl propionate ([$^{125}$I]-Bolton-Hunter Bolton-Hunter Reagent-monoiodinated), and purified by passing through a gel filtration chromatography to prepare the labeled antibodies. The titer of the resulting labeled antibodies was calculated using EIA method described in EXAMPLE 2.

Example 52

Measurement of the Dissociation Constant of cF1232-37-2/CHO for Human and Monkey Platelets The dissociation constant was calculated using homologous competitive binding assay. First, the washed platelets were incubated with a constant amount of the labeled antibodies and a variable amount of cF1232-37-2/CHO (non-labeled antibody). The amount of the labeled antibodies bound to platelets was determined. Based on the amount of the labeled and non-labeled antibodies added, the dissociation constant of cF1232-37-2/CHO and maximum number of antibodies bound per a platelet were calculated. The following formula was used for calculating each parameter.

$$\text{Total Binding} = B_{max} \times [\text{Hot}] \div ([\text{Hot}] + [\text{Cold}] + KD) + NS$$

Total Binding: number of labeled antibodies bound per a platelet
$B_{max}$: maximum number of antibody bound per a platelet
[Hot]: titer of the labeled antibodies (M)
[Cold]: titer of the non-labeled antibodies (M)
KD: dissociation constant (M)
NS: number of antibodies non-specifically bound per a platelet ACD-A (acid citrate-dextrose) was added to the PRPs prepared from citrated blood obtained from healthy human or cynomolgus monkey to adjust the pH to 6.5. The obtained PRPs were collected by centrifugation at 2,000 rpm. The pelleted platelets were washed with HEPES Buffer (pH was adjusted to 6.5 with ACD-A). An appropriate quantity of HEPES Buffer (pH 7.4) was added to prepare platelet suspension. The number of platelets were determined with SYSMEX® F-820 (Sysmex Co.), then the above-described platelet suspension was diluted with HEPES buffer (pH 7.4) to platelet count at $6\times10^5$ cells/μL.

To the diluted washed platelets, the labeled and non-labeled antibodies were added at final concentrations of 3 nM and 0-1250 nM, respectively, and mixed to obtain platelet count at $3\times10^5$ cells/μL. After incubating the mixture on the ice for one hour, the reactant was passed through 30% sucrose/HEPE buffer (pH 7.4) layered column and centrifuged at 12,000 g for 5 min in order to separate the platelets and non-bound antibodies. The radioactivity of each fraction was measured using automatic gamma counter 1470 WIZARD (PerkinElmer Japan). Data was analyzed using GraphPad Prism software (Graph Pad Software, Inc.).

As for human platelets, $KD=1.7\pm0.4\times10^{-8}$ (M), and maximum number of antibody bound per a platelet=925±254 (n=3, mean±S.E.). As for simian platelets, $KD=2.0\pm0.1\times10^{-8}$ (M), and maximum number of antibody bound per a platelet=1007±64.4 (n=3, mean±S.E.).

INDUSTRIAL APPLICABILITY

The antibody of the present invention may be useful for prevention and/or treatment of especially human diseases such as diseases caused by activation or aggregation of platelet, or vascular endothelial disorders or arteriosclerotic reaction, and can be used for prevention and/or treatment of the disease caused by the thrombus or the embolism, for example, thrombosis, embolism, or arteriosclerotic diseases. Further, by the method of detecting GPVI in the test samples using the antibody of the present invention, diagnosis of diseases can be performed. Especially, it is possible to use for diagnosis of especially human diseases such as thrombus, embolism or arteriosclerotic diseases.

The invention claimed is:

1. An isolated antibody or antigen-binding fragment thereof that specifically binds to loop 9 in domain 2 of human platelet glycoprotein VI (GPVI) protein, wherein said antibody or antigen-binding fragment thereof comprises a variable heavy chain (VH) with 3 complementarity determining regions (CDR) and a variable light chain (VL) with 3 complementarity determining regions (CDR), comprising the following VH CDR1, VH CDR2, VH CDR3, VL CDR1, VL CDR2, and VL CDR3, respectively of:
   (i) SEQ ID NOs: 18, 19, 20, 54, 55 and 56;
   (ii) SEQ ID NOs: 24, 25, 26, 60, 61 and 62;
   (iii) SEQ ID NOs: 48, 49, 50, 84, 85 and 86;
   (iv) SEQ ID NOs: 362, 363, 364, 404, 405, and 406; and
   (v) SEQ ID NOs: 365, 366, 367, 407, 408, and 409.

2. The antibody or antigen-binding fragment thereof of claim 1, which is a chimeric antibody.

3. The antibody or antigen-binding fragment thereof of claim 1, which is a humanized antibody.

4. The antibody or antigen-binding fragment thereof of claim 1, wherein its antigen-binding valency is monovalent.

5. The antibody or antigen-binding fragment thereof of claim 1, which is polyethyleneglycolated (PEGylated).

6. A pharmaceutical composition comprising the antibody or antigen binding fragment thereof of claim 1, and a pharmaceutically acceptable excipient.

7. The antigen binding fragment according to claim 1, which is an Fab, Fab', F(ab')2, single-chain antibody (scFv), sc(Fv)2, disulfide-stabilized Fv(dsFv), or a diabody.

8. The antibody or antigen-binding fragment according to claim 1, which is labeled with a labeling substance; conjugated to a radioisotope, protein, peptide, or low molecular weight compound, or fused to another protein or peptide.

* * * * *